US011685901B2

(12) United States Patent
Evans et al.

(10) Patent No.: US 11,685,901 B2
(45) Date of Patent: Jun. 27, 2023

(54) COMPOSITIONS AND METHODS FOR ORGANOID GENERATION AND DISEASE MODELING

(71) Applicant: Salk Institute for Biological Studies, La Jolla, CA (US)

(72) Inventors: Ronald Evans, La Jolla, CA (US); Michael Downes, La Jolla, CA (US); Annette Atkins, La Jolla, CA (US); Eiji Yoshihara, La Jolla, CA (US); Ruth Yu, La Jolla, CA (US)

(73) Assignee: Salk Institute for Biological Studies, La Jolla, CA (US)

(*) Notice: Subject to any disclaimer, the term of this patent is extended or adjusted under 35 U.S.C. 154(b) by 0 days.

(21) Appl. No.: 17/706,272

(22) Filed: Mar. 28, 2022

(65) Prior Publication Data

US 2022/0220446 A1 Jul. 14, 2022

Related U.S. Application Data

(62) Division of application No. 16/301,671, filed as application No. PCT/US2017/034278 on May 24, 2017.

(60) Provisional application No. 62/341,461, filed on May 25, 2016.

(51) Int. Cl.

| | |
|---|---|
| ***C12N 5/071*** | (2010.01) |
| ***G01N 33/50*** | (2006.01) |
| ***A61K 35/39*** | (2015.01) |

(52) U.S. Cl.

CPC ............ *C12N 5/0677* (2013.01); *A61K 35/39* (2013.01); *G01N 33/5088* (2013.01); *C12N 2501/117* (2013.01); *C12N 2501/16* (2013.01); *C12N 2501/385* (2013.01); *C12N 2501/395* (2013.01); *C12N 2501/415* (2013.01); *C12N 2501/727* (2013.01); *C12N 2501/999* (2013.01); *C12N 2502/1382* (2013.01); *C12N 2502/28* (2013.01); *C12N 2503/02* (2013.01); *C12N 2506/02* (2013.01); *C12N 2506/45* (2013.01); *C12N 2513/00* (2013.01); *C12N 2533/52* (2013.01); *C12N 2533/54* (2013.01); *C12N 2533/90* (2013.01); *G01N 2800/04* (2013.01); *G01N 2800/7028* (2013.01)

(58) Field of Classification Search

CPC .................................................... C12N 5/0677

See application file for complete search history.

(56) References Cited

U.S. PATENT DOCUMENTS

| | | | |
|---|---|---|---|
| 4,683,202 | A | 7/1987 | Mullis |
| 5,399,346 | A | 3/1995 | Anderson et al. |
| 5,854,033 | A | 12/1998 | Lizardi |
| 5,942,435 | A | 8/1999 | Wheeler |
| 9,102,920 | B2 | 8/2015 | Feng et al. |
| 9,546,379 | B2 | 1/2017 | Evans et al. |
| 10,520,494 | B2 | 12/2019 | Lickert et al. |
| 10,912,800 | B2 | 2/2021 | Evans et al. |
| 10,920,199 | B2 | 2/2021 | Evans et al. |
| 2009/0281191 | A1 | 11/2009 | Rangwala et al. |
| 2010/0145470 | A1 | 6/2010 | Cohen et al. |
| 2011/0028401 | A1 | 2/2011 | Minchiotti et al. |
| 2011/0165570 | A1 | 7/2011 | Feng et al. |
| 2012/0039919 | A1 | 2/2012 | Yang et al. |
| 2012/0302491 | A1 | 11/2012 | Narkar et al. |
| 2013/0195811 | A1 | 8/2013 | Wang et al. |
| 2014/0289877 | A1 | 9/2014 | Taniguchi et al. |
| 2015/0203818 | A1 | 7/2015 | Mountford et al. |
| 2015/0368667 | A1 | 12/2015 | Evans et al. |
| 2016/0083693 | A1 | 3/2016 | Xu et al. |
| 2017/0087189 | A1 | 3/2017 | Evans et al. |
| 2018/0044642 | A1 | 2/2018 | Evans et al. |
| 2019/0211310 | A1 | 7/2019 | Evans et al. |
| 2021/0283187 | A1 | 9/2021 | Evans et al. |
| 2021/0363490 | A1 | 11/2021 | Yoshihara et al. |

FOREIGN PATENT DOCUMENTS

| | | | |
|---|---|---|---|
| CA | 2937882 | A1 | 9/2015 |
| EP | 2878664 | A1 | 6/2015 |
| EP | 2940127 | A1 | 11/2015 |
| JP | 2009533017 | A | 9/2009 |
| JP | 2011522520 | A | 8/2011 |
| JP | 2016514481 | A | 5/2016 |
| WO | 2001015755 | A2 | 3/2001 |
| WO | 2006063733 | A1 | 6/2006 |
| WO | 2006063734 | A2 | 6/2006 |

(Continued)

OTHER PUBLICATIONS

Jaramillo et al. (2014, PLOS One, vol. 9(4), pp. 1-14) (Year: 2014).*

(Continued)

*Primary Examiner* — Anoop K Singh
*Assistant Examiner* — David A Montanari
(74) *Attorney, Agent, or Firm* — Melissa Hunter-Ensor; Leslie Serunian; Greenberg Traurig, LLP

(57) ABSTRACT

The invention features pancreatic islet and pancreatic organoids, and cell cultures and methods that are useful for the rapid and reliable generation of pancreatic islet and pancreatic islet organoids. The invention also features methods of treating pancreatic diseases and methods of identifying agents that are useful for treatment of pancreatic diseases, such as type 2 diabetes and pancreatic cancer, using the pancreatic islet and pancreatic organoids of the invention.

19 Claims, 38 Drawing Sheets

Specification includes a Sequence Listing.

(56) References Cited

FOREIGN PATENT DOCUMENTS

| | | | |
|---|---|---|---|
| WO | 2006063735 | A1 | 6/2006 |
| WO | 2006063736 | A1 | 6/2006 |
| WO | 2006119886 | A1 | 11/2006 |
| WO | 2006119887 | A1 | 11/2006 |
| WO | 2006119888 | A2 | 11/2006 |
| WO | 2009136867 | A1 | 11/2009 |
| WO | 2011160066 | A1 | 12/2011 |
| WO | 2012044486 | A1 | 4/2012 |
| WO | 2013159103 | A1 | 10/2013 |
| WO | 2014017513 | A1 | 1/2014 |
| WO | 2014104364 | A1 | 7/2014 |
| WO | 2014145625 | A1 | 9/2014 |
| WO | 2015148832 | A1 | 10/2015 |
| WO | 2016015158 | A1 | 2/2016 |
| WO | 2016100898 | A1 | 6/2016 |
| WO | 2016100909 | A1 | 6/2016 |
| WO | 2016100921 | A1 | 6/2016 |
| WO | 2016100925 | A1 | 6/2016 |
| WO | 2016100930 | A1 | 6/2016 |
| WO | 2017205511 | A1 | 11/2017 |
| WO | 2018156955 | A1 | 8/2018 |

OTHER PUBLICATIONS

Liu et al. (2017, Genes and Development, vol. 31(3), pp. 228-240) (Year: 2017).*
Bosnak et al., "Somatostatin Therapy in the Management of Resistant Diabetic Ketoacidosis," Diabetes Care, Mar. 2002, vol. 25, No. 3, pp. 629-630.
Office Action dated Mar. 30, 2022 in corresponding Japanese Patent Application No. 2018-561550 (4 pages).
English translation of the Office Action dated Mar. 30, 2022 in corresponding Japanese Patent Application No. 2018-561550 (4 pages).
Baidal et al., "Bioengineering of an Intraabdominal Endocrine Pancreas," The New England Journal of Medicine, May 11, 2017, vol. 376, No. 19, pp. 1887-1889.
Burns et al., "High-Throughput Luminescent Reporter of Insulin Secretion for Discovering Regulators of Pancreatic Beta-Cell Function," Cell Metabolism, Jan. 6, 2015, vol. 21, pp. 126-137.
D'Amour et al., "Production of pancreatic hormone-expressing endocrine cells from human embryonic stem cells," Nature Biotechnology, Nov. 2006, vol. 24, No. 11, pp. 1392-1401.
Kroon et al., "Pancreatic endoderm derived from human embryonic stem cells generates glucose-responsive insulin-secreting cells in vivo," Nature Biotechnology, Apr. 2008, vol. 26, No. 4, pp. 443-452.
Mandel et al., "SERKAL Syndrome: An Autosomal-Recessive Disorder Caused by a Loss-of-Function Mutation in WNT4," The American Journal of Human Genetics, Jan. 2008, vol. 82, No. 1, pp. 39-47.
Pagliuca et al., "Generation of Functional Human Pancreatic β Cells In Vitro," Cell, Oct. 9, 2014, vol. 159, p. 428-439.
Raikwar et al., "Human iPS Cell-Derived Insulin Producing Cells Form Vascularized Organoids under the Kidney Capsules of Diabetic Mice," PLoS One, Jan. 28, 2015, vol. 10, No. 1, e0116582.
Rezania et al., "Reversal of diabetes with insulin-producing cells derived in vitro from human pluripotent stem cells," Nature Biotechnology, Nov. 2014, vol. 32, No. 11, pp. 1121-1133.
Russ et al., "Controlled induction of human pancreatic progenitors produces functional beta-like cells in vitro," The EMBO Journal, 2015, vol. 34, No. 13, pp. 1759-1772.
Sneddon et al., "Self-renewal of embryonic-stem-cell-derived progenitors by organ-matched mesenchyme," Nature, Nov. 29, 2012, vol. 491, No. 7426, pp. 765-768.
Soltanian et al., "Morphogenesis of Human Pluripotent Stem Cell Aggregates toward Pancreatic Progenitors in Suspension Culture," Cell Journal (Yakhteh), 2015, vol. 17, Suppl. 1, Ps-86, p. 59.
Saito et al., "Generation of Glucose-Responsive Functional Islets with a Three-Dimensional Structure from Mouse Fetal Pancreatic Cells and iPS Cells In Vitro," PLoS One, Dec. 1, 2011, vol. 6, No. 12, e28209, pp. 1-7.
Takebe et al., "Vascularized and functional human liver from an iPSC-derived organ bud transplant," Nature, Jul. 2013, vol. 499, No. 7459, pp. 481-484.
Vegas et al., "Combinatorial hydrogel library enables identification of materials that mitigate the foreign body response in primates," Nature Biotechnology, Mar. 2016, vol. 34, No. 3, pp. 345-352.
Vegas et al., "Long-term glycemic control using polymer-encapsulated human stem cell-derived beta cells in immune-competent mice," Nature Medicine, Mar. 2016, vol. 22, No. 3, pp. 306-311.
Willert et al., "Wnt Proteins," Cold Spring Harbor Perspectives in Biology, Sep. 1, 2012, vol. 4, No. 9, a007864, pp. 1-13.
Yoshihara et al., "Disruption of TBP-2 ameliorates insulin sensitivity and secretion without affecting obesity," Nature Communications, 2010, vol. 1, Article No. 127, pp. 1-12.
Yoshihara et al., "ERRγ Is Required for the Metabolic Maturation of Therapeutically Functional Glucose-Responsive 3 Cells," Cell Metabolism, Apr. 12, 2016, vol. 23, pp. 622-634.
Yu et al., "Human induced pluripotent stem cells free of vector and transgene sequences," Science, May 8, 2009 [Corrected: Jun. 5, 2009], vol. 324, No. 5928, pp. 797-801.
International Search Report and Written Opinion dated Oct. 31, 2017 in corresponding International PCT Patent Application No. PCT/US2017/034278 (22 pages).
Partial Supplementary European Search Report dated Apr. 7, 2020 in corresponding European Patent Application No. 17803511.9 (13 pages).
Extended European Search Report dated Jul. 9, 2020 in corresponding European Patent Application No. 17803511.9 (12 pages).
Office Action dated Apr. 30, 2021 in corresponding Japanese Patent Application No. 2018-561550 (9 pages).
English translation of the Office Action dated Apr. 30, 2021 in corresponding Japanese Patent Application No. 2018-561550 (6 pages).
Examination Report dated Jul. 26, 2021 in corresponding European Patent Application No. 17803511.9 (4 pages).
Extended European Search Report dated Dec. 1, 2021 in corresponding European Patent Application No. 21180343.2 (9 pages).
Akinci et al., "Reprogramming of Various Cell Types to a Beta-Like State by Pdx1, Ngn3 and MafA," PLOS one, Nov. 2013, vol. 8, No. 11, pp. e82424.
Alaynick et al., "ERRγ Directs and Maintains the Transition to Oxidative Metabolism in the Postnatal Heart," Cell Metabolism, Jul. 2007, vol. 6, pp. 13-24.
Anderson, W. French, "Prospects for Human Gene Therapy," Science, Oct. 26, 1984, vol. 226, No. 4673, pp. 401-409.
Anello et al., "Functional and morphological alterations of mitochondria in pancreatic beta cells from type 2 diabetic patients," Diabetologia, 2005, vol. 48, pp. 282-289.
Ansari et al., "The Programmed Death-1 (PD-1) Pathway Regulates Autoimmune Diabetes in Nonobese Diabetic (NOD) Mice," Journal of Experimental Medicine, Jul. 7, 2003, vol. 198, No. 1, pp. 63-69.
Bader et al., "Identification of proliferative and mature β-cells in the islets of Langerhans," Nature, Jul. 21, 2016, vol. 535, pp. 430-434.
Barany, F., "Genetic disease detection and DNA amplification using cloned thermostable ligase," PNAS, Jan. 1991, vol. 88, pp. 189-193.
Bar-Ephraim et al., "Modelling cancer immunomodulation using epithelial organoid cultures," BioRxiv, 2018.
Blomer et al., "Highly efficient and sustained gene transfer in adult neurons with a lentivirus vector," Journal of Virology, Sep. 1997, vol. 71, No. 9, pp. 6641-6649.
Brevini et al., "No shortcuts to pig embryonic stem cells," Theriogenology, 2010, vol. 74, pp. 544-550.
Buenrostro et al., "ATAC-seq: A Method for Assaying Chromatin Accessibility Genome-Wide," Current Protocols in Molecular Biology, 2016, vol. 109, pp. 21.29.1-21.29.9.
Buganim et al., "Single-Cell Expression Analyses during Cellular Reprogramming Reveal an Early Stochastic and a Late Hierarchic Phase," Cell, Sep. 14, 2012, vol. 150, pp. 1209-1222.

(56) References Cited

OTHER PUBLICATIONS

Buganim et al., "The Developmental Potential of iPSCs Is Greatly Influenced by Reprogramming Factor Selection," Cell Stem Cell, Sep. 4, 2014, vol. 15, pp. 295-309.
Carey et al., "Single-gene transgenic mouse strains for reprogramming adult somatic cells," Nature Methods, Jan. 2010, vol. 7, No. 1, pp. 56-59.
Cayouette et al., "Adenovirus-Mediated Gene Transfer of Ciliary Neurotrophic Factor Can Prevent Photoreceptor Degeneration in the Retinal Degeneration (rd) Mouse," Human Gene Therapy, Mar. 1, 1997, vol. 8, pp. 423-430.
Chen et al., "Integration of External Signaling Pathways with the Core Transcriptional Network in Embryonic Stem Cells," Cell, Jun. 13, 2008, vol. 133, pp. 1106-1117.
Chen et al., "PDGF signalling controls age-dependent proliferation in pancreatic β-cells," Nature, 2012, vol. 478, No. 7369, pp. 349-355.
Colli et al., "PDL1 is expressed in the islets of people with type 1 diabetes and is up-regulated by interferons-α and-γ via IRF1 induction," EBioMedicine, 2018, vol. 36, pp. 367-375.
Conrad et al., "Revealing transcription factors during human pancreatic β cell development," Trends in Endocrinology & Metabolism, Aug. 2014, vol. 25, No. 8, pp. 407-414.
Crunkhorn, Sarah, "Human iPSC-derived β-like cells rescue diabetic mice," Nature Reviews Drug Discovery, 2016. vol 15, No. 383.
Ding et al., "Activation of CD4+ T cells by delivery of the B7 costimulatory signal on bystander antigen-presenting cells (transcostimulation)," European Journal of Immunology, 1994, vol. 24, pp. 859-866.
Dobin et al., "STAR: ultrafast universal RNA-seq aligner," Bioinformatics, 2013, vol. 29, No. 1, pp. 15-21.
Dor et al., "Adult pancreatic β-cells are formed by self-duplication rather than stem-cell differentiation," Nature, May 6, 2004, vol. 429, pp. 41-46.
Dufour et al., "Genome-wide Orchestration of Cardiac Functions by the Orphan Nuclear Receptors ERRα and γ," Cell Metabolism, May 2007, vol. 5, pp. 345-356.
Felgner et al., "Lipofection: a highly efficient, lipid-mediated DNA-transfection procedure," PNAS, Nov. 1987, vol. 84, pp. 7413-7417.
Feng et al., "Reprogramming of fibroblasts into induced pluripotent stem cells with orphan nuclear receptor Esrrb," Nature Cell Biology, Feb. 2009, vol. 11, No. 2, pp. 197-203.
Festuccia et al., "Esrrb Is a Direct Nanog Target Gene that Can Substitute for Nanog Function in Pluripotent Cells," Cell Stem Cell, Oct. 5, 2012, vol. 11, pp. 477-490.
Foks et al., "Immune checkpoint proteins: exploring their therapeutic potential to regulate atherosclerosis," British Journal of Pharmacology, 2017, vol. 174, pp. 3940-3955.
Folmes et al., "Somatic Oxidative Bioenergetics Transitions into Pluripotency-Dependent Glycolysis to Facilitate Nuclear Reprogramming," Cell Metabolism, Aug. 3, 2011, vol. 14, pp. 264-271.
Friedmann, Theodore, "Progress Toward Human Gene Therapy," Science, Jun. 16, 1989, vol. 244, No. 4910, pp. 1275-1281.
Guatelli et al., "Isothermal, in vitro amplification of nucleic acids by a multienzyme reaction modeled after retroviral replication," PNAS, Mar. 1990, vol. 87, pp. 1874-1878.
Hackenbrock, Charles R., "Ultrastructural Bases for Metabolically Linked Mechanical Activity in Mitochondria : I. Reversible Ultrastructural Changes with Change in Metabolic Steady State in Isolated Liver Mitochondria," Journal of Cell Biology, 1966, vol. 30, pp. 269-297.
Hart et al., "Attenuation of FGF signalling in mouse β-cells leads to diabetes," Nature, Dec. 14, 2000, vol. 408, pp. 864-868.
Heinz et al., "Simple Combinations of Lineage-Determining Transcription Factors Prime cis-Regulatory Elements Required for Macrophage and B Cell Identities," Molecular Cell, May 28, 2010, vol. 38, pp. 576-589.
Hickey et al., "Generation of islet-like cells from mouse gall bladder by direct ex vivo reprogramming," Stem Cell Research, 2013, vol. 11, pp. 503-515.
Hrvatin et al., "Differentiated human stem cells resemble fetal, not adult, β cells," PNAS, Feb. 25, 2014, vol. 111, No. 8, pp. 3038-3043.
Huang et al., "Enhanced Differentiation of Three-Gene-Reprogrammed Induced Pluripotent Stem Cells into Adipocytes via Adenoviral-Mediated PGC-1α Overexpression," International Journal of Molecular Sciences, 2011, vol. 12, pp. 7554-7568.
Huang et al., "Systematic and integrative analysis of large gene lists using DAVID bioinformatics resources," Nature Protocols, 2009, vol. 4, pp. 44-57.
Johnson, Larry G., "Gene Therapy for Cystic Fibrosis," Chest, Feb. 1995, vol. 107, pp. 77S-83S.
Kapturczak et al., "Transduction of Human and Mouse Pancreatic Islet Cells Using a Bicistronic Recombinant Adeno-associated Viral Vector," Molecular Therapy, Feb. 2002, vol. 5, No. 2, pp. 154-160.
Kawaguchi et al., "Generation of Naïve Bovine Induced Pluripotent Stem Cells Using PiggyBac Transposition of Doxycycline-Inducible Transcription Factors," PLOS one, Aug. 19, 2015, vol. 10, pp. 1-18.
Kawamure et al., "Linking the p53 tumour suppressor pathway to somatic cell reprogramming," Nature, Aug. 27, 2009, vol. 460, No. 7259, pp. 1140-1144.
Kida et al., "ERRs Mediate a Metabolic Switch Required for Somatic Cell Reprogramming to Pluripotency," Cell Stem Cell, May 7, 2015, vol. 16, pp. 547-555.
Kwoh et al., "Transcription-based amplification system and detection of amplified human immunodeficiency virus type 1 with a bead-based sandwich hybridization format," PNAS, Feb. 1989, vol. 86, pp. 1173-1177.
Le Gal La Salle et al., "An Adenovirus Vector for Gene Transfer into Neurons and Glia in the Brain," Science, Feb. 12, 1993, vol. 259, No. 5097, pp. 988-990.
Lee et al., "Decoding the Pluripotency Network: The Emergence of New Transcription Factors," Biomedicines, 2013, vol. 1, pp. 49-78.
Li et al., "Small Molecules Facilitate the Reprogramming of Mouse Fibroblasts into Pancreatic Lineages," Cell Stem Cell, Feb. 6, 2014, vol. 14, pp. 228-236.
Liu et al., "Cells that present both specific ligand and costimulatory activity are the most efficient inducers of clonal expansion of normal CD4 T cells," PNAS, May 1992, vol. 89, pp. 3845-3849.
Ludwig et al., "Feeder-independent culture of human embryonic stem cells," Nature Methods, Aug. 2006, vol. 3, No. 8, pp. 637-646.
Ludwig et al., "Transplantation of human islets without immunosuppression," PNAS, Nov. 19, 2013, vol. 110, No. 47, pp. 19054-19058.
Mangelsdorf et al., "The Nuclear Receptor Superfamily: The Second Decade," Cell, Dec. 15, 1995, vol. 83, No. 6, pp. 835-839.
Mao et al., "Automated genome annotation and pathway identification using the KEGG Orthology (KO) as a controlled vocabulary," Bioinformatics, 2005, vol. 21, No. 19, pp. 3787-3793.
Mao et al., "Lentiviral Vectors Mediate Long-Term and High Efficiency Transgene Expression in HEK 293T cells," International Journal of Medical Sciences, 2015, vol. 12, No. 5, pp. 407-415.
Martello et al., "Esrrb Is a Pivotal Target of the Gsk3/Tcf3 Axis Regulating Embryonic Stem Cell Self-Renewal," Cell Stem Cell, Oct. 5, 2012, vol. 11, pp. 491-504.
Mathieu et al., "Investigating the real role of HIF-1 and HIF-2 in iron recycling by macrophages," Haematologica, 2014, vol. 99, pp. e112-e114.
Miller et al., "Improved Retroviral Vectors for Gene Transfer and Expression," Biotechniques, Oct. 1989, vol. 7, No. 9, pp. 980-990.
Miller, Dusty A., "Retrovirus Packaging Cells," Human Gene Therapy, 1990, vol. 1, pp. 5-14.
Miyoshi et al., "Stable and efficient gene transfer into the retina using an HIV-based lentiviral vector," PNAS, Sep. 1997, vol. 94, pp. 10319-10323.
Morizane et al., "MHC matching improves engraftment of iPSC-derived neurons in non-human primates," Nature Communications, 2017, vol. 8, No. 385, pp. 1-12.

(56) References Cited

OTHER PUBLICATIONS

Munoz et al., "Conventional pluripotency markers are unspecific for bovine embryonic-derived cell-lines," Theriogenology, 2008, vol. 69, pp. 1159-1164.
Naldini et al., "In Vivo Gene Delivery and Stable Transduction of Nondividing Cells by a Lentiviral Vector," Science, Apr. 12, 1996, vol. 272, pp. 263-267.
Narkar et al., "Exercise and PGC-1α-Independent Synchronization of Type I Muscle Metabolism and Vasculature by ERRγ," Cell Metabolism, Mar. 2, 2011, vol. 13, pp. 283-293.
Nasr et al., "PD-L1 genetic overexpression or pharmacological restoration in hematopoietic stem and progenitor cells reverses autoimmune diabetes," Science Translational Medicine, Nov. 15, 2017, vol. 9, No. 416, pp. 1-14.
Nemajerova et al., "Two-factor reprogramming of somatic cells to pluripotent stem cells reveals partial functional fedundancy of Sox2 and Klf4," Cell Death & Differentiation, 2012, vol. 19, pp. 1268-1276.
Nichols et al., "Adult tissue sources for new β cells," Translational Research, Apr. 2014, vol. 163, No. 4, pp. 418-431.
Ono et al., "Plasmid DNAs directly injected into mouse brain with lipofectin can be incorporated and expressed by brain cells," Neurosceince Letters, 1990, vol. 117, pp. 259-263.
Osum et al., "Interferon-gamma drives programmed death-ligand 1 expression on islet β cells to limit T cell function during autoimmune diabetes," Scientific Reports, 2018, vol. 8, No. 8295, pp. 1-12.
Pagliuca et al., "How to make a functional β-cell," Development, 2013, vol. 140, No. 12, pp. 2472-2483.
Panopoulos et al., "The metabolome of induced pluripotent stem cells reveals metabolic changes occurring in somatic cell reprogramming," Cell Research, 2012, vol. 22, pp. 168-177.
Paris et al., "Equine embryos and embryonic stem cells: Defining reliable markers of pluripotency," Theriogenology, Sep. 1, 2010, vol. 74, No. 4, pp. 516-524.
Ravassard et al., "A genetically engineered human pancreatic β cell line exhibiting glucose-inducible insulin secretion," The Journal of Clinical Investigation, 2011, vol. 121, No. 9, pp. 3589-3597.
Roberts et al., "Identification of novel transcripts in annotated genomes using RNA-Seq," Bioinformatics, 2011, vol. 27, No. 17, pp. 2325-2329.
Rosenberg et al., "Gene Transfer into Humans—Immunotherapy of Patients with Advanced Melanoma, Using Tumor-Infiltrating Lymphocytes Modified by Retroviral Gene Transduction," The New England Journal of Medicine, Aug. 30, 1990, vol. 323, No. 9, pp. 570-578.
Roska et al., "Dissection of the functions of antigen-presenting cells in the induction of T cell activation." The Journal of Immunology, 1985, vol. 135, pp. 2953-2961.
Said et al., "Programmed death-1-induced interleukin-10 production by monocytes impairs CD4+ T cell activation during HIV infection," Nature Medicine, Apr. 2010, vol. 16, No. 4, pp. 452-459.
Schulz et al., "A Scalable System for Production of Functional Pancreatic Progenitors from Human Embryonic Stem Cells," PLOS one, May 2012, vol. 7, No. 5, pp. e37004.
Shyh-Chang et al., "Influence of Threonine Metabolism on S-Adenosylmethionine and Histone Methylation," Science, Jan. 11, 2013, vol. 339, No. 6116, pp. 222-226.
Subudhi et al., "Local expression of B7-H1 promotes organ-specific autoimmunity and transplant rejection," The Journal of Clinical Investigation, 2004, vol. 113, No. 5, pp. 694-700.
Sugii et al., "Human and mouse adipose-derived cells support feeder-independent induction of pluripotent stem cells," PNAS, Feb. 23, 2010, vol. 107, No. 8, pp. 3558-3563.
Sutton et al., "Isolation of Rat Pancreatic Islets By Ductal Injection of Collagenase," Transplantation, Dec. 1986, vol. 42, No. 6, pp. 689-690.
Takahashi et al., "Induction of Pluripotent Stem Cells from Adult Human Fibroblasts by Defined Factors," Cell, Nov. 30, 2007, vol. 131, pp. 861-872.
Takahashi et al., "Induction of Pluripotent Stem Cells from Mouse Embryonic and Adult Fibroblast Cultures by Defined Factors," Cell, Aug. 25, 2006, vol. 126, pp. 663-676.
Tang et al., "Desnutrin/ATGL Activates PPARδ to Promote Mitochondrial Function for Insulin Secretion in Islet β Cells," Cell Metabolism, Dec. 3, 2013, vol. 18, pp. 883-895.
Teta et al., "Very Slow Turnover of β-Cells in Aged Adult Mice," Diabetes , Sep. 2005, vol. 54, pp. 2557-2567.
Tolstoshev et al., "Gene expression using retroviral vectors," Current Opinion in Biotechnology, 1990, vol. 1, pp. 55-61.
Trapnell et al., "Differential analysis of gene regulation at transcript resolution with RNA-seq," Nature Biotechnology, Jan. 2013, vol. 31, No. 1, pp. 1-19.
Tsonkova et al., "The EndoC-βH1 cell line is a valid model of human beta cells and applicable for screenings to identify novel drug target candidates," Molecular Metabolism, 2018, vol. 8, pp. 144-157.
Vaithilingam et al., "Co-encapsulation and co-transplantation of mesenchymal stem cells reduces pericapsular fibrosis and improves encapsulated islet survival and function when allografted," Scientific Reports, 2017, vol. 7, No. 10059, pp. 1-13.
Vethe et al., "The Effect of Wnt Pathway Modulators on Human iPSC-Derived Pancreatic Beta Cell Maturation," Frontiers in Endocrinology, May 2019, vol. 10, No. 293, pp. 1-13.
Wei et al., "Klf4 Interacts Directly with Oct4 and Sox2 to Promote Reprogramming," Stem Cells, 2009, vol. 27, No. 12, pp. 2969-2978.
Wei et al., "Klf4 Organizes Long-Range Chromosomal Interactions with the Oct4 Locus in Reprogramming and Pluripotency," Cell Stem Cell, Jul. 3, 2013, vol. 13, pp. 36-47.
Wendeln et al., "Innate immune memory in the brain shapes neurological disease hallmarks," Nature, Apr. 2018, vol. 556, No. 7701, pp. 332-338.
Wolff et al., "Direct Gene Transfer into Mouse Muscle in Vivo," Science, Mar. 23, 1990, vol. 247, pp. 1465-1468.
Wu et al., "Receptor-mediated Gene Delivery and Expression in Vivo," Journal of Biological Chemistry, Oct. 15, 1988, vol. 263, No. 29, pp. 14621-14624.
Wu et al., "Targeting Genes: Delivery and Persistent Expression of a Foreign Gene Driven by Mammalian Regulatory Elements in Vivo," Journal of Biological Chemistry, Oct. 15, 1989, vol. 264, No. 29, pp. 16985-16987.
Wulfing et al., "A Receptor/Cytoskeletal Movement Triggered by Costimulation During T Cell Activation," Science, Dec. 18, 1998, vol. 282, pp. 2266-2269.
Xu et al., "The role of pyruvate carboxylase in insulin secretion and proliferation in rat pancreatic beta cells," Diabetologia, 2008, vol. 51, pp. 2022-2030.
Yang et al., "Nuclear Receptor Expression Links the Circadian Clock to Metabolism," Cell, Aug. 25, 2006, vol. 126, pp. 801-810.
Yu et al., "Induced Pluripotent Stem Cell Lines Derived from Human Somatic Cells," Science, 2007, vol. 318, pp. 1917-1920.
Zhang et al., "Efficient Reprogramming of Naïve-Like Induced Pluripotent Stem Cells from Porcine Adipose-Derived Stem Cells with a Feeder-Independent and Serum-Free System," PLOS one, Jan. 2014, vol. 9, No. 1, pp. e85089.
Zhang et al., "Esrrb Activates Oct4 Transcription and Sustains Self-renewal and Pluripotency in Embryonic Stem Cells," Molecular Basis of Cell and Developmental Biology, Dec. 19, 2008, vol. 283, No. 51, pp. 35825-35833.
Zhang et al., "Metabolic Regulation in Pluripotent Stem Cells during Reprogramming and Self-Renewal," Cell Stem Cell, Nov. 2, 2012, vol. 11, pp. 589-595.
Zhao et al., "Overexpression of lactate dehydrogenase A attenuates glucose-induced insulin secretion in stable MIN-6 β-cell lines," FEBS Letters, 1998, vol. 430, pp. 213-216.
Zuckermann et al., "Discovery of Nanomolar Ligands for 7-Transmembrane G-Protein-Coupled Receptors from a Diverse N-(Substituted)glycine Peptoid Library," Journal of Medicinal Chemistry, 1994, vol. 37, pp. 2678-2685.
Examination Report dated Aug. 18, 2022 in corresponding Australian Patent Application No. 2017269364 (4 pages).
Kemp et al., "Transplantation of Isolated Pancreatic Islets into the Portal Vein of Diabetic Rats," Nature, 1973, vol. 244, p. 447.

(56) References Cited

OTHER PUBLICATIONS

Office Action dated Feb. 20, 2023 in corresponding European Patent Application No. 17803511.9 (5 pages).

* cited by examiner

Human ADSC 3D culture

Systematic Self-organization to sphere formation

Cell number in 1well of 24well with 30μl Matrigel

FIG. 2D-2

Cluster 1

| Term | Count | P-Value |
|---|---|---|
| Pyrimidine metabolism | 16 | 3.80E-03 |
| Endocytosis | 25 | 4.20E-03 |
| Pathways in cancer | 36 | 1.60E-02 |
| Propanoate metabolism | 7 | 2.70E-02 |
| Aminoacyl-tRNA biosynthesis | 8 | 2.90E-02 |
| Spliceosome | 16 | 4.40E-02 |
| DNA replication | 7 | 4.60E-02 |
| Lysosome | 15 | 4.90E-02 |

Cluster 2

| Term | Count | P-Value |
|---|---|---|
| Cytokine-cytokine receptor interaction | 14 | 2.40E-04 |
| Bladder cancer | 5 | 4.40E-03 |
| Pathways in cancer | 12 | 1.50E-02 |
| Fructose and mannose metabolism | 4 | 1.70E-02 |
| Neurotrophin signaling pathway | 6 | 4.90E-02 |
| Hematopoietic cell lineage | 5 | 4.90E-02 |

Cluster 3

| Term | Count | P-Value |
|---|---|---|
| Calcium signaling pathway | 15 | 1.00E-03 |
| NOD-like receptor signaling pathway | 8 | 2.90E-03 |
| p53 signaling pathway | 8 | 4.80E-03 |
| MAPK signaling pathway | 17 | 8.30E-03 |
| Pathways in cancer | 18 | 2.50E-02 |
| Inositol phosphate metabolism | 6 | 2.50E-02 |
| Cytokine-cytokine receptor interaction | 15 | 3.20E-02 |
| Melanogenesis | 8 | 3.40E-02 |
| Dorso-ventral axis formation | 4 | 4.10E-02 |

FIG. 2D-3

Cluster 4

| Term | Count | P-Value |
| --- | --- | --- |
| TGF-beta signaling pathway | 16 | 2.30E-04 |
| Adherens junction | 14 | 7.50E-04 |
| Axon guidance | 19 | 8.50E-04 |
| Chronic myeloid leukemia | 13 | 1.90E-03 |
| ErbB signaling pathway | 14 | 2.40E-03 |
| Pathways in cancer | 34 | 3.20E-03 |
| Pancreatic cancer | 12 | 4.20E-03 |
| Lysine degradation | 9 | 4.80E-03 |
| Wnt signaling pathway | 19 | 5.10E-03 |
| Neurotrophin signaling pathway | 16 | 8.90E-03 |

Cluster 5

| Term | Count | P-Value |
| --- | --- | --- |
| Cell cycle | 17 | 4.60E-06 |
| Oocyte meiosis | 14 | 8.70E-05 |
| Terpenoid backbone biosynthesis | 5 | 1.40E-03 |
| Progesterone-mediated oocyte maturation | 10 | 2.60E-03 |
| Valine, leucine and isoleucine degradation | 7 | 3.60E-03 |
| Biosynthesis of unsaturated fatty acids | 5 | 6.10E-03 |
| Pathogenic Escherichia coli infection | 7 | 1.30E-03 |
| Butanoate metabolism | 5 | 2.80E-02 |
| p53 signaling pathway | 7 | 2.90E-02 |
| Gap junction | 8 | 3.30E-02 |

Cluster 6

| Term | Count | P-Value |
| --- | --- | --- |
| Lysosome | 20 | 5.00E-04 |
| ErbB signaling pathway | 14 | 7.80E-03 |
| MAPK signaling pathway | 30 | 1.30E-02 |
| Basal cell carcinoma | 10 | 1.40E-02 |
| Adipocytokine signaling pathway | 11 | 1.90E-02 |
| Acute myeloid leukemia | 10 | 2.00E-02 |
| Complement and coagulation cascades | 11 | 2.30E-02 |

FIG. 2D-4

Cluster 7

| Term | Count | P-Value |
|---|---|---|
| Parkinson's disease | 51 | 1.90E-16 |
| Huntington's disease | 60 | 5.50E-15 |
| Oxidative phosphorylation | 46 | 1.30E-12 |
| Proteasome | 26 | 2.20E-12 |
| Spliceosome | 43 | 3.10E-11 |
| Alzheimer's disease | 45 | 1.90E-08 |
| Citrate cycle (TCA cycle) | 16 | 3.20E-07 |
| Pathogenic Escherichia coli infection | 19 | 3.50E-05 |
| Glyoxylate and dicarboxylate metabolism | 8 | 6.80E-04 |
| Pyruvate metabolism | 12 | 4.00E-03 |

Cluster 8

| Term | Count | P-Value |
|---|---|---|
| Cytokine-cytokine receptor interaction | 25 | 9.00E-06 |
| Hematopoietic cell lineage | 11 | 6.90E-04 |
| Pathways in cancer | 24 | 8.20E-04 |
| Jak-STAT signaling pathway | 15 | 8.60E-04 |
| Dorso-ventral axis formation | 6 | 1.40E-03 |
| Melanoma | 9 | 2.90E-03 |
| VEGF signaling pathway | 9 | 4.10E-03 |
| MAPK signaling pathway | 19 | 4.70E-03 |
| Fructose and mannose metabolism | 6 | 5.80E-03 |
| Natural killer cell mediated cytotoxicity | 12 | 6.00E-03 |

3D Gellan gum

FIG. 4G *In vitro* Vascularization
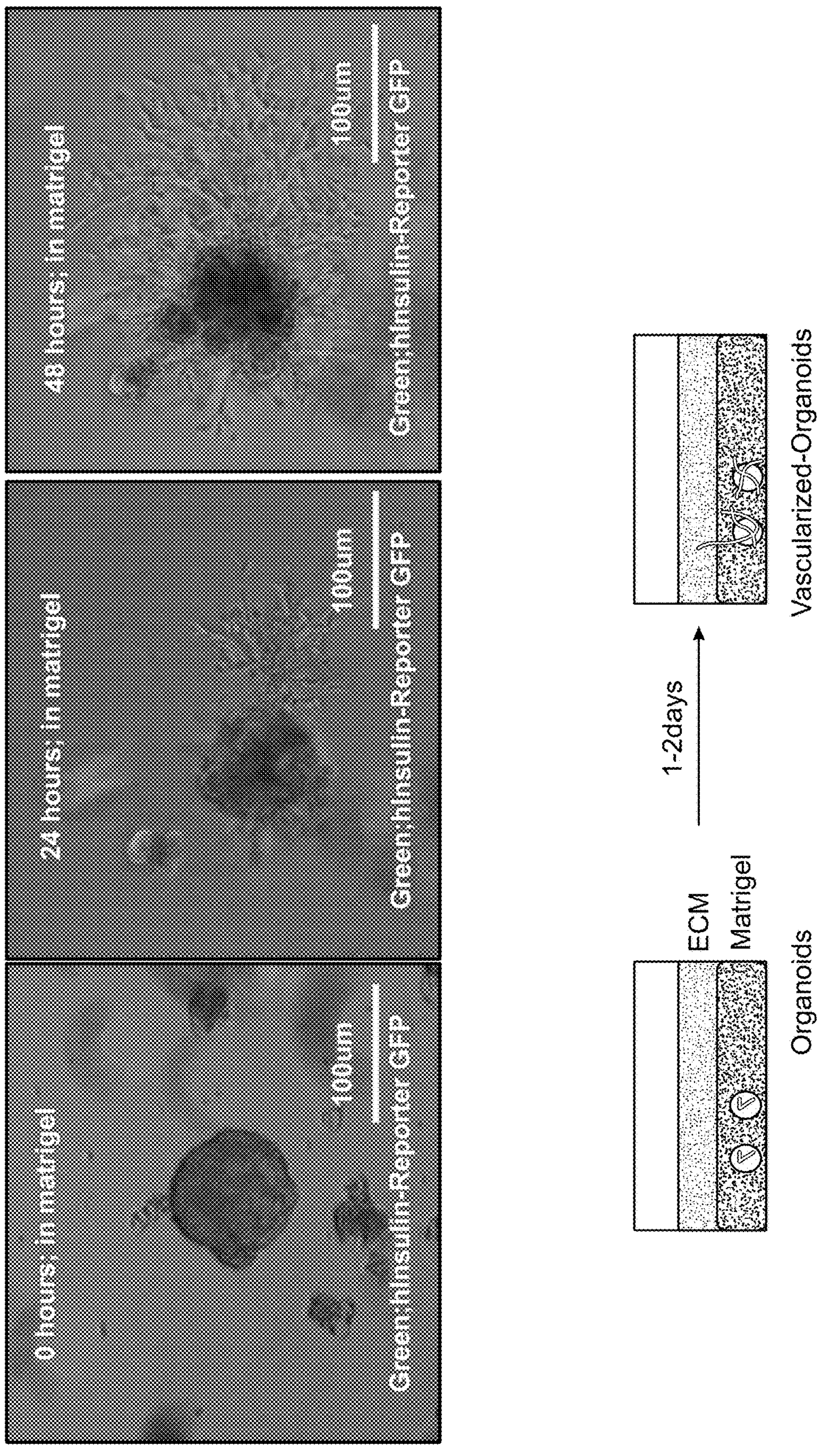

SEQUENCE LISTING

<160> NUMBER OF SEQ ID NOS: 52

<210> SEQ ID NO 1
<211> LENGTH: 609
<212> TYPE: PRT
<213> ORGANISM: Homo sapiens

<400> SEQUENCE: 1

```
Met Lys Trp Val Glu Ser Ile Phe Leu Ile Phe Leu Leu Asn Phe Thr
1               5                   10                  15

Glu Ser Arg Thr Leu His Arg Asn Glu Tyr Gly Ile Ala Ser Ile Leu
            20                  25                  30

Asp Ser Tyr Gln Cys Thr Ala Glu Ile Ser Leu Ala Asp Leu Ala Thr
        35                  40                  45

Ile Phe Phe Ala Gln Phe Val Gln Glu Ala Thr Tyr Lys Glu Val Ser
    50                  55                  60

Lys Met Val Lys Asp Ala Leu Thr Ala Ile Glu Lys Pro Thr Gly Asp
65                  70                  75                  80

Glu Gln Ser Ser Gly Cys Leu Glu Asn Gln Leu Pro Ala Phe Leu Glu
                85                  90                  95

Glu Leu Cys His Glu Lys Glu Ile Leu Glu Lys Tyr Gly His Ser Asp
            100                 105                 110

Cys Cys Ser Gln Ser Glu Glu Gly Arg His Asn Cys Phe Leu Ala His
        115                 120                 125

Lys Lys Pro Thr Pro Ala Ser Ile Pro Leu Phe Gln Val Pro Glu Pro
    130                 135                 140

Val Thr Ser Cys Glu Ala Tyr Glu Glu Asp Arg Glu Thr Phe Met Asn
145                 150                 155                 160

Lys Phe Ile Tyr Glu Ile Ala Arg Arg His Pro Phe Leu Tyr Ala Pro
                165                 170                 175

Thr Ile Leu Leu Trp Ala Ala Arg Tyr Asp Lys Ile Ile Pro Ser Cys
            180                 185                 190

Cys Lys Ala Glu Asn Ala Val Glu Cys Phe Gln Thr Lys Ala Ala Thr
        195                 200                 205

Val Thr Lys Glu Leu Arg Glu Ser Ser Leu Leu Asn Gln His Ala Cys
    210                 215                 220

Ala Val Met Lys Asn Phe Gly Thr Arg Thr Phe Gln Ala Ile Thr Val
225                 230                 235                 240

Thr Lys Leu Ser Gln Lys Phe Thr Lys Val Asn Phe Thr Glu Ile Gln
                245                 250                 255

Lys Leu Val Leu Asp Val Ala His Val His Glu His Cys Cys Arg Gly
            260                 265                 270

Asp Val Leu Asp Cys Leu Gln Asp Gly Glu Lys Ile Met Ser Tyr Ile
        275                 280                 285

Cys Ser Gln Gln Asp Thr Leu Ser Asn Lys Ile Thr Glu Cys Cys Lys
    290                 295                 300

Leu Thr Thr Leu Glu Arg Gly Gln Cys Ile Ile His Ala Glu Asn Asp
305                 310                 315                 320

Glu Lys Pro Glu Gly Leu Ser Pro Asn Leu Asn Arg Phe Leu Gly Asp
                325                 330                 335

Arg Asp Phe Asn Gln Phe Ser Ser Gly Glu Lys Asn Ile Phe Leu Ala
            340                 345                 350

Ser Phe Val His Glu Tyr Ser Arg Arg His Pro Gln Leu Ala Val Ser
        355                 360                 365
```

-continued

```
Val Ile Leu Arg Val Ala Lys Gly Tyr Gln Glu Leu Leu Glu Lys Cys
    370                 375                 380

Phe Gln Thr Glu Asn Pro Leu Glu Cys Gln Asp Lys Gly Glu Glu Glu
385                 390                 395                 400

Leu Gln Lys Tyr Ile Gln Glu Ser Gln Ala Leu Ala Lys Arg Ser Cys
                405                 410                 415

Gly Leu Phe Gln Lys Leu Gly Glu Tyr Tyr Leu Gln Asn Ala Phe Leu
            420                 425                 430

Val Ala Tyr Thr Lys Lys Ala Pro Gln Leu Thr Ser Ser Glu Leu Met
        435                 440                 445

Ala Ile Thr Arg Lys Met Ala Ala Thr Ala Ala Thr Cys Cys Gln Leu
    450                 455                 460

Ser Glu Asp Lys Leu Leu Ala Cys Gly Glu Gly Ala Ala Asp Ile Ile
465                 470                 475                 480

Ile Gly His Leu Cys Ile Arg His Glu Met Thr Pro Val Asn Pro Gly
                485                 490                 495

Val Gly Gln Cys Cys Thr Ser Ser Tyr Ala Asn Arg Arg Pro Cys Phe
            500                 505                 510

Ser Ser Leu Val Val Asp Glu Thr Tyr Val Pro Pro Ala Phe Ser Asp
        515                 520                 525

Asp Lys Phe Ile Phe His Lys Asp Leu Cys Gln Ala Gln Gly Val Ala
    530                 535                 540

Leu Gln Thr Met Lys Gln Glu Phe Leu Ile Asn Leu Val Lys Gln Lys
545                 550                 555                 560

Pro Gln Ile Thr Glu Glu Gln Leu Glu Ala Val Ile Ala Asp Phe Ser
                565                 570                 575

Gly Leu Leu Glu Lys Cys Cys Gln Gly Gln Glu Gln Glu Val Cys Phe
            580                 585                 590

Ala Glu Glu Gly Gln Lys Leu Ile Ser Lys Thr Arg Ala Ala Leu Gly
        595                 600                 605

Val
```

```
<210> SEQ ID NO 2
<211> LENGTH: 2057
<212> TYPE: DNA
<213> ORGANISM: Homo sapiens

<400> SEQUENCE: 2

atattgtgct tccaccactg ccaataacaa aataactagc aaccatgaag tgggtggaat      60

caattttttt aattttccta ctaaatttta ctgaatccag aacactgcat agaaatgaat     120

atggaatagc ttccatattg gattcttacc aatgtactgc agagataagt ttagctgacc     180

tggctaccat atttttgcc cagtttgttc aagaagccac ttacaaggaa gtaagcaaaa     240

tggtgaaaga tgcattgact gcaattgaga aacccactgg agatgaacag tcttcagggt     300

gtttagaaaa ccagctacct gcctttctgg aagaactttg ccatgagaaa gaaattttgg     360

agaagtacgg acattcagac tgctgcagcc aaagtgaaga gggaagacat aactgttttc     420

ttgcacacaa aaagcccact ccagcatcga tcccactttt ccaagttcca gaacctgtca     480

caagctgtga agcatatgaa gaagacaggg agacattcat gaacaaattc atttatgaga     540

tagcaagaag gcatcccttc ctgtatgcac ctacaattct tctttgggct gctcgctatg     600

acaaaataat tccatcttgc tgcaaagctg aaaatgcagt tgaatgcttc caaacaaagg     660

cagcaacagt tacaaaagaa ttaagagaaa gcagcttgtt aaatcaacat gcatgtgcag     720
```

```
taatgaaaaa ttttgggacc cgaactttcc aagccataac tgttactaaa ctgagtcaga    780

agtttaccaa agttaatttt actgaaatcc agaaactagt cctggatgtg gcccatgtac    840

atgagcactg ttgcagagga gatgtgctgg attgtctgca ggatggggaa aaaatcatgt    900

cctacatatg ttctcaacaa gacactctgt caaacaaaat aacagaatgc tgcaaactga    960

ccacgctgga acgtggtcaa tgtataattc atgcagaaaa tgatgaaaaa cctgaaggtc   1020

tatctccaaa tctaaacagg tttttaggag atagagattt taaccaattt tcttcagggg   1080

aaaaaaatat cttcttggca agttttgttc atgaatattc aagaagacat cctcagcttg   1140

ctgtctcagt aattctaaga gttgctaaag gataccagga gttattggag aagtgtttcc   1200

agactgaaaa ccctcttgaa tgccaagata aaggagaaga agaattacag aaatacatcc   1260

aggagagcca agcattggca aagcgaagct gcggcctctt ccagaaacta ggagaatatt   1320

acttacaaaa tgcgtttctc gttgcttaca caaagaaagc cccccagctg acctcgtcgg   1380

agctgatggc catcaccaga aaaatggcag ccacagcagc cacttgttgc caactcagtg   1440

aggacaaact attggcctgt ggcgagggag cggctgacat tattatcgga cacttatgta   1500

tcagacatga aatgactcca gtaaaccctg gtgttggcca gtgctgcact tcttcatatg   1560

ccaacaggag gccatgcttc agcagcttgg tggtggatga aacatatgtc cctcctgcat   1620

tctctgatga caagttcatt ttccataagg atctgtgcca agctcagggt gtagcgctgc   1680

aaacgatgaa gcaagagttt ctcattaacc ttgtgaagca aaagccacaa ataacagagg   1740

aacaacttga ggctgtcatt gcagatttct caggcctgtt ggagaaatgc tgccaaggcc   1800

aggaacagga agtctgcttt gctgaagagg gacaaaaact gatttcaaaa actcgtgctg   1860

ctttgggagt ttaaattact tcaggggaag agaagacaaa acgagtcttt cattcggtgt   1920

gaacttttct ctttaatttt aactgattta acactttttg tgaattaatg aaatgataaa   1980

gacttttatg tgagatttcc ttatcacaga aataaaatat ctccaaatgt ttccttttca   2040

aaaaaaaaaa aaaaaaa                                                  2057
```

<210> SEQ ID NO 3
<211> LENGTH: 609
<212> TYPE: PRT
<213> ORGANISM: Homo sapiens

<400> SEQUENCE: 3

```
Met Lys Trp Val Thr Phe Ile Ser Leu Leu Phe Leu Phe Ser Ser Ala
1               5                   10                  15

Tyr Ser Arg Gly Val Phe Arg Arg Asp Ala His Lys Ser Glu Val Ala
            20                  25                  30

His Arg Phe Lys Asp Leu Gly Glu Glu Asn Phe Lys Ala Leu Val Leu
        35                  40                  45

Ile Ala Phe Ala Gln Tyr Leu Gln Gln Cys Pro Phe Glu Asp His Val
    50                  55                  60

Lys Leu Val Asn Glu Val Thr Glu Phe Ala Lys Thr Cys Val Ala Asp
65                  70                  75                  80

Glu Ser Ala Glu Asn Cys Asp Lys Ser Leu His Thr Leu Phe Gly Asp
                85                  90                  95

Lys Leu Cys Thr Val Ala Thr Leu Arg Glu Thr Tyr Gly Glu Met Ala
            100                 105                 110

Asp Cys Cys Ala Lys Gln Glu Pro Glu Arg Asn Glu Cys Phe Leu Gln
        115                 120                 125

His Lys Asp Asp Asn Pro Asn Leu Pro Arg Leu Val Arg Pro Glu Val
```

```
    130                 135                 140

Asp Val Met Cys Thr Ala Phe His Asp Asn Glu Glu Thr Phe Leu Lys
145                 150                 155                 160

Lys Tyr Leu Tyr Glu Ile Ala Arg Arg His Pro Tyr Phe Tyr Ala Pro
                165                 170                 175

Glu Leu Leu Phe Phe Ala Lys Arg Tyr Lys Ala Ala Phe Thr Glu Cys
            180                 185                 190

Cys Gln Ala Ala Asp Lys Ala Ala Cys Leu Leu Pro Lys Leu Asp Glu
        195                 200                 205

Leu Arg Asp Glu Gly Lys Ala Ser Ser Ala Lys Gln Arg Leu Lys Cys
    210                 215                 220

Ala Ser Leu Gln Lys Phe Gly Glu Arg Ala Phe Lys Ala Trp Ala Val
225                 230                 235                 240

Ala Arg Leu Ser Gln Arg Phe Pro Lys Ala Glu Phe Ala Glu Val Ser
                245                 250                 255

Lys Leu Val Thr Asp Leu Thr Lys Val His Thr Glu Cys Cys His Gly
            260                 265                 270

Asp Leu Leu Glu Cys Ala Asp Asp Arg Ala Asp Leu Ala Lys Tyr Ile
        275                 280                 285

Cys Glu Asn Gln Asp Ser Ile Ser Ser Lys Leu Lys Glu Cys Cys Glu
    290                 295                 300

Lys Pro Leu Leu Glu Lys Ser His Cys Ile Ala Glu Val Glu Asn Asp
305                 310                 315                 320

Glu Met Pro Ala Asp Leu Pro Ser Leu Ala Ala Asp Phe Val Glu Ser
                325                 330                 335

Lys Asp Val Cys Lys Asn Tyr Ala Glu Ala Lys Asp Val Phe Leu Gly
            340                 345                 350

Met Phe Leu Tyr Glu Tyr Ala Arg Arg His Pro Asp Tyr Ser Val Val
        355                 360                 365

Leu Leu Leu Arg Leu Ala Lys Thr Tyr Glu Thr Thr Leu Glu Lys Cys
    370                 375                 380

Cys Ala Ala Ala Asp Pro His Glu Cys Tyr Ala Lys Val Phe Asp Glu
385                 390                 395                 400

Phe Lys Pro Leu Val Glu Glu Pro Gln Asn Leu Ile Lys Gln Asn Cys
                405                 410                 415

Glu Leu Phe Glu Gln Leu Gly Glu Tyr Lys Phe Gln Asn Ala Leu Leu
            420                 425                 430

Val Arg Tyr Thr Lys Lys Val Pro Gln Val Ser Thr Pro Thr Leu Val
        435                 440                 445

Glu Val Ser Arg Asn Leu Gly Lys Val Gly Ser Lys Cys Cys Lys His
    450                 455                 460

Pro Glu Ala Lys Arg Met Pro Cys Ala Glu Asp Tyr Leu Ser Val Val
465                 470                 475                 480

Leu Asn Gln Leu Cys Val Leu His Glu Lys Thr Pro Val Ser Asp Arg
                485                 490                 495

Val Thr Lys Cys Cys Thr Glu Ser Leu Val Asn Arg Arg Pro Cys Phe
            500                 505                 510

Ser Ala Leu Glu Val Asp Glu Thr Tyr Val Pro Lys Glu Phe Asn Ala
        515                 520                 525

Glu Thr Phe Thr Phe His Ala Asp Ile Cys Thr Leu Ser Glu Lys Glu
    530                 535                 540

Arg Gln Ile Lys Lys Gln Thr Ala Leu Val Glu Leu Val Lys His Lys
545                 550                 555                 560
```

```
Pro Lys Ala Thr Lys Glu Gln Leu Lys Ala Val Met Asp Asp Phe Ala
                565                 570                 575

Ala Phe Val Glu Lys Cys Cys Lys Ala Asp Asp Lys Glu Thr Cys Phe
            580                 585                 590

Ala Glu Glu Gly Lys Lys Leu Val Ala Ala Ser Gln Ala Ala Leu Gly
        595                 600                 605

Leu


<210> SEQ ID NO 4
<211> LENGTH: 2264
<212> TYPE: DNA
<213> ORGANISM: Homo sapiens

<400> SEQUENCE: 4

agtatattag tgctaatttc cctccgtttg tcctagcttt tctcttctgt caaccccaca      60

cgcctttggc acaatgaagt gggtaacctt tatttccctt ctttttctct ttagctcggc     120

ttattccagg ggtgtgtttc gtcgagatgc acacaagagt gaggttgctc atcggtttaa     180

agatttggga gaagaaaatt tcaaagcctt ggtgttgatt gcctttgctc agtatcttca     240

gcagtgtcca tttgaagatc atgtaaaatt agtgaatgaa gtaactgaat ttgcaaaaac     300

atgtgttgct gatgagtcag ctgaaaattg tgacaaatca cttcataccc tttttggaga     360

caaattatgc acagttgcaa ctcttcgtga aacctatggt gaaatggctg actgctgtgc     420

aaaacaagaa cctgagagaa atgaatgctt cttgcaacac aaagatgaca acccaaacct     480

cccccgattg gtgagaccag aggttgatgt gatgtgcact gcttttcatg acaatgaaga     540

gacatttttg aaaaaatact tatatgaaat tgccagaaga catccttact tttatgcccc     600

ggaactcctt ttctttgcta aaaggtataa agctgctttt acagaatgtt gccaagctgc     660

tgataaagct gcctgcctgt tgccaaagct cgatgaactt cgggatgaag ggaaggcttc     720

gtctgccaaa cagagactca agtgtgccag tctccaaaaa tttggagaaa gagctttcaa     780

agcatgggca gtagctcgcc tgagccagag atttcccaaa gctgagtttg cagaagtttc     840

caagttagtg acagatctta ccaaagtcca cacggaatgc tgccatggag atctgcttga     900

atgtgctgat gacagggcgg accttgccaa gtatatctgt gaaaatcaag attcgatctc     960

cagtaaactg aaggaatgct gtgaaaaacc tctgttggaa aaatcccact gcattgccga    1020

agtggaaaat gatgagatgc ctgctgactt gccttcatta gctgctgatt ttgttgaaag    1080

taaggatgtt tgcaaaaact atgctgaggc aaaggatgtc ttcctgggca tgtttttgta    1140

tgaatatgca agaaggcatc ctgattactc tgtcgtgctg ctgctgagac ttgccaagac    1200

atatgaaacc actctagaga agtgctgtgc cgctgcagat cctcatgaat gctatgccaa    1260

agtgttcgat gaatttaaac ctcttgtgga agagcctcag aatttaatca aacaaaattg    1320

tgagcttttt gagcagcttg gagagtacaa attccagaat gcgctattag ttcgttacac    1380

caagaaagta ccccaagtgt caactccaac tcttgtagag gtctcaagaa acctaggaaa    1440

agtgggcagc aaatgttgta aacatcctga agcaaaaaga atgccctgtg cagaagacta    1500

tctatccgtg gtcctgaacc agttatgtgt gttgcatgag aaaacgccag taagtgacag    1560

agtcaccaaa tgctgcacag aatccttggt gaacaggcga ccatgctttt cagctctgga    1620

agtcgatgaa acatacgttc ccaaagagtt taatgctgaa acattcacct tccatgcaga    1680

tatatgcaca ctttctgaga aggagagaca aatcaagaaa caaactgcac ttgttgagct    1740

cgtgaaacac aagcccaagg caacaaaaga gcaactgaaa gctgttatgg atgatttcgc    1800
```

```
agcttttgta gagaagtgct gcaaggctga cgataaggag acctgctttg ccgaggaggg   1860

taaaaaactt gttgctgcaa gtcaagctgc cttaggctta taacatcaca tttaaaagca   1920

tctcagccta ccatgagaat aagagaaaga aaatgaagat caaaagctta ttcatctgtt   1980

tttctttttc gttggtgtaa agccaacacc ctgtctaaaa aacataaatt tctttaatca   2040

ttttgcctct tttctctgtg cttcaattaa taaaaaatgg aaagaatcta atagagtggt   2100

acagcactgt tatttttcaa agatgtgttg ctatcctgaa aattctgtag gttctgtgga   2160

agttccagtg ttctctctta ttccacttcg gtagaggatt tctagtttct tgtgggctaa   2220

ttaaataaat cattaatact cttctaaaaa aaaaaaaaaa aaaa                    2264


<210> SEQ ID NO 5
<211> LENGTH: 313
<212> TYPE: PRT
<213> ORGANISM: Homo sapiens

<400> SEQUENCE: 5

Met Tyr Val Ser Tyr Leu Leu Asp Lys Asp Val Ser Met Tyr Pro Ser
1               5                   10                  15

Ser Val Arg His Ser Gly Gly Leu Asn Leu Ala Pro Gln Asn Phe Val
            20                  25                  30

Ser Pro Pro Gln Tyr Pro Asp Tyr Gly Gly Tyr His Val Ala Ala Ala
        35                  40                  45

Ala Ala Ala Ala Ala Asn Leu Asp Ser Ala Gln Ser Pro Gly Pro Ser
    50                  55                  60

Trp Pro Ala Ala Tyr Gly Ala Pro Leu Arg Glu Asp Trp Asn Gly Tyr
65                  70                  75                  80

Ala Pro Gly Gly Ala Ala Ala Ala Ala Asn Ala Val Ala His Gly Leu
                85                  90                  95

Asn Gly Gly Ser Pro Ala Ala Ala Met Gly Tyr Ser Ser Pro Ala Asp
            100                 105                 110

Tyr His Pro His His His Pro His His His Pro His His Pro Ala Ala
        115                 120                 125

Ala Pro Ser Cys Ala Ser Gly Leu Leu Gln Thr Leu Asn Pro Gly Pro
    130                 135                 140

Pro Gly Pro Ala Ala Thr Ala Ala Ala Glu Gln Leu Ser Pro Gly Gly
145                 150                 155                 160

Gln Arg Arg Asn Leu Cys Glu Trp Met Arg Lys Pro Ala Gln Gln Ser
                165                 170                 175

Leu Gly Ser Gln Val Lys Thr Arg Thr Lys Asp Lys Tyr Arg Val Val
            180                 185                 190

Tyr Thr Asp His Gln Arg Leu Glu Leu Glu Lys Glu Phe His Tyr Ser
        195                 200                 205

Arg Tyr Ile Thr Ile Arg Arg Lys Ala Glu Leu Ala Ala Thr Leu Gly
    210                 215                 220

Leu Ser Glu Arg Gln Val Lys Ile Trp Phe Gln Asn Arg Arg Ala Lys
225                 230                 235                 240

Glu Arg Lys Ile Asn Lys Lys Lys Leu Gln Gln Gln Gln Gln Gln Gln
                245                 250                 255

Pro Pro Gln Pro Pro Pro Pro Pro Pro Gln Pro Pro Gln Pro Gln Pro
            260                 265                 270

Gly Pro Leu Arg Ser Val Pro Glu Pro Leu Ser Pro Val Ser Ser Leu
        275                 280                 285
```

Gln Ala Ser Val Ser Gly Ser Val Pro Gly Val Leu Gly Pro Thr Gly
290 295 300

Gly Val Leu Asn Pro Thr Val Thr Gln
305 310

<210> SEQ ID NO 6
<211> LENGTH: 2370
<212> TYPE: DNA
<213> ORGANISM: Homo sapiens

<400> SEQUENCE: 6
ctccaaccat tggtgtctgt gtcattacta atagagtctt gtaaacactc gttaatcacg 60
gaaggccgcc ggcctggggc tccgcacgcc agcctgtggc gggtcttccc cgcctctgca 120
gcctagtggg aaggaggtgg gaggaaagaa ggaagaaagg gagggaggga ggaggcaggc 180
cagagggagg gaccgcctcg gaggcagaag agccgcgagg agccagcgga gcaccgcggg 240
ctggggcgca gccacccgcc gctcctcgag tcccctcgcc cctttccctt cgtgcccccc 300
ggcagcctcc agcgtcggtc cccaggcagc atggtgaggt ctgctcccgg accctcgcca 360
ccatgtacgt gagctacctc ctggacaagg acgtgagcat gtaccctagc tccgtgcgcc 420
actctggcgg cctcaacctg gcgccgcaga acttcgtcag ccccccgcag tacccggact 480
acggcggtta ccacgtggcg gccgcagctg cagcggcagc gaacttggac agcgcgcagt 540
ccccggggcc atcctggccg gcagcgtatg gcgccccact ccgggaggac tggaatggct 600
acgcgcccgg aggcgccgcg gccgccgcca acgccgtggc tcacggcctc aacggtggct 660
ccccggccgc agccatgggc tacagcagcc ccgcagacta ccatccgcac caccacccgc 720
atcaccaccc gcaccacccg gccgccgcgc cttcctgcgc ttctgggctg ctgcaaacgc 780
tcaaccccgg ccctcctggg cccgccgcca ccgctgccgc cgagcagctg tctcccggcg 840
gccagcggcg gaacctgtgc gagtggatgc ggaagccggc gcagcagtcc ctcggcagcc 900
aagtgaaaac caggacgaaa gacaaatatc gagtggtgta cacggaccac cagcggctgg 960
agctggagaa ggagtttcac tacagtcgct acatcaccat ccggaggaaa gccgagctag 1020
ccgccacgct ggggctctct gagaggcagg ttaaaatctg gtttcagaac cgcagagcaa 1080
aggagaggaa aatcaacaag aagaagttgc agcagcaaca gcagcagcag ccaccacagc 1140
cgcctccgcc gccaccacag cctccccagc ctcagccagg tcctctgaga agtgtcccag 1200
agcccttgag tccggtgtct tccctgcaag cctcagtgtc tggctctgtc cctggggttc 1260
tggggccaac tgggggggtg ctaaacccca ccgtcaccca gtgacccacc gggttctgca 1320
gcggcagagc aattccaggc tgagccatga ggagcgtgga ctctgctaga ctcctcagga 1380
gagacccctc ccctcccacc cacagccata gacctacaga cctggctctc agaggaaaaa 1440
tgggagccag gagtaagaca agtgggattt ggggcctcaa gaaatatact ctcccagatt 1500
tttacttttt cccatctggc tttttctgcc actgaggaga cagaaagcct ccgctgggct 1560
tcattccgga ctggcagaag cattgcctgg actgaccaca ccaaccaggc cttcatcctc 1620
ctccccagct cttctcttcc tagatctgca ggctgcacct ctggctagag ccgaggggag 1680
agagggactc aagggaaagg caagcttgag gccaagatgg ctgctgcctg ctcatggccc 1740
tcggaggtcc agctgggcct cctgcctccg ggcaggcaag gtttacactg cggaagccaa 1800
aggcagctaa gatagaaagc tggactgacc aaagactgca gaacccccag gtggcctgcg 1860 tctttttct cttcccttcc cagaccagga aaggcttggc tggtgtatgc acagggtgtg 1920
gtatgagggg gtggttattg gactccaggc ctgaccaggg ggcccgaaca gggacttgtt 1980

```
tagagagcct gtcaccagag cttctctggg ctgaatgtat gtcagtgcta taaatgccag   2040

agccaacctg gacttcctgt cattttcaca atcttggggc tgatgaagaa gggggtgggg   2100

ggagtttgtg ttgttgttgc tgctgtttgg gttgttggtc tgtgtaacat ccaagccaga   2160

gtttttaaag ccttctggat ccatgggggg agaagtgata tggtgaaggg aagtggggag   2220

tatttgaaca cagttgaatt ttttctaaaa agaaaaagag ataaatgagc tttccagatt   2280

tcagattctg tatttatctt cagattttgt ctgcaactat tttttatttt ttaaagaaat   2340

gaaatatctt caaaaaaaaa aaaaaaaaaa                                    2370
```

<210> SEQ ID NO 7
<211> LENGTH: 503
<212> TYPE: PRT
<213> ORGANISM: Homo sapiens

<400> SEQUENCE: 7

```
Met Asp Leu Ile Pro Asn Leu Ala Val Glu Thr Trp Leu Leu Leu Ala
1               5                   10                  15

Val Ser Leu Ile Leu Leu Tyr Leu Tyr Gly Thr Arg Thr His Gly Leu
            20                  25                  30

Phe Lys Lys Leu Gly Ile Pro Gly Pro Thr Pro Leu Pro Phe Leu Gly
        35                  40                  45

Asn Ala Leu Ser Phe Arg Lys Gly Tyr Trp Thr Phe Asp Met Glu Cys
    50                  55                  60

Tyr Lys Lys Tyr Arg Lys Val Trp Gly Ile Tyr Asp Cys Gln Gln Pro
65                  70                  75                  80

Met Leu Ala Ile Thr Asp Pro Asp Met Ile Lys Thr Val Leu Val Lys
                85                  90                  95

Glu Cys Tyr Ser Val Phe Thr Asn Arg Arg Pro Phe Gly Pro Val Gly
            100                 105                 110

Phe Met Lys Asn Ala Ile Ser Ile Ala Glu Asp Glu Glu Trp Lys Arg
        115                 120                 125

Ile Arg Ser Leu Leu Ser Pro Thr Phe Thr Ser Gly Lys Leu Lys Glu
    130                 135                 140

Met Val Pro Ile Ile Ala Gln Tyr Gly Asp Val Leu Val Arg Asn Leu
145                 150                 155                 160

Arg Arg Glu Ala Glu Thr Gly Lys Pro Val Thr Leu Lys His Val Phe
                165                 170                 175

Gly Ala Tyr Ser Met Asp Val Ile Thr Ser Thr Ser Phe Gly Val Ser
            180                 185                 190

Ile Asp Ser Leu Asn Asn Pro Gln Asp Pro Phe Val Glu Asn Thr Lys
        195                 200                 205

Lys Leu Leu Arg Phe Asn Pro Leu Asp Pro Phe Val Leu Ser Ile Lys
    210                 215                 220

Val Phe Pro Phe Leu Thr Pro Ile Leu Glu Ala Leu Asn Ile Thr Val
225                 230                 235                 240

Phe Pro Arg Lys Val Ile Ser Phe Leu Thr Lys Ser Val Lys Gln Ile
                245                 250                 255

Lys Glu Gly Arg Leu Lys Glu Thr Gln Lys His Arg Val Asp Phe Leu
            260                 265                 270

Gln Leu Met Ile Asp Ser Gln Asn Ser Lys Asp Ser Glu Thr His Lys
        275                 280                 285

Ala Leu Ser Asp Leu Glu Leu Met Ala Gln Ser Ile Ile Phe Ile Phe
    290                 295                 300
```

-continued

Ala Gly Tyr Glu Thr Thr Ser Ser Val Leu Ser Phe Ile Ile Tyr Glu
305 310 315 320

Leu Ala Thr His Pro Asp Val Gln Gln Lys Val Gln Lys Glu Ile Asp
325 330 335

Thr Val Leu Pro Asn Lys Ala Pro Pro Thr Tyr Asp Thr Val Leu Gln
340 345 350

Leu Glu Tyr Leu Asp Met Val Val Asn Glu Thr Leu Arg Leu Phe Pro
355 360 365

Val Ala Met Arg Leu Glu Arg Val Cys Lys Lys Asp Val Glu Ile Asn
370 375 380

Gly Met Phe Ile Pro Lys Gly Val Val Val Met Ile Pro Ser Tyr Val
385 390 395 400

Leu His His Asp Pro Lys Tyr Trp Thr Glu Pro Glu Lys Phe Leu Pro
405 410 415

Glu Arg Phe Ser Lys Lys Asn Lys Asp Asn Ile Asp Pro Tyr Ile Tyr
420 425 430

Thr Pro Phe Gly Ser Gly Pro Arg Asn Cys Ile Gly Met Arg Phe Ala
435 440 445

Leu Val Asn Met Lys Leu Ala Leu Val Arg Val Leu Gln Asn Phe Ser
450 455 460

Phe Lys Pro Cys Lys Glu Thr Gln Ile Pro Leu Lys Leu Arg Phe Gly
465 470 475 480

Gly Leu Leu Leu Thr Glu Lys Pro Ile Val Leu Lys Ala Glu Ser Arg
485 490 495

Asp Glu Thr Val Ser Gly Ala
500

<210> SEQ ID NO 8
<211> LENGTH: 2099
<212> TYPE: DNA
<213> ORGANISM: Homo sapiens

<400> SEQUENCE: 8
aatcactgct gtgcagggca ggaaagctcc acacacacag cccagcaaac agcagcacgc 60
tgctgaaaaa aagactcaga ggagagagat aaggaaggaa agtagtgatg gatctcatcc 120
caaacttggc cgtggaaacc tggcttctcc tggctgtcag cctgatactc ctctatctat 180
atggaacccg tacacatgga ctttttaaga agcttggaat tccagggccc acacctctgc 240 ctttttttggg aaatgctttg tccttccgta agggctattg gacgtttgac atggaatgtt 300
ataaaaagta tagaaaagtc tggggtattt atgactgtca acagcctatg ctggctatca 360
cagatcccga catgatcaaa acagtgctag tgaaagaatg ttattctgtc ttcacaaacc 420
ggaggccttt cgggccagtg ggatttatga aaaatgccat ctctatagct gaggatgaag 480
aatggaagag aatacgatca ttgctgtctc caacattcac cagcggaaaa ctcaaggaga 540
tggtccctat cattgcccag tatggagatg tgttggtgag aaatctgagg cgggaagcag 600
agacaggcaa gcctgtcacc ttgaaacacg tctttggggc ctacagcatg gatgtgatca 660
ctagcacatc atttggagtg agcatcgact ctctcaacaa tccacaagac ccctttgtgg 720
aaaacaccaa gaagctttta agatttaatc cattagatcc attcgttctc tcaataaaag 780
tctttccatt ccttacccca attcttgaag cattaaatat cactgtgttt ccaagaaaag 840
ttataagttt tctaacaaaa tctgtaaaac agataaaaga aggtcgcctc aaagagacac 900
aaaagcaccg agtggatttc cttcagctga tgattgactc tcagaattca aaagactctg 960

-continued

```
agacccacaa agctctgtct gatctggagc tcatggccca atcaattatc tttatttttg   1020

ctggctatga aaccacgagc agtgttctct ccttcattat atatgaactg gccactcacc   1080

ctgatgtcca gcagaaagtg cagaaggaaa ttgatacagt tttacccaat aaggcaccac   1140

ccacctatga tactgtgcta cagttggagt atcttgacat ggtggtgaat gaaacactca   1200

gattattccc agttgctatg agacttgaga gggtctgcaa aaaagatgtt gaaatcaatg   1260

ggatgtttat tcccaaaggg gtggtggtga tgattccaag ctatgttctt catcatgacc   1320

caaagtactg gacagagcct gagaagttcc tccctgaaag gttcagtaaa aagaacaagg   1380

acaacataga tccttacata tacacaccct ttggaagtgg acccagaaac tgcattggca   1440

tgaggtttgc tctcgtgaac atgaaacttg ctctagtcag agtccttcag aacttctcct   1500

tcaaaccttg taaagaaaca cagatccccc tgaaattacg ctttggagga cttcttctaa   1560

cagaaaaacc cattgttcta aaggctgagt caagggatga gaccgtaagt ggagcctgat   1620

ttccctaagg acttctggtt tgctctttaa gaaagctgtg ccccagaaca ccagagacct   1680

caaattactt tacaaataga accctgaaat gaagacgggc ttcatccaat gtgctgcata   1740

aataatcagg gattctgtac gtgcattgtg ctctctcatg gtctgtatag agtgttatac   1800

ttggtaatat agaggagatg accaaatcag tgctggggaa gtagatttgg cttctctgct   1860

tctcatagga ctatctccac cacccccagt tagcaccatt aactcctcct gagctctgat   1920

aacataatta acatttctca ataatttcaa ccacaatcat taataaaaat aggaattatt   1980

ttgatggctc taacagtgac atttatatca tgtgttatat ctgtagtatt ctatagtaag   2040

ctttatatta agcaaatcaa taaaaacctc tttacaaaag taaaaaaaaa aaaaaaaaa    2099
```

<210> SEQ ID NO 9
<211> LENGTH: 435
<212> TYPE: PRT
<213> ORGANISM: Homo sapiens

<400> SEQUENCE: 9

```
Met Ser Asn Lys Asp Arg His Ile Asp Ser Ser Cys Ser Ser Phe Ile
1               5                   10                  15

Lys Thr Glu Pro Ser Ser Pro Ala Ser Leu Thr Asp Ser Val Asn His
            20                  25                  30

His Ser Pro Gly Gly Ser Ser Asp Ala Ser Gly Ser Tyr Ser Ser Thr
        35                  40                  45

Met Asn Gly His Gln Asn Gly Leu Asp Ser Pro Pro Leu Tyr Pro Ser
    50                  55                  60

Ala Pro Ile Leu Gly Gly Ser Gly Pro Val Arg Lys Leu Tyr Asp Asp
65                  70                  75                  80

Cys Ser Ser Thr Ile Val Glu Asp Pro Gln Thr Lys Cys Glu Tyr Met
                85                  90                  95

Leu Asn Ser Met Pro Lys Arg Leu Cys Leu Val Cys Gly Asp Ile Ala
            100                 105                 110

Ser Gly Tyr His Tyr Gly Val Ala Ser Cys Glu Ala Cys Lys Ala Phe
        115                 120                 125

Phe Lys Arg Thr Ile Gln Gly Asn Ile Glu Tyr Ser Cys Pro Ala Thr
    130                 135                 140

Asn Glu Cys Glu Ile Thr Lys Arg Arg Arg Lys Ser Cys Gln Ala Cys
145                 150                 155                 160

Arg Phe Met Lys Cys Leu Lys Val Gly Met Leu Lys Glu Gly Val Arg
                165                 170                 175
```

```
Leu Asp Arg Val Arg Gly Gly Arg Gln Lys Tyr Lys Arg Arg Ile Asp
            180                 185                 190

Ala Glu Asn Ser Pro Tyr Leu Asn Pro Gln Leu Val Gln Pro Ala Lys
        195                 200                 205

Lys Pro Tyr Asn Lys Ile Val Ser His Leu Leu Val Ala Glu Pro Glu
    210                 215                 220

Lys Ile Tyr Ala Met Pro Asp Pro Thr Val Pro Asp Ser Asp Ile Lys
225                 230                 235                 240

Ala Leu Thr Thr Leu Cys Asp Leu Ala Asp Arg Glu Leu Val Val Ile
                245                 250                 255

Ile Gly Trp Ala Lys His Ile Pro Gly Phe Ser Thr Leu Ser Leu Ala
            260                 265                 270

Asp Gln Met Ser Leu Leu Gln Ser Ala Trp Met Glu Ile Leu Ile Leu
        275                 280                 285

Gly Val Val Tyr Arg Ser Leu Ser Phe Glu Asp Glu Leu Val Tyr Ala
    290                 295                 300

Asp Asp Tyr Ile Met Asp Glu Asp Gln Ser Lys Leu Ala Gly Leu Leu
305                 310                 315                 320

Asp Leu Asn Asn Ala Ile Leu Gln Leu Val Lys Lys Tyr Lys Ser Met
                325                 330                 335

Lys Leu Glu Lys Glu Glu Phe Val Thr Leu Lys Ala Ile Ala Leu Ala
            340                 345                 350

Asn Ser Asp Ser Met His Ile Glu Asp Val Glu Ala Val Gln Lys Leu
        355                 360                 365

Gln Asp Val Leu His Glu Ala Leu Gln Asp Tyr Glu Ala Gly Gln His
    370                 375                 380

Met Glu Asp Pro Arg Arg Ala Gly Lys Met Leu Met Thr Leu Pro Leu
385                 390                 395                 400

Leu Arg Gln Thr Ser Thr Lys Ala Val Gln His Phe Tyr Asn Ile Lys
                405                 410                 415

Leu Glu Gly Lys Val Pro Met His Lys Leu Phe Leu Glu Met Leu Glu
            420                 425                 430

Ala Lys Val
        435
```

<210> SEQ ID NO 10
<211> LENGTH: 5559
<212> TYPE: DNA
<213> ORGANISM: Homo sapiens

<400> SEQUENCE: 10

```
aagctccaat cggggcttta agtccttgat taggagagtg tgagagcttt ggtcccaact      60

ggctgtgcct ataggcttgt cactaggaga acatttgtgt taattgcact gtgctctgtc     120

aaggaaactt tgatttatag ctggggtgca caaataatgg ttgccggtcg cacatggatt     180

cggtagaact ttgccttcct gaatcttttt ccctgcacta cgaggaagag tagacttgaa     240

tgagacctgc ctcatcagtc atgggatcat agtgtcacag atggaaaagc aactatcagc     300

tgaattgtac tgaactacac acttggctaa ttcatcttat tgctctacac atctaaagga     360

aggctcattc tgttcttgga gtctagacag catcaggagt tgggctcagt gaacaaaact     420

ttaatgtcta gagcatttat gagggtttta atgattggaa aatctatcct gagaatgtgg     480

tcaccatatg tgacagcctt gctttctatc ttgtcttcag tttctggggc ttctctgcag     540

aatgtcaaac aaagatcgac acattgattc cagctgttcg tccttcatca agacggaacc     600
```

-continued

```
ttccagccca gcctccctga cggacagcgt caaccaccac agccctggtg gctcttcaga    660
cgccagtggg agctacagtt caaccatgaa tggccatcag aacggacttg actcgccacc    720
tctctaccct tctgctccta tcctgggagg tagtgggcct gtcaggaaac tgtatgatga    780
ctgctccagc accattgttg aagatcccca gaccaagtgt gaatacatgc tcaactcgat    840
gcccaagaga ctgtgtttag tgtgtggtga catcgcttct gggtaccact atggggtagc    900
atcatgtgaa gcctgcaagg cattcttcaa gaggacaatt caaggcaata tagaatacag    960
ctgccctgcc acgaatgaat gtgaaatcac aaagcgcaga cgtaaatcct gccaggcttg   1020
ccgcttcatg aagtgtttaa aagtgggcat gctgaaagaa ggggtgcgtc ttgacagagt   1080
acgtggaggt cggcagaagt acaagcgcag gatagatgcg gagaacagcc catacctgaa   1140
ccctcagctg gttcagccag ccaaaaagcc atataacaag attgtctcac atttgttggt   1200
ggctgaaccg gagaagatct atgccatgcc tgaccctact gtccccgaca gtgacatcaa   1260
agccctcact acactgtgtg acttggccga ccgagagttg gtggttatca ttggatgggc   1320
gaagcatatt ccaggcttct ccacgctgtc cctggcggac cagatgagcc ttctgcagag   1380
tgcttggatg gaaattttga tccttggtgt cgtataccgg tctctttcgt ttgaggatga   1440
acttgtctat gcagacgatt atataatgga cgaagaccag tccaaattag caggccttct   1500
tgatctaaat aatgctatcc tgcagctggt aaagaaatac aagagcatga agctggaaaa   1560
agaagaattt gtcaccctca aagctatagc tcttgctaat tcagactcca tgcacataga   1620
agatgttgaa gccgttcaga agcttcagga tgtcttacat gaagcgctgc aggattatga   1680
agctggccag cacatggaag accctcgtcg agctggcaag atgctgatga cactgccact   1740
cctgaggcag acctctacca aggccgtgca gcatttctac aacatcaaac tagaaggcaa   1800
agtcccaatg cacaaacttt ttttggaaat gttggaggcc aaggtctgac taaaagctcc   1860
ctgggccttc ccatccttca tgttgaaaaa gggaaaataa acccaagagt gatgtcgaag   1920
aaacttagag tttagttaac aacatcaaaa atcaacagac tgcactgata atttagcagc   1980
aagactatga agcagctttc agattcctcc ataggttcct gatgagtttc tttctacttt   2040
ctccatcatc ttctttcctc tttcttccca catttctctt tctctttatt ttttctcctt   2100
ttcttctttc acctccctta tttctttgct tctttcattc ctagttccca ttctccttta   2160
ttttcttccc gtctgcctgc cttctttctt ttctttacct actctcattc ctctcttttc   2220
tcatccttcc cctttttttct aaatttgaaa tagctttagt ttaaaaaaaa atcctccctt   2280
ccccctttcc tttccctttc tttcctttt ccctttcctt ttccctttcc tttcctttcc   2340
tcttgacctt ctttccatct ttctttttct tccttctgct gctgaacttt taaaagaggt   2400
ctctaactga agagagatgg aagccagccc tgccaaagga tggagatcca taatatggat   2460
gccagtgaac ttattgtgaa ccatactgtc cccaatgact aaggaatcaa agagagagaa   2520
ccaacgttcc taaaagtaca gtgcaacata tacaaattga ctgagtgcag tattagattt   2580
catgggagca gcctctaatt agacaactta agcaacgttg catcggctgc ttcttatcat   2640
tgcttttcca tctagatcag ttacagccat ttgattcctt aattgttttt tcaagtcttc   2700
caggtatttg ttagtttagc tactatgtaa ctttttcagg gaatagttta agctttattc   2760
attcatgcaa tactaaagag aaataagaat actgcaattt tgtgctggct ttgaacaatt   2820
acgaacaata atgaaggaca aatgaatcct gaaggaagat ttttaaaaat gttttgtttc   2880
ttcttacaaa tggagatttt tttgtaccag ctttaccact tttcagccat ttattaatat   2940
```

-continued

```
gggaatttaa cttactcaag caatagttga agggaaggtg catattatca cggatgcaat   3000
ttatgttgtg tgccagtctg gtcccaaaca tcaatttctt aacatgagct ccagtttacc   3060
taaatgttca ctgacacaaa ggatgagatt acacctacag tgactctgag tagtcacata   3120
tataagcact gcacatgaga tatagatccg tagaattgtc aggagtgcac ctctctactt   3180
gggaggtaca attgccatat gatttctagc tgccatggtg gttaggaatg tgatactgcc   3240
tgtttgcaaa gtcacagacc ttgcctcaga aggagctgtg agccagtatt catttaagag   3300
gcaataaggc aaatgccaga attaaaaaaa aaaatcatca aagacagaaa atgcctgacc   3360
aaattctaaa acctaatcca tataagttta ttcatttagg aatgttcgtt taaattaatc   3420
tgcagttttt accaagagct aagccaatat atgtgctttt caaccagtat tgtcacagca   3480
tgaaagtcaa gtcaggttcc agactgttaa gaggtgtaat ctaatgaaga aatcaattag   3540
atgccccgaa atctacagtc gctgaataac caataaacag taacctccat caaatgctat   3600
accaatggac cagtgttagt agctgctccc tgtattatgt gaacagtctt attctatgta   3660
cacagatgta attaaaattg taatcctaac aaacaaaaga aatgtagttc agcttttcaa   3720
tgtttcatgt ttgctgtgct tttctgaatt ttatgttgca ttcaaagact gttgtcttgt   3780
tcttgtggtg tttggattct tgtggtgtgt gcttttagac acagggtaga attagagaca   3840
atattggatg tacaattcct caggagacta cagtagtata ttctattcct taccagtaat   3900
aaggttcttc ctaataataa ttaagagatt gaaactccaa acaagtattc attatgaaca   3960
gatacacatc aaaatcataa taatattttc aaaacaagga ataatttctc taatggttta   4020
ttatagaata ccaatgtata gcttagaaat aaaactttga atatttcaag aatatagata   4080
agtctaattt ttaaatgctg tatatatggc tttcactcaa tcatctctca gatgttgtta   4140
ttaactcgct ctgtgttgtt gcaaaacttt ttggtgcaga ttcgtttcca aaactattgc   4200
tactttgtgt gctttaaaca aaataccttg ggttgatgaa acatcaaccc agtgctagga   4260
atactgtgta tctatcatta gctatatggg actatattgt agattgtggt ttctcagtag   4320
agaagtgact gtagtgtgat tctagataaa tcatcattag caattcattc agatggtcaa   4380
taacttgaaa tttatagctg tgataggagt tcagaaattg gcacatccct ttaaaaataa   4440
caacagaaaa tacaactcct gggaaaaaag gtgctgattc tataagatta tttatatatg   4500
taagtgttta aaaagattat tttccagaaa gtttgtgcag ggtttaagtt gctactattc   4560
aactacacta tatataaata aaatatatac aatatataca ttgttttcac tgtatcacat   4620
taaagtactt gggcttcaga agtaagagcc aaccaactga aaacctgaga tggagatatg   4680
ttcaaagaat gagatacaat tttttagttt tcagtttaag taactctcag cattacaaaa   4740
gagtaagtat ctcacaaata ggaaataaaa ctaaaacgtg gatttaaaaa gaactgcacg   4800
ggctttaggg taaatgctca tcttaaacct cactagaggg aagtcttctc aagtttcaag   4860
caagaccatt tacttaatgt gaagttttgg aaagttataa aggtgtatgt tttagccata   4920
tgattttaat tttaatttg cttcttttag gttcgttctt atttaaagca atatgattgt   4980
gtgactcctt gtagttacac ttgtgtttca atcagatcag attgttgtat ttattccact   5040
attttgcatt taaatgataa cataaaagat ataaaaaatt taaaactgct atttttctta   5100
tagaagagaa aatgggtgtt ggtgattgta ttttaattat ttaagcgtct ctgtttacct   5160
gcctaggaaa acattttatg gcagtcttat gtgcaaagat cgtaaaagga caaaaaattt   5220
aaactgctta taataatcca ggagttgcat tatagccagt agtaaaaata ataataataa   5280
taataaaacc atgtctatag ctgtagatgg gcttcacatc tgtaaagcaa tcaattgtat   5340
```

```
atttttgtga tgtgtaccat actgtgtgct ccagcaaatg tccatttgtg taaatgtatt   5400

tattttatat tgtatatatt gttaaatgca aaaaggagat atgattctgt aactccaatc   5460

agttcagatg tgtaactcaa attattatgc ctttcaggat gatggtagag caatattaaa   5520

caagcttcca cttttgactg ctaaaaaaaa aaaaaaaaa                          5559


<210> SEQ ID NO 11
<211> LENGTH: 463
<212> TYPE: PRT
<213> ORGANISM: Homo sapiens

<400> SEQUENCE: 11

Met His Ser Ala Ser Ser Met Leu Gly Ala Val Lys Met Glu Gly His
1               5                   10                  15

Glu Pro Ser Asp Trp Ser Ser Tyr Tyr Ala Glu Pro Glu Gly Tyr Ser
            20                  25                  30

Ser Val Ser Asn Met Asn Ala Gly Leu Gly Met Asn Gly Met Asn Thr
        35                  40                  45

Tyr Met Ser Met Ser Ala Ala Ala Met Gly Ser Gly Ser Gly Asn Met
    50                  55                  60

Ser Ala Gly Ser Met Asn Met Ser Ser Tyr Val Gly Ala Gly Met Ser
65                  70                  75                  80

Pro Ser Leu Ala Gly Met Ser Pro Gly Ala Gly Ala Met Ala Gly Met
                85                  90                  95

Gly Gly Ser Ala Gly Ala Ala Gly Val Ala Gly Met Gly Pro His Leu
            100                 105                 110

Ser Pro Ser Leu Ser Pro Leu Gly Gly Gln Ala Ala Gly Ala Met Gly
        115                 120                 125

Gly Leu Ala Pro Tyr Ala Asn Met Asn Ser Met Ser Pro Met Tyr Gly
    130                 135                 140

Gln Ala Gly Leu Ser Arg Ala Arg Asp Pro Lys Thr Tyr Arg Arg Ser
145                 150                 155                 160

Tyr Thr His Ala Lys Pro Pro Tyr Ser Tyr Ile Ser Leu Ile Thr Met
                165                 170                 175

Ala Ile Gln Gln Ser Pro Asn Lys Met Leu Thr Leu Ser Glu Ile Tyr
            180                 185                 190

Gln Trp Ile Met Asp Leu Phe Pro Phe Tyr Arg Gln Asn Gln Gln Arg
        195                 200                 205

Trp Gln Asn Ser Ile Arg His Ser Leu Ser Phe Asn Asp Cys Phe Leu
    210                 215                 220

Lys Val Pro Arg Ser Pro Asp Lys Pro Gly Lys Gly Ser Phe Trp Thr
225                 230                 235                 240

Leu His Pro Asp Ser Gly Asn Met Phe Glu Asn Gly Cys Tyr Leu Arg
                245                 250                 255

Arg Gln Lys Arg Phe Lys Cys Glu Lys Gln Leu Ala Leu Lys Glu Ala
            260                 265                 270

Ala Gly Ala Ala Gly Ser Gly Lys Lys Ala Ala Ala Gly Ala Gln Ala
        275                 280                 285

Ser Gln Ala Gln Leu Gly Glu Ala Ala Gly Pro Ala Ser Glu Thr Pro
    290                 295                 300

Ala Gly Thr Glu Ser Pro His Ser Ser Ala Ser Pro Cys Gln Glu His
305                 310                 315                 320

Lys Arg Gly Gly Leu Gly Glu Leu Lys Gly Thr Pro Ala Ala Ala Leu
                325                 330                 335
```

```
Ser Pro Pro Glu Pro Ala Pro Ser Pro Gly Gln Gln Gln Gln Ala Ala
            340                 345                 350

Ala His Leu Leu Gly Pro Pro His His Pro Gly Leu Pro Pro Glu Ala
        355                 360                 365

His Leu Lys Pro Glu His His Tyr Ala Phe Asn His Pro Phe Ser Ile
    370                 375                 380

Asn Asn Leu Met Ser Ser Glu Gln Gln His His His Ser His His His
385                 390                 395                 400

His Gln Pro His Lys Met Asp Leu Lys Ala Tyr Glu Gln Val Met His
                405                 410                 415

Tyr Pro Gly Tyr Gly Ser Pro Met Pro Gly Ser Leu Ala Met Gly Pro
            420                 425                 430

Val Thr Asn Lys Thr Gly Leu Asp Ala Ser Pro Leu Ala Ala Asp Thr
        435                 440                 445

Ser Tyr Tyr Gln Gly Val Tyr Ser Arg Pro Ile Met Asn Ser Ser
    450                 455                 460


<210> SEQ ID NO 12
<211> LENGTH: 2428
<212> TYPE: DNA
<213> ORGANISM: Homo sapiens

<400> SEQUENCE: 12

cccgcccact tccaactacc gcctccggcc tgcccaggga gagagaggga gtggagccca      60

gggagaggga gcgcgagaga gggagggagg aggggacggt gctttggctg acttttttt     120

aaaagagggt gggggtgggg ggtgattgct ggtcgtttgt tgtggctgtt aaattttaaa     180

ctgccatgca ctcggcttcc agtatgctgg gagcggtgaa gatggaaggg cacgagccgt     240

ccgactggag cagctactat gcagagcccg agggctactc ctccgtgagc aacatgaacg     300

ccggcctggg gatgaacggc atgaacacgt acatgagcat gtcggcggcc gccatgggca     360

gcggctcggg caacatgagc gcgggctcca tgaacatgtc gtcgtacgtg ggcgctggca     420

tgagcccgtc cctggcgggg atgtcccccg gcgcgggcgc catggcgggc atgggcggct     480

cggccggggc ggccggcgtg gcgggcatgg ggccgcactt gagtcccagc ctgagcccgc     540

tcggggggca ggcggccggg gccatgggcg gcctggcccc ctacgccaac atgaactcca     600

tgagccccat gtacgggcag gcgggcctga gccgcgcccg cgaccccaag acctacaggc     660

gcagctacac gcacgcaaag ccgccctact cgtacatctc gctcatcacc atggccatcc     720

agcagagccc caacaagatg ctgacgctga gcgagatcta ccagtggatc atggacctct     780

tccccttcta ccggcagaac cagcagcgct ggcagaactc catccgccac tcgctctcct     840

tcaacgactg tttcctgaag gtgccccgct cgcccgacaa gcccggcaag ggctccttct     900

ggaccctgca ccctgactcg ggcaacatgt tcgagaacgg ctgctacctg cgccgccaga     960

agcgcttcaa gtgcgagaag cagctggcgc tgaaggaggc cgcaggcgcc gccggcagcg    1020

gcaagaaggc ggccgccgga gcccaggcct cacaggctca actcggggag gccgccgggc    1080

cggcctccga gactccggcg ggcaccgagt cgcctcactc gagcgcctcc ccgtgccagg    1140

agcacaagcg agggggcctg ggagagctga aggggacgcc ggctgcggcg ctgagccccc    1200

cagagccggc gccctctccc gggcagcagc agcaggccgc ggcccacctg ctgggcccgc    1260

cccaccaccc gggcctgccg cctgaggccc acctgaagcc ggaacaccac tacgccttca    1320

accacccgtt ctccatcaac aacctcatgt cctcggagca gcagcaccac cacagccacc    1380
```

-continued

```
accaccacca accccacaaa atggacctca aggcctacga acaggtgatg cactaccccg   1440

gctacggttc ccccatgcct ggcagcttgg ccatgggccc ggtcacgaac aaaacgggcc   1500

tggacgcctc gcccctggcc gcagatacct cctactacca gggggtgtac tcccggccca   1560

ttatgaactc ctcttaagaa gacgacggct tcaggcccgg ctaactctgg caccccggat   1620

cgaggacaag tgagagagca agtgggggtc gagactttgg ggagacggtg ttgcagagac   1680

gcaagggaga agaaatccat aacacccccca ccccaacacc cccaagacag cagtcttctt   1740

cacccgctgc agccgttccg tcccaaacag agggccacac agataccccca cgttctatat   1800

aaggaggaaa acgggaaaga atataaagtt aaaaaaaagc ctccggtttc cactactgtg   1860

tagactcctg cttcttcaag cacctgcaga ttctgatttt tttgttgttg ttgttctcct   1920

ccattgctgt tgttgcaggg aagtcttact taaaaaaaaa aaaaaatttt gtgagtgact   1980

cggtgtaaaa ccatgtagtt ttaacagaac cagagggttg tactattgtt taaaaacagg   2040

aaaaaaaata atgtaagggt ctgttgtaaa tgaccaagaa aaagaaaaaa aaagcattcc   2100

caatcttgac acggtgaaat ccaggtctcg ggtccgatta atttatggtt tctgcgtgct   2160

ttatttatgg cttataaatg tgtattctgg ctgcaagggc cagagttcca caaatctata   2220

ttaaagtgtt atacccggtt ttatcccttg aatcttttct tccagatttt tcttttcttt   2280

acttggctta caaaatatac aggcttggaa attatttcaa gaaggaggga gggataccct   2340

gtctggttgc aggttgtatt ttattttggc ccagggagtg ttgctgtttt cccaacattt   2400

tattaataaa attttcagac ataaaaaa                                       2428
```

<210> SEQ ID NO 13
<211> LENGTH: 595
<212> TYPE: PRT
<213> ORGANISM: Homo sapiens

<400> SEQUENCE: 13

```
Met Ala Leu Thr Asp Gly Gly Trp Cys Leu Pro Lys Arg Phe Gly Ala
1               5                   10                  15

Ala Gly Ala Asp Ala Ser Asp Ser Arg Ala Phe Pro Ala Arg Glu Pro
            20                  25                  30

Ser Thr Pro Pro Ser Pro Ile Ser Ser Ser Ser Ser Ser Cys Ser Arg
        35                  40                  45

Gly Gly Glu Arg Gly Pro Gly Gly Ala Ser Asn Cys Gly Thr Pro Gln
    50                  55                  60

Leu Asp Thr Glu Ala Ala Ala Gly Pro Pro Ala Arg Ser Leu Leu Leu
65                  70                  75                  80

Ser Ser Tyr Ala Ser His Pro Phe Gly Ala Pro His Gly Pro Ser Ala
                85                  90                  95

Pro Gly Val Ala Gly Pro Gly Gly Asn Leu Ser Ser Trp Glu Asp Leu
            100                 105                 110

Leu Leu Phe Thr Asp Leu Asp Gln Ala Ala Thr Ala Ser Lys Leu Leu
        115                 120                 125

Trp Ser Ser Arg Gly Ala Lys Leu Ser Pro Phe Ala Pro Glu Gln Pro
    130                 135                 140

Glu Glu Met Tyr Gln Thr Leu Ala Ala Leu Ser Ser Gln Gly Pro Ala
145                 150                 155                 160

Ala Tyr Asp Gly Ala Pro Gly Gly Phe Val His Ser Ala Ala Ala Ala
                165                 170                 175

Ala Ala Ala Ala Ala Ala Ala Ser Ser Pro Val Tyr Val Pro Thr Thr
            180                 185                 190
```

-continued

```
Arg Val Gly Ser Met Leu Pro Gly Leu Pro Tyr His Leu Gln Gly Ser
        195                 200                 205

Gly Ser Gly Pro Ala Asn His Ala Gly Gly Ala Gly Ala His Pro Gly
    210                 215                 220

Trp Pro Gln Ala Ser Ala Asp Ser Pro Pro Tyr Gly Ser Gly Gly Gly
225                 230                 235                 240

Ala Ala Gly Gly Gly Ala Ala Gly Pro Gly Gly Ala Gly Ser Ala Ala
                245                 250                 255

Ala His Val Ser Ala Arg Phe Pro Tyr Ser Pro Ser Pro Pro Met Ala
            260                 265                 270

Asn Gly Ala Ala Arg Glu Pro Gly Gly Tyr Ala Ala Ala Gly Ser Gly
        275                 280                 285

Gly Ala Gly Gly Val Ser Gly Gly Gly Ser Ser Leu Ala Ala Met Gly
    290                 295                 300

Gly Arg Glu Pro Gln Tyr Ser Ser Leu Ser Ala Ala Arg Pro Leu Asn
305                 310                 315                 320

Gly Thr Tyr His His His His His His His His His His Pro Ser Pro
                325                 330                 335

Tyr Ser Pro Tyr Val Gly Ala Pro Leu Thr Pro Ala Trp Pro Ala Gly
            340                 345                 350

Pro Phe Glu Thr Pro Val Leu His Ser Leu Gln Ser Arg Ala Gly Ala
        355                 360                 365

Pro Leu Pro Val Pro Arg Gly Pro Ser Ala Asp Leu Leu Glu Asp Leu
    370                 375                 380

Ser Glu Ser Arg Glu Cys Val Asn Cys Gly Ser Ile Gln Thr Pro Leu
385                 390                 395                 400

Trp Arg Arg Asp Gly Thr Gly His Tyr Leu Cys Asn Ala Cys Gly Leu
                405                 410                 415

Tyr Ser Lys Met Asn Gly Leu Ser Arg Pro Leu Ile Lys Pro Gln Lys
            420                 425                 430

Arg Val Pro Ser Ser Arg Arg Leu Gly Leu Ser Cys Ala Asn Cys His
        435                 440                 445

Thr Thr Thr Thr Thr Leu Trp Arg Arg Asn Ala Glu Gly Glu Pro Val
    450                 455                 460

Cys Asn Ala Cys Gly Leu Tyr Met Lys Leu His Gly Val Pro Arg Pro
465                 470                 475                 480

Leu Ala Met Lys Lys Glu Gly Ile Gln Thr Arg Lys Arg Lys Pro Lys
                485                 490                 495

Asn Ile Asn Lys Ser Lys Thr Cys Ser Gly Asn Ser Asn Asn Ser Ile
            500                 505                 510

Pro Met Thr Pro Thr Ser Thr Ser Ser Asn Ser Asp Asp Cys Ser Lys
        515                 520                 525

Asn Thr Ser Pro Thr Thr Gln Pro Thr Ala Ser Gly Ala Gly Ala Pro
    530                 535                 540

Val Met Thr Gly Ala Gly Glu Ser Thr Asn Pro Glu Asn Ser Glu Leu
545                 550                 555                 560

Lys Tyr Ser Gly Gln Asp Gly Leu Tyr Ile Gly Val Ser Leu Ala Ser
                565                 570                 575

Pro Ala Glu Val Thr Ser Ser Val Arg Pro Asp Ser Trp Cys Ala Leu
            580                 585                 590

Ala Leu Ala
        595
```

<210> SEQ ID NO 14
<211> LENGTH: 3785
<212> TYPE: DNA
<213> ORGANISM: Homo sapiens

<400> SEQUENCE: 14
agttccgacc cacagcctgg caccccttcgg cgagcgctgt ttgtttaggg ctcggtgagt 60
ccaatcagga gcccaggctg cagttttccg gcagagcagt aagaggcgcc tcctctctcc 120
tttttattca ccagcagcgc ggcgcagacc ccggactcgc gctcgcccgc tggcgccctc 180
ggcttctctc cgcgcctggg agcaccctcc gccgcggccg ttctccatgc gcagcgcccg 240
cccgaggagc tagacgtcag cttggagcgg cgccggaccg tggatggcct tgactgacgg 300
cggctggtgc ttgccgaagc gcttcggggc cgcgggtgcg gacgccagcg actccagagc 360
ctttccagcg cgggagccct ccacgccgcc ttccccccatc tcttcctcgt cctcctcctg 420
ctcccggggc ggagagcggg gccccggcgg cgccagcaac tgcgggacgc ctcagctcga 480
cacggaggcg gcggccggac ccccggcccg ctcgctgctg ctcagttcct acgcttcgca 540
tcccttcggg gctccccacg gaccttcggc gcctggggtc gcgggccccg ggggcaacct 600
gtcgagctgg gaggacttgc tgctgttcac tgacctcgac caagccgcga ccgccagcaa 660
gctgctgtgg tccagccgcg gcgccaagct gagccccttc gcacccgagc agccggagga 720
gatgtaccag accctcgccg ctctctccag ccagggtccg gccgcctacg acggcgcgcc 780
cggcggcttc gtgcactctg cggccgcggc ggcagcagcc gcggcggcgg ccagctcccc 840
ggtctacgtg cccaccaccc gcgtgggttc catgctgccc ggcctaccgt accacctgca 900
ggggtcgggc agtgggccag ccaaccacgc gggcggcgcg ggcgcgcacc ccggctggcc 960
tcaggcctcg gccgacagcc ctccatacgg cagcggaggc ggcgcggctg gcggcggggc 1020
cgcggggcct ggcggcgctg gctcagccgc ggcgcacgtc tcggcgcgct tcccctactc 1080
tcccagcccg cccatggcca acggcgccgc gcgggagccg ggaggctacg cggcggcggg 1140
cagtgggggc gcgggaggcg tgagcggcgg cggcagtagc ctggcggcca tgggcggccg 1200
cgagccccag tacagctcgc tgtcggccgc gcggccgctg aacgggacgt accaccacca 1260
ccaccaccac caccaccacc atccgagccc ctactcgccc tacgtggggg cgccactgac 1320
gcctgcctgg cccgccggac ccttcgagac cccggtgctg cacagcctgc agagccgcgc 1380
cggagccccg ctcccggtgc cccggggtcc cagtgcagac ctgctggagg acctgtccga 1440
gagccgcgag tgcgtgaact gcggctccat ccagacgccg ctgtggcggc gggacggcac 1500
cggccactac ctgtgcaacg cctgcgggct ctacagcaag atgaacggcc tcagccggcc 1560
cctcatcaag ccgcagaagc gcgtgccttc atcacggcgg cttggattgt cctgtgccaa 1620
ctgtcacacc acaactacca ccttatggcg cagaaacgcc gagggtgaac ccgtgtgcaa 1680
tgcttgtgga ctctacatga aactccatgg ggtgcccaga ccacttgcta tgaaaaaaga 1740
gggaattcaa accaggaaac gaaaacctaa gaacataaat aaatcaaaga cttgctctgg 1800
taatagcaat aattccattc ccatgactcc aacttccacc tcttctaact cagatgattg 1860
cagcaaaaat acttccccca caacacaacc tacagcctca ggggcgggtg ccccggtgat 1920
gactggtgcg ggagagagca ccaatcccga gaacagcgag ctcaagtatt cgggtcaaga 1980
tgggctctac ataggcgtca gtctcgcctc gccggccgaa gtcacgtcct ccgtgcgacc 2040
ggattcctgg tgcgccctgg ccctggcctg agcccacgcc gccaggaggc agggagggct 2100
ccgccgcggg cctcactcca ctcgtgtctg cttttgtgca gcggtccaga cagtggcgac 2160

```
tgcgctgaca gaacgtgatt ctcgtgcctt tattttgaaa gagatgtttt tcccaagagg   2220

cttgctgaaa gagtgagaga agatggaagg gaagggccag tgcaactggg cgcttgggcc   2280

actccagcca gcccgcctcc ggggcggacc ctgctccact tccagaagcc aggactagga   2340

cctgggcctt gcctgctatg gaatattgag agagattttt taaaaaagat tttgcatttt   2400

gtccaaaatc atgtgcttct tctgatcaat tttggttgtt ccagaatttc ttcatacctt   2460

ttccacatcc agatttcatg tgcgttcatg gagaagatca cttgaggcca tttggtacac   2520

atctctggag gctgagtcgg ttcatgaggt ctcttatcaa aatattact cagtttgcaa   2580

gactgcattg taactttaac atacactgtg actgacgttt ctcaaagttc atattgtgtg   2640

gctgatctga agtcagtcgg aatttgtaaa cagggtagca aacaagatat ttttcttcca   2700

tgtatacaat aattttttta aaaagtgcaa tttgcgttgc agcaatcagt gttaaatcat   2760

ttgcataaga tttaacagca ttttttataa tgaatgtaaa cattttaact taatggtact   2820

taaaataatt taaaagaaaa atgttaactt agacattctt atgcttcttt tacaactaca   2880

tcccatttta tatttccaat tgttaaagaa aaatatttca agaacaaatc ttctctcagg   2940

aaaattgcct ttctctattt gttaagaatt tttatacaag aacaccaata tacccccttt   3000

attttactgt ggaatatgtg ctggaaaaat tgcaacaaca ctttactacc taacggatag   3060

catttgtaaa tactctaggt atctgtaaac actctgatga agtctgtata gtgtgactaa   3120

cccacaggca ggttggttta cattaatttt tttttttgaa tgggatgtcc tatggaaacc   3180

tatttcacca gagttttaaa aataaaaagg gtattgtttt gtcttctgta cagtgagttc   3240

cttccctttt caaagctttc tttttatgct gtatgtgact atagatattc atataaaaca   3300

agtgcacgtg aagtttgcaa aatgctttaa ggccttcctt tcaaagcata gtccttttgg   3360

agccgttttg tacctttat accttggctt atttgaagtt gacacatggg gttagttact   3420

actctccatg tgcattgggg acagttttta taagtgggaa ggactcagta ttattatatt   3480

tgagatgata agcattttgt ttgggaacaa tgcttaaaaa tattccagaa agttcagatt   3540

tttttctttt gtgaatgaaa tatattctgg cccacgaaca gggcgatttc ctttcagttt   3600

tttccttttg caacgtgcct tgaagtctca aagctcacct gaggttgcag acgttacccc   3660

caacagaaga taggtagaaa tgattccagt ggcctctttg tattttcttc attgttgagt   3720

agatttcagg aaatcaggag gtgtttcaca atacagaatg atggccttta actgtgaaaa   3780

aaaaa                                                               3785
```

```
<210> SEQ ID NO 15
<211> LENGTH: 394
<212> TYPE: PRT
<213> ORGANISM: Homo sapiens

<400> SEQUENCE: 15

Met Lys Arg Gln Asn Val Arg Thr Leu Ala Leu Ile Val Cys Thr Phe
1               5                   10                  15

Thr Tyr Leu Leu Val Gly Ala Ala Val Phe Asp Ala Leu Glu Ser Glu
            20                  25                  30

Pro Glu Leu Ile Glu Arg Gln Arg Leu Glu Leu Arg Gln Gln Glu Leu
        35                  40                  45

Arg Ala Arg Tyr Asn Leu Ser Gln Gly Gly Tyr Glu Glu Leu Glu Arg
    50                  55                  60

Val Val Leu Arg Leu Lys Pro His Lys Ala Gly Val Gln Trp Arg Phe
65                  70                  75                  80
```

```
Ala Gly Ser Phe Tyr Phe Ala Ile Thr Val Ile Thr Thr Ile Gly Tyr
                85                  90                  95

Gly His Ala Ala Pro Ser Thr Asp Gly Gly Lys Val Phe Cys Met Phe
            100                 105                 110

Tyr Ala Leu Leu Gly Ile Pro Leu Thr Leu Val Met Phe Gln Ser Leu
        115                 120                 125

Gly Glu Arg Ile Asn Thr Leu Val Arg Tyr Leu Leu His Arg Ala Lys
    130                 135                 140

Lys Gly Leu Gly Met Arg Arg Ala Asp Val Ser Met Ala Asn Met Val
145                 150                 155                 160

Leu Ile Gly Phe Phe Ser Cys Ile Ser Thr Leu Cys Ile Gly Ala Ala
                165                 170                 175

Ala Phe Ser His Tyr Glu His Trp Thr Phe Phe Gln Ala Tyr Tyr Tyr
            180                 185                 190

Cys Phe Ile Thr Leu Thr Thr Ile Gly Phe Gly Asp Tyr Val Ala Leu
        195                 200                 205

Gln Lys Asp Gln Ala Leu Gln Thr Gln Pro Gln Tyr Val Ala Phe Ser
    210                 215                 220

Phe Val Tyr Ile Leu Thr Gly Leu Thr Val Ile Gly Ala Phe Leu Asn
225                 230                 235                 240

Leu Val Val Leu Arg Phe Met Thr Met Asn Ala Glu Asp Glu Lys Arg
                245                 250                 255

Asp Ala Glu His Arg Ala Leu Leu Thr Arg Asn Gly Gln Ala Gly Gly
            260                 265                 270

Gly Gly Gly Gly Gly Ser Ala His Thr Thr Asp Thr Ala Ser Ser Thr
        275                 280                 285

Ala Ala Ala Gly Gly Gly Gly Phe Arg Asn Val Tyr Ala Glu Val Leu
    290                 295                 300

His Phe Gln Ser Met Cys Ser Cys Leu Trp Tyr Lys Ser Arg Glu Lys
305                 310                 315                 320

Leu Gln Tyr Ser Ile Pro Met Ile Ile Pro Arg Asp Leu Ser Thr Ser
                325                 330                 335

Asp Thr Cys Val Glu Gln Ser His Ser Ser Pro Gly Gly Gly Gly Arg
            340                 345                 350

Tyr Ser Asp Thr Pro Ser Arg Arg Cys Leu Cys Ser Gly Ala Pro Arg
        355                 360                 365

Ser Ala Ile Ser Ser Val Ser Thr Gly Leu His Ser Leu Ser Thr Phe
    370                 375                 380

Arg Gly Leu Met Lys Arg Arg Ser Ser Val
385                 390
```

<210> SEQ ID NO 16
<211> LENGTH: 3978
<212> TYPE: DNA
<213> ORGANISM: Homo sapiens

<400> SEQUENCE: 16

```
ggcggcggcg gcggcggcgg ccccgggcgc tgagcgggtg cccggcgcgg agagcggcga      60

gcgcagccat gccccaggcc gcctccgggg cagcagcagc ggcggccggg gccgaggcgc     120

gggccggggg cgccgggggg ccggcggcgg cccgggcggg acgatgaagc ggcagaacgt     180

gcgcacgctg gcgctcatcg tgtgcacctt cacctacctg ctggtgggcg ccgcggtctt     240

cgacgcgctg gagtcggagc ccgagctgat cgagcggcag cggctggagc tgcggcagca     300
```

-continued

```
ggagctgcgg gcgcgctaca acctcagcca gggcggctac gaggagctgg agcgcgtcgt    360
gctgcgcctc aagccgcaca aggccggcgt gcagtggcgc ttcgccggct ccttctactt    420
cgccatcacc gtcatcacca ccatcggcta cgggcacgcg gcacccagca cggatggcgg    480
caaggtgttc tgcatgttct acgcgctgct gggcatcccg ctcacgctcg tcatgttcca    540
gagcctgggc gagcgcatca acaccttggt gaggtacctg ctgcaccgcg ccaagaaggg    600
gctgggcatg cggcgcgccg acgtgtccat ggccaacatg gtgctcatcg gcttcttctc    660
gtgcatcagc acgctgtgca tcggcgccgc cgccttctcc cactacgagc actggacctt    720
cttccaggcc tactactact gcttcatcac cctcaccacc atcggcttcg gcgactacgt    780
ggcgctgcag aaggaccagg ccctgcagac gcagccgcag tacgtggcct tcagcttcgt    840
ctacatcctt acgggcctca cggtcatcgg cgccttcctc aacctcgtgg tgctgcgctt    900
catgaccatg aacgccgagg acgagaagcg cgacgccgag caccgcgcgc tgctcacgcg    960
caacgggcag gcgggcggcg gcggaggggg tggcagcgcg cacactacgg acaccgcctc   1020
atccacggcg gcagcgggcg gcggcggctt ccgcaacgtc tacgcggagg tgctgcactt   1080
ccagtccatg tgctcgtgcc tgtggtacaa gagccgcgag aagctgcagt actccatccc   1140
catgatcatc ccgcgggacc tctccacgtc cgacacgtgc gtggagcaga gccactcgtc   1200
gccgggaggg ggcggccgct acagcgacac gccctcgcga cgctgcctgt gcagcggggc   1260
gccacgctcc gccatcagct cggtgtccac gggtctgcac agcctgtcca ccttccgcgg   1320
cctcatgaag cgcaggagct ccgtgtgact gccccgaggg gcctggagca cctgggggcg   1380
cgggcggggg acccctgctg ggaggccagg agactgcccc tgctgccttc tgcccagtgg   1440
gaccccgcac aacatccctc accactctcc cccagcaccc ccatctccga ctgtgcctgc   1500
ttgcaccagc cggcaggagg ccgggctctg aggacccctg gggcccccat cggagccctg   1560
caaattccga gaaatgtgaa acttggtggg gtcagggagg aaaggcagaa gctgggagcc   1620
tcccttccct ttgaaaatct aagaagctcc cagtcctcag agaccctgct ggtacccaga   1680
cccccacctt cggaggggac ttcatgttcc gtgtacgttt gcatctctat ttatacctct   1740
gtcctgctag gtctcccacc ttcccttggt tccaaaagcc agggtgtcta tgtccaagtc   1800
accccctactc agccccactc cccttcctca tccccagctg tgtctcccaa cctcccttcg   1860
tgttgttttg catggctttg cagttatgga gaaagtggaa acccagcagt ccctaaagct   1920
ggtccccaga aagcaggaca gaaagaagga gggacaggca ggcagcagga ggggcgagct   1980
gggaggcagg aggcagcggc ctgtcagtct gcagaatggt cgcactggag gttcaagcta   2040
actggcctcc agccacattc tcatagcagg taggacttca gccttccaga cactgccctt   2100
agaatctgga acagaagact tcagactcac cataattgct gataattacc cactcttaaa   2160
tttgtcgagt gatttttagc ctctgaaaac tctatgctgg ccactgattc ctttgagtct   2220
cacaaaaccc tacttaggtc atcagggcag gagttctcac tcccatttta cagatgagaa   2280
tactgaggcc tggacaggtg aagtgaccag agagcaaaag gcaaaggggt gggggctggg   2340
tgcagtggct cacacctgta ttcccaacac ttttggaggc tgaggttgga ggattgcttg   2400
agcccaggaa tttgagacca gcctaggtga catagtgaga ccccatctct acaaaaaata   2460
aaaaattaac caggtgtggt ggcacgtgcc tgggagtccc agcgacttgg gaggctgagg   2520
tgggaggatt gtttgagcct gggaggtcga ggctgtagtg agccctgatt gcaccactgt   2580
actccagcct gggtgacagg gcaagaccct gtctcaaaaa aaaaaaaaaa aatggcaaag   2640
ggagacaaga gcccagcctg cttgttgcta gccaaagtgt tctttccttc cagcttggcc   2700
```

-continued

```
tgctcttaaa agcaaagctc ctgcagtgta catcctggca ttgtgtggct acctgggttt   2760

taaaccagaa tcagaagtcc cggatcagag ggcactgctg aggttcagcc tcttctcttc   2820

ttggccagga ggcagcagct ctgaatgggc ccctgaggct gcacaggggc ctttgtcact   2880

ggggcgcatg cttacaaaca gtgcagttct tgggaccgag gtaagcaggg ctgggtctca   2940

tggcagaaag gccaggatct ggggctctag gaatttggga attgggcaga gtggccaaga   3000

aagctggcag gcatatccta tgggacatca cacctggcac cattgtcatt gttggtgcct   3060

gtgtcccaag tagctagtga taagctgagg ctgcagcaag aaacaccctt cccaggtggg   3120

ggagtttgga ccagaggtgc cctctgccca ccacacctgc aacccagaag cccagatgga   3180

acgcagctga cgaaggtgat gcttgaggct cacttttggg gccccacagc tggagccggt   3240

ataatgactg ggacaacatc aaggggtgga tgaggggcct ctcctcccgc aacactgcct   3300

tcccatgctg ttcccctgcc agctccttaa cactgccgac caaggccagc cctggcattc   3360

agggaaattg gagggcagca cccgtagggt ggccagcctc aggccccacc ccagctgtgt   3420

cctctagtct ctggggaccc ctggggggaa gaagtctacc ctgcttgtga gtcccgtctc   3480

agtgtggagg aactggctgc acgtgggacc tgaaggtgcc ctctgtgttt atgttggggg   3540

tgggggggca gtgctggctg cctctgtcct gtgtgtgacc ctgccctcga agggtcctgt   3600

cctgtcagtc ccgagggagc cacaaccaaa gctgcggaga gaaggtgggg aagggtgcag   3660

aatggccgtg gggcacagcg tggcagactg ttcagtctct gctgggtctt tcctagggac   3720

ctggaaggcc agtgttgctt ccccctcact ccctttcact gcaggcagcc tctctgcttc   3780

cccaatgcct tatgcctggg cacactgcca cagaatatgc aatatgtgtg ggtgaccatg   3840

ccctcacgac cacaccccca ccccgggcag cccccggact ccaaaggtcg tggctgccac   3900

agcctccctc agctcttcct gcctatctgt cttcacactg agaatggcgc ccaataaatg   3960

ctatccacgg agaccagg                                                 3978
```

<210> SEQ ID NO 17
<211> LENGTH: 676
<212> TYPE: PRT
<213> ORGANISM: Homo sapiens

<400> SEQUENCE: 17

```
Met Ala Ala Ala Ser Ser Pro Pro Arg Ala Glu Arg Lys Arg Trp Gly
1               5                   10                  15

Trp Gly Arg Leu Pro Gly Ala Arg Arg Gly Ser Ala Gly Leu Ala Lys
            20                  25                  30

Lys Cys Pro Phe Ser Leu Glu Leu Ala Glu Gly Gly Pro Ala Gly Gly
        35                  40                  45

Ala Leu Tyr Ala Pro Ile Ala Pro Gly Ala Pro Gly Pro Ala Pro Pro
    50                  55                  60

Ala Ser Pro Ala Ala Pro Ala Ala Pro Pro Val Ala Ser Asp Leu Gly
65                  70                  75                  80

Pro Arg Pro Pro Val Ser Leu Asp Pro Arg Val Ser Ile Tyr Ser Thr
                85                  90                  95

Arg Arg Pro Val Leu Ala Arg Thr His Val Gln Gly Arg Val Tyr Asn
            100                 105                 110

Phe Leu Glu Arg Pro Thr Gly Trp Lys Cys Phe Val Tyr His Phe Ala
        115                 120                 125

Val Phe Leu Ile Val Leu Val Cys Leu Ile Phe Ser Val Leu Ser Thr
    130                 135                 140
```

-continued

```
Ile Glu Gln Tyr Ala Ala Leu Ala Thr Gly Thr Leu Phe Trp Met Glu
145                 150                 155                 160

Ile Val Leu Val Val Phe Phe Gly Thr Glu Tyr Val Val Arg Leu Trp
                165                 170                 175

Ser Ala Gly Cys Arg Ser Lys Tyr Val Gly Leu Trp Gly Arg Leu Arg
            180                 185                 190

Phe Ala Arg Lys Pro Ile Ser Ile Ile Asp Leu Ile Val Val Val Ala
        195                 200                 205

Ser Met Val Val Leu Cys Val Gly Ser Lys Gly Gln Val Phe Ala Thr
    210                 215                 220

Ser Ala Ile Arg Gly Ile Arg Phe Leu Gln Ile Leu Arg Met Leu His
225                 230                 235                 240

Val Asp Arg Gln Gly Gly Thr Trp Arg Leu Leu Gly Ser Val Val Phe
                245                 250                 255

Ile His Arg Gln Glu Leu Ile Thr Thr Leu Tyr Ile Gly Phe Leu Gly
            260                 265                 270

Leu Ile Phe Ser Ser Tyr Phe Val Tyr Leu Ala Glu Lys Asp Ala Val
        275                 280                 285

Asn Glu Ser Gly Arg Val Glu Phe Gly Ser Tyr Ala Asp Ala Leu Trp
    290                 295                 300

Trp Gly Val Val Thr Val Thr Thr Ile Gly Tyr Gly Asp Lys Val Pro
305                 310                 315                 320

Gln Thr Trp Val Gly Lys Thr Ile Ala Ser Cys Phe Ser Val Phe Ala
                325                 330                 335

Ile Ser Phe Phe Ala Leu Pro Ala Gly Ile Leu Gly Ser Gly Phe Ala
            340                 345                 350

Leu Lys Val Gln Gln Lys Gln Arg Gln Lys His Phe Asn Arg Gln Ile
        355                 360                 365

Pro Ala Ala Ala Ser Leu Ile Gln Thr Ala Trp Arg Cys Tyr Ala Ala
    370                 375                 380

Glu Asn Pro Asp Ser Ser Thr Trp Lys Ile Tyr Ile Arg Lys Ala Pro
385                 390                 395                 400

Arg Ser His Thr Leu Leu Ser Pro Ser Pro Lys Pro Lys Lys Ser Val
                405                 410                 415

Val Val Lys Lys Lys Lys Phe Lys Leu Asp Lys Asp Asn Gly Val Thr
            420                 425                 430

Pro Gly Glu Lys Met Leu Thr Val Pro His Ile Thr Cys Asp Pro Pro
        435                 440                 445

Glu Glu Arg Arg Leu Asp His Phe Ser Val Asp Gly Tyr Asp Ser Ser
    450                 455                 460

Val Arg Lys Ser Pro Thr Leu Leu Glu Val Ser Met Pro His Phe Met
465                 470                 475                 480

Arg Thr Asn Ser Phe Ala Glu Asp Leu Asp Leu Glu Gly Glu Thr Leu
                485                 490                 495

Leu Thr Pro Ile Thr His Ile Ser Gln Leu Arg Glu His His Arg Ala
            500                 505                 510

Thr Ile Lys Val Ile Arg Arg Met Gln Tyr Phe Val Ala Lys Lys Lys
        515                 520                 525

Phe Gln Gln Ala Arg Lys Pro Tyr Asp Val Arg Asp Val Ile Glu Gln
    530                 535                 540

Tyr Ser Gln Gly His Leu Asn Leu Met Val Arg Ile Lys Glu Leu Gln
545                 550                 555                 560
```

```
Arg Arg Leu Asp Gln Ser Ile Gly Lys Pro Ser Leu Phe Ile Ser Val
                565                 570                 575

Ser Glu Lys Ser Lys Asp Arg Gly Ser Asn Thr Ile Gly Ala Arg Leu
            580                 585                 590

Asn Arg Val Glu Asp Lys Val Thr Gln Leu Asp Gln Arg Leu Ala Leu
        595                 600                 605

Ile Thr Asp Met Leu His Gln Leu Leu Ser Leu His Gly Gly Ser Thr
    610                 615                 620

Pro Gly Ser Gly Gly Pro Pro Arg Glu Gly Gly Ala His Ile Thr Gln
625                 630                 635                 640

Pro Cys Gly Ser Gly Gly Ser Val Asp Pro Glu Leu Phe Leu Pro Ser
                645                 650                 655

Asn Thr Leu Pro Thr Tyr Glu Gln Leu Thr Val Pro Arg Arg Gly Pro
            660                 665                 670

Asp Glu Gly Ser
        675
```

<210> SEQ ID NO 18
<211> LENGTH: 3262
<212> TYPE: DNA
<213> ORGANISM: Homo sapiens

<400> SEQUENCE: 18

```
gcggcggggc tggcagcagt ggctgcccgc actgcgcccg ggcgctcgcc ttcgctgcag      60

ctcccggtgc cgccgctcgg gccggccccc cggcaggccc tcctcgttat ggccgcggcc     120

tcctccccgc ccagggccga gaggaagcgc tggggttggg gccgcctgcc aggcgcccgg     180

cggggcagcg cgggcctggc caagaagtgc cccttctcgc tggagctggc ggagggcggc     240

ccggcgggcg gcgcgctcta cgcgcccatc gcgcccggcg ccccaggtcc cgcgcccccct     300

gcgtccccgg ccgcgcccgc cgcgccccca gttgcctccg accttggccc gcggccgccg     360

gtgagcctag acccgcgcgt ctccatctac agcacgcgcc gcccggtgtt ggcgcgcacc     420

cacgtccagg gccgcgtcta caacttcctc gagcgtccca ccggctggaa atgcttcgtt     480

taccacttcg ccgtcttcct catcgtcctg gtctgcctca tcttcagcgt gctgtccacc     540

atcgagcagt atgccgccct ggccacgggg actctcttct ggatggagat cgtgctggtg     600

gtgttcttcg ggacggagta cgtggtccgc ctctggtccg ccggctgccg cagcaagtac     660

gtgggcctct gggggcggct gcgctttgcc cggaagccca tttccatcat cgacctcatc     720

gtggtcgtgg cctccatggt ggtcctctgc gtgggctcca aggggcaggt gtttgccacg     780

tcggccatca ggggcatccg cttcctgcag atcctgagga tgctacacgt cgaccgccag     840

ggaggcacct ggaggctcct gggctccgtg gtcttcatcc accgccagga gctgataacc     900

accctgtaca tcggcttcct gggcctcatc ttctcctcgt actttgtgta cctggctgag     960

aaggacgcgg tgaacgagtc aggccgcgtg gagttcggca gctacgcaga tgcgctgtgg    1020

tggggggtgg tcacagtcac caccatcggc tatggggaca aggtgcccca gacgtgggtc    1080

gggaagacca tcgcctcctg cttctctgtc tttgccatct ccttctttgc gctcccagcg    1140

gggattcttg gctcggggtt tgccctgaag gtgcagcaga agcagaggca gaagcacttc    1200

aaccggcaga tcccggcggc agcctcactc attcagaccg catggaggtg ctatgctgcc    1260

gagaaccccg actcctccac ctggaagatc tacatccgga aggcccccccg gagccacact    1320

ctgctgtcac ccagccccaa acccaagaag tctgtggtgg taaagaaaaa aaagttcaag    1380

ctggacaaag acaatggggt gactcctgga gagaagatgc tcacagtccc ccatatcacg    1440
```

```
tgcgaccccc cagaagagcg gcggctggac cacttctctg tcgacggcta tgacagttct   1500
gtaaggaaga gcccaacact gctggaagtg agcatgcccc atttcatgag aaccaacagc   1560
ttcgccgagg acctggacct ggaaggggag actctgctga cacccatcac ccacatctca   1620
cagctgcggg aacaccatcg ggccaccatt aaggtcattc gacgcatgca gtactttgtg   1680
gccaagaaga aattccagca agcgcggaag ccttacgatg tgcgggacgt cattgagcag   1740
tactcgcagg gccacctcaa cctcatggtg cgcatcaagg agctgcagag gaggctggac   1800
cagtccattg ggaagccctc actgttcatc tccgtctcag aaaagagcaa ggatcgcggc   1860
agcaacacga tcggcgcccg cctgaaccga gtagaagaca aggtgacgca gctggaccag   1920
aggctggcac tcatcaccga catgcttcac cagctgctct ccttgcacgg tggcagcacc   1980
cccggcagcg gcggcccccc cagagagggc ggggcccaca tcacccagcc ctgcggcagt   2040
ggcggctccg tcgaccctga gctcttcctg cccagcaaca ccctgcccac ctacgagcag   2100
ctgaccgtgc ccaggagggg ccccgatgag ggtcctgag gaggggatgg ggctgggga   2160
tgggcctgag tgagagggga ggccaagagt ggccccacct ggccctctct gaaggaggcc   2220
acctcctaaa aggcccagag agaagagccc cactctcaga ggccccaata ccccatggac   2280
catgctgtct ggcacagcct gcacttgggg gctcagcaag gccacctctt cctggccggt   2340
gtgggggccc cgtctcaggt ctgagttgtt accccaagcg ccctggcccc cacatggtga   2400
tgttgacatc actggcatgg tggttgggac ccagtggcag ggcacagggc ctggcccatg   2460
tatggccagg aagtagcaca ggctgagtgc aggcccaccc tgcttggccc agggggcttc   2520
ctgaggggag acagagcaac ccctggaccc cagcctcaaa tccaggaccc tgccaggcac   2580
aggcagggca ggaccagccc acgctgacta cagggccgcc ggcaataaaa gcccaggagc   2640
ccatttggag ggcctgggcc tggctccctc actctcagga aatgctgacc catgggcagg   2700
agactgtgga gactgctcct gagcccccag cttccagcag gagggacagt ctcaccattt   2760
ccccagggca cgtggttgag tggggggaac gcccacttcc ctgggttaga ctgccagctc   2820
ttcctagctg gagaggagcc ctgcctctcc gcccctgagc ccactgtgcg tggggctccc   2880
gcctccaacc cctcgcccag tcccagcagc cagccaaaca cacagaaggg gactgccacc   2940
tccccttgcc agctgctgag ccgcagagaa gtgacggttc ctacacagga caggggttcc   3000
ttctgggcat tacatcgcat agaaatcaat aatttgtggt gatttggatc tgtgttttaa   3060
tgagtttcac agtgtgattt tgattattaa ttgtgcaagc ttttcctaat aaacgtggag   3120
aatcacaggc tgggctgggc actgctctca ccttggttcc tggggcatcc atggggtctc   3180
tcacagacag gacccctgca gttcccctgg aagcagtgcc caggtggctg tggaatagga   3240
acgctaaaaa aaaaaaaaaa aa                                            3262
```

<210> SEQ ID NO 19
<211> LENGTH: 907
<212> TYPE: PRT
<213> ORGANISM: Homo sapiens

<400> SEQUENCE: 19

```
Met Asp Thr Ser Arg Leu Gly Val Leu Leu Ser Leu Pro Val Leu Leu
1               5                   10                  15

Gln Leu Ala Thr Gly Gly Ser Ser Pro Arg Ser Gly Val Leu Leu Arg
            20                  25                  30

Gly Cys Pro Thr His Cys His Cys Glu Pro Asp Gly Arg Met Leu Leu
        35                  40                  45
```

-continued

```
Arg Val Asp Cys Ser Asp Leu Gly Leu Ser Glu Leu Pro Ser Asn Leu
    50                  55                  60

Ser Val Phe Thr Ser Tyr Leu Asp Leu Ser Met Asn Asn Ile Ser Gln
65                  70                  75                  80

Leu Leu Pro Asn Pro Leu Pro Ser Leu Arg Phe Leu Glu Glu Leu Arg
                85                  90                  95

Leu Ala Gly Asn Ala Leu Thr Tyr Ile Pro Lys Gly Ala Phe Thr Gly
            100                 105                 110

Leu Tyr Ser Leu Lys Val Leu Met Leu Gln Asn Asn Gln Leu Arg His
        115                 120                 125

Val Pro Thr Glu Ala Leu Gln Asn Leu Arg Ser Leu Gln Ser Leu Arg
    130                 135                 140

Leu Asp Ala Asn His Ile Ser Tyr Val Pro Pro Ser Cys Phe Ser Gly
145                 150                 155                 160

Leu His Ser Leu Arg His Leu Trp Leu Asp Asp Asn Ala Leu Thr Glu
                165                 170                 175

Ile Pro Val Gln Ala Phe Arg Ser Leu Ser Ala Leu Gln Ala Met Thr
            180                 185                 190

Leu Ala Leu Asn Lys Ile His His Ile Pro Asp Tyr Ala Phe Gly Asn
        195                 200                 205

Leu Ser Ser Leu Val Val Leu His Leu His Asn Asn Arg Ile His Ser
    210                 215                 220

Leu Gly Lys Lys Cys Phe Asp Gly Leu His Ser Leu Glu Thr Leu Asp
225                 230                 235                 240

Leu Asn Tyr Asn Asn Leu Asp Glu Phe Pro Thr Ala Ile Arg Thr Leu
                245                 250                 255

Ser Asn Leu Lys Glu Leu Gly Phe His Ser Asn Asn Ile Arg Ser Ile
            260                 265                 270

Pro Glu Lys Ala Phe Val Gly Asn Pro Ser Leu Ile Thr Ile His Phe
        275                 280                 285

Tyr Asp Asn Pro Ile Gln Phe Val Gly Arg Ser Ala Phe Gln His Leu
    290                 295                 300

Pro Glu Leu Arg Thr Leu Thr Leu Asn Gly Ala Ser Gln Ile Thr Glu
305                 310                 315                 320

Phe Pro Asp Leu Thr Gly Thr Ala Asn Leu Glu Ser Leu Thr Leu Thr
                325                 330                 335

Gly Ala Gln Ile Ser Ser Leu Pro Gln Thr Val Cys Asn Gln Leu Pro
            340                 345                 350

Asn Leu Gln Val Leu Asp Leu Ser Tyr Asn Leu Leu Glu Asp Leu Pro
        355                 360                 365

Ser Phe Ser Val Cys Gln Lys Leu Gln Lys Ile Asp Leu Arg His Asn
    370                 375                 380

Glu Ile Tyr Glu Ile Lys Val Asp Thr Phe Gln Gln Leu Leu Ser Leu
385                 390                 395                 400

Arg Ser Leu Asn Leu Ala Trp Asn Lys Ile Ala Ile Ile His Pro Asn
                405                 410                 415

Ala Phe Ser Thr Leu Pro Ser Leu Ile Lys Leu Asp Leu Ser Ser Asn
            420                 425                 430

Leu Leu Ser Ser Phe Pro Ile Thr Gly Leu His Gly Leu Thr His Leu
        435                 440                 445

Lys Leu Thr Gly Asn His Ala Leu Gln Ser Leu Ile Ser Ser Glu Asn
    450                 455                 460
```

Phe Pro Glu Leu Lys Val Ile Glu Met Pro Tyr Ala Tyr Gln Cys Cys
465 470 475 480

Ala Phe Gly Val Cys Glu Asn Ala Tyr Lys Ile Ser Asn Gln Trp Asn
485 490 495

Lys Gly Asp Asn Ser Ser Met Asp Asp Leu His Lys Lys Asp Ala Gly
500 505 510

Met Phe Gln Ala Gln Asp Glu Arg Asp Leu Glu Asp Phe Leu Leu Asp
515 520 525

Phe Glu Glu Asp Leu Lys Ala Leu His Ser Val Gln Cys Ser Pro Ser
530 535 540

Pro Gly Pro Phe Lys Pro Cys Glu His Leu Leu Asp Gly Trp Leu Ile
545 550 555 560

Arg Ile Gly Val Trp Thr Ile Ala Val Leu Ala Leu Thr Cys Asn Ala
565 570 575

Leu Val Thr Ser Thr Val Phe Arg Ser Pro Leu Tyr Ile Ser Pro Ile
580 585 590

Lys Leu Leu Ile Gly Val Ile Ala Ala Val Asn Met Leu Thr Gly Val
595 600 605

Ser Ser Ala Val Leu Ala Gly Val Asp Ala Phe Thr Phe Gly Ser Phe
610 615 620

Ala Arg His Gly Ala Trp Trp Glu Asn Gly Val Gly Cys His Val Ile
625 630 635 640

Gly Phe Leu Ser Ile Phe Ala Ser Glu Ser Ser Val Phe Leu Leu Thr
645 650 655

Leu Ala Ala Leu Glu Arg Gly Phe Ser Val Lys Tyr Ser Ala Lys Phe
660 665 670

Glu Thr Lys Ala Pro Phe Ser Ser Leu Lys Val Ile Ile Leu Leu Cys
675 680 685

Ala Leu Leu Ala Leu Thr Met Ala Ala Val Pro Leu Leu Gly Gly Ser
690 695 700

Lys Tyr Gly Ala Ser Pro Leu Cys Leu Pro Leu Pro Phe Gly Glu Pro
705 710 715 720

Ser Thr Met Gly Tyr Met Val Ala Leu Ile Leu Leu Asn Ser Leu Cys
725 730 735

Phe Leu Met Met Thr Ile Ala Tyr Thr Lys Leu Tyr Cys Asn Leu Asp
740 745 750

Lys Gly Asp Leu Glu Asn Ile Trp Asp Cys Ser Met Val Lys His Ile
755 760 765

Ala Leu Leu Leu Phe Thr Asn Cys Ile Leu Asn Cys Pro Val Ala Phe
770 775 780

Leu Ser Phe Ser Ser Leu Ile Asn Leu Thr Phe Ile Ser Pro Glu Val
785 790 795 800

Ile Lys Phe Ile Leu Leu Val Val Val Pro Leu Pro Ala Cys Leu Asn
805 810 815

Pro Leu Leu Tyr Ile Leu Phe Asn Pro His Phe Lys Glu Asp Leu Val
820 825 830

Ser Leu Arg Lys Gln Thr Tyr Val Trp Thr Arg Ser Lys His Pro Ser
835 840 845

Leu Met Ser Ile Asn Ser Asp Asp Val Glu Lys Gln Ser Cys Asp Ser
850 855 860

Thr Gln Ala Leu Val Thr Phe Thr Ser Ser Ser Ile Thr Tyr Asp Leu
865 870 875 880

Pro Pro Ser Ser Val Pro Ser Pro Ala Tyr Pro Val Thr Glu Ser Cys 885 890 895

His Leu Ser Ser Val Ala Phe Val Pro Cys Leu
900 905

<210> SEQ ID NO 20
<211> LENGTH: 4625
<212> TYPE: DNA
<213> ORGANISM: Homo sapiens

<400> SEQUENCE: 20
aaaaaacgag cgtgcaagca gagatgctgc tccacaccgc tcaggccgcg agcagcagca 60
aggcgcaccg ccactgtcgc cgctgcagcc agggctgctc cgaaggccgg cgtggcggca 120
accggcacct ctgtccccgc cgcgcttctc ctcgccgccc acgccgtggg gtcaggaacg 180
cggcgtctgg cgctgcagac gcccgctgag ttgcagaagc ccacggagcg gcgcccggcg 240
cgccacggcc cgtagcagtc cggtgctgct ctccgcccgc gtccggctcg tggcccccta 300
cttcgggcac catggacacc tcccggctcg gtgtgctcct gtccttgcct gtgctgctgc 360
agctggcgac cgggggcagc tctcccaggt ctggtgtgtt gctgaggggc tgccccacac 420
actgtcattg cgagcccgac ggcaggatgt tgctcagggt ggactgctcc gacctggggc 480
tctcggagct gccttccaac ctcagcgtct tcacctccta cctagacctc agtatgaaca 540
acatcagtca gctgctcccg aatcccctgc ccagtctccg cttcctggag gagttacgtc 600
ttgcgggaaa cgctctgaca tacattccca agggagcatt cactggcctt tacagtctta 660
aagttcttat gctgcagaat aatcagctaa gacacgtacc cacagaagct ctgcagaatt 720
tgcgaagcct tcaatccctg cgtctggatg ctaaccacat cagctatgtg cccccaagct 780
gtttcagtgg cctgcattcc ctgaggcacc tgtggctgga tgacaatgcg ttaacagaaa 840
tccccgtcca ggcttttaga agtttatcgg cattgcaagc catgaccttg gccctgaaca 900
aaatacacca cataccagac tatgcctttg gaaacctctc cagcttggta gttctacatc 960
tccataacaa tagaatccac tccctgggaa agaaatgctt tgatgggctc cacagcctag 1020
agactttaga tttaaattac aataaccttg atgaattccc cactgcaatt aggacactct 1080
ccaaccttaa agaactagga tttcatagca acaatatcag gtcgatacct gagaaagcat 1140
ttgtaggcaa cccttctctt attacaatac atttctatga caatcccatc cagtttgttg 1200
ggagatctgc ttttcaacat ttacctgaac taagaacact gactctgaat ggtgcctcac 1260
aaataactga atttcctgat ttaactggaa ctgcaaacct ggagagtctg actttaactg 1320
gagcacagat ctcatctctt cctcaaaccg tctgcaatca gttacctaat ctccaagtgc 1380
tagatctgtc ttacaaccta ttagaagatt tacccagttt ttcagtctgc caaaagcttc 1440
agaaaattga cctaagacat aatgaaatct acgaaattaa agttgacact ttccagcagt 1500
tgcttagcct ccgatcgctg aatttggctt ggaacaaaat tgctattatt caccccaatg 1560
cattttccac tttgccatcc ctaataaagc tggacctatc gtccaacctc ctgtcgtctt 1620
ttcctataac tgggttacat ggtttaactc acttaaaatt aacaggaaat catgccttac 1680
agagcttgat atcatctgaa aactttccag aactcaaggt tatagaaatg ccttatgctt 1740
accagtgctg tgcatttgga gtgtgtgaga atgcctataa gatttctaat caatggaata 1800
aaggtgacaa cagcagtatg gacgaccttc ataagaaaga tgctggaatg tttcaggctc 1860
aagatgaacg tgaccttgaa gatttcctgc ttgactttga ggaagacctg aaagcccttc 1920
attcagtgca gtgttcacct tccccaggcc ccttcaaacc ctgtgaacac ctgcttgatg 1980

-continued

```
gctggctgat cagaattgga gtgtggacca tagcagttct ggcacttact tgtaatgctt   2040
tggtgacttc aacagttttc agatcccctc tgtacatttc ccccattaaa ctgttaattg   2100
gggtcatcgc agcagtgaac atgctcacgg gagtctccag tgccgtgctg gctggtgtgg   2160
atgcgttcac ttttggcagc tttgcacgac atggtgcctg gtgggagaat ggggttggtt   2220
gccatgtcat tggtttttg tccatttttg cttcagaatc atctgttttc ctgcttactc    2280
tggcagccct ggagcgtggg ttctctgtga aatattctgc aaaatttgaa acgaaagctc   2340
cattttctag cctgaaagta atcattttgc tctgtgccct gctggccttg accatggccg   2400
cagttcccct gctgggtggc agcaagtatg gcgcctcccc tctctgcctg cctttgcctt   2460
ttggggagcc cagcaccatg ggctacatgg tcgctctcat cttgctcaat tccctttgct   2520
tcctcatgat gaccattgcc tacaccaagc tctactgcaa tttggacaag ggagacctgg   2580
agaatatttg ggactgctct atggtaaaac acattgccct gttgctcttc accaactgca   2640
tcctaaactg ccctgtggct ttcttgtcct tctcctcttt aataaacctt acatttatca   2700
gtcctgaagt aattaagttt atccttctgg tggtagtccc acttcctgca tgtctcaatc   2760
cccttctcta catcttgttc aatcctcact ttaaggagga tctggtgagc ctgagaaagc   2820
aaacctacgt ctggacaaga tcaaaacacc caagcttgat gtcaattaac tctgatgatg   2880
tcgaaaaaca gtcctgtgac tcaactcaag ccttggtaac ctttaccagc tccagcatca   2940
cttatgacct gcctcccagt tccgtgccat caccagctta tccagtgact gagagctgcc   3000
atctttcctc tgtggcattt gtcccatgtc tctaattaat atgtgaagga aaatgttttc   3060
aaaggttgag aacctgaaaa tgtgagattg agtatatcag agcagtaatt aataagaaga   3120
gctgaggtga aactcggttt aaaaaccaaa aaagaatctc tcagttagta agaaaaggct   3180
gaaaacctct tgatacttga gagtgaatat aagtctaaat gctgctttgt ataatttgtt   3240
cagctaaggg atagatcgat cacactattt aagtgagccc agatcaaaaa agcagattga   3300
aattttcttt agaaaagatt ctccatgatt tgaattgcat tctctttaaa ctcaccaatg   3360
taatcatttt gggaggaggg agaacccact tgctttccaa atgggtttat ttaaacccac   3420
aaactcaaga ggttgttggg ggaattagga aaataagggt tttcaatgac ctacattgct   3480
aggtagaggc tgtgatccat gggatttcat tctaatgacc atgtgaagat gtttgagtcc   3540
tcctttgcct ttcctcagaa agaatccttc taaggcacaa atcccttaga tggataatgt   3600
aaggtattgt taactcactc atattgagat catttttaga gataccaggt tttatgtatc   3660
agcactagat ggttccaccc tcatgggata aaactgctta caagtatttt gaaagaaaaa   3720
ctgaccaaaa ttcttaaatt gttactaagg caatcatgca caggtgacgt atgtcttatc   3780
tgatttgttt ttaactcctt ggtgcccaaa gctcagaagg gaattccact gccagcaatg   3840
aacatacctg gaaaagaaag taagcaatct gggatttttt ttctgggtta gtaaagaatt   3900
tttgcaataa gttttatcag ttgattcaaa ctgatgtgca tcttaatgat caaatgtgca   3960
cattacataa attaagtcca ctgatacaac ttcttacaca tgtatctcta gtagctctgg   4020
caaacccaat atctgacacc actttggact caagagactc agtaacgtat tatcctgttt   4080
atttagcttg gttttagctg tgttctctct ggataaccca cttgatgtta ggaacattac   4140
ttctctgctt attccatatt aatactgtgt taggtatttt aagaagcaag ttattaaata   4200
agaaaagtca aagtattaat tcttaccttc tattatccta tattagcttc aatacatcca   4260
aaccaaatgg ctgttaggta gatttatttt tatataagca tgtttatttt gatcagatgt   4320
tttaacttgg atttgaaaaa atacatttat gagatgtttt ataagatgtg taaatataga   4380
```

```
actgtattta ttactatagt aaaggttcag taacattaag gaccatgata atgataataa   4440

accttgtaca gtggcatatt ctttgattta tattgtgttt ctctgcccat tttctttaaa   4500

ttcattaact gtatatatgt aaatatatag tacttgtaaa tagattccaa atttgctttt   4560

ctattgggta aaaaataaat ttgtaataaa atgtgtgact atgaaacaaa aaaaaaaaaa   4620

aaaaa                                                               4625


<210> SEQ ID NO 21
<211> LENGTH: 332
<212> TYPE: PRT
<213> ORGANISM: Homo sapiens

<400> SEQUENCE: 21

Met Ala Thr Leu Lys Asp Gln Leu Ile Tyr Asn Leu Leu Lys Glu Glu
1               5                   10                  15

Gln Thr Pro Gln Asn Lys Ile Thr Val Val Gly Val Gly Ala Val Gly
            20                  25                  30

Met Ala Cys Ala Ile Ser Ile Leu Met Lys Asp Leu Ala Asp Glu Leu
        35                  40                  45

Ala Leu Val Asp Val Ile Glu Asp Lys Leu Lys Gly Glu Met Met Asp
    50                  55                  60

Leu Gln His Gly Ser Leu Phe Leu Arg Thr Pro Lys Ile Val Ser Gly
65                  70                  75                  80

Lys Asp Tyr Asn Val Thr Ala Asn Ser Lys Leu Val Ile Ile Thr Ala
                85                  90                  95

Gly Ala Arg Gln Gln Glu Gly Glu Ser Arg Leu Asn Leu Val Gln Arg
            100                 105                 110

Asn Val Asn Ile Phe Lys Phe Ile Ile Pro Asn Val Val Lys Tyr Ser
        115                 120                 125

Pro Asn Cys Lys Leu Leu Ile Val Ser Asn Pro Val Asp Ile Leu Thr
    130                 135                 140

Tyr Val Ala Trp Lys Ile Ser Gly Phe Pro Lys Asn Arg Val Ile Gly
145                 150                 155                 160

Ser Gly Cys Asn Leu Asp Ser Ala Arg Phe Arg Tyr Leu Met Gly Glu
                165                 170                 175

Arg Leu Gly Val His Pro Leu Ser Cys His Gly Trp Val Leu Gly Glu
            180                 185                 190

His Gly Asp Ser Ser Val Pro Val Trp Ser Gly Met Asn Val Ala Gly
        195                 200                 205

Val Ser Leu Lys Thr Leu His Pro Asp Leu Gly Thr Asp Lys Asp Lys
    210                 215                 220

Glu Gln Trp Lys Glu Val His Lys Gln Val Val Glu Ser Ala Tyr Glu
225                 230                 235                 240

Val Ile Lys Leu Lys Gly Tyr Thr Ser Trp Ala Ile Gly Leu Ser Val
                245                 250                 255

Ala Asp Leu Ala Glu Ser Ile Met Lys Asn Leu Arg Arg Val His Pro
            260                 265                 270

Val Ser Thr Met Ile Lys Gly Leu Tyr Gly Ile Lys Asp Asp Val Phe
        275                 280                 285

Leu Ser Val Pro Cys Ile Leu Gly Gln Asn Gly Ile Ser Asp Leu Val
    290                 295                 300

Lys Val Thr Leu Thr Ser Glu Glu Glu Ala Arg Leu Lys Lys Ser Ala
305                 310                 315                 320
```

```
Asp Thr Leu Trp Gly Ile Gln Lys Glu Leu Gln Phe
                325                 330


<210> SEQ ID NO 22
<211> LENGTH: 2226
<212> TYPE: DNA
<213> ORGANISM: Homo sapiens

<400> SEQUENCE: 22

gtctgccggt cggttgtctg gctgcgcgcg ccacccgggc ctctccagtg ccccgcctgg     60

ctcggcatcc acccccagcc cgactcacac gtgggttccc gcacgtccgc cggccccccc    120

cgctgacgtc agcatagctg ttccacttaa ggcccctccc gcgcccagct cagagtgctg    180

cagccgctgc cgccgattcc ggatctcatt gccacgcgcc cccgacgacc gcccgacgtg    240

cattcccgat tccttttggt tccaagtcca atatggcaac tctaaaggat cagctgattt    300

ataatcttct aaaggaagaa cagacccccc agaataagat tacagttgtt ggggttggtg    360

ctgttggcat ggcctgtgcc atcagtatct taatgaagga cttggcagat gaacttgctc    420

ttgttgatgt catcgaagac aaattgaagg gagagatgat ggatctccaa catggcagcc    480

ttttccttag aacaccaaag attgtctctg gcaaagacta taatgtaact gcaaactcca    540

agctggtcat tatcacggct ggggcacgtc agcaagaggg agaaagccgt cttaatttgg    600

tccagcgtaa cgtgaacatc tttaaattca tcattcctaa tgttgtaaaa tacagcccga    660

actgcaagtt gcttattgtt tcaaatccag tggatatctt gacctacgtg gcttggaaga    720

taagtggttt tcccaaaaac cgtgttattg gaagcggttg caatctggat tcagcccgat    780

tccgttacct aatgggggaa aggctgggag ttcacccatt aagctgtcat gggtgggtcc    840

ttggggaaca tggagattcc agtgtgcctg tatggagtgg aatgaatgtt gctggtgtct    900

ctctgaagac tctgcaccca gatttaggga ctgataaaga taaggaacag tggaaagagg    960

ttcacaagca ggtggttgag agtgcttatg aggtgatcaa actcaaaggc tacacatcct   1020

gggctattgg actctctgta gcagatttgg cagagagtat aatgaagaat cttaggcggg   1080

tgcacccagt ttccaccatg attaagggtc tttacggaat aaaggatgat gtcttcctta   1140

gtgttccttg cattttggga cagaatggaa tctcagacct tgtgaaggtg actctgactt   1200

ctgaggaaga ggcccgtttg aagaagagtg cagatacact tgggggatc caaaaggagc   1260

tgcaatttta aagtcttctg atgtcatatc atttcactgt ctaggctaca acaggattct   1320

aggtggaggt tgtgcatgtt gtccttttta tctgatctgt gattaaagca gtaatatttt   1380

aagatggact gggaaaaaca tcaactcctg aagttagaaa taagaatggt ttgtaaaatc   1440

cacagctata tcctgatgct ggatggtatt aatcttgtgt agtcttcaac tggttagtgt   1500

gaaatagttc tgccacctct gacgcaccac tgccaatgct gtacgtactg catttgcccc   1560

ttgagccagg tggatgttta ccgtgtgtta tataacttcc tggctccttc actgaacatg   1620

cctagtccaa catttttttcc cagtgagtca catcctggga tccagtgtat aaatccaata   1680

tcatgtcttg tgcataattc ttccaaagga tcttattttg tgaactatat cagtagtgta   1740

cattaccata taatgtaaaa agatctacat acaaacaatg caaccaacta tccaagtgtt   1800

ataccaacta aaaccccaa taaaccttga acagtgacta ctttggttaa ttcattatat   1860

taagatataa agtcataaag ctgctagtta ttatattaat ttggaaatat taggctattc   1920

ttgggcaacc ctgcaacgat tttttctaac agggatatta ttgactaata gcagaggatg   1980

taatagtcaa ctgagttgta ttggtaccac ttccattgta agtcccaaag tattatatat   2040
```

-continued

```
ttgataataa tgctaatcat aattggaaag taacattcta tatgtaaatg taaaatttat   2100

ttgccaactg aatataggca atgatagtgt gtcactatag ggaacacaga tttttgagat   2160

cttgtcctct ggaagctggt aacaattaaa aacaatctta aggcagggaa aaaaaaaaaa   2220

aaaaaa                                                              2226


<210> SEQ ID NO 23
<211> LENGTH: 353
<212> TYPE: PRT
<213> ORGANISM: Homo sapiens

<400> SEQUENCE: 23

Met Ala Ala Glu Leu Ala Met Gly Ala Glu Leu Pro Ser Ser Pro Leu
1               5                   10                  15

Ala Ile Glu Tyr Val Asn Asp Phe Asp Leu Met Lys Phe Glu Val Lys
            20                  25                  30

Lys Glu Pro Pro Glu Ala Glu Arg Phe Cys His Arg Leu Pro Pro Gly
        35                  40                  45

Ser Leu Ser Ser Thr Pro Leu Ser Thr Pro Cys Ser Ser Val Pro Ser
    50                  55                  60

Ser Pro Ser Phe Cys Ala Pro Ser Pro Gly Thr Gly Gly Gly Gly Gly
65                  70                  75                  80

Ala Gly Gly Gly Gly Gly Ser Ser Gln Ala Gly Gly Ala Pro Gly Pro
                85                  90                  95

Pro Ser Gly Gly Pro Gly Ala Val Gly Gly Thr Ser Gly Lys Pro Ala
            100                 105                 110

Leu Glu Asp Leu Tyr Trp Met Ser Gly Tyr Gln His His Leu Asn Pro
        115                 120                 125

Glu Ala Leu Asn Leu Thr Pro Glu Asp Ala Val Glu Ala Leu Ile Gly
    130                 135                 140

Ser Gly His His Gly Ala His His Gly Ala His His Pro Ala Ala Ala
145                 150                 155                 160

Ala Ala Tyr Glu Ala Phe Arg Gly Pro Gly Phe Ala Gly Gly Gly Gly
                165                 170                 175

Ala Asp Asp Met Gly Ala Gly His His His Gly Ala His His Ala Ala
            180                 185                 190

His His His His Ala Ala His His His His His His His His His His
        195                 200                 205

Gly Gly Ala Gly His Gly Gly Gly Ala Gly His His Val Arg Leu Glu
    210                 215                 220

Glu Arg Phe Ser Asp Asp Gln Leu Val Ser Met Ser Val Arg Glu Leu
225                 230                 235                 240

Asn Arg Gln Leu Arg Gly Phe Ser Lys Glu Glu Val Ile Arg Leu Lys
                245                 250                 255

Gln Lys Arg Arg Thr Leu Lys Asn Arg Gly Tyr Ala Gln Ser Cys Arg
            260                 265                 270

Phe Lys Arg Val Gln Gln Arg His Ile Leu Glu Ser Glu Lys Cys Gln
        275                 280                 285

Leu Gln Ser Gln Val Glu Gln Leu Lys Leu Glu Val Gly Arg Leu Ala
    290                 295                 300

Lys Glu Arg Asp Leu Tyr Lys Glu Lys Tyr Glu Lys Leu Ala Gly Arg
305                 310                 315                 320

Gly Gly Pro Gly Ser Ala Gly Gly Ala Gly Phe Pro Arg Glu Pro Ser
                325                 330                 335
```

```
Pro Pro Gln Ala Gly Pro Gly Gly Ala Lys Gly Thr Ala Asp Phe Phe
            340                 345                 350

Leu


<210> SEQ ID NO 24
<211> LENGTH: 2373
<212> TYPE: DNA
<213> ORGANISM: Homo sapiens

<400> SEQUENCE: 24

gcgcggccgg gcgcgggccc cgggcgatgg ccgcggagct ggcgatgggc gccgagctgc     60

ccagcagccc gctggccatc gagtacgtca acgacttcga cctgatgaag ttcgaggtga    120

agaaggagcc tcccgaggcc gagcgcttct gccaccgcct gccgccaggc tcgctgtcct    180

cgacgccgct cagcacgccc tgctcctccg tgccctcctc gcccagcttc tgcgcgccca    240

gcccgggcac cggcggcggc ggcggcgcgg ggggcggcgg cggctcgtct caggccgggg    300

gcgcccccgg gccgccgagc gggggccccg gcgccgtcgg gggcacctcg ggaagccgg    360

cgctggagga tctgtactgg atgagcggct accagcatca cctcaacccc gaggcgctca    420

acctgacgcc cgaggacgcg gtggaggcgc tcatcggcag cggccaccac ggcgcgcacc    480

acggcgcgca ccacccggcg gccgccgcag cctacgaggc tttccgcggc ccgggcttcg    540

cgggcggcgg cggagcggac gacatgggcg ccggccacca ccacggcgcg caccacgccg    600

cccaccatca ccacgccgcc caccaccacc accaccacca ccaccaccat ggcggcgcgg    660

gacacggcgg tggcgcgggc caccacgtgc gcctggagga gcgcttctcc gacgaccagc    720

tggtgtccat gtcggtgcgc gagctgaacc ggcagctccg cggcttcagc aaggaggagg    780

tcatccggct caagcagaag cggcgcacgc tcaagaaccg cggctacgcg cagtcctgcc    840

gcttcaagcg ggtgcagcag cggcacattc tggagagcga gaagtgccaa ctccagagcc    900

aggtggagca gctgaagctg gaggtggggc gcctggccaa agagcgggac ctgtacaagg    960

agaaatacga gaagctggcg ggccggggcg gccccgggag cgcgggcggg gccggtttcc   1020

cgcgggagcc ttcgccgccg caggccggtc ccggcggggc caagggcacg gccgacttct   1080

tcctgtaggc gccggacccc gagcccgcgc cgccgtcgcc ggggacaagt tcgcgcaggc   1140

ctctcggggc ctcggctcgg actccgcggt acaggacgtg gacaccaggc ccggcccggc   1200

cgtgctggcc ccggtgccaa gtctgcgggc gcggggctgg aggccccttc gctcccggtc   1260

cccgttcgcg cgcgtcggcc cgggtcgccg tcctgaggtt gagcggagaa cggtgatttc   1320

taaggaaact tgagccaggt ctaacttctt tccaagcgtc cgcttgtaca tacgttgaac   1380

gtggttctcc gttcccacct tcgccctgcc agcctagagg gaccgcgctg ccgtcccttc   1440

ccgggtggcc cctgcctgcc cccgccctcc ttcgttctct tctcagcctc cctttccttg   1500

cctttttaa cttcccctcc ccgttttaaa atcggtctta ttttcgaagt atttataatt   1560

attatgcttg gtgattagaa aagaaaacct tggaggaagc cccttctttc cccagccggg   1620

gtccgccctc agtcgcgagt cacagcatga gtcgctcgcc aggaggggcc cggcccctgc   1680

ctgccccctc cccgcttgcc cccgaccctg ctaccggcgt tccttggagg tcgaagccag   1740

ggacgtcacc cgtgctgtgt ccaggcctgc tgtcctacta tgctcaaccg ggggtggggg   1800

gagggggtg agtcctgtgc tcagtcgggt gggggctggc ccggatcccg agctgctgtc   1860

tctctatgca ccagaacata tctgtaactc ctggggaaat acatcttgtt ttaaccttca   1920

agagaagtga aagaaaaaag taatgcacag tatttctagc agaaaatttt ttttttaag   1980
```

-continued

```
aggaggcttg ggccagagcc ttctggcatg gggcgggtgg agaaagtgtt tttattttaa   2040

tttaaattgt gtttcgtttt gtttgtggaa tctttcttta atgcttcgtc gctctttgga   2100

ctagccggga gagagggcga ggaggcgggt gctccaggcc ctgtaggctg ggccaggcgc   2160

ctgggggatc tgcccgtttt cggaggccct caggggccat cagtgggatt ccagccgctc   2220

cacacccctc ccctgagcac tcggagtgga aggcgcgccg actcgttgaa agttttgttg   2280

tgtagttggt tttcgttgag ttcttttttc atttgctacg aaactgagaa aaagaaaaaa   2340

atacacaaaa taaatctgtt cagatccaag tca                                 2373
```

```
<210> SEQ ID NO 25
<211> LENGTH: 1939
<212> TYPE: PRT
<213> ORGANISM: Homo sapiens

<400> SEQUENCE: 25

Met Thr Asp Ala Gln Met Ala Asp Phe Gly Ala Ala Ala Gln Tyr Leu
1               5                   10                  15

Arg Lys Ser Glu Lys Glu Arg Leu Glu Ala Gln Thr Arg Pro Phe Asp
            20                  25                  30

Ile Arg Thr Glu Cys Phe Val Pro Asp Asp Lys Glu Glu Phe Val Lys
        35                  40                  45

Ala Lys Ile Leu Ser Arg Glu Gly Gly Lys Val Ile Ala Glu Thr Glu
    50                  55                  60

Asn Gly Lys Thr Val Thr Val Lys Glu Asp Gln Val Leu Gln Gln Asn
65                  70                  75                  80

Pro Pro Lys Phe Asp Lys Ile Glu Asp Met Ala Met Leu Thr Phe Leu
                85                  90                  95

His Glu Pro Ala Val Leu Phe Asn Leu Lys Glu Arg Tyr Ala Ala Trp
            100                 105                 110

Met Ile Tyr Thr Tyr Ser Gly Leu Phe Cys Val Thr Val Asn Pro Tyr
        115                 120                 125

Lys Trp Leu Pro Val Tyr Asn Ala Glu Val Val Ala Ala Tyr Arg Gly
    130                 135                 140

Lys Lys Arg Ser Glu Ala Pro Pro His Ile Phe Ser Ile Ser Asp Asn
145                 150                 155                 160

Ala Tyr Gln Tyr Met Leu Thr Asp Arg Glu Asn Gln Ser Ile Leu Ile
                165                 170                 175

Thr Gly Glu Ser Gly Ala Gly Lys Thr Val Asn Thr Lys Arg Val Ile
            180                 185                 190

Gln Tyr Phe Ala Ser Ile Ala Ala Ile Gly Asp Arg Gly Lys Lys Asp
        195                 200                 205

Asn Ala Asn Ala Asn Lys Gly Thr Leu Glu Asp Gln Ile Ile Gln Ala
    210                 215                 220

Asn Pro Ala Leu Glu Ala Phe Gly Asn Ala Lys Thr Val Arg Asn Asp
225                 230                 235                 240

Asn Ser Ser Arg Phe Gly Lys Phe Ile Arg Ile His Phe Gly Ala Thr
                245                 250                 255

Gly Lys Leu Ala Ser Ala Asp Ile Glu Thr Tyr Leu Leu Glu Lys Ser
            260                 265                 270

Arg Val Ile Phe Gln Leu Lys Ala Glu Arg Asn Tyr His Ile Phe Tyr
        275                 280                 285

Gln Ile Leu Ser Asn Lys Lys Pro Glu Leu Leu Asp Met Leu Leu Val
    290                 295                 300
```

-continued

```
Thr Asn Asn Pro Tyr Asp Tyr Ala Phe Val Ser Gln Gly Glu Val Ser
305                 310                 315                 320

Val Ala Ser Ile Asp Asp Ser Glu Glu Leu Met Ala Thr Asp Ser Ala
                325                 330                 335

Phe Asp Val Leu Gly Phe Thr Ser Glu Glu Lys Ala Gly Val Tyr Lys
            340                 345                 350

Leu Thr Gly Ala Ile Met His Tyr Gly Asn Met Lys Phe Lys Gln Lys
        355                 360                 365

Gln Arg Glu Glu Gln Ala Glu Pro Asp Gly Thr Glu Asp Ala Asp Lys
    370                 375                 380

Ser Ala Tyr Leu Met Gly Leu Asn Ser Ala Asp Leu Leu Lys Gly Leu
385                 390                 395                 400

Cys His Pro Arg Val Lys Val Gly Asn Glu Tyr Val Thr Lys Gly Gln
                405                 410                 415

Ser Val Gln Gln Val Tyr Tyr Ser Ile Gly Ala Leu Ala Lys Ala Val
            420                 425                 430

Tyr Glu Lys Met Phe Asn Trp Met Val Thr Arg Ile Asn Ala Thr Leu
        435                 440                 445

Glu Thr Lys Gln Pro Arg Gln Tyr Phe Ile Gly Val Leu Asp Ile Ala
    450                 455                 460

Gly Phe Glu Ile Phe Asp Phe Asn Ser Phe Glu Gln Leu Cys Ile Asn
465                 470                 475                 480

Phe Thr Asn Glu Lys Leu Gln Gln Phe Phe Asn His His Met Phe Val
                485                 490                 495

Leu Glu Gln Glu Glu Tyr Lys Lys Glu Gly Ile Glu Trp Thr Phe Ile
            500                 505                 510

Asp Phe Gly Met Asp Leu Gln Ala Cys Ile Asp Leu Ile Glu Lys Pro
        515                 520                 525

Met Gly Ile Met Ser Ile Leu Glu Glu Glu Cys Met Phe Pro Lys Ala
    530                 535                 540

Thr Asp Met Thr Phe Lys Ala Lys Leu Tyr Asp Asn His Leu Gly Lys
545                 550                 555                 560

Ser Asn Asn Phe Gln Lys Pro Arg Asn Ile Lys Gly Lys Gln Glu Ala
                565                 570                 575

His Phe Ser Leu Ile His Tyr Ala Gly Thr Val Asp Tyr Asn Ile Leu
            580                 585                 590

Gly Trp Leu Glu Lys Asn Lys Asp Pro Leu Asn Glu Thr Val Val Ala
        595                 600                 605

Leu Tyr Gln Lys Ser Ser Leu Lys Leu Met Ala Thr Leu Phe Ser Ser
    610                 615                 620

Tyr Ala Thr Ala Asp Thr Gly Asp Ser Gly Lys Ser Lys Gly Gly Lys
625                 630                 635                 640

Lys Lys Gly Ser Ser Phe Gln Thr Val Ser Ala Leu His Arg Glu Asn
                645                 650                 655

Leu Asn Lys Leu Met Thr Asn Leu Arg Thr Thr His Pro His Phe Val
            660                 665                 670

Arg Cys Ile Ile Pro Asn Glu Arg Lys Ala Pro Gly Val Met Asp Asn
        675                 680                 685

Pro Leu Val Met His Gln Leu Arg Cys Asn Gly Val Leu Glu Gly Ile
    690                 695                 700

Arg Ile Cys Arg Lys Gly Phe Pro Asn Arg Ile Leu Tyr Gly Asp Phe
705                 710                 715                 720

Arg Gln Arg Tyr Arg Ile Leu Asn Pro Val Ala Ile Pro Glu Gly Gln
```

-continued

```
                725                 730                 735

Phe Ile Asp Ser Arg Lys Gly Thr Glu Lys Leu Leu Ser Ser Leu Asp
            740                 745                 750

Ile Asp His Asn Gln Tyr Lys Phe Gly His Thr Lys Val Phe Phe Lys
        755                 760                 765

Ala Gly Leu Leu Gly Leu Leu Glu Glu Met Arg Asp Glu Arg Leu Ser
    770                 775                 780

Arg Ile Ile Thr Arg Met Gln Ala Gln Ala Arg Gly Gln Leu Met Arg
785                 790                 795                 800

Ile Glu Phe Lys Lys Ile Val Glu Arg Arg Asp Ala Leu Leu Val Ile
                805                 810                 815

Gln Trp Asn Ile Arg Ala Phe Met Gly Val Lys Asn Trp Pro Trp Met
            820                 825                 830

Lys Leu Tyr Phe Lys Ile Lys Pro Leu Leu Lys Ser Ala Glu Thr Glu
        835                 840                 845

Lys Glu Met Ala Thr Met Lys Glu Glu Phe Gly Arg Ile Lys Glu Thr
    850                 855                 860

Leu Glu Lys Ser Glu Ala Arg Arg Lys Glu Leu Glu Glu Lys Met Val
865                 870                 875                 880

Ser Leu Leu Gln Glu Lys Asn Asp Leu Gln Leu Gln Val Gln Ala Glu
                885                 890                 895

Gln Asp Asn Leu Asn Asp Ala Glu Glu Arg Cys Asp Gln Leu Ile Lys
            900                 905                 910

Asn Lys Ile Gln Leu Glu Ala Lys Val Lys Glu Met Asn Glu Arg Leu
        915                 920                 925

Glu Asp Glu Glu Glu Met Asn Ala Glu Leu Thr Ala Lys Lys Arg Lys
    930                 935                 940

Leu Glu Asp Glu Cys Ser Glu Leu Lys Lys Asp Ile Asp Asp Leu Glu
945                 950                 955                 960

Leu Thr Leu Ala Lys Val Glu Lys Glu Lys His Ala Thr Glu Asn Lys
                965                 970                 975

Val Lys Asn Leu Thr Glu Glu Met Ala Gly Leu Asp Glu Ile Ile Ala
            980                 985                 990

Lys Leu Thr Lys Glu Lys Lys Ala  Leu Gln Glu Ala His  Gln Gln Ala
        995                 1000                1005

Leu Asp  Asp Leu Gln Val Glu  Glu Asp Lys Val Asn  Ser Leu Ser
    1010                1015                1020

Lys Ser  Lys Val Lys Leu Glu  Gln Gln Val Asp Asp  Leu Glu Gly
    1025                1030                1035

Ser Leu  Glu Gln Glu Lys Lys  Val Arg Met Asp Leu  Glu Arg Ala
    1040                1045                1050

Lys Arg  Lys Leu Glu Gly Asp  Leu Lys Leu Thr Gln  Glu Ser Ile
    1055                1060                1065

Met Asp  Leu Glu Asn Asp Lys  Leu Gln Leu Glu Glu  Lys Leu Lys
    1070                1075                1080

Lys Lys  Glu Phe Asp Ile Asn  Gln Gln Asn Ser Lys  Ile Glu Asp
    1085                1090                1095

Glu Gln  Val Leu Ala Leu Gln  Leu Gln Lys Lys Leu  Lys Glu Asn
    1100                1105                1110

Gln Ala  Arg Ile Glu Glu Leu  Glu Glu Glu Leu Glu  Ala Glu Arg
    1115                1120                1125

Thr Ala  Arg Ala Lys Val Glu  Lys Leu Arg Ser Asp  Leu Ser Arg
    1130                1135                1140
```

```
Glu Leu  Glu Glu Ile Ser Glu  Arg Leu Glu Glu Ala  Gly Gly Ala
    1145                 1150                 1155

Thr Ser  Val Gln Ile Glu Met  Asn Lys Lys Arg Glu  Ala Glu Phe
    1160                 1165                 1170

Gln Lys  Met Arg Arg Asp Leu  Glu Glu Ala Thr Leu  Gln His Glu
    1175                 1180                 1185

Ala Thr  Ala Ala Ala Leu Arg  Lys Lys His Ala Asp  Ser Val Ala
    1190                 1195                 1200

Glu Leu  Gly Glu Gln Ile Asp  Asn Leu Gln Arg Val  Lys Gln Lys
    1205                 1210                 1215

Leu Glu  Lys Glu Lys Ser Glu  Phe Lys Leu Glu Leu  Asp Asp Val
    1220                 1225                 1230

Thr Ser  Asn Met Glu Gln Ile  Ile Lys Ala Lys Ala  Asn Leu Glu
    1235                 1240                 1245

Lys Val  Ser Arg Thr Leu Glu  Asp Gln Ala Asn Glu  Tyr Arg Val
    1250                 1255                 1260

Lys Leu  Glu Glu Ala Gln Arg  Ser Leu Asn Asp Phe  Thr Thr Gln
    1265                 1270                 1275

Arg Ala  Lys Leu Gln Thr Glu  Asn Gly Glu Leu Ala  Arg Gln Leu
    1280                 1285                 1290

Glu Glu  Lys Glu Ala Leu Ile  Ser Gln Leu Thr Arg  Gly Lys Leu
    1295                 1300                 1305

Ser Tyr  Thr Gln Gln Met Glu  Asp Leu Lys Arg Gln  Leu Glu Glu
    1310                 1315                 1320

Glu Gly  Lys Ala Lys Asn Ala  Leu Ala His Ala Leu  Gln Ser Ala
    1325                 1330                 1335

Arg His  Asp Cys Asp Leu Leu  Arg Glu Gln Tyr Glu  Glu Glu Thr
    1340                 1345                 1350

Glu Ala  Lys Ala Glu Leu Gln  Arg Val Leu Ser Lys  Ala Asn Ser
    1355                 1360                 1365

Glu Val  Ala Gln Trp Arg Thr  Lys Tyr Glu Thr Asp  Ala Ile Gln
    1370                 1375                 1380

Arg Thr  Glu Glu Leu Glu Glu  Ala Lys Lys Lys Leu  Ala Gln Arg
    1385                 1390                 1395

Leu Gln  Asp Ala Glu Glu Ala  Val Glu Ala Val Asn  Ala Lys Cys
    1400                 1405                 1410

Ser Ser  Leu Glu Lys Thr Lys  His Arg Leu Gln Asn  Glu Ile Glu
    1415                 1420                 1425

Asp Leu  Met Val Asp Val Glu  Arg Ser Asn Ala Ala  Ala Ala Ala
    1430                 1435                 1440

Leu Asp  Lys Lys Gln Arg Asn  Phe Asp Lys Ile Leu  Ala Glu Trp
    1445                 1450                 1455

Lys Gln  Lys Tyr Glu Glu Ser  Gln Ser Glu Leu Glu  Ser Ser Gln
    1460                 1465                 1470

Lys Glu  Ala Arg Ser Leu Ser  Thr Glu Leu Phe Lys  Leu Lys Asn
    1475                 1480                 1485

Ala Tyr  Glu Glu Ser Leu Glu  His Leu Glu Thr Phe  Lys Arg Glu
    1490                 1495                 1500

Asn Lys  Asn Leu Gln Glu Glu  Ile Ser Asp Leu Thr  Glu Gln Leu
    1505                 1510                 1515

Gly Glu  Gly Gly Lys Asn Val  His Glu Leu Glu Lys  Val Arg Lys
    1520                 1525                 1530
```

-continued

```
Gln Leu  Glu Val Glu Lys Leu  Glu Leu Gln Ser Ala  Leu Glu Glu
    1535                 1540                 1545

Ala Glu  Ala Ser Leu Glu His  Glu Glu Gly Lys Ile  Leu Arg Ala
    1550                 1555                 1560

Gln Leu  Glu Phe Asn Gln Ile  Lys Ala Glu Ile Glu  Arg Lys Leu
    1565                 1570                 1575

Ala Glu  Lys Asp Glu Glu Met  Glu Gln Ala Lys Arg  Asn His Gln
    1580                 1585                 1590

Arg Val  Val Asp Ser Leu Gln  Thr Ser Leu Asp Ala  Glu Thr Arg
    1595                 1600                 1605

Ser Arg  Asn Glu Val Leu Arg  Val Lys Lys Lys Met  Glu Gly Asp
    1610                 1615                 1620

Leu Asn  Glu Met Glu Ile Gln  Leu Ser His Ala Asn  Arg Met Ala
    1625                 1630                 1635

Ala Glu  Ala Gln Lys Gln Val  Lys Ser Leu Gln Ser  Leu Leu Lys
    1640                 1645                 1650

Asp Thr  Gln Ile Gln Leu Asp  Asp Ala Val Arg Ala  Asn Asp Asp
    1655                 1660                 1665

Leu Lys  Glu Asn Ile Ala Ile  Val Glu Arg Arg Asn  Asn Leu Leu
    1670                 1675                 1680

Gln Ala  Glu Leu Glu Glu Leu  Arg Ala Val Val Glu  Gln Thr Glu
    1685                 1690                 1695

Arg Ser  Arg Lys Leu Ala Glu  Gln Glu Leu Ile Glu  Thr Ser Glu
    1700                 1705                 1710

Arg Val  Gln Leu Leu His Ser  Gln Asn Thr Ser Leu  Ile Asn Gln
    1715                 1720                 1725

Lys Lys  Lys Met Glu Ser Asp  Leu Thr Gln Leu Gln  Ser Glu Val
    1730                 1735                 1740

Glu Glu  Ala Val Gln Glu Cys  Arg Asn Ala Glu Glu  Lys Ala Lys
    1745                 1750                 1755

Lys Ala  Ile Thr Asp Ala Ala  Met Met Ala Glu Glu  Leu Lys Lys
    1760                 1765                 1770

Glu Gln  Asp Thr Ser Ala His  Leu Glu Arg Met Lys  Lys Asn Met
    1775                 1780                 1785

Glu Gln  Thr Ile Lys Asp Leu  Gln His Arg Leu Asp  Glu Ala Glu
    1790                 1795                 1800

Gln Ile  Ala Leu Lys Gly Gly  Lys Lys Gln Leu Gln  Lys Leu Glu
    1805                 1810                 1815

Ala Arg  Val Arg Glu Leu Glu  Gly Glu Leu Glu Ala  Glu Gln Lys
    1820                 1825                 1830

Arg Asn  Ala Glu Ser Val Lys  Gly Met Arg Lys Ser  Glu Arg Arg
    1835                 1840                 1845

Ile Lys  Glu Leu Thr Tyr Gln  Thr Glu Glu Asp Lys  Lys Asn Leu
    1850                 1855                 1860

Leu Arg  Leu Gln Asp Leu Val  Asp Lys Leu Gln Leu  Lys Val Lys
    1865                 1870                 1875

Ala Tyr  Lys Arg Gln Ala Glu  Glu Ala Glu Glu Gln  Ala Asn Thr
    1880                 1885                 1890

Asn Leu  Ser Lys Phe Arg Lys  Val Gln His Glu Leu  Asp Glu Ala
    1895                 1900                 1905

Glu Glu  Arg Ala Asp Ile Ala  Glu Ser Gln Val Asn  Lys Leu Arg
    1910                 1915                 1920

Ala Lys  Ser Arg Asp Ile Gly  Ala Lys Gln Lys Met  His Asp Glu
```

1925 1930 1935

Glu

<210> SEQ ID NO 26
<211> LENGTH: 5941
<212> TYPE: DNA
<213> ORGANISM: Homo sapiens

<400> SEQUENCE: 26
agatagagag actcctgcgg cccagattct tcaggattct ccgtgaaggg ataaccaggg 60
gaagcaccaa gatgaccgat gcccagatgg ctgactttgg ggcagcggcc cagtacctcc 120
gcaagtcaga gaaggagcgt ctagaggccc agacccggcc ctttgacatt cgcactgagt 180
gcttcgtgcc cgatgacaag gaagagtttg tcaaagccaa gattttgtcc cgggagggag 240
gcaaggtcat tgctgaaacc gagaatggga agacggtgac tgtgaaggag gaccaggtgt 300
tgcagcagaa cccacccaag ttcgacaaga ttgaggacat ggccatgctg accttcctgc 360
acgagcccgc ggtgcttttc aacctcaagg agcgctacgc ggcctggatg atatatacct 420
actcgggcct cttctgtgtc actgtcaacc cctacaagtg gctgccggtg tacaatgccg 480
aggtggtggc cgcctaccgg ggcaagaaga ggagtgaggc cccgccccac atcttctcca 540
tctccgacaa cgcctatcag tacatgctga cagatcggga gaaccagtcc atcctcatca 600
cgggagaatc cggggcgggg aagactgtga acaccaagcg tgtcatccag tactttgcca 660
gcattgcagc cataggtgac cgtggcaaga aggacaatgc caatgcgaac aagggcaccc 720
tggaggacca gatcatccag gccaaccccg ctctggaggc cttcggcaat gccaagactg 780
tccggaacga caactcctcc cgctttggga aattcattag gatccacttt ggggccactg 840
gaaagctggc ttctgcagac atagagacct acctgctgga gaagtcccgg gtgatcttcc 900
agctgaaagc tgagagaaac taccacatct tctaccagat tctgtccaac aagaagccgg 960
agttgctgga catgctgctg gtcaccaaca atccctacga ctacgccttc gtgtctcagg 1020
gagaggtgtc cgtggcctcc attgatgact ccgaggagct catggccacc gatagtgcct 1080
ttgacgtgct gggcttcact tcagaggaga aagctggcgt ctacaagctg acgggagcca 1140
tcatgcacta cgggaacatg aagttcaagc agaagcagcg ggaggagcag gcggagccag 1200
acggcaccga agatgctgac aagtcggcct acctcatggg gctgaactca gctgacctgc 1260
tcaaggggct gtgccaccct cgggtgaaag tgggcaacga gtatgtcacc aaggggcaga 1320
gcgtgcagca ggtgtactac tccatcgggg ctctggccaa ggcagtgtat gagaagatgt 1380
tcaactggat ggtgacgcgc atcaacgcca ccctggagac caagcagcca cgccagtact 1440
tcataggagt cctggacatc gctggcttcg agatcttcga cttcaacagc tttgagcagc 1500
tctgcatcaa cttcaccaac gagaagctgc agcagttctt caaccaccac atgttcgtgc 1560
tggagcagga ggagtacaag aaggagggca ttgagtggac attcattgac tttggcatgg 1620
acctgcaggc ctgcattgac ctcatcgaga agcccatggg catcatgtcc atcctggagg 1680
aggagtgcat gttccccaag gccactgaca tgaccttcaa ggccaagctg tacgacaacc 1740
acctgggcaa gtccaacaat ttccagaagc cacgcaacat caaggggaag caggaagccc 1800
acttctccct gatccactac gccggcactg tggactacaa catcctgggc tggctggaaa 1860
aaaacaagga tcctctcaac gagactgttg tggccctgta ccagaagtcc tccctcaagc 1920
tcatggccac tctcttctcc tcctacgcaa ctgccgatac tggggacagt ggtaaaagca 1980
aaggaggcaa gaaaaagggc tcatccttcc agacggtgtc ggctctccac cgggaaaatc 2040

```
tcaacaagct aatgaccaac ctgaggacca cccatcctca ctttgtgcgt tgcatcatcc   2100
ccaatgagcg gaaggctcca ggggtgatgg acaacccccct ggtcatgcac cagctgcgct   2160
gcaatggcgt gctggagggc atccgcatct gcaggaaggg cttccccaac cgcatcctct   2220
acggggactt ccggcagagg tatcgcatcc tgaacccagt ggccatccct gagggacagt   2280
tcattgatag caggaagggg acagagaagc tgctcagctc tctggacatt gatcacaacc   2340
agtacaagtt tggccacacc aaggtgttct tcaaggcagg gctgcttggg ctgctggagg   2400
agatgcggga tgagaggctg agccgcatca tcacgcgcat gcaggcccaa gcccggggcc   2460
agctcatgcg cattgagttc aagaagatag tggaacgcag ggatgccctg ctggtaatcc   2520
agtggaacat tcgggccttc atgggggtca agaattggcc ctggatgaag ctctacttca   2580
agatcaagcc gctgctgaag agcgcagaga cggagaagga gatggccacc atgaaggaag   2640
agttcgggcg catcaaagag acgctggaga agtccgaggc tcgccgcaag gagctggagg   2700
agaagatggt gtccctgctg caggagaaga atgacctgca gctccaagtg caggcggaac   2760
aagacaacct caatgatgct gaggagcgct gcgaccagct gatcaaaaac aagattcagc   2820
tggaggccaa agtaaaggag atgaatgaga ggctggagga tgaggaggag atgaacgcgg   2880
agctcactgc caagaagcgc aagctggaag acgagtgctc agagctcaag aaggacattg   2940
atgacctgga gctgacactg gccaaggtgg agaaggagaa gcatgcaaca gagaacaagg   3000
tgaagaacct aacagaggag atggctgggc tggatgaaat catcgctaag ctgaccaagg   3060
agaagaaagc tctacaagag gcccatcagc aggccctgga tgaccttcag gttgaggaag   3120
acaaggtcaa cagcctgtcc aagtctaagg tcaagctgga gcagcaggtg gatgatctgg   3180
agggatccct agagcaagag aagaaggtgc gcatggacct ggagcgagca aagcggaaac   3240
tggagggcga cctgaagctg acccaggaga gcatcatgga cctggaaaat gataaactgc   3300
agctggaaga aaagcttaag aagaaggagt ttgacattaa tcagcagaac agtaagattg   3360
aggatgagca ggtgctggcc cttcaactac agaagaaact gaaggaaaac caggcacgca   3420
tcgaggagct ggaggaggag ctggaggccg agcgcaccgc cagggctaag gtggagaagc   3480
tgcgctcaga cctgtctcgg gagctggagg agatcagcga gcggctggaa gaggccggcg   3540
gggccacgtc cgtgcagatc gagatgaaca agaagcgcga ggccgagttc cagaagatgc   3600
ggcgggacct ggaggaggcc acgctgcagc acgaggccac tgccgcggcc ctgcgcaaga   3660
agcacgccga cagcgtggcc gagctgggcg agcagatcga caacctgcag cgggtgaagc   3720
agaagctgga gaaggagaag agcgagttca agctggagct ggatgacgtc acctccaaca   3780
tggagcagat catcaaggcc aaggcaaacc tggagaaagt gtctcggacg ctggaggacc   3840
aggccaatga gtaccgcgtg aagctagaag aggcccaacg ctccctcaat gatttcacca   3900
cccagcgagc caagctgcag accgagaatg gagagttggc ccggcagcta gaggaaaagg   3960
aggcgctaat ctcgcagctg acccggggga agctctctta tacccagcaa atggaggacc   4020
tcaaaaggca gctggaggag gagggcaagg cgaagaacgc cctggcccat gcactgcagt   4080
cggcccggca tgactgcgac ctgctgcggg agcagtacga ggaggagaca gaggccaagg   4140
ccgagctgca gcgcgtcctg tccaaggcca actcggaggt ggcccagtgg aggaccaagt   4200
atgagacgga cgccattcag cggactgagg agctcgaaga ggccaaaaag aagctggccc   4260
agcggctgca ggatgccgag gaggccgtgg aggctgttaa tgccaagtgc tcctcactgg   4320
agaagaccaa gcaccggcta cagaatgaga tagaggactt gatggtggac gtagagcgct   4380
```

```
ccaatgctgc tgctgcagcc ctggacaaga agcagagaaa ctttgacaag atcctggccg   4440

agtggaagca gaagtatgag gagtcgcagt ctgagctgga gtcctcacag aaggaggctc   4500

gctccctcag cacagagctc ttcaagctca agaacgccta cgaggagtcc ctggagcacc   4560

tagagacctt caagcgggag aacaagaacc ttcaggagga aatctcggac cttactgagc   4620

agctaggaga aggaggaaag aatgtgcatg agctggagaa ggtccgcaaa cagctggagg   4680

tggagaagct ggagctgcag tcagccctgg aggaggcaga ggcctccctg gagcacgagg   4740

agggcaagat cctccgggcc cagctagagt tcaaccagat caaggcagag atcgagcgga   4800

agctggcaga gaaggacgag gagatggaac aggccaagcg caaccaccag cgggtggtgg   4860

actcgctgca gacctccctg gatgcagaga cacgcagccg caacgaggtc ctgagggtga   4920

agaagaagat ggaaggagac ctcaatgaga tggagatcca gctcagccac gccaaccgca   4980

tggctgccga ggcccagaag caagtcaaga gcctccagag cttgctgaag gacacccaga   5040

tccagctgga cgatgcggtc cgtgccaacg acgacctgaa ggagaacatc gccatcgtgg   5100

agcggcgcaa caacctgctg caggctgagc tggaggagct gcgtgccgtg gtggagcaga   5160

cagagcggtc ccggaagctg gcggagcagg agctgattga gaccagcgag cgggtgcagc   5220

tgctgcattc ccagaacacc agcctcatca accagaagaa gaagatggag tcggatctga   5280

cccagctcca gtcggaagtg gaggaggcag tgcaggagtg cagaaacgcc gaggagaagg   5340

ccaagaaggc catcacggat gccgccatga tggcagagga gctgaagaag gagcaggaca   5400

ccagcgccca cctggagcgc atgaagaaga acatggagca gaccattaag gacctgcagc   5460

accggctgga cgaggccgag cagatcgccc tcaagggagg caagaagcag ctgcagaagc   5520

tggaagcgcg ggtgcgggag ctggagggtg agctggaggc cgagcagaag cgcaacgcag   5580

agtcggtgaa gggcatgagg aagagcgagc ggcgcatcaa ggagctcacc taccagacag   5640

aggaagacaa aaagaacctg ctgcggctac aggacctggt ggacaagctg caactgaagg   5700

tcaaggccta caagcgccag gccgaggagg cggaggagca agccaacacc aacctgtcca   5760

agttccgcaa ggtgcagcat gagctggatg aggcagagga gcgggcggac atcgctgagt   5820

cccaggtcaa caagcttcga gccaagagcc gtgacattgg tgccaagcaa aaaatgcacg   5880

atgaggagtg acactgcctc gggaacctca ctcttgccaa cctgtaataa atatgagtgc   5940

c                                                                   5941
```

<210> SEQ ID NO 27
<211> LENGTH: 175
<212> TYPE: PRT
<213> ORGANISM: Homo sapiens

<400> SEQUENCE: 27

```
Met Ala Ser Arg Lys Ala Gly Thr Arg Gly Lys Val Ala Ala Thr Lys
1               5                   10                  15

Gln Ala Gln Arg Gly Ser Ser Asn Val Phe Ser Met Phe Glu Gln Ala
            20                  25                  30

Gln Ile Gln Glu Phe Lys Glu Ala Phe Ser Cys Ile Asp Gln Asn Arg
        35                  40                  45

Asp Gly Ile Ile Cys Lys Ala Asp Leu Arg Glu Thr Tyr Ser Gln Leu
    50                  55                  60

Gly Lys Val Ser Val Pro Glu Glu Glu Leu Asp Ala Met Leu Gln Glu
65                  70                  75                  80

Gly Lys Gly Pro Ile Asn Phe Thr Val Phe Leu Thr Leu Phe Gly Glu
                85                  90                  95
```

Lys Leu Asn Gly Thr Asp Pro Glu Glu Ala Ile Leu Ser Ala Phe Arg
            100                 105                 110

Met Phe Asp Pro Ser Gly Lys Gly Val Val Asn Lys Asp Glu Phe Lys
        115                 120                 125

Gln Leu Leu Leu Thr Gln Ala Asp Lys Phe Ser Pro Ala Glu Val Glu
    130                 135                 140

Gln Met Phe Ala Leu Thr Pro Met Asp Leu Ala Gly Asn Ile Asp Tyr
145                 150                 155                 160

Lys Ser Leu Cys Tyr Ile Ile Thr His Gly Asp Glu Lys Glu Glu
                165                 170                 175

<210> SEQ ID NO 28
<211> LENGTH: 619
<212> TYPE: DNA
<213> ORGANISM: Homo sapiens

<400> SEQUENCE: 28
tctgcagaga gaatggccag caggaaggcg gggacccggg gcaaggtggc agccaccaag 60
caggcccaac gtggttcttc caacgtcttt tccatgtttg aacaagccca gatacaggag 120
ttcaaagaag ccttcagctg tatcgaccag aatcgtgatg gcatcatctg caaggcagac 180
ctgagggaga cctactccca gctggggaag gtgagtgtcc cagaggagga gctggacgcc 240
atgctgcaag agggcaaggg ccccatcaac ttcaccgtct tcctcacgct ctttggggag 300
aagctcaatg ggacagaccc cgaggaagcc atcctgagtg ccttccgcat gtttgacccc 360
agcggcaaag gggtggtgaa caaggatgag ttcaagcagc ttctcctgac ccaggcagac 420
aagttctctc cagctgaggt ggagcagatg ttcgccctga cacccatgga cctggcgggg 480
aacatcgact acaagtcact gtgctacatc atcacccatg gagacgagaa agaggaatga 540
ggggcagggc caggcccacg ggggggcacc tcaataaact ctgttgcaaa attggaaaaa 600
aaaaaaaaaa aaaaaaaaa 619

<210> SEQ ID NO 29
<211> LENGTH: 5179
<212> TYPE: PRT
<213> ORGANISM: Homo sapiens

<400> SEQUENCE: 29

Met Gly Leu Pro Leu Ala Arg Leu Ala Ala Val Cys Leu Ala Leu Ser
1               5                   10                  15

Leu Ala Gly Gly Ser Glu Leu Gln Thr Glu Gly Arg Thr Arg Asn His
            20                  25                  30

Gly His Asn Val Cys Ser Thr Trp Gly Asn Phe His Tyr Lys Thr Phe
        35                  40                  45

Asp Gly Asp Val Phe Arg Phe Pro Gly Pro Cys Asp Tyr Asn Phe Ala
    50                  55                  60

Ser Asp Cys Arg Gly Ser Tyr Lys Glu Phe Ala Val His Leu Lys Arg
65                  70                  75                  80

Gly Pro Gly Gln Ala Glu Ala Pro Ala Gly Val Glu Ser Ile Leu Leu
                85                  90                  95

Thr Ile Lys Asp Asp Thr Ile Tyr Leu Thr Arg His Leu Ala Val Leu
            100                 105                 110

Asn Gly Ala Val Val Ser Thr Pro His Tyr Ser Pro Gly Leu Leu Ile
        115                 120                 125

Glu Lys Ser Asp Ala Tyr Thr Lys Val Tyr Ser Arg Ala Gly Leu Thr

```
    130                 135                 140

Leu Met Trp Asn Arg Glu Asp Ala Leu Met Leu Glu Leu Asp Thr Lys
145                 150                 155                 160

Phe Arg Asn His Thr Cys Gly Leu Cys Gly Asp Tyr Asn Gly Leu Gln
                165                 170                 175

Ser Tyr Ser Glu Phe Leu Ser Asp Gly Val Leu Phe Ser Pro Leu Glu
            180                 185                 190

Phe Gly Asn Met Gln Lys Ile Asn Gln Pro Asp Val Val Cys Glu Asp
        195                 200                 205

Pro Glu Glu Glu Val Ala Pro Ala Ser Cys Ser Glu His Arg Ala Glu
    210                 215                 220

Cys Glu Arg Leu Leu Thr Ala Glu Ala Phe Ala Asp Cys Gln Asp Leu
225                 230                 235                 240

Val Pro Leu Glu Pro Tyr Leu Arg Ala Cys Gln Gln Asp Arg Cys Arg
                245                 250                 255

Cys Pro Gly Gly Asp Thr Cys Val Cys Ser Thr Val Ala Glu Phe Ser
            260                 265                 270

Arg Gln Cys Ser His Ala Gly Gly Arg Pro Gly Asn Trp Arg Thr Ala
        275                 280                 285

Thr Leu Cys Pro Lys Thr Cys Pro Gly Asn Leu Val Tyr Leu Glu Ser
    290                 295                 300

Gly Ser Pro Cys Met Asp Thr Cys Ser His Leu Glu Val Ser Ser Leu
305                 310                 315                 320

Cys Glu Glu His Arg Met Asp Gly Cys Phe Cys Pro Glu Gly Thr Val
                325                 330                 335

Tyr Asp Asp Ile Gly Asp Ser Gly Cys Val Pro Val Ser Gln Cys His
            340                 345                 350

Cys Arg Leu His Gly His Leu Tyr Thr Pro Gly Gln Glu Ile Thr Asn
        355                 360                 365

Asp Cys Glu Gln Cys Val Cys Asn Ala Gly Arg Trp Val Cys Lys Asp
    370                 375                 380

Leu Pro Cys Pro Gly Thr Cys Ala Leu Glu Gly Gly Ser His Ile Thr
385                 390                 395                 400

Thr Phe Asp Gly Lys Thr Tyr Thr Phe His Gly Asp Cys Tyr Tyr Val
                405                 410                 415

Leu Ala Lys Gly Asp His Asn Asp Ser Tyr Ala Leu Leu Gly Glu Leu
            420                 425                 430

Ala Pro Cys Gly Ser Thr Asp Lys Gln Thr Cys Leu Lys Thr Val Val
        435                 440                 445

Leu Leu Ala Asp Lys Lys Lys Asn Val Val Val Phe Lys Ser Asp Gly
    450                 455                 460

Ser Val Leu Leu Asn Glu Leu Gln Val Asn Leu Pro His Val Thr Ala
465                 470                 475                 480

Ser Phe Ser Val Phe Arg Pro Ser Ser Tyr His Ile Met Val Ser Met
                485                 490                 495

Ala Ile Gly Val Arg Leu Gln Val Gln Leu Ala Pro Val Met Gln Leu
            500                 505                 510

Phe Val Thr Leu Asp Gln Ala Ser Gln Gly Gln Val Gln Gly Leu Cys
        515                 520                 525

Gly Asn Phe Asn Gly Leu Glu Gly Asp Asp Phe Lys Thr Ala Ser Gly
    530                 535                 540

Leu Val Glu Ala Thr Gly Ala Gly Phe Ala Asn Thr Trp Lys Ala Gln
545                 550                 555                 560
```

```
Ser Thr Cys His Asp Lys Leu Asp Trp Leu Asp Asp Pro Cys Ser Leu
                565                 570                 575

Asn Ile Glu Ser Ala Asn Tyr Ala Glu His Trp Cys Ser Leu Leu Lys
            580                 585                 590

Lys Thr Glu Thr Pro Phe Gly Arg Cys His Ser Ala Val Asp Pro Ala
        595                 600                 605

Glu Tyr Tyr Lys Arg Cys Lys Tyr Asp Thr Cys Asn Cys Gln Asn Asn
    610                 615                 620

Glu Asp Cys Leu Cys Ala Ala Leu Ser Ser Tyr Ala Arg Ala Cys Thr
625                 630                 635                 640

Ala Lys Gly Val Met Leu Trp Gly Trp Arg Glu His Val Cys Asn Lys
                645                 650                 655

Asp Val Gly Ser Cys Pro Asn Ser Gln Val Phe Leu Tyr Asn Leu Thr
            660                 665                 670

Thr Cys Gln Gln Thr Cys Arg Ser Leu Ser Glu Ala Asp Ser His Cys
        675                 680                 685

Leu Glu Gly Phe Ala Pro Val Asp Gly Cys Gly Cys Pro Asp His Thr
    690                 695                 700

Phe Leu Asp Glu Lys Gly Arg Cys Val Pro Leu Ala Lys Cys Ser Cys
705                 710                 715                 720

Tyr His Arg Gly Leu Tyr Leu Glu Ala Gly Asp Val Val Val Arg Gln
                725                 730                 735

Glu Glu Arg Cys Val Cys Arg Asp Gly Arg Leu His Cys Arg Gln Ile
            740                 745                 750

Arg Leu Ile Gly Gln Ser Cys Thr Ala Pro Lys Ile His Met Asp Cys
        755                 760                 765

Ser Asn Leu Thr Ala Leu Ala Thr Ser Lys Pro Arg Ala Leu Ser Cys
    770                 775                 780

Gln Thr Leu Ala Ala Gly Tyr Tyr His Thr Glu Cys Val Ser Gly Cys
785                 790                 795                 800

Val Cys Pro Asp Gly Leu Met Asp Asp Gly Arg Gly Gly Cys Val Val
                805                 810                 815

Glu Lys Glu Cys Pro Cys Val His Asn Asn Asp Leu Tyr Ser Ser Gly
            820                 825                 830

Ala Lys Ile Lys Val Asp Cys Asn Thr Cys Thr Cys Lys Arg Gly Arg
        835                 840                 845

Trp Val Cys Thr Gln Ala Val Cys His Gly Thr Cys Ser Ile Tyr Gly
    850                 855                 860

Ser Gly His Tyr Ile Thr Phe Asp Gly Lys Tyr Tyr Asp Phe Asp Gly
865                 870                 875                 880

His Cys Ser Tyr Val Ala Val Gln Asp Tyr Cys Gly Gln Asn Ser Ser
                885                 890                 895

Leu Gly Ser Phe Ser Ile Ile Thr Glu Asn Val Pro Cys Gly Thr Thr
            900                 905                 910

Gly Val Thr Cys Ser Lys Ala Ile Lys Ile Phe Met Gly Arg Thr Glu
        915                 920                 925

Leu Lys Leu Glu Asp Lys His Arg Val Val Ile Gln Arg Asp Glu Gly
    930                 935                 940

His His Val Ala Tyr Thr Thr Arg Glu Val Gly Gln Tyr Leu Val Val
945                 950                 955                 960

Glu Ser Ser Thr Gly Ile Ile Val Ile Trp Asp Lys Arg Thr Thr Val
                965                 970                 975
```

```
Phe Ile Lys Leu Ala Pro Ser Tyr Lys Gly Thr Val Cys Gly Leu Cys
            980                 985                 990

Gly Asn Phe Asp His Arg Ser Asn  Asn Asp Phe Thr Thr  Arg Asp His
        995                 1000                 1005

Met Val  Val Ser Ser Glu Leu  Asp Phe Gly Asn Ser  Trp Lys Glu
    1010                 1015                 1020

Ala Pro  Thr Cys Pro Asp Val  Ser Thr Asn Pro Glu  Pro Cys Ser
    1025                 1030                 1035

Leu Asn  Pro His Arg Arg Ser  Trp Ala Glu Lys Gln  Cys Ser Ile
    1040                 1045                 1050

Leu Lys  Ser Ser Val Phe Ser  Ile Cys His Ser Lys  Val Asp Pro
    1055                 1060                 1065

Lys Pro  Phe Tyr Glu Ala Cys  Val His Asp Ser Cys  Ser Cys Asp
    1070                 1075                 1080

Thr Gly  Gly Asp Cys Glu Cys  Phe Cys Ser Ala Val  Ala Ser Tyr
    1085                 1090                 1095

Ala Gln  Glu Cys Thr Lys Glu  Gly Ala Cys Val Phe  Trp Arg Thr
    1100                 1105                 1110

Pro Asp  Leu Cys Pro Ile Phe  Cys Asp Tyr Tyr Asn  Pro Pro His
    1115                 1120                 1125

Glu Cys  Glu Trp His Tyr Glu  Pro Cys Gly Asn Arg  Ser Phe Glu
    1130                 1135                 1140

Thr Cys  Arg Thr Ile Asn Gly  Ile His Ser Asn Ile  Ser Val Ser
    1145                 1150                 1155

Tyr Leu  Glu Gly Cys Tyr Pro  Arg Cys Pro Lys Asp  Arg Pro Ile
    1160                 1165                 1170

Tyr Glu  Glu Asp Leu Lys Lys  Cys Val Thr Ala Asp  Lys Cys Gly
    1175                 1180                 1185

Cys Tyr  Val Glu Asp Thr His  Tyr Pro Pro Gly Ala  Ser Val Pro
    1190                 1195                 1200

Thr Glu  Glu Thr Cys Lys Ser  Cys Val Cys Thr Asn  Ser Ser Gln
    1205                 1210                 1215

Val Val  Cys Arg Pro Glu Glu  Gly Lys Ile Leu Asn  Gln Thr Gln
    1220                 1225                 1230

Asp Gly  Ala Phe Cys Tyr Trp  Glu Ile Cys Gly Pro  Asn Gly Thr
    1235                 1240                 1245

Val Glu  Lys His Phe Asn Ile  Cys Ser Ile Thr Thr  Arg Pro Ser
    1250                 1255                 1260

Thr Leu  Thr Thr Phe Thr Thr  Ile Thr Leu Pro Thr  Thr Pro Thr
    1265                 1270                 1275

Thr Phe  Thr Thr Thr Thr Thr  Thr Thr Thr Pro Thr  Ser Ser Thr
    1280                 1285                 1290

Val Leu  Ser Thr Thr Pro Lys  Leu Cys Cys Leu Trp  Ser Asp Trp
    1295                 1300                 1305

Ile Asn  Glu Asp His Pro Ser  Ser Gly Ser Asp Asp  Gly Asp Arg
    1310                 1315                 1320

Glu Thr  Phe Asp Gly Val Cys  Gly Ala Pro Glu Asp  Ile Glu Cys
    1325                 1330                 1335

Arg Ser  Val Lys Asp Pro His  Leu Ser Leu Glu Gln  Leu Gly Gln
    1340                 1345                 1350

Lys Val  Gln Cys Asp Val Ser  Val Gly Phe Ile Cys  Lys Asn Glu
    1355                 1360                 1365

Asp Gln  Phe Gly Asn Gly Pro  Phe Gly Leu Cys Tyr  Asp Tyr Lys
```

```
    1370                1375                1380

Ile Arg  Val Asn Cys Cys Trp  Pro Met Asp Lys Cys  Ile Thr Thr
    1385                1390                1395

Pro Ser  Pro Pro Thr Thr Thr  Pro Ser Pro Pro Pro  Thr Ser Thr
    1400                1405                1410

Thr Thr  Leu Pro Pro Thr Thr  Thr Pro Ser Pro Pro  Thr Thr Thr
    1415                1420                1425

Thr Thr  Thr Pro Pro Pro Thr  Thr Thr Pro Ser Pro  Pro Ile Thr
    1430                1435                1440

Thr Thr  Thr Thr Pro Pro Pro  Thr Thr Thr Pro Ser  Pro Pro Ile
    1445                1450                1455

Ser Thr  Thr Thr Thr Pro Pro  Pro Thr Thr Thr Pro  Ser Pro Pro
    1460                1465                1470

Thr Thr  Thr Pro Ser Pro Pro  Thr Thr Thr Pro Ser  Pro Pro Thr
    1475                1480                1485

Thr Thr  Thr Thr Thr Pro Pro  Pro Thr Thr Thr Pro  Ser Pro Pro
    1490                1495                1500

Thr Thr  Thr Pro Ile Thr Pro  Pro Ala Ser Thr Thr  Thr Leu Pro
    1505                1510                1515

Pro Thr  Thr Thr Pro Ser Pro  Pro Thr Thr Thr Thr  Thr Thr Pro
    1520                1525                1530

Pro Pro  Thr Thr Thr Pro Ser  Pro Pro Thr Thr Thr  Pro Ile Thr
    1535                1540                1545

Pro Pro  Thr Ser Thr Thr Thr  Leu Pro Pro Thr Thr  Thr Pro Ser
    1550                1555                1560

Pro Pro  Pro Thr Thr Thr Thr  Thr Pro Pro Pro Thr  Thr Thr Pro
    1565                1570                1575

Ser Pro  Pro Thr Thr Thr Thr  Pro Ser Pro Pro Thr  Ile Thr Thr
    1580                1585                1590

Thr Thr  Pro Pro Pro Thr Thr  Thr Pro Ser Pro Pro  Thr Thr Thr
    1595                1600                1605

Thr Thr  Thr Pro Pro Pro Thr  Thr Thr Pro Ser Pro  Pro Thr Thr
    1610                1615                1620

Thr Pro  Ile Thr Pro Pro Thr  Ser Thr Thr Thr Leu  Pro Pro Thr
    1625                1630                1635

Thr Thr  Pro Ser Pro Pro Pro  Thr Thr Thr Thr Thr  Pro Pro Pro
    1640                1645                1650

Thr Thr  Thr Pro Ser Pro Pro  Thr Thr Thr Thr Pro  Ser Pro Pro
    1655                1660                1665

Ile Thr  Thr Thr Thr Thr Pro  Pro Pro Thr Thr Thr  Pro Ser Ser
    1670                1675                1680

Pro Ile  Thr Thr Thr Pro Ser  Pro Pro Thr Thr Thr  Met Thr Thr
    1685                1690                1695

Pro Ser  Pro Thr Thr Thr Pro  Ser Ser Pro Ile Thr  Thr Thr Thr
    1700                1705                1710

Thr Pro  Ser Ser Thr Thr Thr  Pro Ser Pro Pro Pro  Thr Thr Met
    1715                1720                1725

Thr Thr  Pro Ser Pro Thr Thr  Thr Pro Ser Pro Pro  Thr Thr Thr
    1730                1735                1740

Met Thr  Thr Leu Pro Pro Thr  Thr Thr Ser Ser Pro  Leu Thr Thr
    1745                1750                1755

Thr Pro  Leu Pro Pro Ser Ile  Thr Pro Pro Thr Phe  Ser Pro Phe
    1760                1765                1770
```

```
Ser Thr  Thr Thr Pro Thr Thr  Pro Cys Val Pro Leu  Cys Asn Trp
    1775                 1780                 1785

Thr Gly  Trp Leu Asp Ser Gly  Lys Pro Asn Phe His  Lys Pro Gly
    1790                 1795                 1800

Gly Asp  Thr Glu Leu Ile Gly  Asp Val Cys Gly Pro  Gly Trp Ala
    1805                 1810                 1815

Ala Asn  Ile Ser Cys Arg Ala  Thr Met Tyr Pro Asp  Val Pro Ile
    1820                 1825                 1830

Gly Gln  Leu Gly Gln Thr Val  Val Cys Asp Val Ser  Val Gly Leu
    1835                 1840                 1845

Ile Cys  Lys Asn Glu Asp Gln  Lys Pro Gly Gly Val  Ile Pro Met
    1850                 1855                 1860

Ala Phe  Cys Leu Asn Tyr Glu  Ile Asn Val Gln Cys  Cys Glu Cys
    1865                 1870                 1875

Val Thr  Gln Pro Thr Thr Met  Thr Thr Thr Thr Thr  Glu Asn Pro
    1880                 1885                 1890

Thr Pro  Pro Thr Thr Thr Pro  Ile Thr Thr Thr Thr  Thr Val Thr
    1895                 1900                 1905

Pro Thr  Pro Thr Pro Thr Gly  Thr Gln Thr Pro Thr  Thr Thr Pro
    1910                 1915                 1920

Ile Thr  Thr Thr Thr Thr Val  Thr Pro Thr Pro Thr  Pro Thr Gly
    1925                 1930                 1935

Thr Gln  Thr Pro Thr Thr Thr  Pro Ile Thr Thr Thr  Thr Thr Val
    1940                 1945                 1950

Thr Pro  Thr Pro Thr Pro Thr  Gly Thr Gln Thr Pro  Thr Thr Thr
    1955                 1960                 1965

Pro Ile  Thr Thr Thr Thr Thr  Val Thr Pro Thr Pro  Thr Pro Thr
    1970                 1975                 1980

Gly Thr  Gln Thr Pro Thr Thr  Thr Pro Ile Thr Thr  Thr Thr Thr
    1985                 1990                 1995

Val Thr  Pro Thr Pro Thr Pro  Thr Gly Thr Gln Thr  Pro Thr Thr
    2000                 2005                 2010

Thr Pro  Ile Thr Thr Thr Thr  Thr Val Thr Pro Thr  Pro Thr Pro
    2015                 2020                 2025

Thr Gly  Thr Gln Thr Pro Thr  Thr Thr Pro Ile Thr  Thr Thr Thr
    2030                 2035                 2040

Thr Val  Thr Pro Thr Pro Thr  Pro Thr Gly Thr Gln  Thr Pro Thr
    2045                 2050                 2055

Thr Thr  Pro Ile Thr Thr Thr  Thr Thr Val Thr Pro  Thr Pro Thr
    2060                 2065                 2070

Pro Thr  Gly Thr Gln Thr Pro  Thr Thr Thr Pro Ile  Thr Thr Thr
    2075                 2080                 2085

Thr Thr  Val Thr Pro Thr Pro  Thr Pro Thr Gly Thr  Gln Thr Pro
    2090                 2095                 2100

Thr Thr  Thr Pro Ile Thr Thr  Thr Thr Thr Val Thr  Pro Thr Pro
    2105                 2110                 2115

Thr Pro  Thr Gly Thr Gln Thr  Pro Thr Thr Thr Pro  Ile Thr Thr
    2120                 2125                 2130

Thr Thr  Thr Val Thr Pro Thr  Pro Thr Pro Thr Gly  Thr Gln Thr
    2135                 2140                 2145

Pro Thr  Thr Thr Pro Ile Thr  Thr Thr Thr Thr Val  Thr Pro Thr
    2150                 2155                 2160
```

-continued

Pro Thr Pro Thr Gly Thr Gln Thr Pro Thr Thr Thr Pro Ile Thr
2165 2170 2175

Thr Thr Thr Thr Val Thr Pro Thr Pro Thr Pro Thr Gly Thr Gln
2180 2185 2190

Thr Pro Thr Thr Thr Pro Ile Thr Thr Thr Thr Thr Val Thr Pro
2195 2200 2205

Thr Pro Thr Pro Thr Gly Thr Gln Thr Pro Thr Thr Thr Pro Ile
2210 2215 2220

Thr Thr Thr Thr Thr Val Thr Pro Thr Pro Thr Pro Thr Gly Thr
2225 2230 2235

Gln Thr Pro Thr Thr Thr Pro Ile Thr Thr Thr Thr Thr Val Thr
2240 2245 2250

Pro Thr Pro Thr Pro Thr Gly Thr Gln Thr Pro Thr Thr Thr Pro
2255 2260 2265

Ile Thr Thr Thr Thr Thr Val Thr Pro Thr Pro Thr Pro Thr Gly
2270 2275 2280

Thr Gln Thr Pro Thr Thr Thr Pro Ile Thr Thr Thr Thr Thr Val
2285 2290 2295

Thr Pro Thr Pro Thr Pro Thr Gly Thr Gln Thr Pro Thr Thr Thr
2300 2305 2310

Pro Ile Thr Thr Thr Thr Thr Val Thr Pro Thr Pro Thr Pro Thr
2315 2320 2325

Gly Thr Gln Thr Pro Thr Thr Thr Pro Ile Thr Thr Thr Thr Thr
2330 2335 2340

Val Thr Pro Thr Pro Thr Pro Thr Gly Thr Gln Thr Pro Thr Thr
2345 2350 2355

Thr Pro Ile Thr Thr Thr Thr Thr Val Thr Pro Thr Pro Thr Pro
2360 2365 2370

Thr Gly Thr Gln Thr Pro Thr Thr Thr Pro Ile Thr Thr Thr Thr
2375 2380 2385

Thr Val Thr Pro Thr Pro Thr Pro Thr Gly Thr Gln Thr Pro Thr
2390 2395 2400

Thr Thr Pro Ile Thr Thr Thr Thr Thr Val Thr Pro Thr Pro Thr
2405 2410 2415

Pro Thr Gly Thr Gln Thr Pro Thr Thr Thr Pro Ile Thr Thr Thr
2420 2425 2430

Thr Thr Val Thr Pro Thr Pro Thr Pro Thr Gly Thr Gln Thr Pro
2435 2440 2445

Thr Thr Thr Pro Ile Thr Thr Thr Thr Thr Val Thr Pro Thr Pro
2450 2455 2460

Thr Pro Thr Gly Thr Gln Thr Pro Thr Thr Thr Pro Ile Thr Thr
2465 2470 2475

Thr Thr Thr Val Thr Pro Thr Pro Thr Pro Thr Gly Thr Gln Thr
2480 2485 2490

Pro Thr Thr Thr Pro Ile Thr Thr Thr Thr Thr Val Thr Pro Thr
2495 2500 2505

Pro Thr Pro Thr Gly Thr Gln Thr Pro Thr Thr Thr Pro Ile Thr
2510 2515 2520

Thr Thr Thr Thr Val Thr Pro Thr Pro Thr Pro Thr Gly Thr Gln
2525 2530 2535

Thr Pro Thr Thr Thr Pro Ile Thr Thr Thr Thr Thr Val Thr Pro
2540 2545 2550

Thr Pro Thr Pro Thr Gly Thr Gln Thr Pro Thr Thr Thr Pro Ile

-continued

```
    2555                2560                2565

Thr Thr  Thr Thr Thr Val Thr  Pro Thr Pro Thr Pro  Thr Gly Thr
    2570                2575                2580

Gln Thr  Pro Thr Thr Thr Pro  Ile Thr Thr Thr Thr  Thr Val Thr
    2585                2590                2595

Pro Thr  Pro Thr Pro Thr Gly  Thr Gln Thr Pro Thr  Thr Thr Pro
    2600                2605                2610

Ile Thr  Thr Thr Thr Thr Val  Thr Pro Thr Pro Thr  Pro Thr Gly
    2615                2620                2625

Thr Gln  Thr Pro Thr Thr Thr  Pro Ile Thr Thr Thr  Thr Thr Val
    2630                2635                2640

Thr Pro  Thr Pro Thr Pro Thr  Gly Thr Gln Thr Pro  Thr Thr Thr
    2645                2650                2655

Pro Ile  Thr Thr Thr Thr Thr  Val Thr Pro Thr Pro  Thr Pro Thr
    2660                2665                2670

Gly Thr  Gln Thr Pro Thr Thr  Thr Pro Ile Thr Thr  Thr Thr Thr
    2675                2680                2685

Val Thr  Pro Thr Pro Thr Pro  Thr Gly Thr Gln Thr  Pro Thr Thr
    2690                2695                2700

Thr Pro  Ile Thr Thr Thr Thr  Thr Val Thr Pro Thr  Pro Thr Pro
    2705                2710                2715

Thr Gly  Thr Gln Thr Pro Thr  Thr Thr Pro Ile Thr  Thr Thr Thr
    2720                2725                2730

Thr Val  Thr Pro Thr Pro Thr  Pro Thr Gly Thr Gln  Thr Pro Thr
    2735                2740                2745

Thr Thr  Pro Ile Thr Thr Thr  Thr Thr Val Thr Pro  Thr Pro Thr
    2750                2755                2760

Pro Thr  Gly Thr Gln Thr Pro  Thr Thr Thr Pro Ile  Thr Thr Thr
    2765                2770                2775

Thr Thr  Val Thr Pro Thr Pro  Thr Pro Thr Gly Thr  Gln Thr Pro
    2780                2785                2790

Thr Thr  Thr Pro Ile Thr Thr  Thr Thr Thr Val Thr  Pro Thr Pro
    2795                2800                2805

Thr Pro  Thr Gly Thr Gln Thr  Pro Thr Thr Thr Pro  Ile Thr Thr
    2810                2815                2820

Thr Thr  Thr Val Thr Pro Thr  Pro Thr Pro Thr Gly  Thr Gln Thr
    2825                2830                2835

Pro Thr  Thr Thr Pro Ile Thr  Thr Thr Thr Thr Val  Thr Pro Thr
    2840                2845                2850

Pro Thr  Pro Thr Gly Thr Gln  Thr Pro Thr Thr Thr  Pro Ile Thr
    2855                2860                2865

Thr Thr  Thr Thr Val Thr Pro  Thr Pro Thr Pro Thr  Gly Thr Gln
    2870                2875                2880

Thr Pro  Thr Thr Thr Pro Ile  Thr Thr Thr Thr Thr  Val Thr Pro
    2885                2890                2895

Thr Pro  Thr Pro Thr Gly Thr  Gln Thr Pro Thr Thr  Thr Pro Ile
    2900                2905                2910

Thr Thr  Thr Thr Thr Val Thr  Pro Thr Pro Thr Pro  Thr Gly Thr
    2915                2920                2925

Gln Thr  Pro Thr Thr Thr Pro  Ile Thr Thr Thr Thr  Thr Val Thr
    2930                2935                2940

Pro Thr  Pro Thr Pro Thr Gly  Thr Gln Thr Pro Thr  Thr Thr Pro
    2945                2950                2955
```

-continued

```
Ile Thr Thr Thr Thr Thr Val Thr Pro Thr Pro Thr Pro Thr Gly
    2960                2965                2970

Thr Gln Thr Pro Thr Thr Thr Pro Ile Thr Thr Thr Thr Thr Val
    2975                2980                2985

Thr Pro Thr Pro Thr Pro Thr Gly Thr Gln Thr Pro Thr Thr Thr
    2990                2995                3000

Pro Ile Thr Thr Thr Thr Thr Val Thr Pro Thr Pro Thr Pro Thr
    3005                3010                3015

Gly Thr Gln Thr Pro Thr Thr Thr Pro Ile Thr Thr Thr Thr Thr
    3020                3025                3030

Val Thr Pro Thr Pro Thr Pro Thr Gly Thr Gln Thr Pro Thr Thr
    3035                3040                3045

Thr Pro Ile Thr Thr Thr Thr Thr Val Thr Pro Thr Pro Thr Pro
    3050                3055                3060

Thr Gly Thr Gln Thr Pro Thr Thr Thr Pro Ile Thr Thr Thr Thr
    3065                3070                3075

Thr Val Thr Pro Thr Pro Thr Pro Thr Gly Thr Gln Thr Pro Thr
    3080                3085                3090

Thr Thr Pro Ile Thr Thr Thr Thr Thr Val Thr Pro Thr Pro Thr
    3095                3100                3105

Pro Thr Gly Thr Gln Thr Pro Thr Thr Thr Pro Ile Thr Thr Thr
    3110                3115                3120

Thr Thr Val Thr Pro Thr Pro Thr Pro Thr Gly Thr Gln Thr Pro
    3125                3130                3135

Thr Thr Thr Pro Ile Thr Thr Thr Thr Thr Val Thr Pro Thr Pro
    3140                3145                3150

Thr Pro Thr Gly Thr Gln Thr Pro Thr Thr Thr Pro Ile Thr Thr
    3155                3160                3165

Thr Thr Thr Val Thr Pro Thr Pro Thr Pro Thr Gly Thr Gln Thr
    3170                3175                3180

Pro Thr Thr Thr Pro Ile Thr Thr Thr Thr Thr Val Thr Pro Thr
    3185                3190                3195

Pro Thr Pro Thr Gly Thr Gln Thr Pro Thr Thr Thr Pro Ile Thr
    3200                3205                3210

Thr Thr Thr Thr Val Thr Pro Thr Pro Thr Pro Thr Gly Thr Gln
    3215                3220                3225

Thr Pro Thr Thr Thr Pro Ile Thr Thr Thr Thr Thr Val Thr Pro
    3230                3235                3240

Thr Pro Thr Pro Thr Gly Thr Gln Thr Pro Thr Thr Thr Pro Ile
    3245                3250                3255

Thr Thr Thr Thr Thr Val Thr Pro Thr Pro Thr Pro Thr Gly Thr
    3260                3265                3270

Gln Thr Pro Thr Thr Thr Pro Ile Thr Thr Thr Thr Thr Val Thr
    3275                3280                3285

Pro Thr Pro Thr Pro Thr Gly Thr Gln Thr Pro Thr Thr Thr Pro
    3290                3295                3300

Ile Thr Thr Thr Thr Thr Val Thr Pro Thr Pro Thr Pro Thr Gly
    3305                3310                3315

Thr Gln Thr Pro Thr Thr Thr Pro Ile Thr Thr Thr Thr Thr Val
    3320                3325                3330

Thr Pro Thr Pro Thr Pro Thr Gly Thr Gln Thr Pro Thr Thr Thr
    3335                3340                3345
```

```
Pro Ile Thr Thr Thr Thr Thr Val Thr Pro Thr Pro Thr Pro Thr
    3350                3355                3360

Gly Thr Gln Thr Pro Thr Thr Thr Pro Ile Thr Thr Thr Thr Thr
    3365                3370                3375

Val Thr Pro Thr Pro Thr Pro Thr Gly Thr Gln Thr Pro Thr Thr
    3380                3385                3390

Thr Pro Ile Thr Thr Thr Thr Thr Val Thr Pro Thr Pro Thr Pro
    3395                3400                3405

Thr Gly Thr Gln Thr Pro Thr Thr Thr Pro Ile Thr Thr Thr Thr
    3410                3415                3420

Thr Val Thr Pro Thr Pro Thr Pro Thr Gly Thr Gln Thr Pro Thr
    3425                3430                3435

Thr Thr Pro Ile Thr Thr Thr Thr Thr Val Thr Pro Thr Pro Thr
    3440                3445                3450

Pro Thr Gly Thr Gln Thr Pro Thr Thr Thr Pro Ile Thr Thr Thr
    3455                3460                3465

Thr Thr Val Thr Pro Thr Pro Thr Pro Thr Gly Thr Gln Thr Pro
    3470                3475                3480

Thr Thr Thr Pro Ile Thr Thr Thr Thr Thr Val Thr Pro Thr Pro
    3485                3490                3495

Thr Pro Thr Gly Thr Gln Thr Pro Thr Thr Thr Pro Ile Thr Thr
    3500                3505                3510

Thr Thr Thr Val Thr Pro Thr Pro Thr Pro Thr Gly Thr Gln Thr
    3515                3520                3525

Pro Thr Thr Thr Pro Ile Thr Thr Thr Thr Thr Val Thr Pro Thr
    3530                3535                3540

Pro Thr Pro Thr Gly Thr Gln Thr Pro Thr Thr Thr Pro Ile Thr
    3545                3550                3555

Thr Thr Thr Thr Val Thr Pro Thr Pro Thr Pro Thr Gly Thr Gln
    3560                3565                3570

Thr Pro Thr Thr Thr Pro Ile Thr Thr Thr Thr Thr Val Thr Pro
    3575                3580                3585

Thr Pro Thr Pro Thr Gly Thr Gln Thr Pro Thr Thr Thr Pro Ile
    3590                3595                3600

Thr Thr Thr Thr Thr Val Thr Pro Thr Pro Thr Pro Thr Gly Thr
    3605                3610                3615

Gln Thr Pro Thr Thr Thr Pro Ile Thr Thr Thr Thr Thr Val Thr
    3620                3625                3630

Pro Thr Pro Thr Pro Thr Gly Thr Gln Thr Pro Thr Thr Thr Pro
    3635                3640                3645

Ile Thr Thr Thr Thr Thr Val Thr Pro Thr Pro Thr Pro Thr Gly
    3650                3655                3660

Thr Gln Thr Pro Thr Thr Thr Pro Ile Thr Thr Thr Thr Thr Val
    3665                3670                3675

Thr Pro Thr Pro Thr Pro Thr Gly Thr Gln Thr Pro Thr Thr Thr
    3680                3685                3690

Pro Ile Thr Thr Thr Thr Thr Val Thr Pro Thr Pro Thr Pro Thr
    3695                3700                3705

Gly Thr Gln Thr Pro Thr Thr Thr Pro Ile Thr Thr Thr Thr Thr
    3710                3715                3720

Val Thr Pro Thr Pro Thr Pro Thr Gly Thr Gln Thr Pro Thr Thr
    3725                3730                3735

Thr Pro Ile Thr Thr Thr Thr Thr Val Thr Pro Thr Pro Thr Pro
```

```
    3740                3745                3750

Thr Gly  Thr Gln Thr Pro Thr  Thr Thr Pro Ile Thr  Thr Thr Thr
    3755                3760                3765

Thr Val  Thr Pro Thr Pro Thr  Pro Thr Gly Thr Gln  Thr Pro Thr
    3770                3775                3780

Thr Thr  Pro Ile Thr Thr Thr  Thr Thr Val Thr Pro  Thr Pro Thr
    3785                3790                3795

Pro Thr  Gly Thr Gln Thr Pro  Thr Thr Thr Pro Ile  Thr Thr Thr
    3800                3805                3810

Thr Thr  Val Thr Pro Thr Pro  Thr Pro Thr Gly Thr  Gln Thr Pro
    3815                3820                3825

Thr Thr  Thr Pro Ile Thr Thr  Thr Thr Thr Val Thr  Pro Thr Pro
    3830                3835                3840

Thr Pro  Thr Gly Thr Gln Thr  Pro Thr Thr Thr Pro  Ile Thr Thr
    3845                3850                3855

Thr Thr  Thr Val Thr Pro Thr  Pro Thr Pro Thr Gly  Thr Gln Thr
    3860                3865                3870

Pro Thr  Thr Thr Pro Ile Thr  Thr Thr Thr Thr Val  Thr Pro Thr
    3875                3880                3885

Pro Thr  Pro Thr Gly Thr Gln  Thr Pro Thr Thr Thr  Pro Ile Thr
    3890                3895                3900

Thr Thr  Thr Thr Val Thr Pro  Thr Pro Thr Pro Thr  Gly Thr Gln
    3905                3910                3915

Thr Pro  Thr Thr Thr Pro Ile  Thr Thr Thr Thr Thr  Val Thr Pro
    3920                3925                3930

Thr Pro  Thr Pro Thr Gly Thr  Gln Thr Pro Thr Thr  Thr Pro Ile
    3935                3940                3945

Thr Thr  Thr Thr Thr Val Thr  Pro Thr Pro Thr Pro  Thr Gly Thr
    3950                3955                3960

Gln Thr  Pro Thr Thr Thr Pro  Ile Thr Thr Thr Thr  Thr Val Thr
    3965                3970                3975

Pro Thr  Pro Thr Pro Thr Gly  Thr Gln Thr Pro Thr  Thr Thr Pro
    3980                3985                3990

Ile Thr  Thr Thr Thr Thr Val  Thr Pro Thr Pro Thr  Pro Thr Gly
    3995                4000                4005

Thr Gln  Thr Pro Thr Thr Thr  Pro Ile Thr Thr Thr  Thr Thr Val
    4010                4015                4020

Thr Pro  Thr Pro Thr Pro Thr  Gly Thr Gln Thr Pro  Thr Thr Thr
    4025                4030                4035

Pro Ile  Thr Thr Thr Thr Thr  Val Thr Pro Thr Pro  Thr Pro Thr
    4040                4045                4050

Gly Thr  Gln Thr Pro Thr Thr  Thr Pro Ile Thr Thr  Thr Thr Thr
    4055                4060                4065

Val Thr  Pro Thr Pro Thr Pro  Thr Gly Thr Gln Thr  Pro Thr Thr
    4070                4075                4080

Thr Pro  Ile Thr Thr Thr Thr  Thr Val Thr Pro Thr  Pro Thr Pro
    4085                4090                4095

Thr Gly  Thr Gln Thr Pro Thr  Thr Thr Pro Ile Thr  Thr Thr Thr
    4100                4105                4110

Thr Val  Thr Pro Thr Pro Thr  Pro Thr Gly Thr Gln  Thr Pro Thr
    4115                4120                4125

Thr Thr  Pro Ile Thr Thr Thr  Thr Thr Val Thr Pro  Thr Pro Thr
    4130                4135                4140
```

```
Pro Thr  Gly Thr Gln Thr Pro  Thr Thr Thr Pro Ile  Thr Thr Thr
    4145                 4150                 4155

Thr Thr  Val Thr Pro Thr Pro  Thr Pro Thr Gly Thr  Gln Thr Pro
    4160                 4165                 4170

Thr Thr  Thr Pro Ile Thr Thr  Thr Thr Thr Val Thr  Pro Thr Pro
    4175                 4180                 4185

Thr Pro  Thr Gly Thr Gln Thr  Gly Pro Pro Thr His  Thr Ser Thr
    4190                 4195                 4200

Ala Pro  Ile Ala Glu Leu Thr  Thr Ser Asn Pro Pro  Pro Glu Ser
    4205                 4210                 4215

Ser Thr  Pro Gln Thr Ser Arg  Ser Thr Ser Ser Pro  Leu Thr Glu
    4220                 4225                 4230

Ser Thr  Thr Leu Leu Ser Thr  Leu Pro Pro Ala Ile  Glu Met Thr
    4235                 4240                 4245

Ser Thr  Ala Pro Pro Ser Thr  Pro Thr Ala Pro Thr  Thr Thr Ser
    4250                 4255                 4260

Gly Gly  His Thr Leu Ser Pro  Pro Pro Ser Thr Thr  Thr Ser Pro
    4265                 4270                 4275

Pro Gly  Thr Pro Thr Arg Gly  Thr Thr Thr Gly Ser  Ser Ser Ala
    4280                 4285                 4290

Pro Thr  Pro Ser Thr Val Gln  Thr Thr Thr Thr Ser  Ala Trp Thr
    4295                 4300                 4305

Pro Thr  Pro Thr Pro Leu Ser  Thr Pro Ser Ile Ile  Arg Thr Thr
    4310                 4315                 4320

Gly Leu  Arg Pro Tyr Pro Ser  Ser Val Leu Ile Cys  Cys Val Leu
    4325                 4330                 4335

Asn Asp  Thr Tyr Tyr Ala Pro  Gly Glu Glu Val Tyr  Asn Gly Thr
    4340                 4345                 4350

Tyr Gly  Asp Thr Cys Tyr Phe  Val Asn Cys Ser Leu  Ser Cys Thr
    4355                 4360                 4365

Leu Glu  Phe Tyr Asn Trp Ser  Cys Pro Ser Thr Pro  Ser Pro Thr
    4370                 4375                 4380

Pro Thr  Pro Ser Lys Ser Thr  Pro Thr Pro Ser Lys  Pro Ser Ser
    4385                 4390                 4395

Thr Pro  Ser Lys Pro Thr Pro  Gly Thr Lys Pro Pro  Glu Cys Pro
    4400                 4405                 4410

Asp Phe  Asp Pro Pro Arg Gln  Glu Asn Glu Thr Trp  Trp Leu Cys
    4415                 4420                 4425

Asp Cys  Phe Met Ala Thr Cys  Lys Tyr Asn Asn Thr  Val Glu Ile
    4430                 4435                 4440

Val Lys  Val Glu Cys Glu Pro  Pro Pro Met Pro Thr  Cys Ser Asn
    4445                 4450                 4455

Gly Leu  Gln Pro Val Arg Val  Glu Asp Pro Asp Gly  Cys Cys Trp
    4460                 4465                 4470

His Trp  Glu Cys Asp Cys Tyr  Cys Thr Gly Trp Gly  Asp Pro His
    4475                 4480                 4485

Tyr Val  Thr Phe Asp Gly Leu  Tyr Tyr Ser Tyr Gln  Gly Asn Cys
    4490                 4495                 4500

Thr Tyr  Val Leu Val Glu Glu  Ile Ser Pro Ser Val  Asp Asn Phe
    4505                 4510                 4515

Gly Val  Tyr Ile Asp Asn Tyr  His Cys Asp Pro Asn  Asp Lys Val
    4520                 4525                 4530
```

-continued

Ser Cys Pro Arg Thr Leu Ile Val Arg His Glu Thr Gln Glu Val
4535 4540 4545

Leu Ile Lys Thr Val His Met Met Pro Met Gln Val Gln Val Gln
4550 4555 4560

Val Asn Arg Gln Ala Val Ala Leu Pro Tyr Lys Lys Tyr Gly Leu
4565 4570 4575

Glu Val Tyr Gln Ser Gly Ile Asn Tyr Val Val Asp Ile Pro Glu
4580 4585 4590

Leu Gly Val Leu Val Ser Tyr Asn Gly Leu Ser Phe Ser Val Arg
4595 4600 4605

Leu Pro Tyr His Arg Phe Gly Asn Asn Thr Lys Gly Gln Cys Gly
4610 4615 4620

Thr Cys Thr Asn Thr Thr Ser Asp Asp Cys Ile Leu Pro Ser Gly
4625 4630 4635

Glu Ile Val Ser Asn Cys Glu Ala Ala Ala Asp Gln Trp Leu Val
4640 4645 4650

Asn Asp Pro Ser Lys Pro His Cys Pro His Ser Ser Ser Thr Thr
4655 4660 4665

Lys Arg Pro Ala Val Thr Val Pro Gly Gly Gly Lys Thr Thr Pro
4670 4675 4680

His Lys Asp Cys Thr Pro Ser Pro Leu Cys Gln Leu Ile Lys Asp
4685 4690 4695

Ser Leu Phe Ala Gln Cys His Ala Leu Val Pro Pro Gln His Tyr
4700 4705 4710

Tyr Asp Ala Cys Val Phe Asp Ser Cys Phe Met Pro Gly Ser Ser
4715 4720 4725

Leu Glu Cys Ala Ser Leu Gln Ala Tyr Ala Ala Leu Cys Ala Gln
4730 4735 4740

Gln Asn Ile Cys Leu Asp Trp Arg Asn His Thr His Gly Ala Cys
4745 4750 4755

Leu Val Glu Cys Pro Ser His Arg Glu Tyr Gln Ala Cys Gly Pro
4760 4765 4770

Ala Glu Glu Pro Thr Cys Lys Ser Ser Ser Ser Gln Gln Asn Asn
4775 4780 4785

Thr Val Leu Val Glu Gly Cys Phe Cys Pro Glu Gly Thr Met Asn
4790 4795 4800

Tyr Ala Pro Gly Phe Asp Val Cys Val Lys Thr Cys Gly Cys Val
4805 4810 4815

Gly Pro Asp Asn Val Pro Arg Glu Phe Gly Glu His Phe Glu Phe
4820 4825 4830

Asp Cys Lys Asn Cys Val Cys Leu Glu Gly Gly Ser Gly Ile Ile
4835 4840 4845

Cys Gln Pro Lys Arg Cys Ser Gln Lys Pro Val Thr His Cys Val
4850 4855 4860

Glu Asp Gly Thr Tyr Leu Ala Thr Glu Val Asn Pro Ala Asp Thr
4865 4870 4875

Cys Cys Asn Ile Thr Val Cys Lys Cys Asn Thr Ser Leu Cys Lys
4880 4885 4890

Glu Lys Pro Ser Val Cys Pro Leu Gly Phe Glu Val Lys Ser Lys
4895 4900 4905

Met Val Pro Gly Arg Cys Cys Pro Phe Tyr Trp Cys Glu Ser Lys
4910 4915 4920

Gly Val Cys Val His Gly Asn Ala Glu Tyr Gln Pro Gly Ser Pro

-continued

```
    4925                 4930                 4935

Val Tyr  Ser Ser Lys Cys Gln  Asp Cys Val Cys Thr  Asp Lys Val
    4940                 4945                 4950

Asp Asn  Asn Thr Leu Leu Asn  Val Ile Ala Cys Thr  His Val Pro
    4955                 4960                 4965

Cys Asn  Thr Ser Cys Ser Pro  Gly Phe Glu Leu Met  Glu Ala Pro
    4970                 4975                 4980

Gly Glu  Cys Cys Lys Lys Cys  Glu Gln Thr His Cys  Ile Ile Lys
    4985                 4990                 4995

Arg Pro  Asp Asn Gln His Val  Ile Leu Lys Pro Gly  Asp Phe Lys
    5000                 5005                 5010

Ser Asp  Pro Lys Asn Asn Cys  Thr Phe Phe Ser Cys  Val Lys Ile
    5015                 5020                 5025

His Asn  Gln Leu Ile Ser Ser  Val Ser Asn Ile Thr  Cys Pro Asn
    5030                 5035                 5040

Phe Asp  Ala Ser Ile Cys Ile  Pro Gly Ser Ile Thr  Phe Met Pro
    5045                 5050                 5055

Asn Gly  Cys Cys Lys Thr Cys  Thr Pro Arg Asn Glu  Thr Arg Val
    5060                 5065                 5070

Pro Cys  Ser Thr Val Pro Val  Thr Thr Glu Val Ser  Tyr Ala Gly
    5075                 5080                 5085

Cys Thr  Lys Thr Val Leu Met  Asn His Cys Ser Gly  Ser Cys Gly
    5090                 5095                 5100

Thr Phe  Val Met Tyr Ser Ala  Lys Ala Gln Ala Leu  Asp His Ser
    5105                 5110                 5115

Cys Ser  Cys Cys Lys Glu Glu  Lys Thr Ser Gln Arg  Glu Val Val
    5120                 5125                 5130

Leu Ser  Cys Pro Asn Gly Gly  Ser Leu Thr His Thr  Tyr Thr His
    5135                 5140                 5145

Ile Glu  Ser Cys Gln Cys Gln  Asp Thr Val Cys Gly  Leu Pro Thr
    5150                 5155                 5160

Gly Thr  Ser Arg Arg Ala Arg  Arg Ser Pro Arg His  Leu Gly Ser
    5165                 5170                 5175

Gly
```

<210> SEQ ID NO 30
<211> LENGTH: 15720
<212> TYPE: DNA
<213> ORGANISM: Homo sapiens

<400> SEQUENCE: 30

```
caacccacac cgcccctgcc agccaccatg gggctgccac tagcccgcct ggcggctgtg      60

tgcctggccc tgtctttggc agggggctcg gagctccaga cagagggcag aacccgaaac     120

cacggccaca acgtctgcag cacctggggc aacttccact acaagacctt cgacggggac     180

gtcttccgct tccccggccc ctgcgactac aacttcgcct ccgactgccg aggctcctac     240

aaggaatttg ctgtgcacct gaagcggggt ccgggccagg ctgaggcccc cgccggggtg     300

gagtccatcc tgctgaccat caaggatgac accatctacc tcacccgcca cctggctgtg     360

cttaacgggg ccgtggtcag caccccgcac tacagccccg ggctgctcat tgagaagagc     420

gatgcctaca ccaaagtcta ctcccgcgcc ggcctcaccc tcatgtggaa ccgggaggat     480

gcactcatgc tggagctgga cactaagttc cggaaccaca cctgtggcct ctgcggggac     540

tacaacggcc tgcagagcta ttcagaattc ctctctgacg gcgtgctctt cagtcccctg     600
```

```
gagtttggga acatgcagaa gatcaaccag cccgatgtgg tgtgtgagga tcccgaggag    660
gaggtggccc ccgcatcctg ctccgagcac cgcgccgagt gtgagaggct gctgaccgcc    720
gaggccttcg cggactgtca ggacctggtg ccgctggagc cgtatctgcg cgcctgccag    780
caggaccgct gccggtgccc gggcggtgac acctgcgtct gcagcaccgt ggccgagttc    840
tcccgccagt gctcccacgc cggcggccgg cccgggaact ggaggaccgc cacgctctgc    900
cccaagacct gccccgggaa cctggtgtac ctggagagcg gctcgccctg catggacacc    960
tgctcacacc tggaggtgag cagcctgtgc gaggagcacc gcatggacgg ctgtttctgc   1020
ccagaaggca ccgtatatga cgacatcggg gacagtggct gcgttcctgt gagccagtgc   1080
cactgcaggc tgcacggaca cctgtacaca ccgggccagg agatcaccaa tgactgcgag   1140
cagtgtgtct gtaacgctgg ccgctgggtg tgcaaagacc tgccctgccc cggcacctgt   1200
gccctggaag gcggctccca catcaccacc ttcgatggga agacgtacac cttccacggg   1260
gactgctact atgtcctggc caagggtgac cacaacgatt cctacgctct cctgggcgag   1320
ctggcccccct gtggctccac agacaagcag acctgcctga agacggtggt gctgctggct   1380
gacaagaaga agaatgtggt ggtcttcaag tccgatggca gtgtactgct caacgagctg   1440
caggtgaacc tgccccacgt gaccgcgagc ttctctgtct tccgcccgtc ttcctaccac   1500
atcatggtga gcatggccat tggcgtccgg ctgcaggtgc agctggcccc agtcatgcaa   1560
ctctttgtga cactggacca ggcctcccag gggcaggtgc agggcctctg cgggaacttc   1620
aacggcctgg aaggtgacga cttcaagacg gccagcgggc tggtggaggc cacgggggcc   1680
ggctttgcca acacctggaa ggcacagtca acctgccatg acaagctgga ctggttggac   1740
gatccctgct ccctgaacat cgagagcgcc aactacgccg agcactggtg ctccctcctg   1800
aagaagacag agaccccctt tggcaggtgc cactcggctg tggaccctgc tgagtattac   1860
aagaggtgca aatatgacac gtgtaactgt cagaacaatg aggactgcct gtgcgccgcc   1920
ctgtcctcct acgcgcgcgc ctgcaccgcc aagggcgtca tgctgtgggg ctggcgggag   1980
catgtctgca acaaggatgt gggctcctgc cccaactcgc aggtcttcct gtacaacctg   2040
accacctgcc agcagacctg ccgctccctc tccgaggccg acagccactg tctcgagggc   2100
tttgcgcctg tggacggctg cggctgccct gaccacacct tcctggacga gaagggccgc   2160
tgcgtacccc tggccaagtg ctcctgttac caccgcggtc tctacctgga ggcgggggac   2220
gtggtcgtca ggcaggaaga acgatgtgtg tgccgggatg ggcggctgca ctgtaggcag   2280
atccggctga tcggccagag ctgcacggcc ccaaagatcc acatggactg cagcaacctg   2340
actgcactgg ccacctcgaa gccccgagcc ctcagctgcc agacgctggc cgccggctat   2400
taccacacag agtgtgtcag tggctgtgtg tgccccgacg ggctgatgga tgacggccgg   2460
ggtggctgcg tggtggagaa ggaatgccct tgcgtccata acaacgacct gtattcttcc   2520
ggcgccaaga tcaaggtgga ctgcaatacc tgcacctgca agagaggacg ctgggtgtgc   2580
acccaggctg tgtgccatgg cacctgctcc atttacggga gtggccacta catcaccttt   2640
gacgggaagt actacgactt tgacggacac tgctcctacg tggctgttca ggactactgc   2700
ggccagaact cctcactggg ctcattcagc atcatcaccg agaacgtccc ctgtggcact   2760
acgggcgtca cctgctccaa ggccatcaag atcttcatgg ggaggacgga gctgaagttg   2820
gaagacaagc accgtgtggt gatccagcgt gatgagggtc accacgtggc ctacaccacg   2880
cgggaggtgg gccagtacct ggtggtggag tccagcacgg gcatcatcgt catctgggac   2940
```

-continued

```
aagaggacca ccgtgttcat caagctggct ccctcctaca agggcaccgt gtgtggcctg   3000

tgtgggaact ttgaccaccg ctccaacaac gacttcacca cgcgggacca catggtggtg   3060

agcagcgagc tggacttcgg gaacagctgg aaggaggccc ccacctgccc agatgtgagc   3120

accaaccccg agccctgcag cctgaacccg caccgccgct cctgggccga gaagcagtgc   3180

agcatcctca aaagcagcgt gttcagcatc tgccacagca aggtggaccc caagcccttc   3240

tacgaggcct gtgtgcacga ctcgtgctcc tgtgacacgg gtggggactg tgagtgcttc   3300

tgctctgccg tggcctccta cgcccaggag tgtaccaaag agggggcctg cgtgttctgg   3360

aggacgccgg acctgtgccc catattctgc gactactaca accctccgca tgagtgtgag   3420

tggcactatg agccatgtgg gaaccggagc ttcgagacct gcaggaccat caatggcatc   3480

cactccaaca tctccgtgtc ctacctggag ggctgctacc cccggtgccc caaggacagg   3540

cccatctatg aggaggatct gaagaagtgt gtcactgcag acaagtgtgg ctgctatgtc   3600

gaggacaccc actacccacc tggagcatcg gttcccaccg aggagacctg caagtcctgc   3660

gtgtgtacca actcctccca agtcgtctgc aggccggagg aaggaaagat tcttaaccag   3720

acccaggatg gcgccttctg ctactgggag atctgtggcc ccaacgggac ggtggagaag   3780

cacttcaaca tctgttccat tacgacacgc ccgtccaccc tgaccacctt caccaccatc   3840

accctcccca ccaccccac caccttcacc actaccacca ccaccaccac cccgacctcc   3900

agcacagttt tatcaacaac tccgaagctg tgctgcctct ggtctgactg gatcaatgag   3960

gaccacccca gcagtggcag cgacgacggt gaccgagaaa catttgatgg ggtctgcggg   4020

gcccctgagg acatcgagtg caggtcggtc aaggatcccc acctcagctt ggagcagcta   4080

ggccagaagg tgcagtgtga tgtctctgtt gggttcattt gcaagaatga agaccagttt   4140

ggaaatggac catttggact gtgttacgac tacaagatac gtgtcaattg ttgctggccc   4200

atggataagt gtatcaccac tcccagccct ccaactacca ctcccagccc tccaccaacc   4260

agcacgacca ccccttccacc aaccaccacc cccagccctc caaccaccac cacaaccacc   4320

cctccaccaa ccaccacccc cagccctcca ataaccacca cgaccacccc tccaccaacc   4380

accactccca gccctccaat aagcaccaca accacccctc caccaaccac cactcccagc   4440

cctccaacca ccactcccag ccctccaacc accactccca gccctccaac aaccaccaca   4500

accacccctc caccaaccac cactcccagc cctccaacga ctacgcccat cactccacca   4560

gccagcacta ccacccttcc accaaccacc actcccagcc ctccaacaac caccacaacc   4620

acccctccac caaccaccac tcccagtcct ccaacgacta cgcccatcac tccaccaacc   4680

agcactacta cccttccacc aaccaccact cccagccctc caccaaccac cacaaccacc   4740

cctccaccaa ccaccactcc cagccctcca acaaccacca ctcccagtcc tccaacaatc   4800

accacaacca cccctccacc aaccaccact cccagccctc caacaacgac cacaaccacc   4860

cctccaccaa ccaccactcc cagccctcca acgactacac ccatcactcc accaaccagc   4920

actaccaccc ttccaccaac caccactccc agccctccac caaccaccac aaccacccct   4980

ccaccaacca ccactcccag ccctccaaca accaccactc ccagccctcc aataaccacc   5040

acaaccaccc ctccaccaac caccactccc agctctccaa taaccaccac tcccagccct   5100

ccaacaacca ccatgaccac cccttcacca accaccaccc ccagctctcc aataaccacc   5160

acaaccaccc cttcctcaac taccactccc agccctccac caaccaccat gaccacccct   5220

tcaccaacca ccactcccag ccctccaaca accaccatga ccacccttcc accaaccacc   5280

acttccagcc ctctaacaac tactcctcta cctccatcaa taactcctcc tacattttca   5340
```

ccattctcaa cgacaacccc tactacccca tgcgtgcctc tctgcaattg gactggctgg 5400
ctggattctg gaaaacccaa ctttcacaaa ccaggtggag acacagaatt gattggagac 5460
gtctgtggac caggctgggc agctaacatc tcttgcagag ccaccatgta tcctgatgtt 5520
cccattggac agcttggaca aacagtggtg tgtgatgtct ctgtggggct gatatgcaaa 5580
aatgaagacc aaaagccagg tggggtcatc cctatggcct tctgcctcaa ctacgagatc 5640
aacgttcagt gctgtgagtg tgtcacccaa cccaccacca tgacaaccac caccacagag 5700
aacccaactc cgccaaccac gacacccatc accaccacca ctacggtgac cccaacccca 5760
acacccaccg gcacacagac cccaaccacg acacccatca ccaccaccac tacggtgacc 5820
ccaaccccaa cacccaccgg cacacagacc ccaaccacga cacccatcac caccaccact 5880
acggtgaccc caaccccaac acccaccggc acacagaccc caaccacgac acccatcacc 5940
accaccacta cggtgacccc aaccccaaca cccaccggca cacagacccc aaccacgaca 6000
cccatcacca ccaccactac ggtgacccca accccaacac ccaccggcac acagacccca 6060
accacgacac ccatcaccac caccactacg gtgaccccaa ccccaacacc caccggcaca 6120
cagaccccaa ccacgacacc catcaccacc accactacgg tgaccccaac cccaacaccc 6180
accggcacac agaccccaac cacgacaccc atcaccacca ccactacggt gaccccaacc 6240
ccaacaccca ccggcacaca gaccccaacc acgacaccca tcaccaccac cactacggtg 6300
accccaaccc caacacccac cggcacacag accccaacca cgacacccat caccaccacc 6360
actacggtga ccccaacccc aacacccacc ggcacacaga ccccaaccac gacacccatc 6420
accaccacca ctacggtgac cccaacccca acacccaccg gcacacagac cccaaccacg 6480
acacccatca ccaccaccac tacggtgacc ccaaccccaa cacccaccgg cacacagacc 6540
ccaaccacga cacccatcac caccaccact acggtgaccc caaccccaac acccaccggc 6600
acacagaccc caaccacgac acccatcacc accaccacta cggtgacccc aaccccaaca 6660
cccaccggca cacagacccc aaccacgaca cccatcacca ccaccactac ggtgacccca 6720
accccaacac ccaccggcac acagacccca accacgacac ccatcaccac caccactacg 6780
gtgaccccaa ccccaacacc caccggcaca cagaccccaa ccacgacacc catcaccacc 6840
accactacgg tgaccccaac cccaacaccc accggcacac agaccccaac cacgacaccc 6900
atcaccacca ccactacggt gaccccaacc ccaacaccca ccggcacaca gaccccaacc 6960
acgacaccca tcaccaccac cactacggtg accccaaccc caacacccac cggcacacag 7020
accccaacca cgacacccat caccaccacc actacggtga ccccaacccc aacacccacc 7080
ggcacacaga ccccaaccac gacacccatc accaccacca ctacggtgac cccaacccca 7140
acacccaccg gcacacagac cccaaccacg acacccatca ccaccaccac tacggtgacc 7200
ccaaccccaa cacccaccgg cacacagacc ccaaccacga cacccatcac caccaccact 7260
acggtgaccc caaccccaac acccaccggc acacagaccc caaccacgac acccatcacc 7320
accaccacta cggtgacccc aaccccaaca cccaccggca cacagacccc aaccacgaca 7380
cccatcacca ccaccactac ggtgacccca accccaacac ccaccggcac acagacccca 7440
accacgacac ccatcaccac caccactacg gtgaccccaa ccccaacacc caccggcaca 7500
cagaccccaa ccacgacacc catcaccacc accactacgg tgaccccaac cccaacaccc 7560
accggcacac agaccccaac cacgacaccc atcaccacca ccactacggt gaccccaacc 7620
ccaacaccca ccggcacaca gaccccaacc acgacaccca tcaccaccac cactacggtg 7680
accccaaccc caacacccac cggcacacag accccaacca cgacacccat caccaccacc 7740
actacggtga ccccaacccc aacacccacc ggcacacaga ccccaaccac gacacccatc 7800
accaccacca ctacggtgac cccaacccca acacccaccg gcacacagac cccaaccacg 7860
acacccatca ccaccaccac tacggtgacc ccaaccccaa cacccaccgg cacacagacc 7920
ccaaccacga cacccatcac caccaccact acggtgaccc caaccccaac acccaccggc 7980
acacagaccc caaccacgac acccatcacc accaccacta cggtgacccc aaccccaaca 8040
cccaccggca cacagacccc aaccacgaca cccatcacca ccaccactac ggtgacccca 8100
accccaacac ccaccggcac acagacccca accacgacac ccatcaccac caccactacg 8160
gtgaccccaa ccccaacacc caccggcaca cagaccccaa ccacgacacc catcaccacc 8220
accactacgg tgaccccaac cccaacaccc accggcacac agaccccaac cacgacaccc 8280
atcaccacca ccactacggt gaccccaacc ccaacaccca ccggcacaca gaccccaacc 8340
acgacaccca tcaccaccac cactacggtg accccaaccc caacacccac cggcacacag 8400
accccaacca cgacacccat caccaccacc actacggtga ccccaacccc aacacccacc 8460
ggcacacaga ccccaaccac gacacccatc accaccacca ctacggtgac cccaacccca 8520
acacccaccg gcacacagac cccaaccacg acacccatca ccaccaccac tacggtgacc 8580
ccaaccccaa cacccaccgg cacacagacc ccaaccacga cacccatcac caccaccact 8640
acggtgaccc caaccccaac acccaccggc acacagaccc caaccacgac acccatcacc 8700
accaccacta cggtgacccc aaccccaaca cccaccggca cacagacccc aaccacgaca 8760
cccatcacca ccaccactac ggtgacccca accccaacac ccaccggcac acagacccca 8820
accacgacac ccatcaccac caccactacg gtgaccccaa ccccaacacc caccggcaca 8880
cagaccccaa ccacgacacc catcaccacc accactacgg tgaccccaac cccaacaccc 8940
accggcacac agaccccaac cacgacaccc atcaccacca ccactacggt gaccccaacc 9000
ccaacaccca ccggcacaca gaccccaacc acgacaccca tcaccaccac cactacggtg 9060
accccaaccc caacacccac cggcacacag accccaacca cgacacccat caccaccacc 9120
actacggtga ccccaacccc aacacccacc ggcacacaga ccccaaccac gacacccatc 9180
accaccacca ctacggtgac cccaacccca acacccaccg gcacacagac cccaaccacg 9240
acacccatca ccaccaccac tacggtgacc ccaaccccaa cacccaccgg cacacagacc 9300
ccaaccacga cacccatcac caccaccact acggtgaccc caaccccaac acccaccggc 9360
acacagaccc caaccacgac acccatcacc accaccacta cggtgacccc aaccccaaca 9420
cccaccggca cacagacccc aaccacgaca cccatcacca ccaccactac ggtgacccca 9480
accccaacac ccaccggcac acagacccca accacgacac ccatcaccac caccactacg 9540
gtgaccccaa ccccaacacc caccggcaca cagaccccaa ccacgacacc catcaccacc 9600
accactacgg tgaccccaac cccaacaccc accggcacac agaccccaac cacgacaccc 9660
atcaccacca ccactacggt gaccccaacc ccaacaccca ccggcacaca gaccccaacc 9720
acgacaccca tcaccaccac cactacggtg accccaaccc caacacccac cggcacacag 9780
accccaacca cgacacccat caccaccacc actacggtga ccccaacccc aacacccacc 9840
ggcacacaga ccccaaccac gacacccatc accaccacca ctacggtgac cccaacccca 9900
acacccaccg gcacacagac cccaaccacg acacccatca ccaccaccac tacggtgacc 9960
ccaaccccaa cacccaccgg cacacagacc ccaaccacga cacccatcac caccaccact 10020
acggtgaccc caaccccaac acccaccggc acacagaccc caaccacgac acccatcacc 10080

```
accaccacta cggtgacccc aaccccaaca cccaccggca cacagacccc aaccacgaca  10140
cccatcacca ccaccactac ggtgacccca accccaacac ccaccggcac acagacccca  10200
accacgacac ccatcaccac caccactacg gtgaccccaa ccccaacacc caccggcaca  10260
cagaccccaa ccacgacacc catcaccacc accactacgg tgaccccaac cccaacaccc  10320
accggcacac agaccccaac cacgacaccc atcaccacca ccactacggt gaccccaacc  10380
ccaacaccca ccggcacaca gaccccaacc acgacaccca tcaccaccac cactacggtg  10440
accccaaccc caacacccac cggcacacag accccaacca cgacacccat caccaccacc  10500
actacggtga ccccaacccc aacacccacc ggcacacaga ccccaaccac gacacccatc  10560
accaccacca ctacggtgac cccaacccca acacccaccg gcacacagac cccaaccacg  10620
acacccatca ccaccaccac tacggtgacc ccaaccccaa cacccaccgg cacacagacc  10680
ccaaccacga cacccatcac caccaccact acggtgaccc caaccccaac acccaccggc  10740
acacagaccc caaccacgac acccatcacc accaccacta cggtgacccc aaccccaaca  10800
cccaccggca cacagacccc aaccacgaca cccatcacca ccaccactac ggtgacccca  10860
accccaacac ccaccggcac acagacccca accacgacac ccatcaccac caccactacg  10920
gtgaccccaa ccccaacacc caccggcaca cagaccccaa ccacgacacc catcaccacc  10980
accactacgg tgaccccaac cccaacaccc accggcacac agaccccaac cacgacaccc  11040
atcaccacca ccactacggt gaccccaacc ccaacaccca ccggcacaca gaccccaacc  11100
acgacaccca tcaccaccac cactacggtg accccaaccc caacacccac cggcacacag  11160
accccaacca cgacacccat caccaccacc actacggtga ccccaacccc aacacccacc  11220
ggcacacaga ccccaaccac gacacccatc accaccacca ctacggtgac cccaacccca  11280
acacccaccg gcacacagac cccaaccacg acacccatca ccaccaccac tacggtgacc  11340
ccaaccccaa cacccaccgg cacacagacc ccaaccacga cacccatcac caccaccact  11400
acggtgaccc caaccccaac acccaccggc acacagaccc caaccacgac acccatcacc  11460
accaccacta cggtgacccc aaccccaaca cccaccggca cacagacccc aaccacgaca  11520
cccatcacca ccaccactac ggtgacccca accccaacac ccaccggcac acagacccca  11580
accacgacac ccatcaccac caccactacg gtgaccccaa ccccaacacc caccggcaca  11640
cagaccccaa ccacgacacc catcaccacc accactacgg tgaccccaac cccaacaccc  11700
accggcacac agaccccaac cacgacaccc atcaccacca ccactacggt gaccccaacc  11760
ccaacaccca ccggcacaca gaccccaacc acgacaccca tcaccaccac cactacggtg  11820
accccaaccc caacacccac cggcacacag accccaacca cgacacccat caccaccacc  11880
actacggtga ccccaacccc aacacccacc ggcacacaga ccccaaccac gacacccatc  11940
accaccacca ctacggtgac cccaacccca acacccaccg gcacacagac cccaaccacg  12000
acacccatca ccaccaccac tacggtgacc ccaaccccaa cacccaccgg cacacagacc  12060
ccaaccacga cacccatcac caccaccact acggtgaccc caaccccaac acccaccggc  12120
acacagaccc caaccacgac acccatcacc accaccacta cggtgacccc aaccccaaca  12180
cccaccggca cacagacccc aaccacgaca cccatcacca ccaccactac ggtgacccca  12240
accccaacac ccaccggcac acagacccca accacgacac ccatcaccac caccactacg  12300
gtgaccccaa ccccaacacc caccggcaca cagaccccaa ccacgacacc catcaccacc  12360
accactacgg tgaccccaac cccaacaccc accggcacac agaccccaac cacgacaccc  12420
```

```
atcaccacca ccactacggt gaccccaacc ccaacaccca ccggcacaca gaccccaacc  12480
acgacaccca tcaccaccac cactacggtg accccaaccc caacacccac cggcacacag  12540
accccaacca cgacacccat caccaccacc actacggtga ccccaacccc aacacccacc  12600
ggcacacaga ccgggccccc cacccacaca agcacagcac cgattgctga gttgaccaca  12660
tccaatcctc cgcctgagtc ctcaacccct cagacctctc ggtccacctc ttcccctctc  12720
acggagtcaa ccacccttct gagtacccta ccacctgcca ttgagatgac cagcacggcc  12780
ccaccctcca cacccacggc acccacgacc acgagcggag gccacacact gtctccaccg  12840
cccagcacca ccacgtcccc tccaggcacc cccactcgcg gtaccacgac tgggtcatct  12900
tcagccccca cccccagcac tgtgcagacg accaccacca gtgcctggac ccccacgccg  12960
accccactct ccacacccag catcatcagg accacaggcc tgaggcccta cccttcctct  13020
gtgcttatct gctgtgtcct gaacgacacc tactacgcac caggtgagga ggtgtacaac  13080
ggcacatacg gagacacctg ttatttcgtc aactgctcac tgagctgtac gttggagttc  13140
tataactggt cctgcccatc cacgccctcc ccaacaccca cgccctccaa gtcgacgccc  13200
acgccttcca agccatcgtc cacgccctcc aagccgacgc ccggcaccaa gccccccgag  13260
tgcccagact ttgatcctcc cagacaggag aacgagactt ggtggctgtg cgactgcttc  13320
atggccacgt gcaagtacaa caacacggtg gagatcgtga aggtggagtg tgagccgccg  13380
cccatgccca cctgctccaa cggcctccaa cccgtgcgcg tcgaggaccc cgacggctgc  13440
tgctggcact gggagtgcga ctgctactgc acgggctggg gcgacccgca ctatgtcacc  13500
ttcgacggac tctactacag ctaccagggc aactgcacct acgtgctggt ggaggagatc  13560
agcccctccg tggacaactt cggagtttac atcgacaact accactgcga tcccaacgac  13620
aaggtgtcct gcccccgcac cctcatcgtg cgccacgaga cccaggaggt gctgatcaag  13680
accgtgcata tgatgcccat gcaggtgcag gtgcaggtga acaggcaggc ggtggcactg  13740
ccctacaaga agtacgggct ggaggtgtac cagtctggca tcaactacgt ggtggacatc  13800
cccgagctgg gtgtcctcgt ctcctacaat ggcctgtcct tctccgtcag gctgccctac  13860
caccggtttg gcaacaacac caagggccag tgtggcacct gcaccaacac cacctccgac  13920
gactgcattc tgcccagcgg ggagatcgtc tccaactgtg aggctgcggc tgaccagtgg  13980
ctggtgaacg accccctccaa gccacactgc ccccacagca gctccacgac caagcgcccg  14040
gccgtcactg tgcccggggg cggtaaaacg accccacaca aggactgcac cccatctccc  14100
ctctgccagc tcatcaagga cagcctgttt gcccagtgcc acgcactggt gcccccgcag  14160
cactactacg atgcctgcgt gttcgacagc tgcttcatgc cgggctcgag cctggagtgc  14220
gccagtctgc aggcctacgc agccctctgt gcccagcaga acatctgcct cgactggcgg  14280
aaccacacgc atggggcctg cttggtggag tgcccatctc acagggagta ccaggcctgt  14340
ggccctgcag aagagcccac gtgcaaatcc agctcctccc agcagaacaa cacagtcctg  14400
gtggaaggct gcttctgtcc tgagggcacc atgaactacg ctcctggctt tgatgtctgc  14460
gtgaagacct gcggctgtgt gggacctgac aatgtgccca gagagtttgg ggagcacttc  14520
gagttcgact gcaagaactg tgtctgcctg gagggtggaa gtggcatcat ctgccaaccc  14580
aagaggtgca gccagaagcc cgttacccac tgcgtggaag acggcaccta cctcgccacg  14640
gaggtcaacc ctgccgacac ctgctgcaac attaccgtct gcaagtgcaa caccagcctg  14700
tgcaaagaga agccctccgt gtgcccgctg ggattcgaag tgaagagcaa gatggtgcct  14760
ggaaggtgct gtcctttcta ctggtgtgag tccaaggggg tgtgtgttca cgggaatgct  14820
```

```
gagtaccagc ccggttctcc agtttattcc tccaagtgcc aggactgcgt gtgcacggac  14880

aaggtggaca acaacaccct gctcaacgtc atcgcctgca cccacgtgcc ctgcaacacc  14940

tcctgcagcc ctggcttcga actcatggag gcccccgggg agtgctgtaa gaagtgtgaa  15000

cagacgcact gtatcatcaa acggcccgac aaccagcacg tcatcctgaa gcccggggac  15060

ttcaagagcg acccgaagaa caactgcaca ttcttcagct gcgtgaagat ccacaaccag  15120

ctcatctcgt ccgtctccaa catcacctgc cccaactttg atgccagcat ttgcatcccg  15180

ggctccatca cattcatgcc caatggatgc tgcaagacct gcacccctcg caatgagacc  15240

agggtgccct gctccaccgt ccccgtcacc acggaggttt cgtacgccgg ctgcaccaag  15300

accgtcctca tgaatcattg ctccgggtcc tgcgggacat ttgtcatgta ctcggccaag  15360

gcccaggccc tggaccacag ctgctcctgc tgcaaagagg agaaaaccag ccagcgtgag  15420

gtggtcctga gctgccccaa tggcggctcg ctgacacaca cctacaccca catcgagagc  15480

tgccagtgcc aggacaccgt ctgcgggctc ccccaccggca cctcccgccg ggcccggcgc  15540

tcccctaggc atctggggag cgggtgagcg gggtgggcac agccccccttc actgccctcg  15600

acagctttac ctcccccgga ccctctgagc ctcctaagct cggcttcctc tcttcagata  15660

tttattgtct gagtctttgt tcagtccttg ctttccaata ataaactcag gggacatgc  15720
```

<210> SEQ ID NO 31
<211> LENGTH: 324
<212> TYPE: PRT
<213> ORGANISM: Homo sapiens

<400> SEQUENCE: 31

```
Met Phe Pro Ser Pro Ala Leu Thr Pro Thr Pro Phe Ser Val Lys Asp
1               5                   10                  15

Ile Leu Asn Leu Glu Gln Gln Gln Arg Ser Leu Ala Ala Ala Gly Glu
            20                  25                  30

Leu Ser Ala Arg Leu Glu Ala Thr Leu Ala Pro Ser Ser Cys Met Leu
        35                  40                  45

Ala Ala Phe Lys Pro Glu Ala Tyr Ala Gly Pro Glu Ala Ala Ala Pro
    50                  55                  60

Gly Leu Pro Glu Leu Arg Ala Glu Leu Gly Arg Ala Pro Ser Pro Ala
65                  70                  75                  80

Lys Cys Ala Ser Ala Phe Pro Ala Ala Pro Ala Phe Tyr Pro Arg Ala
                85                  90                  95

Tyr Ser Asp Pro Asp Pro Ala Lys Asp Pro Arg Ala Glu Lys Lys Glu
            100                 105                 110

Leu Cys Ala Leu Gln Lys Ala Val Glu Leu Glu Lys Thr Glu Ala Asp
        115                 120                 125

Asn Ala Glu Arg Pro Arg Ala Arg Arg Arg Arg Lys Pro Arg Val Leu
    130                 135                 140

Phe Ser Gln Ala Gln Val Tyr Glu Leu Glu Arg Arg Phe Lys Gln Gln
145                 150                 155                 160

Arg Tyr Leu Ser Ala Pro Glu Arg Asp Gln Leu Ala Ser Val Leu Lys
                165                 170                 175

Leu Thr Ser Thr Gln Val Lys Ile Trp Phe Gln Asn Arg Arg Tyr Lys
            180                 185                 190

Cys Lys Arg Gln Arg Gln Asp Gln Thr Leu Glu Leu Val Gly Leu Pro
        195                 200                 205

Pro Pro Pro Pro Pro Pro Ala Arg Arg Ile Ala Val Pro Val Leu Val
```

```
    210                 215                 220

Arg Asp Gly Lys Pro Cys Leu Gly Asp Ser Ala Pro Tyr Ala Pro Ala
225                 230                 235                 240

Tyr Gly Val Gly Leu Asn Pro Tyr Gly Tyr Asn Ala Tyr Pro Ala Tyr
                245                 250                 255

Pro Gly Tyr Gly Gly Ala Ala Cys Ser Pro Gly Tyr Ser Cys Thr Ala
            260                 265                 270

Ala Tyr Pro Ala Gly Pro Ser Pro Ala Gln Pro Ala Thr Ala Ala Ala
        275                 280                 285

Asn Asn Asn Phe Val Asn Phe Gly Val Gly Asp Leu Asn Ala Val Gln
    290                 295                 300

Ser Pro Gly Ile Pro Gln Ser Asn Ser Gly Val Ser Thr Leu His Gly
305                 310                 315                 320

Ile Arg Ala Trp


<210> SEQ ID NO 32
<211> LENGTH: 1669
<212> TYPE: DNA
<213> ORGANISM: Homo sapiens

<400> SEQUENCE: 32

gctcctgtca tcgaggcccc tggcccaatg gcaggctgag tccccctcct ctggcctggt     60

cccgcctctc ctgccccttg tgctcagcgc tacctgctgc ccggacacat ccagagctgg    120

ccgacgggtg cgcgggcggg cggcggcacc atgcagggaa gctgccaggg gccgtgggca    180

gcgccgcttt ctgccgccca cctggcgctg tgagactggc gctgccacca tgttccccag    240

ccctgctctc acgcccacgc ccttctcagt caaagacatc ctaaacctgg aacagcagca    300

gcgcagcctg gctgccgccg gagagctctc tgcccgcctg gaggcgaccc tggcgccctc    360

ctcctgcatg ctggccgcct tcaagccaga ggcctacgct gggcccgagg cggctgcgcc    420

gggcctccca gagctgcgcg cagagctggg ccgcgcgcct tcaccggcca agtgtgcgtc    480

tgcctttccc gccgcccccg ccttctatcc acgtgcctac agcgaccccg acccagccaa    540

ggaccctaga gccgaaaaga aagagctgtg cgcgctgcag aaggcggtgg agctggagaa    600

gacagaggcg gacaacgcgg agcggccccg ggcgcgacgg cggaggaagc cgcgcgtgct    660

cttctcgcag gcgcaggtct atgagctgga gcggcgcttc aagcagcagc ggtacctgtc    720

ggcccccgaa cgcgaccagc tggccagcgt gctgaaactc acgtccacgc aggtcaagat    780

ctggttccag aaccggcgct acaagtgcaa gcggcagcgg caggaccaga ctctggagct    840

ggtggggctg cccccgccgc cgccgccgcc tgcccgcagg atcgcggtgc cagtgctggt    900

gcgcgatggc aagccatgcc taggggactc ggcgccctac gcgcctgcct acggcgtggg    960

cctcaatccc tacggttata acgcctaccc cgcctatccg ggttacggcg gcgcggcctg   1020

cagccctggc tacagctgca ctgccgctta ccccgccggg ccttccccag cgcagccggc   1080

cactgccgcc gccaacaaca acttcgtgaa cttcggcgtc ggggacttga atgcggttca   1140

gagccccggg attccgcaga gcaactcggg agtgtccacg ctgcatggta tccgagcctg   1200

gtagggaagg gacccgcgtg gcgcgaccct gaccgatccc acctcaacag ctccctgact   1260

ctcgggggga gaaggggctc ccaacatgac cctgagtccc ctggattttg cattcactcc   1320

tgcggagacc taggaacttt ttctgtccca cgcgcgtttg ttcttgcgca cgggagagtt   1380

tgtggcggcg attatgcagc gtgcaatgag tgatcctgca gcctggtgtc ttagctgtcc   1440

ccccaggagt gccctccgag agtccatggg cacccccggt tggaactggg actgagctcg   1500
```

-continued

```
ggcacgcagg gcctgagatc tggccgccca ttccgcgagc cagggccggg cgcccgggcc   1560

tttgctatct cgccgtcgcc cgcccacgca cccacccgta tttatgtttt tacctattgc   1620

tgtaagaaat gacgatcccc ttcccattaa agagagtgcg ttgaccccg               1669
```

```
<210> SEQ ID NO 33
<211> LENGTH: 356
<212> TYPE: PRT
<213> ORGANISM: Homo sapiens

<400> SEQUENCE: 33

Met Thr Lys Ser Tyr Ser Glu Ser Gly Leu Met Gly Glu Pro Gln Pro
1               5                   10                  15

Gln Gly Pro Pro Ser Trp Thr Asp Glu Cys Leu Ser Ser Gln Asp Glu
            20                  25                  30

Glu His Glu Ala Asp Lys Lys Glu Asp Asp Leu Glu Ala Met Asn Ala
        35                  40                  45

Glu Glu Asp Ser Leu Arg Asn Gly Gly Glu Glu Glu Asp Glu Asp Glu
    50                  55                  60

Asp Leu Glu Glu Glu Glu Glu Glu Glu Glu Glu Asp Asp Asp Gln Lys
65                  70                  75                  80

Pro Lys Arg Arg Gly Pro Lys Lys Lys Lys Met Thr Lys Ala Arg Leu
                85                  90                  95

Glu Arg Phe Lys Leu Arg Arg Met Lys Ala Asn Ala Arg Glu Arg Asn
            100                 105                 110

Arg Met His Gly Leu Asn Ala Ala Leu Asp Asn Leu Arg Lys Val Val
        115                 120                 125

Pro Cys Tyr Ser Lys Thr Gln Lys Leu Ser Lys Ile Glu Thr Leu Arg
    130                 135                 140

Leu Ala Lys Asn Tyr Ile Trp Ala Leu Ser Glu Ile Leu Arg Ser Gly
145                 150                 155                 160

Lys Ser Pro Asp Leu Val Ser Phe Val Gln Thr Leu Cys Lys Gly Leu
                165                 170                 175

Ser Gln Pro Thr Thr Asn Leu Val Ala Gly Cys Leu Gln Leu Asn Pro
            180                 185                 190

Arg Thr Phe Leu Pro Glu Gln Asn Gln Asp Met Pro Pro His Leu Pro
        195                 200                 205

Thr Ala Ser Ala Ser Phe Pro Val His Pro Tyr Ser Tyr Gln Ser Pro
    210                 215                 220

Gly Leu Pro Ser Pro Pro Tyr Gly Thr Met Asp Ser Ser His Val Phe
225                 230                 235                 240

His Val Lys Pro Pro Pro His Ala Tyr Ser Ala Ala Leu Glu Pro Phe
                245                 250                 255

Phe Glu Ser Pro Leu Thr Asp Cys Thr Ser Pro Ser Phe Asp Gly Pro
            260                 265                 270

Leu Ser Pro Pro Leu Ser Ile Asn Gly Asn Phe Ser Phe Lys His Glu
        275                 280                 285

Pro Ser Ala Glu Phe Glu Lys Asn Tyr Ala Phe Thr Met His Tyr Pro
    290                 295                 300

Ala Ala Thr Leu Ala Gly Ala Gln Ser His Gly Ser Ile Phe Ser Gly
305                 310                 315                 320

Thr Ala Ala Pro Arg Cys Glu Ile Pro Ile Asp Asn Ile Met Ser Phe
                325                 330                 335

Asp Ser His Ser His His Glu Arg Val Met Ser Ala Gln Leu Asn Ala
```

```
            340                 345                 350

Ile Phe His Asp
        355


<210> SEQ ID NO 34
<211> LENGTH: 3002
<212> TYPE: DNA
<213> ORGANISM: Homo sapiens

<400> SEQUENCE: 34

ggggaggagg ggagaacggg gagcgcacag cctggacgcg tgcgcaggcg tcaggcgcat     60

agacctgcta gcccctcagc tagcggcccc gcccgcgctt agcatcacta actgggctat    120

ataacctgag cgcccgcgcg gccacgacac gaggaattcg cccacgcagg aggcgcggcg    180

tccggaggcc ccagggttat gagactatca ctgctcagga cctactaaca acaaaggaaa    240

tcgaaacatg accaaatcgt acagcgagag tgggctgatg ggcgagcctc agccccaagg    300

tcctccaagc tggacagacg agtgtctcag ttctcaggac gaggagcacg aggcagacaa    360

gaaggaggac gacctcgaag ccatgaacgc agaggaggac tcactgagga acgggggaga    420

ggaggaggac gaagatgagg acctggaaga ggaggaagaa gaggaagagg aggatgacga    480

tcaaaagccc aagagacgcg gccccaaaaa gaagaagatg actaaggctc gcctggagcg    540

ttttaaattg agacgcatga aggctaacgc ccgggagcgg aaccgcatgc acggactgaa    600

cgcggcgcta gacaacctgc gcaaggtggt gccttgctat tctaagacgc agaagctgtc    660

caaaatcgag actctgcgct tggccaagaa ctacatctgg gctctgtcgg agatcctgcg    720

ctcaggcaaa agcccagacc tggtctcctt cgttcagacg ctttgcaagg gcttatccca    780

acccaccacc aacctggttg cgggctgcct gcaactcaat cctcggactt ttctgcctga    840

gcagaaccag gacatgcccc cccacctgcc gacggccagc gcttccttcc ctgtacaccc    900

ctactcctac cagtcgcctg ggctgcccag tccgccttac ggtaccatgg acagctccca    960

tgtcttccac gttaagcctc cgccgcacgc ctacagcgca gcgctggagc ccttctttga   1020

aagccctctg actgattgca ccagcccttc ctttgatgga cccctcagcc cgccgctcag   1080

catcaatggc aacttctctt tcaaacacga accgtccgcc gagtttgaga aaaattatgc   1140

ctttaccatg cactatcctg cagcgacact ggcaggggcc caaagccacg gatcaatctt   1200

ctcaggcacc gctgcccctc gctgcgagat ccccatagac aatattatgt ccttcgatag   1260

ccattcacat catgagcgag tcatgagtgc ccagctcaat gccatatttc atgattagag   1320

gcacgccagt ttcaccattt ccgggaaacg aacccactgt gcttacagtg actgtcgtgt   1380

ttacaaaagg cagccctttg ggtactactg ctgcaaagtg caaatactcc aagcttcaag   1440

tgatatatgt atttattgtc attactgcct ttggaagaaa caggggatca aagttcctgt   1500

tcaccttatg tattattttc tatagctctt ctatttaaaa aataaaaaaa tacagtaaag   1560

tttaaaaaat acaccacgaa tttggtgtgg ctgtattcag atcgtattaa ttatctgatc   1620

gggataacaa aatcacaagc aataattagg atctatgcaa tttttaaact agtaatgggc   1680

caattaaaat atatataaat atatattttt caaccagcat tttactactt gttacctttc   1740

ccatgctgaa ttattttgtt gtgattttgt acagaatttt taatgacttt ttataatgtg   1800

gatttcctat tttaaaacca tgcagcttca tcaattttta tacatatcag aaaagtagaa   1860

ttatatctaa tttatacaaa ataatttaac taatttaaac cagcagaaaa gtgcttagaa   1920

agttattgtg ttgccttagc acttctttcc tctccaattg taaaaaaaaa aaaaaaaaaa   1980
```

```
aaaaaaaaaa aaaaattgca caatttgagc aattcatttc actttaaagt ctttccgtct   2040

ccctaaaata aaaaccagaa tcataatttt caagagaaga aaaaattaag agatacattc   2100

cctatcaaaa catatcaatt caacacatta cttgcacaag cttgtatata catattataa   2160

ataaatgcca acataccctt ctttaaatca aaagctgctt gactatcaca tacaatttgc   2220

actgttactt tttagtcttt tactcctttg cattccatga ttttacagag aatctgaagc   2280

tattgatgtt tccagaaaat ataaatgcat gattttatac atagtcacaa aaatggtggt   2340

ttgtcatata ttcatgtaat aaatctgagc ctaaatctaa tcaggttgtt aatgttggga   2400

tttatatcta tagtagtcaa ttagtacagt agcttaaata aattcaaacc atttaattca   2460

taattagaac aatagctatt gcatgtaaaa tgcagtccag aataagtgct gtttgagatg   2520

tgatgctggt accactggaa tcgatctgta ctgtaatttt gtttgtaatc ctgtatatta   2580

tggtgtaatg cacaatttag aaaacattca tccagttgca ataaaatagt attgaaagtg   2640

agagcaattg ttgcatttct tcttaaaggg attctgtttt tatttttggg gaaagtagtt   2700

gctttttgc tgagttaaaa aatactaaac actatatgta gaataaaaga aaagaaaaaa   2760

gtttaccttg gcatatgctc ttgtctgttt atcttgcaca gggagtcacc agttctatgt   2820

agataatgaa aagacctaac tgatatttca ttatttggaa tatgggactg gacggcagta   2880

caaacagtgt gttttttct ttgttttaag tggcttagcc tttaggtttt ttatttccat   2940

ttttaaaaat gattgttaca tgttttcttc tatttctttt tttaaaaggt ggattttaat   3000

aa                                                                  3002


<210> SEQ ID NO 35
<211> LENGTH: 367
<212> TYPE: PRT
<213> ORGANISM: Homo sapiens

<400> SEQUENCE: 35

Met Leu Ala Val Gly Ala Met Glu Gly Thr Arg Gln Ser Ala Phe Leu
1               5                   10                  15

Leu Ser Ser Pro Pro Leu Ala Ala Leu His Ser Met Ala Glu Met Lys
            20                  25                  30

Thr Pro Leu Tyr Pro Ala Ala Tyr Pro Pro Leu Pro Ala Gly Pro Pro
        35                  40                  45

Ser Ser Ser Ser Ser Ser Ser Ser Ser Ser Ser Pro Ser Pro Pro Leu
    50                  55                  60

Gly Thr His Asn Pro Gly Gly Leu Lys Pro Pro Ala Thr Gly Gly Leu
65                  70                  75                  80

Ser Ser Leu Gly Ser Pro Pro Gln Gln Leu Ser Ala Ala Thr Pro His
                85                  90                  95

Gly Ile Asn Asp Ile Leu Ser Arg Pro Ser Met Pro Val Ala Ser Gly
            100                 105                 110

Ala Ala Leu Pro Ser Ala Ser Pro Ser Gly Ser Ser Ser Ser Ser Ser
        115                 120                 125

Ser Ser Ala Ser Ala Ser Ser Ala Ser Ala Ala Ala Ala Ala Ala Ala
    130                 135                 140

Ala Ala Ala Ala Ala Ala Ser Ser Pro Ala Gly Leu Leu Ala Gly Leu
145                 150                 155                 160

Pro Arg Phe Ser Ser Leu Ser Pro Pro Pro Pro Pro Pro Gly Leu Tyr
                165                 170                 175

Phe Ser Pro Ser Ala Ala Ala Val Ala Ala Val Gly Arg Tyr Pro Lys
            180                 185                 190
```

```
Pro Leu Ala Glu Leu Pro Gly Arg Thr Pro Ile Phe Trp Pro Gly Val
        195                 200                 205

Met Gln Ser Pro Pro Trp Arg Asp Ala Arg Leu Ala Cys Thr Pro His
    210                 215                 220

Gln Gly Ser Ile Leu Leu Asp Lys Asp Gly Lys Arg Lys His Thr Arg
225                 230                 235                 240

Pro Thr Phe Ser Gly Gln Gln Ile Phe Ala Leu Glu Lys Thr Phe Glu
                245                 250                 255

Gln Thr Lys Tyr Leu Ala Gly Pro Glu Arg Ala Arg Leu Ala Tyr Ser
            260                 265                 270

Leu Gly Met Thr Glu Ser Gln Val Lys Val Trp Phe Gln Asn Arg Arg
        275                 280                 285

Thr Lys Trp Arg Lys Lys His Ala Ala Glu Met Ala Thr Ala Lys Lys
    290                 295                 300

Lys Gln Asp Ser Glu Thr Glu Arg Leu Lys Gly Ala Ser Glu Asn Glu
305                 310                 315                 320

Glu Glu Asp Asp Asp Tyr Asn Lys Pro Leu Asp Pro Asn Ser Asp Asp
                325                 330                 335

Glu Lys Ile Thr Gln Leu Leu Lys Lys His Lys Ser Ser Ser Gly Gly
            340                 345                 350

Gly Gly Gly Leu Leu Leu His Ala Ser Glu Pro Glu Ser Ser Ser
        355                 360                 365
```

<210> SEQ ID NO 36
<211> LENGTH: 1116
<212> TYPE: DNA
<213> ORGANISM: Homo sapiens

<400> SEQUENCE: 36

```
cgtgggatgt tagcggtggg ggcaatggag ggcacccggc agagcgcatt cctgctcagc     60

agccctcccc tggccgccct gcacagcatg gccgagatga agaccccgct gtaccctgcc    120

gcgtatcccc cgctgcctgc cggccccccc tcctcctcgt cctcgtcgtc gtcctcctcg    180

tcgccctccc cgcctctggg cacccacaac ccaggcggcc tgaagccccc ggccacgggg    240

gggctctcat ccctcggcag ccccccgcag cagctctcgg ccgccacccc acacggcatc    300

aacgatatcc tgagccggcc ctccatgccc gtggcctcgg gggccgccct gccctccgcc    360

tcgccctccg gttcctcctc ctcctcttcc tcgtccgcct ctgcctcctc cgcctctgcc    420

gccgccgcgg ctgctgccgc ggccgcagcc gccgcctcat ccccggcggg gctgctggcc    480

ggactgccac gctttagcag cctgagcccg ccgccgccgc cgcccgggct ctacttcagc    540

cccagcgccg cggccgtggc cgccgtgggc cggtacccca agccgctggc tgagctgcct    600

ggccggacgc ccatcttctg gcccggagtg atgcagagcc cgccctggag ggacgcacgc    660

ctggcctgta cccctcatca aggatccatt ttgttggaca aagacgggaa gagaaaacac    720

acgagaccca ctttttccgg acagcagatc ttcgccctgg agaagacttt cgaacaaaca    780

aaatacttgg cggggcccga gagggctcgt ttggcctatt cgttggggat gacagagagt    840

caggtcaagg tctggttcca gaaccgccgg accaagtgga ggaagaagca cgctgccgag    900

atggccacgg ccaagaagaa gcaggactcg gagacagagc gcctcaaggg ggcctcggag    960

aacgaggaag aggacgacga ctacaataag cctctggatc ccaactcgga cgacgagaaa   1020

atcacgcagc tgttgaagaa gcacaagtcc agcagcggcg gcggcggcgg cctcctactg   1080

cacgcgtccg agccggagag ctcatcctga acgccg                             1116
```

<210> SEQ ID NO 37
<211> LENGTH: 353
<212> TYPE: PRT
<213> ORGANISM: Homo sapiens

<400> SEQUENCE: 37

```
Met Ala Ala Glu Leu Ala Met Gly Ala Glu Leu Pro Ser Ser Pro Leu
1               5                   10                  15

Ala Ile Glu Tyr Val Asn Asp Phe Asp Leu Met Lys Phe Glu Val Lys
            20                  25                  30

Lys Glu Pro Pro Glu Ala Glu Arg Phe Cys His Arg Leu Pro Pro Gly
        35                  40                  45

Ser Leu Ser Ser Thr Pro Leu Ser Thr Pro Cys Ser Ser Val Pro Ser
    50                  55                  60

Ser Pro Ser Phe Cys Ala Pro Ser Pro Gly Thr Gly Gly Gly Gly Gly
65                  70                  75                  80

Ala Gly Gly Gly Gly Gly Ser Ser Gln Ala Gly Gly Ala Pro Gly Pro
                85                  90                  95

Pro Ser Gly Gly Pro Gly Ala Val Gly Gly Thr Ser Gly Lys Pro Ala
            100                 105                 110

Leu Glu Asp Leu Tyr Trp Met Ser Gly Tyr Gln His His Leu Asn Pro
        115                 120                 125

Glu Ala Leu Asn Leu Thr Pro Glu Asp Ala Val Glu Ala Leu Ile Gly
    130                 135                 140

Ser Gly His His Gly Ala His His Gly Ala His His Pro Ala Ala Ala
145                 150                 155                 160

Ala Ala Tyr Glu Ala Phe Arg Gly Pro Gly Phe Ala Gly Gly Gly Gly
                165                 170                 175

Ala Asp Asp Met Gly Ala Gly His His His Gly Ala His His Ala Ala
            180                 185                 190

His His His His Ala Ala His His His His His His His His His His
        195                 200                 205

Gly Gly Ala Gly His Gly Gly Gly Ala Gly His His Val Arg Leu Glu
    210                 215                 220

Glu Arg Phe Ser Asp Asp Gln Leu Val Ser Met Ser Val Arg Glu Leu
225                 230                 235                 240

Asn Arg Gln Leu Arg Gly Phe Ser Lys Glu Glu Val Ile Arg Leu Lys
                245                 250                 255

Gln Lys Arg Arg Thr Leu Lys Asn Arg Gly Tyr Ala Gln Ser Cys Arg
            260                 265                 270

Phe Lys Arg Val Gln Gln Arg His Ile Leu Glu Ser Glu Lys Cys Gln
        275                 280                 285

Leu Gln Ser Gln Val Glu Gln Leu Lys Leu Glu Val Gly Arg Leu Ala
    290                 295                 300

Lys Glu Arg Asp Leu Tyr Lys Glu Lys Tyr Glu Lys Leu Ala Gly Arg
305                 310                 315                 320

Gly Gly Pro Gly Ser Ala Gly Gly Ala Gly Phe Pro Arg Glu Pro Ser
                325                 330                 335

Pro Pro Gln Ala Gly Pro Gly Gly Ala Lys Gly Thr Ala Asp Phe Phe
            340                 345                 350

Leu
```

<210> SEQ ID NO 38

<211> LENGTH: 2058
<212> TYPE: DNA
<213> ORGANISM: Homo sapiens

<400> SEQUENCE: 38
gggtccttca ggtaggaggt cctgggtgac tttggaagtc cgtagtgtct cattgcagat 60
aatttttagc ttagggcctg gtggctaggt cggttctctc ctttccagtc ggagacctct 120
gccgcaaaca tgctccgcca gatcatcggt caggccaaga agcatccgag cttgatcccc 180
ctctttgtat ttattggaac tggagctact ggagcaacac tgtatctctt gcgtctggca 240
ttgttcaatc cagatgtttg ttgggacaga aataacccag agccctggaa caaactgggt 300
cccaatgatc aatacaagtt ctactcagtg aatgtggatt acagcaagct gaagaaggaa 360
cgtccagatt tctaaatgaa atgtttcact ataacgctgc tttagaatga aggtcttcca 420
gaagccacat ccgcacaatt ttccacttaa ccaggaaata tttctcctct aaatgcatga 480
aatcatgttg gagatctcta ttgtaatctc tattggagat tacaatgatt aaatcaataa 540
ataactgaaa cttgatatgt gtcacttttt tatgctgaaa gtatgctctg aactttagag 600
tataggaaat taactattag aatttaaaga atttcttgaa tttctgtagt ttgaaaatac 660
gactttaagc tgctttagta aaacacttcc attttgtgta tagactgttg gtaacttcac 720
tagagcatac ataacaactg gaactggaaa ttatacaaaa gtaaattggg aaggatactc 780
cagcatctga cactggcaaa atggaaacct ttgagtttct cttactggct gttgaagtgt 840
gtgcagtttt taacaatggt ttttacttgg catctctttg ttgtgatttt caaggttata 900
agttgctttg gtcctaggat tgaagttgaa atctgagttt atcagtgcta accatggtgc 960
tagtagtcaa gagatcttga gaattttggc tgctgagtct tggtgcaggg tgcaggtttt 1020
cttttctttt ttcttttttt ttttttgag atagtctctg tcacccaggc tggagtgcag 1080
tggtacaaac atggatcact gcagcctcta cctcccgggc ttaagtgatc ctcctgcctc 1140
agcccctaag tagccgggac tacaggtatg tgccaccatg cccagttaat ttttgtaatt 1200
ttttttagag acagggtttt gccatgttgc ccaggctggt ctcaaactct tgagctcaag 1260
cgatccattc tcctcagcct cccagggtgc tgggattaca ggcgtgagcc attgcgctta 1320
gccatggtgc aggttttcaa aggccaggaa gtatattcat aattttaaga tggggaatat 1380
agcaagtttt cacataggtg tgtgtaagtc atcacatcat agaaacttga ggaattcagt 1440
gacattaatt ttggattttc atacgtaagt atacaattaa atgtttacag ggtagtagaa 1500
gcacatttta aatgtcagga actgaactaa gtatttgaat tacgtggatt atctcaaaaa 1560
ttttgaaatt gttaaacgag ttgaattact tgaattcatt ctgttagtca aatggtggat 1620
atttacaccc atgtagtttt gaatttagag tgtgtagagt gttttcagtt accagactcc 1680
atgcttttac ctcctatgtg tcaggtataa tttgaacctc taagaacagg gtttctcaac 1740
cttgccactg ttgactattt ctgaaagaca gtttggttta gcagaccatc ccatgcgctt 1800
tagcttgttt agtagctaac ttgggctctg ccactacaga caaaaagcac tctttccctc 1860
caattcccac aggctatgag aagaatggag acattaccaa atgtccattg gtgggcaaaa 1920
ttgcttcatt cctacctctg ttgagaatta ctctagatcc tttggcacaa attacctcaa 1980
agtttaaaat tgtgtaaaca aacagtgtgt catgtaattg aaaaacatta agcaactcca 2040
aataaatgct acattaag 2058

<210> SEQ ID NO 39
<211> LENGTH: 343

<212> TYPE: PRT
<213> ORGANISM: Homo sapiens

<400> SEQUENCE: 39

Met Asn Gln Leu Gly Gly Leu Phe Val Asn Gly Arg Pro Leu Pro Leu
1 5 10 15

Asp Thr Arg Gln Gln Ile Val Arg Leu Ala Val Ser Gly Met Arg Pro
20 25 30

Cys Asp Ile Ser Arg Ile Leu Lys Val Ser Asn Gly Cys Val Ser Lys
35 40 45

Ile Leu Gly Arg Tyr Tyr Arg Thr Gly Val Leu Glu Pro Lys Gly Ile
50 55 60

Gly Gly Ser Lys Pro Arg Leu Ala Thr Pro Pro Val Val Ala Arg Ile
65 70 75 80

Ala Gln Leu Lys Gly Glu Cys Pro Ala Leu Phe Ala Trp Glu Ile Gln
85 90 95

Arg Gln Leu Cys Ala Glu Gly Leu Cys Thr Gln Asp Lys Thr Pro Ser
100 105 110

Val Ser Ser Ile Asn Arg Val Leu Arg Ala Leu Gln Glu Asp Gln Gly
115 120 125

Leu Pro Cys Thr Arg Leu Arg Ser Pro Ala Val Leu Ala Pro Ala Val
130 135 140

Leu Thr Pro His Ser Gly Ser Glu Thr Pro Arg Gly Thr His Pro Gly
145 150 155 160

Thr Gly His Arg Asn Arg Thr Ile Phe Ser Pro Ser Gln Ala Glu Ala
165 170 175

Leu Glu Lys Glu Phe Gln Arg Gly Gln Tyr Pro Asp Ser Val Ala Arg
180 185 190

Gly Lys Leu Ala Thr Ala Thr Ser Leu Pro Glu Asp Thr Val Arg Val
195 200 205

Trp Phe Ser Asn Arg Arg Ala Lys Trp Arg Arg Gln Glu Lys Leu Lys
210 215 220

Trp Glu Met Gln Leu Pro Gly Ala Ser Gln Gly Leu Thr Val Pro Arg
225 230 235 240

Val Ala Pro Gly Ile Ile Ser Ala Gln Gln Ser Pro Gly Ser Val Pro
245 250 255

Thr Ala Ala Leu Pro Ala Leu Glu Pro Leu Gly Pro Ser Cys Tyr Gln
260 265 270

Leu Cys Trp Ala Thr Ala Pro Glu Arg Cys Leu Ser Asp Thr Pro Pro
275 280 285

Lys Ala Cys Leu Lys Pro Cys Trp Gly His Leu Pro Pro Gln Pro Asn
290 295 300

Ser Leu Asp Ser Gly Leu Leu Cys Leu Pro Cys Pro Ser Ser His Cys
305 310 315 320

His Leu Ala Ser Leu Ser Gly Ser Gln Ala Leu Leu Trp Pro Gly Cys
325 330 335

Pro Leu Leu Tyr Gly Leu Glu
340

<210> SEQ ID NO 40
<211> LENGTH: 2010
<212> TYPE: DNA
<213> ORGANISM: Homo sapiens

<400> SEQUENCE: 40

-continued

```
caaagactca cccgtgagcc agctctcaaa gaaagcagct tgcgttgaca gcctgggggc     60

agcaaggatg cagtctccca ggagaggatg cactcggtgg tgggaagcca ggctggaggg    120

gcctgagtga ccctctccac aggcgggcag ggcagtggga gaggtggtgt gtggatacct    180

ctgtctcacg cccagggatc agcagcatga accagcttgg ggggctcttt gtgaatggcc    240

ggcccctgcc tctggatacc cggcagcaga ttgtgcggct agcagtcagt ggaatgcggc    300

cctgtgacat ctcacggatc cttaaggtat ctaatggctg tgtgagcaag atcctagggc    360

gttactaccg cacaggtgtc ttggagccaa agggcattgg gggaagcaag ccacggctgg    420

ctacaccccc tgtggtggct cgaattgccc agctgaaggg tgagtgtcca gccctctttg    480

cctgggaaat ccaacgccag ctttgtgctg aagggctttg cacccaggac aagactccca    540

gtgtctcctc catcaaccga gtcctgcggg cattacagga ggaccaggga ctaccgtgca    600

cacggctcag gtcaccagct gttttggctc cagctgtcct cactccccat agtggctctg    660

agactccccg gggtacccac ccagggaccg gccaccggaa tcggactatc ttctccccaa    720

gccaagcaga ggcactggag aaagagttcc agcgtgggca gtatcctgat tcagtggccc    780

gtggaaagct ggctactgcc acctctctgc ctgaggacac ggtgagggtc tggttttcca    840

acagaagagc caaatggcgt cggcaagaga agctcaagtg ggaaatgcag ctgccaggtg    900

cttcccaggg gctgactgta ccaagggttg ccccaggaat catctctgca cagcagtccc    960

ctggcagtgt gcccacagca gccctgcctg ccctggaacc actgggtccc tcctgctatc   1020

agctgtgctg ggcaacagca ccagaaaggt gtctgagtga cacccccacct aaagcctgtc  1080

tcaagccctg ctggggccac ttgcccccac agccgaattc cctggactca ggactgcttt   1140

gccttccttg cccttcctcc cactgtcacc tggccagtct tagtggctct caggccctgc   1200

tctggcctgg ctgcccacta ctgtatggct tggaatgagg caggagtggg aaggagatgg   1260

catagagaag atctaatacc atcctgccca ttgtccttac cgtcctgccc atacagactg   1320

tggctccttc ctccttcctg tgattgctcc ctcctgtgtg gacgttgcct ggccctgcct   1380

cgatgcctct ctggcgcatc acctgattgg aggggctggt aaagcaacac ccacccactt   1440

ctcacactag ccttaagagg cctccactca gcagtaataa aagctgtttt tattagcagt   1500

agttctgttg tccatcatgt tttccctatg agcacccctc tgcccactct aatattcaac   1560

aattatagac aatttgccct atcatttatt tacatctatg tatctaccat ctaatctatg   1620

catgtatgta ggcaatacat gtatctaaac aatgtatttg tcaatgcatc aatttaccta   1680

ctctatgtat gcatctatat gtgtattatg tatgcgtgca tgcgtgcgcg cacacacaca   1740

cacacacaca cacactgaca ttatatcatg gcattttatt cctaaatctt ccagcatgca   1800

tccccaaaaa acaagaaact tgtcttacat aatcacaata atatatccac atctaagaaa   1860

atttactgta acttcttaat ctaagaaaat tatgtatttt tgtcatatgt attttgtcat   1920

atgtattttg tatttgcata tgtattttgt atttgcatat gtatttttgt catagcagca   1980

aacagagtga aatgccattt ttcatattct                                    2010
```

<210> SEQ ID NO 41
<211> LENGTH: 286
<212> TYPE: PRT
<213> ORGANISM: Homo sapiens

<400> SEQUENCE: 41

```
Met Gly Ala Asp Gly Met Tyr Asp Lys Leu Arg Met Leu Asn Gly Gln
1               5                   10                  15
```

```
Thr Gly Ser Trp Gly Thr Arg Pro Gly Trp Tyr Pro Gly Thr Ser Val
            20                  25                  30

Pro Gly Gln Pro Thr Gln Asp Gly Cys Gln Gln Gln Glu Gly Gly Gly
        35                  40                  45

Glu Asn Thr Asn Ser Ile Ser Ser Asn Gly Glu Asp Ser Asp Glu Ala
    50                  55                  60

Gln Met Arg Leu Gln Leu Lys Arg Lys Leu Gln Arg Asn Arg Thr Ser
65                  70                  75                  80

Phe Thr Gln Glu Gln Ile Glu Ala Leu Glu Lys Glu Phe Glu Arg Thr
                85                  90                  95

His Tyr Pro Asp Val Phe Ala Arg Glu Arg Leu Ala Ala Lys Ile Asp
            100                 105                 110

Leu Pro Glu Ala Arg Ile Gln Val Trp Phe Ser Asn Arg Arg Ala Lys
        115                 120                 125

Trp Arg Arg Glu Glu Lys Leu Arg Asn Gln Arg Arg Gln Ala Ser Asn
    130                 135                 140

Thr Pro Ser His Ile Pro Ile Ser Ser Ser Phe Ser Thr Ser Val Tyr
145                 150                 155                 160

Gln Pro Ile Pro Gln Pro Thr Thr Pro Val Ser Ser Phe Thr Ser Gly
                165                 170                 175

Ser Met Leu Gly Arg Thr Asp Thr Ala Leu Thr Asn Thr Tyr Ser Ala
            180                 185                 190

Leu Pro Pro Met Pro Ser Phe Thr Met Ala Asn Asn Leu Pro Met Gln
        195                 200                 205

Pro Pro Val Pro Ser Gln Thr Ser Ser Tyr Ser Cys Met Leu Pro Thr
    210                 215                 220

Ser Pro Ser Val Asn Gly Arg Ser Tyr Asp Thr Tyr Thr Pro Pro His
225                 230                 235                 240

Met Gln Thr His Met Asn Ser Gln Pro Met Gly Thr Ser Gly Thr Thr
                245                 250                 255

Ser Thr Gly Leu Ile Ser Pro Gly Val Ser Val Pro Val Gln Val Pro
            260                 265                 270

Gly Ser Glu Pro Asp Met Ser Gln Tyr Trp Pro Arg Leu Gln
        275                 280                 285
```

<210> SEQ ID NO 42
<211> LENGTH: 6732
<212> TYPE: DNA
<213> ORGANISM: Homo sapiens

<400> SEQUENCE: 42

```
cttttcaatt agccttccat gcatgatccg gagcgacttc cgcctatttc cagaaattaa     60

gctcaaactt gacgtgcagc tagttttatt ttaaagacaa atgtcagaga ggctcatcat    120

atttttcccc ctcttctata tttggagctt atttattgct aagaagctca ggctcctggc    180

gtcaatttat cagtaggctc caaggagaag agaggagagg agaggagagc tgaacaggga    240

gccacgtctt ttcctgggag ggctgctatc taagtcgggg ctgcaggtca cagcggagtg    300

aatcagctcg gtggtgtctt tgtcaacggg cggccactgc cggactccac ccggcagaag    360

attgtagagc tagctcacag cggggcccgg ccgtgcgaca tttcccgaat tctgcagacc    420

catgcagatg caaaagtcca agtgctggac aatcaaaacg tgtccaacgg atgtgtgagt    480

aaaattctgg gcaggtatta cgagactggc tccatcagac ccagggcaat cggtggtagt    540

aaaccgagag tagcgactcc agaagttgta agcaaaatag cccagtataa gcgggagtgc    600
```

-continued

```
ccgtccatct ttgcttggga aatccgagac agattactgt ccgagggggt ctgtaccaac    660
gataacatac caagcgtgtc atcaataaac agagttcttc gcaacctggc tagcgaaaag    720
caacagatgg gcgcagacgg catgtatgat aaactaagga tgttgaacgg gcagaccgga    780
agctggggca cccgccctgg ttggtatccg gggacttcgg tgccagggca acctacgcaa    840
gatggctgcc agcaacagga aggagggggga gagaatacca actccatcag ttccaacgga   900
gaagattcag atgaggctca aatgcgactt cagctgaagc ggaagctgca aagaaataga    960
acatccttta cccaagagca aattgaggcc ctggagaaag agtttgagag aacccattat   1020
ccagatgtgt ttgcccgaga aagactagca gccaaaatag atctacctga agcaagaata   1080
caggtatggt tttctaatcg aagggccaaa tggagaagag aagaaaaact gaggaatcag   1140
agaagacagg ccagcaacac acctagtcat attcctatca gcagtagttt cagcaccagt   1200
gtctaccaac caattccaca acccaccaca ccggtttcct ccttcacatc tggctccatg   1260
ttgggccgaa cagacacagc cctcacaaac acctacagcg ctctgccgcc tatgcccagc   1320
ttcaccatgg caaataacct gcctatgcaa cccccagtcc ccagccagac ctcctcatac   1380
tcctgcatgc tgcccaccag cccttcggtg aatgggcgga gttatgatac ctacaccccc   1440
ccacatatgc agacacacat gaacagtcag ccaatgggca cctcgggcac cacttcaaca   1500
ggactcattt cccctggtgt gtcagttcca gttcaagttc ccggaagtga acctgatatg   1560
tctcaatact ggccaagatt acagtaaaaa aaaaaaaaaa aaaaaaaagg aaaggaaata   1620
ttgtgttaat tcagtcagtg actatgggga cacaacagtt gagctttcag gaaagaaaga   1680
aaaatggctg ttagagccgc ttcagttcta caattgtgtc ctgtattgta ccactgggga   1740
aggaatggac ttgaaacaag gacctttgta tacagaaggc acgatatcag ttggaacaaa   1800
tcttcatttt ggtatccaaa cttttattca ttttggtgta ttatttgtaa atgggcattt   1860
gtatgttata atgaaaaaaa gaacaatgta gactggatgg atgtttgatc tgtgttggtc   1920
atgaagttgt tttttttttt tttaaaaaga aaaccatgat caacaagctt tgccacgaat   1980
ttaagagttt tatcaagata tatcgaatac ttctacccat ctgttcatag tttatggact   2040
gatgttccaa gtttgtatca ttcctttgca tataattaaa cctggaacaa catgcactag   2100
atttatgtca gaaatatctg ttggttttcc aaaggttgtt aacagatgaa gtttatgtgc   2160
aaaaaagggt aagatataaa ttcaaggaag aaaaaaagtt gatagctaaa aggtagagtg   2220
tgtcttcgat ataatccaat ttgttttatg tcaaaatgta agtatttgtc ttccctagaa   2280
atcctcagaa tgatttctat aataaagtta atttcattta tatttgacaa gaatatagat   2340
gttttataca cattttcatg caatcatacg tttctttttt ggccagcaaa agttaattgt   2400
tcttagatat agttgtatta ctgttcacgg tccaatcatt ttgtgcatct agagttcatt   2460
cctaatcaat taaaagtgct tgcaagagtt ttaaacttaa gtgttttgaa gttgttcaca   2520
actacatatc aaaattaacc attgttgatt gtaaaaaacc atgccaaagc ctttgtattt   2580
cctttattat acagttttct ttttaacctt atagtgtggt gttacaaatt ttatttccat   2640
gttagatcaa cattctaaac caatggttac tttcacacac actctgtttt acatcctgat   2700
gatccttaaa aaataatcct tatagatacc ataaatcaaa aacgtgttag aaaaaaattc   2760
cacttacagc agggtgtaga tctgtgccca tttataccca caacatatat acaaaatggt   2820
aacatttccc agttagccat ttaattctaa agctcaaagt ctagaaataa tttaaaaatg   2880
caacaagcga ttagctagga attgtttttt gaattaggac tggcattttc aatctgggca   2940
gatttccatt gtcagcctat ttcaacaatg atttcactga agtatattca aaagtagatt   3000
```

tcttaaagga gactttctga aagctgttgc ctttttcaaa taggccctct ccctttctg 3060
tctccctccc ctttgcacaa gaggcatcat ttcccattga accactacag ctgttcccat 3120
ttgaatcttg ctttctgtgc ggttgtggat ggttggaggg tggagggggg atgttgcatg 3180
tcaaggaata atgagcacag acacatcaac agacaacaac aaagcagact gtgactggcc 3240
ggtgggaatt aaaggccttc agtcattggc agcttaagcc aaacattccc aaatctatga 3300
agcagggccc attgttggtc agttgttatt tgcaatgaag cacagttctg atcatgttta 3360
aagtggaggc acgcagggca ggagtgcttg agcccaagca aaggatggaa aaaaataagc 3420
ctttgttggg taaaaaagga ctgtctgaga ctttcatttg ttctgtgcaa catataagtc 3480
aatacagata agtcttcctc tgcaaacttc actaaaaagc ctgggggttc tggcagtcta 3540
gattaaaatg cttgcacatg cagaaacctc tggggacaaa gacacacttc cactgaatta 3600
tactctgctt taaaaaaatc cccaaaagca aatgatcaga aatgtagaaa ttaatggaag 3660
gatttaaaca tgaccttctc gttcaatatc tactgttttt tagttaagga attacttgtg 3720
aacagataat tgagattcat tgctccggca tgaaatatac taataatttt attccaccag 3780
agttgctgca catttggaga caccttccta agttgcagtt tttgtatgtg tgcatgtagt 3840
tttgttcagt gtcagcctgc actgcacagc agcacatttc tgcaggggag tgagcacaca 3900
tacgcactgt tggtacaatt gccggtgcag acatttctac ctcctgacat tttgcagcct 3960
acattccctg agggctgtgt gctgagggaa ctgtcagaga agggctatgt gggagtgcat 4020
gccacagctg ctggctggct tacttcttcc ttctcgctgg ctgtaatttc caccacggtc 4080
aggcagccag ttccggccca cggttctgtt gtgtagacag cagagacttt ggagacccgg 4140
atgtcgcacg ccaggtgcaa gaggtgggaa tgggagaaaa ggagtgacgt gggagcggag 4200
ggtctgtatg tgtgcacttg ggcacgtata tgtgtgctct gaaggtcagg attgccaggg 4260
caaagtagca cagtctggta tagtctgaag aagcggctgc tcagctgcag aagccctctg 4320
gtccggcagg atgggaacgg ctgccttgcc ttctgcccac accctaggga catgagctgt 4380
ccttccaaac agagctccag gcactctctt ggggacagca tggcaggctc tgtgtggtag 4440
cagtgcctgg gagttggcct tttactcatt gttgaaataa tttttgttta ttatttattt 4500
aacgatacat atatttatat atttatcaat ggggtatctg cagggatgtt ttgacaccat 4560
cttccaggat ggagattatt tgtgaagact tcagtagaat cccaggacta aacgtctaaa 4620
ttttttctcc aaacttgact gacttgggaa aaccaggtga atagaataag agctgaatgt 4680
tttaagtaat aaacgttcaa actgctctaa gtaaaaaaat gcattttact gcaatgaatt 4740
tctagaatat ttttccccca aagctatgcc tcctaaccct taaatggtga acaactggtt 4800
tcttgctaca gctcactgcc atttcttctt actatcatca ctaggtttcc taagattcac 4860
tcatacagta ttatttgaag attcagcttt gttctgtgaa tgtcatctta ggattgtgtc 4920
tatattcttt tgcttatttc tttttactct gggcctctca tactagtaag attttaaaaa 4980
gccttttctt ctctgtatgt ttggctcacc aaggcgaaat atatattctt ctctttttca 5040
tttctcaaga ataaacctca tctgcttttt tgtttttctg tgttttggct tggtactgaa 5100
tgactcaact gctcggtttt aaagttcaaa gtgtaagtac ttagggttag tactgcttat 5160
ttcaataatg ttgacggtga ctatctttgg aaagcagtaa catgctgtct tagaaatgac 5220
attaataatg ggcttaaaca aatgaatagg ggggtccccc cactctcctt ttgtatgcct 5280
atgtgtgtct gatttgttaa aagatggaca gggaattgat tgcagagtgt cgcttccttc 5340

```
taaagtagtt ttattttgtc tactgttagt atttaaagat cctggaggtg gacataagga   5400

ataaatggaa gagaaaagta gatattgtat ggtggctact aaaaggaaat tcaaaaagtc   5460

ttagaacccg agcacctgag caaactgcag tagtcaaaat atttatctca tgttaaagaa   5520

aggcaaatct agtgtaagaa atgagtacca tatagggttt tgaagttcat atactagaaa   5580

cacttaaaag atatcatttc agatattacg tttggcattg ttcttaagta tttatatctt   5640

tgagtcaagc tgataattaa aaaaaatctg ttaatggagt gtatatttca taatgtatca   5700

aaatggtgtc tatacctaag gtagcattat tgaagagaga tatgtttatg tagtaagtta   5760

ttaacataat gagtaacaaa taatgtttcc agaagaaagg aaaacacatt ttcagagtgc   5820

gtttttatca gaggaagaca aaaatacaca cccctctcca gtagcttatt tttacaaagc   5880

cggcccagtg aattagaaaa acaaagcact tggatatgat ttttggaaag cccaggtaca   5940

cttattattc aaaatgcact tttactgagt ttgaaaagtt tcttttatat ttaaaataag   6000

ggttcaaata tgcatattca atttttatag tagttatcta tttgcaaagc atatattaac   6060

tagtaattgg ctgttaattt tatagacatg gtagccaggg aagtatatca atgacctatt   6120

aagtattttg acaagcaatt tacatatctg atgacctcgt atctcttttt cagcaagtca   6180

aatgctatgt aattgttcca ttgtgtgttg tataaaatga atcaacacgg taagaaaaag   6240

gttagagtta ttaaaataat aaactgacta aaatactcat ttgaatttat tcagaatgtt   6300

cataatgctt tcaaaggaca tagcagagct tttgtggagt atccgcacaa cattatttat   6360

tatctatgga ctaaatcaat tttttgaagt tgctttaaaa tttaaaagca cctttgctta   6420

atataaagcc ctttaatttt aactgacaga tcaattctga aactttattt tgaaaagaaa   6480

atggggaaga atctgtgtct ttagaattaa aagaaatgaa aaaaataaac ccgacattct   6540

aaaaaaatag aataagaaac ctgattttta gtactaatga aatagcgggt gacaaaatag   6600

ttgtcttttt gattttgatc acaaaaaata aactggtagt gacaggatat gatggagaga   6660

tttgacatcc tggcaaatca ctgtcattga ttcaattatt ctaattctga ataaaagctg   6720

tatacagtaa aa                                                       6732
```

<210> SEQ ID NO 43
<211> LENGTH: 283
<212> TYPE: PRT
<213> ORGANISM: Homo sapiens

<400> SEQUENCE: 43

```
Met Asn Gly Glu Glu Gln Tyr Tyr Ala Ala Thr Gln Leu Tyr Lys Asp
1               5                   10                  15

Pro Cys Ala Phe Gln Arg Gly Pro Ala Pro Glu Phe Ser Ala Ser Pro
            20                  25                  30

Pro Ala Cys Leu Tyr Met Gly Arg Gln Pro Pro Pro Pro Pro Pro His
        35                  40                  45

Pro Phe Pro Gly Ala Leu Gly Ala Leu Glu Gln Gly Ser Pro Pro Asp
    50                  55                  60

Ile Ser Pro Tyr Glu Val Pro Pro Leu Ala Asp Asp Pro Ala Val Ala
65                  70                  75                  80

His Leu His His His Leu Pro Ala Gln Leu Ala Leu Pro His Pro Pro
                85                  90                  95

Ala Gly Pro Phe Pro Glu Gly Ala Glu Pro Gly Val Leu Glu Glu Pro
            100                 105                 110

Asn Arg Val Gln Leu Pro Phe Pro Trp Met Lys Ser Thr Lys Ala His
        115                 120                 125
```

```
Ala Trp Lys Gly Gln Trp Ala Gly Gly Ala Tyr Ala Ala Glu Pro Glu
    130                 135                 140

Glu Asn Lys Arg Thr Arg Thr Ala Tyr Thr Arg Ala Gln Leu Leu Glu
145                 150                 155                 160

Leu Glu Lys Glu Phe Leu Phe Asn Lys Tyr Ile Ser Arg Pro Arg Arg
                165                 170                 175

Val Glu Leu Ala Val Met Leu Asn Leu Thr Glu Arg His Ile Lys Ile
            180                 185                 190

Trp Phe Gln Asn Arg Arg Met Lys Trp Lys Lys Glu Glu Asp Lys Lys
        195                 200                 205

Arg Gly Gly Gly Thr Ala Val Gly Gly Gly Gly Val Ala Glu Pro Glu
    210                 215                 220

Gln Asp Cys Ala Val Thr Ser Gly Glu Glu Leu Leu Ala Leu Pro Pro
225                 230                 235                 240

Pro Pro Pro Pro Gly Gly Ala Val Pro Pro Ala Ala Pro Val Ala Ala
                245                 250                 255

Arg Glu Gly Arg Leu Pro Pro Gly Leu Ser Ala Ser Pro Gln Pro Ser
            260                 265                 270

Ser Val Ala Pro Arg Arg Pro Gln Glu Pro Arg
        275                 280
```

<210> SEQ ID NO 44
<211> LENGTH: 2573
<212> TYPE: DNA
<213> ORGANISM: Homo sapiens

<400> SEQUENCE: 44

```
gggtggcgcc gggagtggga acgccacaca gtgccaaatc cccggctcca gctcccgact     60

cccggctccc ggctcccggc tcccggtgcc caatcccggg ccgcagccat gaacggcgag    120

gagcagtact acgcggccac gcagctttac aaggacccat gcgcgttcca gcgaggcccg    180

gcgccggagt tcagcgccag ccccccctgcg tgcctgtaca tgggccgcca gcccccgccg    240

ccgccgccgc acccgttccc tggcgccctg ggcgcgctgg agcagggcag ccccccggac    300

atctccccgt acgaggtgcc cccctcgcc gacgaccccg cggtggcgca ccttcaccac    360

cacctcccgg ctcagctcgc gctcccccac ccgcccgccg ggcccttccc ggagggagcc    420

gagccgggcg tcctggagga gcccaaccgc gtccagctgc ctttcccatg gatgaagtct    480

accaaagctc acgcgtggaa aggccagtgg gcaggcggcg cctacgctgc ggagccggag    540

gagaacaagc ggacgcgcac ggcctacacg cgcgcacagc tgctagagct ggagaaggag    600

ttcctattca acaagtacat ctcacggccg cgccgggtgg agctggctgt catgttgaac    660

ttgaccgaga gacacatcaa gatctggttc caaaaccgcc gcatgaagtg gaaaaaggag    720

gaggacaaga agcgcggcgg cgggacagct gtcgggggtg gcggggtcgc ggagcctgag    780

caggactgcg ccgtgacctc cggcgaggag cttctggcgc tgccgccgcc gccgcccccc    840

ggaggtgctg tgccgcccgc tgccccgtt gccgcccgag agggccgcct gccgcctggc    900

cttagcgcgt cgccacagcc ctccagcgtc gcgcctcggc ggccgcagga accacgatga    960

gaggcaggag ctgctcctgg ctgaggggct tcaaccactc gccgaggagg agcagagggc   1020

ctaggaggac cccgggcgtg gaccacccgc cctggcagtt gaatggggcg gcaattgcgg   1080

ggcccacctt agaccgaagg ggaaaacccg ctctctcagg cgcatgtgcc agttggggcc   1140

ccgcgggtag atgccggcag gccttccgga agaaaaagag ccattggttt ttgtagtatt   1200
```

```
ggggccctct tttagtgata ctggattggc gttgtttgtg gctgttgcgc acatccctgc   1260

cctcctacag cactccacct tgggacctgt ttagagaagc cggctcttca aagacaatgg   1320

aaactgtacc atacacattg gaaggctccc taacacacac agcggggaag ctgggccgag   1380

taccttaatc tgccataaag ccattcttac tcgggcgacc cctttaagtt tagaaataat   1440

tgaaaggaaa tgtttgagtt ttcaaagatc ccgtgaaatt gatgccagtg gaatacagtg   1500

agtcctcctc ttcctcctcc tcctcttccc cctcccttc ctcctcctcc tcttcttttc   1560

cctcctcttc ctcttcctcc tgctctcctt tcctcccct cctcttttcc ctcctcttcc   1620

tcttcctcct gctctccttt cctcccctc ctctttctcc tcctcctcct cttcttcccc   1680

ctcctctccc tcctcctctt cttcccctc ctctccctcc tcctcttctt ctccctcctc   1740

ttcctcttcc tcctcttcca cgtgctctcc tttcctcccc ctcctcttgc tccccttctt   1800

ccccgtcctc ttcctcctcc tcctcttctt ctccctcctc ttcctcctcc tctttcttcc   1860

tgacctcttt ctttctcctc ctcctccttc tacctcccct tctcatccct cctcttcctc   1920

ttctctagct gcacacttca ctactgcaca tcttataact tgcacccctt tcttctgagg   1980

aagagaacat cttgcaaggc agggcgagca gcggcagggc tggcttagga gcagtgcaag   2040

agtccctgtg ctccagttcc acactgctgg cagggaaggc aagggggac gggcctggat   2100

ctgggggtga gggagaaaga tggacccctg ggtgaccact aaaccaaaga tattcggaac   2160

tttctattta ggatgtggac gtaattcctg ttccgaggta gaggctgtgc tgaagacaag   2220

cacagtggcc tggtgcgcct tggaaaccaa caactattca cgagccagta tgaccttcac   2280

atctttagaa attatgaaaa cgtatgtgat tggagggttt ggaaaaccag ttatcttatt   2340

taacatttta aaaattacct aacagttatt tacaaacagg tctgtgcatc ccaggtctgt   2400

cttcttttca aggtctgggc cttgtgctcg ggttatgttt gtgggaaatg cttaataaat   2460

actgataata tgggaagaga tgaaaactga ttctcctcac tttgtttcaa acctttctgg   2520

cagtgggatg attcgaattc acttttaaaa ttaaattagc gtgttttgtt ttg          2573
```

```
<210> SEQ ID NO 45
<211> LENGTH: 328
<212> TYPE: PRT
<213> ORGANISM: Homo sapiens

<400> SEQUENCE: 45

Met Asp Ala Val Leu Leu Glu His Phe Pro Gly Gly Leu Asp Ala Phe
1               5                   10                  15

Pro Ser Ser Tyr Phe Asp Glu Asp Asp Phe Phe Thr Asp Gln Ser Ser
            20                  25                  30

Arg Asp Pro Leu Glu Asp Gly Asp Glu Leu Leu Ala Asp Glu Gln Ala
        35                  40                  45

Glu Val Glu Phe Leu Ser His Gln Leu His Glu Tyr Cys Tyr Arg Asp
    50                  55                  60

Gly Ala Cys Leu Leu Leu Gln Pro Ala Pro Pro Ala Ala Pro Leu Ala
65                  70                  75                  80

Leu Ala Pro Pro Ser Ser Gly Gly Leu Gly Glu Pro Asp Asp Gly Gly
                85                  90                  95

Gly Gly Gly Tyr Cys Cys Glu Thr Gly Ala Pro Pro Gly Gly Phe Pro
            100                 105                 110

Tyr Ser Pro Gly Ser Pro Pro Ser Cys Leu Ala Tyr Pro Cys Ala Gly
        115                 120                 125

Ala Ala Val Leu Ser Pro Gly Ala Arg Leu Arg Gly Leu Ser Gly Ala
```

```
    130                 135                 140

Ala Ala Ala Ala Ala Arg Arg Arg Arg Arg Val Arg Ser Glu Ala Glu
145                 150                 155                 160

Leu Gln Gln Leu Arg Gln Ala Ala Asn Val Arg Glu Arg Arg Arg Met
                165                 170                 175

Gln Ser Ile Asn Asp Ala Phe Glu Gly Leu Arg Ser His Ile Pro Thr
            180                 185                 190

Leu Pro Tyr Glu Lys Arg Leu Ser Lys Val Asp Thr Leu Arg Leu Ala
        195                 200                 205

Ile Gly Tyr Ile Asn Phe Leu Ser Glu Leu Val Gln Ala Asp Leu Pro
    210                 215                 220

Leu Arg Gly Gly Gly Ala Gly Gly Cys Gly Gly Pro Gly Gly Gly Gly
225                 230                 235                 240

Arg Leu Gly Gly Asp Ser Pro Gly Ser Gln Ala Gln Lys Val Ile Ile
                245                 250                 255

Cys His Arg Gly Thr Arg Ser Pro Ser Pro Ser Asp Pro Asp Tyr Gly
            260                 265                 270

Leu Pro Pro Leu Ala Gly His Ser Leu Ser Trp Thr Asp Glu Lys Gln
        275                 280                 285

Leu Lys Glu Gln Asn Ile Ile Arg Thr Ala Lys Val Trp Thr Pro Glu
    290                 295                 300

Asp Pro Arg Lys Leu Asn Ser Lys Ser Ser Phe Asn Asn Ile Glu Asn
305                 310                 315                 320

Glu Pro Pro Phe Glu Phe Val Ser
                325


<210> SEQ ID NO 46
<211> LENGTH: 1339
<212> TYPE: DNA
<213> ORGANISM: Homo sapiens

<400> SEQUENCE: 46

atggacgcgg tgttgctgga gcacttcccc gggggcctag acgcctttcc ttcttcgtac      60

ttcgacgagg acgacttctt caccgaccag tcttcacggg accccctgga ggacggcgat     120

gagctgctgg cggacgagca ggccgaggtg gagttcctta gccaccagct ccacgagtac     180

tgctaccgcg acggggcgtg cctgctgctg cagcccgcgc ccccggccgc cccgctagcg     240

ctcgccccgc cgtcctcggg gggcctcggt gagccagacg acggcggcgg cggcggctac     300

tgctgcgaga cgggggcgcc cccaggcggc ttcccctact cgcccggctc gccgccctcg     360

tgcctggcct acccgtgcgc cggggcggca gtactgtctc ccggggcgcg gctgcgcggc     420

ctgagcggag cggcggctgc ggcggcgcgg cgccggcggc gggtgcgctc cgaggcggag     480

ctgcagcagc tgcggcaggc ggccaacgtg cgcgagcggc ggcgcatgca gtccatcaac     540

gacgccttcg aggggctgcg ctcgcacatc cccacgctgc cctacgagaa gcgcctctcc     600

aaggtggaca cgctgcgcct ggccatcggc tacatcaact tcctcagcga gctcgtgcag     660

gccgacctgc ccttgcgcgg cggtggcgcg ggcggctgcg gggggccggg cggcggcggg     720

cgcctgggcg gggacagccc gggcagccag gcccagaagg tcatcatctg ccatcggggc     780

acccggtccc cctcccccag cgaccctgat tatggcctcc ctcccctagc aggacactct     840

ctctcatgga ctgatgaaaa acaactcaag gaacaaaata ttatccgaac agccaaagtc     900

tggaccccag aggaccccag aaaactcaac agcaaatctt ccttcaacaa catagaaaac     960

gaaccaccat ttgagtttgt gtcctgagaa gtcccagact cggctgaaga tctgattatg    1020
```

-continued

```
tctctgtgca tattgtacat gtaaatatct ataatgtaaa tgtaatttaa gaatcaaatt   1080

tttcgaatgg caatcaactg tttattattt atctatttat tatcctgttg agttgatgaa   1140

atagatgatt tctttttaaa tatataattt atataactta tcctgatttt ctgaaaatat   1200

gcaatagcct atgattttcc tgaactctgt gttgttggga gaactctggc cagaaaacgt   1260

cctgcttatt tattgccaga tatggtttat ttctaagcgt tgtcaataaa tgctatttac   1320

accttttcct gaaaaaaaa                                                1339
```

<210> SEQ ID NO 47
<211> LENGTH: 1555
<212> TYPE: DNA
<213> ORGANISM: Homo sapiens

<400> SEQUENCE: 47

```
cggcgatggc cccactcgga tacttcttac tcctctgcag cctgaagcag gctctgggca     60

gctacccgat ctggtggtcg ctggctgttg ggccacagta ttcctccctg ggctcgcagc    120

ccatcctgtg tgccagcatc ccgggcctgg tccccaagca gctccgcttc tgcaggaact    180

acgtggagat catgcccagc gtggccgagg gcatcaagat tggcatccag gagtgccagc    240

accagttccg cggccgccgg tggaactgca ccaccgtcca cgacagcctg gccatcttcg    300

ggcccgtgct ggacaaagct accagggagt cggcctttgt ccacgccatt gcctcagccg    360

gtgtggcctt tgcagtgaca cgctcatgtg cagaaggcac ggccgccatc tgtggctgca    420

gcagccgcca ccagggctca ccaggcaagg gctggaagtg ggtggctgt agcgaggaca    480

tcgagtttgg tgggatggtg tctcgggagt tcgccgacgc ccgggagaac cggccagatg    540

cccgctcagc catgaaccgc cacaacaacg aggctgggcg ccaggccatc gccagccaca    600

tgcacctcaa gtgcaagtgc cacgggctgt cgggcagctg cgaggtgaag acatgctggt    660

ggtcgcaacc cgacttccgc gccatcggtg acttcctcaa ggacaagtac gacagcgcct    720

cggagatggt ggtggagaag caccgggagt cccgcggctg ggtggagacc ctgcggccgc    780

gctacaccta cttcaaggtg cccacggagc gcgacctggt ctactacgag gcctcgccca    840

acttctgcga gcccaaccct gagacgggct ccttcggcac gcgcgaccgc acctgcaacg    900

tcagctcgca cggcatcgac ggctgcgacc tgctgtgctg cggccgcggc cacaacgcgc    960

gagcggagcg gcgccgggag aagtgccgct gcgtgttcca ctggtgctgc tacgtcagct   1020

gccaggagtg cacgcgcgtc tacgacgtgc acacctgcaa gtaggcaccg gccgcggctc   1080

cccctggacg gggcgggccc tgcctgaggg tgggcttttc cctgggtgga gcaggactcc   1140

cacctaaacg gggcagtact cctccctggg ggcgggactc ctccctgggg gtggggctcc   1200

tacctggggg cagaactcct acctgaaggc agggctcctc cctggagcta gtgtctcctc   1260

tctggtggct gggctgctcc tgaatgaggc ggagctccag gatggggagg ggctctgcgt   1320

tggcttctcc ctggggacgg ggctcccctg gacagaggcg gggctacaga ttgggcgggg   1380

cttctcttgg gtgggacagg gcttctcctg cgggggcgag gcccctccca gtaagggcgt   1440

ggctctgggt gggcggggca ctaggtaggc ttctacctgc aggcggggct cctcctgaag   1500

gaggcggggc tctaggatgg ggcacggctc tggggtaggc tgctccctga gggcg        1555
```

<210> SEQ ID NO 48
<211> LENGTH: 385
<212> TYPE: PRT
<213> ORGANISM: Homo sapiens

<400> SEQUENCE: 48

```
Met Ala Pro Leu Gly Tyr Phe Leu Leu Leu Cys Ser Leu Lys Gln Ala
1               5                   10                  15

Leu Gly Ser Tyr Pro Ile Trp Trp Ser Leu Ala Val Gly Pro Gln Tyr
            20                  25                  30

Ser Ser Leu Gly Ser Gln Pro Ile Leu Cys Ala Ser Ile Pro Gly Leu
        35                  40                  45

Val Pro Lys Gln Leu Arg Phe Cys Arg Asn Tyr Val Glu Ile Met Pro
    50                  55                  60

Ser Val Ala Glu Gly Ile Lys Ile Gly Ile Gln Glu Cys Gln His Gln
65                  70                  75                  80

Phe Arg Gly Arg Arg Trp Asn Cys Thr Thr Val His Asp Ser Leu Ala
                85                  90                  95

Ile Phe Gly Pro Val Leu Asp Lys Ala Thr Arg Glu Ser Ala Phe Val
            100                 105                 110

His Ala Ile Ala Ser Ala Gly Val Ala Phe Ala Val Thr Arg Ser Cys
        115                 120                 125

Ala Glu Gly Thr Ala Ala Ile Cys Gly Cys Ser Ser Arg His Gln Gly
    130                 135                 140

Ser Pro Gly Lys Gly Trp Lys Trp Gly Gly Cys Ser Glu Asp Ile Glu
145                 150                 155                 160

Phe Gly Gly Met Val Ser Arg Glu Phe Ala Asp Ala Arg Glu Asn Arg
                165                 170                 175

Pro Asp Ala Arg Ser Ala Met Asn Arg His Asn Asn Glu Ala Gly Arg
            180                 185                 190

Gln Ala Ile Ala Ser His Met His Leu Lys Cys Lys Cys His Gly Leu
        195                 200                 205

Ser Gly Ser Cys Glu Val Lys Thr Cys Trp Trp Ser Gln Pro Asp Phe
    210                 215                 220

Arg Ala Ile Gly Asp Phe Leu Lys Asp Lys Tyr Asp Ser Ala Ser Glu
225                 230                 235                 240

Met Val Val Glu Lys His Arg Glu Ser Arg Gly Trp Val Glu Thr Leu
                245                 250                 255

Arg Pro Arg Tyr Thr Tyr Phe Lys Val Pro Thr Glu Arg Asp Leu Val
            260                 265                 270

Tyr Tyr Glu Ala Ser Pro Asn Phe Cys Glu Pro Asn Pro Glu Thr Gly
        275                 280                 285

Ser Phe Gly Thr Arg Asp Arg Thr Cys Asn Val Ser Ser His Gly Ile
    290                 295                 300

Asp Gly Cys Asp Leu Leu Cys Cys Gly Arg Gly His Asn Ala Arg Ala
305                 310                 315                 320

Glu Arg Arg Arg Glu Lys Cys Arg Cys Val Phe His Trp Cys Cys Tyr
                325                 330                 335

Val Ser Cys Gln Glu Cys Thr Arg Val Tyr Asp Val His Thr Cys Lys
            340                 345                 350

Asn Pro Gly Ser Arg Ala Gly Asn Ser Ala His Gln Pro Pro His Pro
        355                 360                 365

Gln Pro Pro Val Arg Phe His Pro Pro Leu Arg Arg Ala Gly Lys Val
    370                 375                 380

Pro
385
```

<210> SEQ ID NO 49

<211> LENGTH: 1056
<212> TYPE: DNA
<213> ORGANISM: Homo sapiens

<400> SEQUENCE: 49
atgagtcccc gctcgtgcct gcgttcgctg cgcctcctcg tcttcgccgt cttctcagcc 60
gccgcgagca actggctgta cctggccaag ctgtcgtcgg tggggagcat ctcagaggag 120
gagacgtgcg agaaactcaa gggcctgatc cagaggcagg tgcagatgtg caagcggaac 180
ctggaagtca tggactcggt gcgccgcggt gcccagctgg ccattgagga gtgccagtac 240
cagttccgga accggcgctg gaactgctcc acactcgact ccttgcccgt cttcggcaag 300
gtggtgacgc aagggattcg ggaggcggcc ttggtgtacg ccatctcttc ggcaggtgtg 360
gcctttgcag tgacgcgggc gtgcagcagt ggggagctgg agaagtgcgg ctgtgacagg 420
acagtgcatg gggtcagccc acagggcttc cagtggtcag gatgctctga caacatcgcc 480
tacggtgtgg ccttctcaca gtcgtttgtg gatgtgcggg agagaagcaa gggggcctcg 540
tccagcagag ccctcatgaa cctccacaac aatgaggccg gcaggaaggc catcctgaca 600
cacatgcggg tggaatgcaa gtgccacggg gtgtcaggct cctgtgaggt aaagacgtgc 660
tggcgagccg tgccgccctt ccgccaggtg ggtcacgcac tgaaggagaa gtttgatggt 720
gccactgagg tggagccacg ccgcgtgggc tcctccaggg cactggtgcc acgcaacgca 780
cagttcaagc cgcacacaga tgaggacttg gtgtacttgg agcctagccc cgacttctgt 840
gagcaggaca tgcgcagcgg cgtgctgggc acgaggggcc gcacatgcaa caagacgtcc 900
aaggccatcg acggctgtga gctgctgtgc tgtggccgcg gcttccacac ggcgcaggtg 960
gagctggctg aacgctgcag ctgcaaattc cactggtgct gcttcgtcaa gtgccggcag 1020
tgccagcggc tcgtggagtt gcacacgtgc cgatga 1056

<210> SEQ ID NO 50
<211> LENGTH: 351
<212> TYPE: PRT
<213> ORGANISM: Homo sapiens

<400> SEQUENCE: 50

Met Ser Pro Arg Ser Cys Leu Arg Ser Leu Arg Leu Leu Val Phe Ala
1 5 10 15

Val Phe Ser Ala Ala Ala Ser Asn Trp Leu Tyr Leu Ala Lys Leu Ser
20 25 30

Ser Val Gly Ser Ile Ser Glu Glu Glu Thr Cys Glu Lys Leu Lys Gly
35 40 45

Leu Ile Gln Arg Gln Val Gln Met Cys Lys Arg Asn Leu Glu Val Met
50 55 60

Asp Ser Val Arg Arg Gly Ala Gln Leu Ala Ile Glu Glu Cys Gln Tyr
65 70 75 80

Gln Phe Arg Asn Arg Arg Trp Asn Cys Ser Thr Leu Asp Ser Leu Pro
85 90 95

Val Phe Gly Lys Val Val Thr Gln Gly Ile Arg Glu Ala Ala Leu Val
100 105 110

Tyr Ala Ile Ser Ser Ala Gly Val Ala Phe Ala Val Thr Arg Ala Cys
115 120 125

Ser Ser Gly Glu Leu Glu Lys Cys Gly Cys Asp Arg Thr Val His Gly
130 135 140

Val Ser Pro Gln Gly Phe Gln Trp Ser Gly Cys Ser Asp Asn Ile Ala
145 150 155 160

Tyr Gly Val Ala Phe Ser Gln Ser Phe Val Asp Val Arg Glu Arg Ser
165 170 175

Lys Gly Ala Ser Ser Ser Arg Ala Leu Met Asn Leu His Asn Asn Glu
180 185 190

Ala Gly Arg Lys Ala Ile Leu Thr His Met Arg Val Glu Cys Lys Cys
195 200 205

His Gly Val Ser Gly Ser Cys Glu Val Lys Thr Cys Trp Arg Ala Val
210 215 220

Pro Pro Phe Arg Gln Val Gly His Ala Leu Lys Glu Lys Phe Asp Gly
225 230 235 240

Ala Thr Glu Val Glu Pro Arg Arg Val Gly Ser Ser Arg Ala Leu Val
245 250 255

Pro Arg Asn Ala Gln Phe Lys Pro His Thr Asp Glu Asp Leu Val Tyr
260 265 270

Leu Glu Pro Ser Pro Asp Phe Cys Glu Gln Asp Met Arg Ser Gly Val
275 280 285

Leu Gly Thr Arg Gly Arg Thr Cys Asn Lys Thr Ser Lys Ala Ile Asp
290 295 300

Gly Cys Glu Leu Leu Cys Cys Gly Arg Gly Phe His Thr Ala Gln Val
305 310 315 320

Glu Leu Ala Glu Arg Cys Ser Cys Lys Phe His Trp Cys Cys Phe Val
325 330 335

Lys Cys Arg Gln Cys Gln Arg Leu Val Glu Leu His Thr Cys Arg
340 345 350

<210> SEQ ID NO 51
<211> LENGTH: 1143
<212> TYPE: DNA
<213> ORGANISM: Homo sapiens

<400> SEQUENCE: 51
atgaagaagt ccattggaat attaagccca ggagttgctt tggggatggc tggaagtgca 60
atgtcttcca agttcttcct agtggctttg gccatatttt tctccttcgc ccaggttgta 120
attgaagcca attcttggtg gtcgctaggt atgaataacc ctgttcagat gtcagaagta 180
tatattatag gagcacagcc tctctgcagc caactggcag gactttctca aggacagaag 240
aaactgtgcc acttgtatca ggaccacatg cagtacatcg gagaaggcgc gaagacaggc 300
atcaaagaat gccagtatca attccgacat cgaaggtgga actgcagcac tgtggataac 360
acctctgttt ttggcagggt gatgcagata ggcagccgcg agacggcctt cacatacgcg 420
gtgagcgcag caggggtggt gaacgccatg agccgggcgt gccgcgaggg cgagctgtcc 480
acctgcggct gcagccgcgc cgcgcgcccc aaggacctgc cgcgggactg gctctggggc 540
ggctgcggcg acaacatcga ctatggctac cgctttgcca aggagttcgt ggacgcccgc 600
gagcgggagc gcatccacgc caagggctcc tacgagagtg ctcgcatcct catgaacctg 660
cacaacaacg aggccggccg caggacggtg tacaacctgg ctgatgtggc ctgcaagtgc 720
catggggtgt ccggctcatg tagcctgaag acatgctggc tgcagctggc agacttccgc 780
aaggtgggtg atgccctgaa ggagaagtac gacagcgcgg cggccatgcg gctcaacagc 840
cggggcaagt tggtacaggt caacagccgc ttcaactcgc ccaccacaca agacctggtc 900
tacatcgacc ccagccctga ctactgcgtg cgcaatgaga gcaccggctc gctgggcacg 960
cagggccgcc tgtgcaacaa gacgtcggag ggcatggatg gctgcgagct catgtgctgc 1020

```
ggccgtggct acgaccagtt caagaccgtg cagacggagc gctgccactg caagttccac   1080

tggtgctgct acgtcaagtg caagaagtgc acggagatcg tggaccagtt tgtgtgcaag   1140

tag                                                                 1143


<210> SEQ ID NO 52
<211> LENGTH: 380
<212> TYPE: PRT
<213> ORGANISM: Homo sapiens

<400> SEQUENCE: 52

Met Lys Lys Ser Ile Gly Ile Leu Ser Pro Gly Val Ala Leu Gly Met
1               5                   10                  15

Ala Gly Ser Ala Met Ser Ser Lys Phe Phe Leu Val Ala Leu Ala Ile
            20                  25                  30

Phe Phe Ser Phe Ala Gln Val Val Ile Glu Ala Asn Ser Trp Trp Ser
        35                  40                  45

Leu Gly Met Asn Asn Pro Val Gln Met Ser Glu Val Tyr Ile Ile Gly
    50                  55                  60

Ala Gln Pro Leu Cys Ser Gln Leu Ala Gly Leu Ser Gln Gly Gln Lys
65                  70                  75                  80

Lys Leu Cys His Leu Tyr Gln Asp His Met Gln Tyr Ile Gly Glu Gly
                85                  90                  95

Ala Lys Thr Gly Ile Lys Glu Cys Gln Tyr Gln Phe Arg His Arg Arg
            100                 105                 110

Trp Asn Cys Ser Thr Val Asp Asn Thr Ser Val Phe Gly Arg Val Met
        115                 120                 125

Gln Ile Gly Ser Arg Glu Thr Ala Phe Thr Tyr Ala Val Ser Ala Ala
    130                 135                 140

Gly Val Val Asn Ala Met Ser Arg Ala Cys Arg Glu Gly Glu Leu Ser
145                 150                 155                 160

Thr Cys Gly Cys Ser Arg Ala Ala Arg Pro Lys Asp Leu Pro Arg Asp
                165                 170                 175

Trp Leu Trp Gly Gly Cys Gly Asp Asn Ile Asp Tyr Gly Tyr Arg Phe
            180                 185                 190

Ala Lys Glu Phe Val Asp Ala Arg Glu Arg Glu Arg Ile His Ala Lys
        195                 200                 205

Gly Ser Tyr Glu Ser Ala Arg Ile Leu Met Asn Leu His Asn Asn Glu
    210                 215                 220

Ala Gly Arg Arg Thr Val Tyr Asn Leu Ala Asp Val Ala Cys Lys Cys
225                 230                 235                 240

His Gly Val Ser Gly Ser Cys Ser Leu Lys Thr Cys Trp Leu Gln Leu
                245                 250                 255

Ala Asp Phe Arg Lys Val Gly Asp Ala Leu Lys Glu Lys Tyr Asp Ser
            260                 265                 270

Ala Ala Ala Met Arg Leu Asn Ser Arg Gly Lys Leu Val Gln Val Asn
        275                 280                 285

Ser Arg Phe Asn Ser Pro Thr Thr Gln Asp Leu Val Tyr Ile Asp Pro
    290                 295                 300

Ser Pro Asp Tyr Cys Val Arg Asn Glu Ser Thr Gly Ser Leu Gly Thr
305                 310                 315                 320

Gln Gly Arg Leu Cys Asn Lys Thr Ser Glu Gly Met Asp Gly Cys Glu
                325                 330                 335

Leu Met Cys Cys Gly Arg Gly Tyr Asp Gln Phe Lys Thr Val Gln Thr
            340                 345                 350
```

-continued

```
Glu Arg Cys His Cys Lys Phe His Trp Cys Cys Tyr Val Lys Cys Lys
        355                 360                 365

Lys Cys Thr Glu Ile Val Asp Gln Phe Val Cys Lys
    370                 375                 380
```

COMPOSITIONS AND METHODS FOR ORGANOID GENERATION AND DISEASE MODELING

SEQUENCE LISTING The instant application contains a Sequence Listing which has been submitted electronically in ASCII format and is hereby incorporated by reference in its entirety. The ASCII copy, created on Jun. 26, 2017, is named 167776-010908USDIV-SL.txt and is 262,334 bytes in size.

CROSS REFERENCE TO RELATED APPLICATIONS

This application is a divisional of patent application U.S. Ser. No. 16/301,671, filed Nov. 14, 2018, which is a U.S. national stage application under 35 U.S.C. § 371 of International PCT Application No. PCT/US2017/034278, filed May 24, 2017, which claims priority to and benefit of U.S. Provisional Patent Application No. 62/341,461, filed May 25, 2016, the contents of all of which are hereby incorporated by reference herein in their entireties.

STATEMENT OF RIGHTS TO INVENTIONS MADE UNDER FEDERALLY SPONSORED RESEARCH

This invention was made with government support under Grant Nos. DK057978 and DK0909962 awarded by the National Institutes of Health. The government has certain rights in the invention.

BACKGROUND OF THE INVENTION

Although animal disease models can yield insight into the pathogenesis of diseases, drugs screened and selected using animal models often fail to be adopted in human patients. Because evolutionary biology, molecular biology, and genetic studies show animals and humans can profoundly differ, recapitulating human disease using human cells and generation of functional human organs is urgently needed.

SUMMARY OF THE INVENTION

As described below, the present invention features compositions and methods for generating an organoid, including a pancreatic islet organoid or a pancreatic organoid.

In one aspect, the invention provides a method of generating a pancreatic islet organoid, the method involving culturing an induced pluripotent stem cell (iPSC)-derived beta-like cell in a 3-dimensional matrix containing gellan gum, thereby generating a pancreatic islet organoid.

In another aspect, the invention provides a cell culture including an iPSC-derived beta-like cell in a three-dimensional matrix containing gellan gum.

In another aspect, the invention provides a cell culture including a human iPSC-derived beta-like cell, a human adipose-derived stem cell (hADSC), and a human umbilical vein endothelial cell (HUVEC) in a three-dimensional matrix containing gellan gum.

In various embodiments of any aspect delineated herein, the cell culture includes an adipose-derived stem cell and/or an endothelial cell.

In another aspect, the invention provides a pancreatic islet organoid containing an iPSC-derived beta-like cell, where the organoid is vascularized and exhibits glucose-stimulated insulin secretion (GSIS).

In another aspect, the invention provides a pancreatic islet organoid containing an iPSC-derived beta-like cell, an iPSC-derived alpha cell, an iPSC-derived delta cell, an iPSC-derived duct cell, an adipose-derived stem cell (hADSC), and an endothelial cell where the organoid is vascularized and exhibits glucose-stimulated insulin secretion (GSIS), KCl-stimulated insulin secretion, GLP-1 stimulated insulin secretion, somatostatin secretion, and glucagon secretion.

In a related aspect, the invention provides a non-human organism transplanted with the organoid of any aspect delineated herein.

In another aspect, the invention provides a method of identifying an agent that modulates pancreatic activity and/or treats a pancreatic disease involving contacting a candidate agent with a pancreatic islet organoid or a pancreatic organoid; and measuring an activity of the organoid contacted with the candidate agent, where the candidate agent is identified as an agent that modulates pancreatic activity and/or treats a pancreatic disease if the activity of the organoid is altered relative to a reference.

In another aspect, the invention provides a method of identifying an agent that modulates pancreatic activity and/or treats a pancreatic disease involving administering a candidate agent to a non-human subject transplanted with a pancreatic islet organoid or a pancreatic organoid; and measuring a pancreatic activity of the non-human subject, where the candidate agent is identified as an agent that modulates pancreatic activity and/or treats a pancreatic disease if the pancreatic activity of the non-human subject is altered relative to a reference.

In another aspect, the invention provides a method of treating a pancreatic disease in a subject involving transplanting a pancreatic islet organoid into the subject, where the pancreatic islet organoid contains an iPSC-derived beta-like cell, is vascularized, and exhibits glucose-stimulated insulin secretion (GSIS).

In another aspect, the invention provides a method of treating type 1 diabetes in a subject, involving transplanting a pancreatic islet organoid into the subject, where the pancreatic islet organoid contains an iPSC-derived beta-like cell, is vascularized, and exhibits glucose-stimulated insulin secretion (GSIS).

In another aspect, the invention provides a pancreatic islet organoid generated by culturing an induced pluripotent stem cell (iPSC)-derived beta-like cell in a 3-dimensional matrix containing gellan gum.

In another aspect, the invention provides a pancreatic organoid generated by culturing an induced pluripotent stem cell (iPSC)-derived beta-like cell and an iPSC-derived exocrine component cell in a 3-dimensional matrix containing gellan gum.

In another aspect, the invention provides a liver organoid generated by culturing an induced pluripotent stem cell (iPSC)-derived hepatocyte in a 3-dimensional matrix containing gellan gum.

In another aspect, the invention provides a heart organoid generated by culturing an induced pluripotent stem cell (iPSC)-derived cardiomyocyte in a 3-dimensional matrix containing gellan gum.

In another aspect, the invention provides an intestinal organoid generated by culturing an induced pluripotent stem cell (iPSC)-derived intestinal cell in a 3-dimensional matrix containing gellan gum.

In various embodiments of any aspect delineated herein, the method involves culturing the iPSC-derived beta-like cell with an adipose-derived stem cell and/or an endothelial cell. In various embodiments of any aspect delineated herein, the method involves culturing the iPSC-derived beta-like cell with an iPSC-derived alpha-like cell, an iPSC-derived delta-like cell, and/or an iPSC-derived duct-like cell.

In various embodiments of any aspect delineated herein, the pancreatic islet organoid contains an iPSC-derived alpha-like cell, an iPSC-derived delta-like cell, and/or an iPSC-derived duct-like cell. In various embodiments of any aspect delineated herein, the pancreatic islet organoid includes an adipose-derived stem cell and/or an endothelial cell. In various embodiments of any aspect delineated herein, the pancreatic islet organoid exhibits KCl-stimulated insulin secretion, GLP-1 stimulated insulin secretion, somatostatin secretion, and/or glucagon secretion. In various embodiments of any aspect delineated herein, the pancreatic islet organoid expresses one or more of the beta cell transcription factors Pdx1, MafA, Pax4, Pax6, NeuroD1, Nkx6-1, Gata6, and Foxa2. In certain embodiments, the pancreatic islet organoid contains an iPSC-derived beta-like cell, an iPSC-derived alpha cell, an iPSC-derived delta cell, an iPSC-derived duct cell, an adipose-derived stem cell (hADSC), and an endothelial cell, where the organoid is vascularized and exhibits glucose-stimulated insulin secretion (GSIS), KCl-stimulated insulin secretion, GLP-1 stimulated insulin secretion, somatostatin secretion, and glucagon secretion. In various embodiments of any aspect delineated herein, the pancreatic islet organoid is surrounded by an iPSC-derived exocrine component. In various embodiments, the iPSC-derived exocrine component expresses one or more of the markers PDX1, Nkx6-1, and Ptf1.

In various embodiments of any aspect delineated herein, the method involves inducing or mimicking a pancreatic disease in the organoid or non-human subject. In various embodiments of any aspect delineated herein, the disease is induced by contacting the organoid with or administering to the non-human subject one or more of the following agents: a free fatty acid (FFA), glucose, and cytokine. In various embodiments of any aspect delineated herein, the disease is mimicked by culturing the organoid with pancreatic cancer cells, stellate cells, and immune cells to create human pancreatic cancer microenvironment. In various embodiments of any aspect delineated herein, the pancreatic activity is one or more of insulin secretion, beta cell apoptosis, expression or activity of a NDUFA4, ESRRG, G6PC2, MDH1, LDHA, KCNK3, or MAFA polypeptide or polynucleotide, amylase secretion, apoptosis of an exocrine component, collagen synthesis, and stellate cell activation. In various embodiments, the non-human subject is also transplanted with a liver organoid.

In various embodiments of any aspect delineated herein, the candidate agent increases insulin secretion. In various embodiments of any aspect delineated herein, the candidate agent identified as an agent that modulates pancreatic activity is tested for the ability to treat a pancreatic disease. In various embodiments, the pancreatic disease is type 2 diabetes or pancreatic cancer.

In various embodiments of any aspect delineated herein, the organoid is an organoid according to any aspect delineated herein.

In various embodiments, the non-human organism is a mammal (e.g., a mouse).

In various embodiments of any aspect delineated herein, the pancreatic islet organoid contains an iPSC-derived alpha-like cell, an iPSC-derived delta-like cell, and/or an iPSC-derived duct-like cell.

In various embodiments of any aspect delineated herein, the pancreatic islet organoid contains an adipose-derived stem cell and/or an endothelial cell.

In various embodiments of any aspect delineated herein, a pancreatic disease is induced or mimicked in the subject. In particular embodiments, the pancreatic disease is type 1 diabetes or type 2 diabetes. In certain embodiments, the subject is a mammal (e.g., human). In various embodiments of any aspect delineated herein, the subject is administered an immunosuppressive agent.

In various embodiments of any aspect delineated herein, the liver organoid expresses one or more of the markers AFP, ALB, and Cyp3a7. In various embodiments of any aspect delineated herein, the liver organoid exhibits insulin signaling, insulin resistance by palmitic acids, and lipid accumulation.

In various embodiments of any aspect delineated herein, the heart organoid expresses one or more of the markers hMlc2a, hNkx2-5, alphaMHC and KCNQ1. In various embodiments of any aspect delineated herein, the heart organoid exhibits cardiac beating.

In various embodiments of any aspect delineated herein, the intestinal organoid expresses one or more of the markers CDX2, Muc2, and Lgr5. In various embodiments of any aspect delineated herein, the intestinal organoid exhibits budding in response to R-spondin.

In various embodiments of any aspect delineated herein, the iPSC-derived beta-like cell, iPSC-derived alpha-like cell, iPSC-derived delta-like cell, and/or iPSC-derived duct-like cell is human. In various embodiments of any aspect delineated herein, the iPSC-derived beta-like cell, iPSC-derived exocrine component cell, iPSC-derived hepatocyte, iPSC-derived cardiomyocyte, or iPSC-derived intestinal cell is human. In various embodiments, the adipose-derived stem cell is a human adipose-derived stem cell (hADSC). In various embodiments of any aspect delineated herein, the endothelial cell is a human umbilical vein endothelial cell (HUVEC).

In various embodiments of any aspect delineated herein, the pancreatic islet organoid, pancreatic organoid, liver organoid, heart organoid, or intestinal organoid, contains an adipose-derived stem cell and/or an endothelial cell. In various embodiments of any aspect delineated herein, the pancreatic islet organoid, pancreatic organoid, liver organoid, heart organoid, or intestinal organoid is vascularized.

In another aspect, the invention provides a method of generating a pancreatic islet organoid, the method comprising culturing an induced pluripotent stem cell (iPSC)-derived beta-like cell in a medium comprising Wnt4 or Wnt5a protein. In an embodiment, the induced pluripotent stem cell (iPSC)-derived beta-like cell is cultured in a 3-dimensional matrix. In an embodiment of the foregoing aspect, the Wnt4 or Wnt5a protein is a recombinant human Wnt4 or Wnt5a protein. In a particular embodiment, the medium comprises recombinant human Wnt4 protein. In another particular embodiment, the medium comprises recombinant human Wnt5a protein.

In another aspect the invention provides a cell culture comprising a human iPSC-derived beta-like cell and Wnt4 or Wnt5a protein. In an embodiment, the human iPSC-derived beta-like cell is in a three-dimensional matrix comprising gellan gum. In an embodiment, the Wnt4 or Wnt5a protein is a recombinant human Wnt4 or Wnt5a protein. In a particular embodiment, the medium comprises recombinant human Wnt4 protein. In another particular embodiment, the medium comprises recombinant human Wnt5a protein.

In another aspect, the invention provides a pancreatic islet organoid comprising an iPSC-derived beta-like cell cultured in medium comprising Wnt4 or Wnt5a protein, wherein the organoid is vascularized and exhibits glucose-stimulated insulin secretion (GSIS). In an embodiment, the organoid further exhibits KCl-stimulated insulin secretion or glucose stimulated insulin secretion. In an embodiment, the pancreatic islet organoid expresses Fltp and Esrrg genes. In an embodiment, the Wnt4 or Wnt5a protein is a recombinant human Wnt4 or Wnt5a protein. In a particular embodiment, the medium comprises recombinant human Wnt4 protein. In another particular embodiment, the medium comprises recombinant human Wnt5a protein.

In another aspect, the invention provides a non-human organism transplanted with the organoid defined in the above described aspects.

In another aspect, the invention provides a method of enhancing self organization of adipose-derived stem cells (ADSCs) for generating an induced pluripotent stem cell (iPSC)-derived organoid, the method comprising culturing the ADSCs in a 3-dimensional (3-D) culture matrix medium comprising a Wnt5a protein. In an embodiment of the method, the ADSCs are cultured in a 3-D culture matrix comprising gellan gum. In an embodiment, the ADSCs are cultured in the 3-D culture matrix medium comprising a Wnt5 protein and an iPSC-derived cell selected from an iPSC-derived beta-like cell, an iPSC-derived exocrine component cell, an iPSC-derived hepatocyte, an iPSC-derived cardiomyocyte, or an iPSC-derived intestinal cell. In an embodiment of the method, the iPSC-derived organoid is selected from a pancreatic islet organoid, pancreatic organoid, a liver organoid, a heart organoid, or an intestinal organoid. In an embodiment of the method, the induced pluripotent stem cell (iPSC)-derived organoid is a human induced pluripotent stem cell (hiPSC)-derived organoid. In an embodiment of the method, the Wnt5a protein is a recombinant human Wnt5a protein. In an embodiment of the method, the pancreatic islet organoid, pancreatic organoid, liver organoid, heart organoid, or intestinal organoid is derived from an iPSC-derived cell selected from an iPSC-derived beta-like cell, an iPSC-derived exocrine component cell, an iPSC-derived hepatocyte, an iPSC-derived cardiomyocyte, or an iPSC-derived intestinal cell, respectively. In an embodiment, of any of the above, the iPSC-derived cell is human. In another aspect, the invention provides a method of enhancing self organization of adipose-derived stem cells (ADSCs) for generating a pancreatic islet or pancreatic organoid, comprising culturing ADSCs in medium comprising Wnt5a protein. In an embodiment, the ADSCs are cultured in a 3-dimensional matrix comprising gellan gum. In another embodiment, the Wnt5a protein a recombinant human Wnt5a protein. In another aspect, the invention provides a pancreatic islet organoid, pancreatic organoid, a liver organoid, a heart organoid, or intestinal organoid produced by any of the above-delineated methods and embodiments thereof.

Compositions and articles defined by the invention were isolated or otherwise manufactured in connection with the examples provided below. Other features and advantages of the invention will be apparent from the detailed description, and from the claims.

Definitions

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them below, unless specified otherwise.

By "AFP polypeptide" or "alpha-fetoprotein" is meant a protein or fragment thereof having at least 85% amino acid sequence identity to the sequence provided at NCBI Accession No. NP_001125.1 and having a biological activity of an AFP polypeptide. Exemplary biological activities of an AFP polypeptide include binding to copper, nickel, fatty acids, and bilirubin. The amino acid sequence provided at NCBI Accession No. NP_001125.1 is shown below:

```
                                                              (SEQ ID NO: 1)
    1   mkwvesifli  fllnftesrt  lhrneygias  ildsyqctae  isladlatif  faqfvqeaty

   61   kevskmvkda  ltaiekptgd  eqssgclenq  lpafleelch  ekeilekygh  sdccsqseeg

  121   rhncflahkk  ptpasiplfq  vpepvtscea  yeedretfmn  kfiyeiarrh  pflyaptill

  181   waarydkiip  scckaenave  cfqtkaatvt  kelresslln  qhacavmknf  gtrtfqaitv

  241   tklsqkftkv  nfteiqklvl  dvahvhehcc  rgdvldclqd  gekimsyics  qqdtlsnkit

  301   eccklttler  gqciihaend  ekpeglspnl  nrflgdrdfn  qfssgeknif  lasfvheysr

  361   rhpqlaysvi  lrvakgygel  lekcfqtenp  lecqdkgeee  lqkyiqesqa  lakrscglfq

  421   klgeyylqna  flvaytkkap  qltsselmai  trkmaataat  ccqlsedkll  acgegaadii

  481   ighlcirhem  tpvnpgvgqc  ctssyanrrp  cfsslvvdet  yvppafsddk  fifhkdlcqa

  541   qgvalgtmkg  eflinlvkqk  pqiteeqlea  viadfsglle  kccqgqeqev  cfaeegqkli

  601   sktraalgv
```

By "AFP polynucleotide" is meant a polynucleotide encoding a AFP polypeptide or fragment thereof. An exemplary AFP polynucleotide sequence is provided at NCBI Ref: NM_001134.2. The sequence provided at NCBI Ref: NM_001134.2 is reproduced below:

(SEQ ID NO: 2)

```
   1 atattgtgct tccaccactg ccaataacaa aataactagc aaccatgaag tgggtggaat
  61 caattttttt aattttccta ctaaatttta ctgaatccag aacactgcat agaaatgaat
 121 atggaatagc ttccatattg gattcttacc aatgtactgc agagataagt ttagctgacc
 181 tggctaccat attttttgcc cagtttgttc aagaagccac ttacaaggaa gtaagcaaaa
 241 tggtgaaaga tgcattgact gcaattgaga aacccactgg agatgaacag tcttcagggt
 301 gtttagaaaa ccagctacct gcctttctgg aagaactttg ccatgagaaa gaaattttgg
 361 agaagtacgg acattcagac tgctgcagcc aaagtgaaga gggaagacat aactgttttc
 421 ttgcacacaa aaagcccact ccagcatcga tcccactttt ccaagttcca gaacctgtca
 481 caagctgtga agcatatgaa gaagacaggg agacattcat gaacaaattc atttatgaga
 541 tagcaagaag gcatcccttc ctgtatgcac ctacaattct tctttgggct gctcgctatg
 601 acaaaataat tccatcttgc tgcaaagctg aaaatgcagt tgaatgcttc caaacaaagg
 661 cagcaacagt tacaaaagaa ttaagagaaa gcagcttgtt aaatcaacat gcatgtgcag
 721 taatgaaaaa ttttgggacc cgaactttcc aagccataac tgttactaaa ctgagtcaga
 781 agtttaccaa agttaatttt actgaaatcc agaaactagt cctggatgtg gcccatgtac
 841 atgagcactg ttgcagagga gatgtgctgg attgtctgca ggatggggaa aaaatcatgt
 901 cctacatatg ttctcaacaa gacactctgt caaacaaaat aacagaatgc tgcaaactga
 961 ccacgctgga acgtggtcaa tgtataattc atgcagaaaa tgatgaaaaa cctgaaggtc
1021 tatctccaaa tctaaacagg tttttaggag atagagattt taaccaattt tcttcagggg
1081 aaaaaaatat cttcttggca agttttgttc atgaatattc aagaagacat cctcagcttg
1141 ctgtctcagt aattctaaga gttgctaaag gataccagga gttattggag aagtgtttcc
1201 agactgaaaa ccctcttgaa tgccaagata aaggagaaga agaattacag aaatacatcc
1261 aggagagcca agcattggca aagcgaagct gcggcctctt ccagaaacta ggagaatatt
1321 acttacaaaa tgcgtttctc gttgcttaca caaagaaagc cccccagctg acctcgtcgg
1381 agctgatggc catcaccaga aaaatggcag ccacagcagc cacttgttgc caactcagtg
1441 aggacaaact attggcctgt ggcgagggag cggctgacat tattatcgga cacttatgta
1501 tcagacatga aatgactcca gtaaaccctg gtgttggcca gtgctgcact tcttcatatg
1561 ccaacaggag gccatgcttc agcagcttgg tggtggatga aacatatgtc cctcctgcat
1621 tctctgatga caagttcatt ttccataagg atctgtgcca agctcagggt gtagcgctgc
1681 aaacgatgaa gcaagagttt ctcattaacc ttgtgaagca aaagccacaa ataacagagg
1741 aacaacttga ggctgtcatt gcagatttct caggcctgtt ggagaaatgc tgccaaggcc
1801 aggaacagga agtctgcttt gctgaagagg gacaaaaact gatttcaaaa actcgtgctg
1861 ctttgggagt ttaaattact tcaggggaag agaagacaaa acgagtcttt cattcggtgt
1921 gaacttttct ctttaatttt aactgattta acactttttg tgaattaatg aaatgataaa
1981 gacttttatg tgagatttcc ttatcacaga aataaaatat ctccaaatgt ttcctttca

2041 aaaaaaaaaa aaaaaaa
```

By "ALB polypeptide" or "albumin" is meant a protein or fragment thereof having at least 85% amino acid sequence identity to the sequence provided at NCBI Accession No. NP_000468.1 and having a biological activity of ALB polypeptide. Exemplary biological activities of ALB polypeptide include binding to fatty acids, calcium ions, sodium ions, potassium ions, hormones, and bilirubin; stabilization of extracellular fluid volume; and, transport of plasma zinc. The amino acid sequence provided at NCBI Accession No. NP_000468.1 is shown below:

(SEQ ID NO: 3)

```
1    mkwvtfisll flfssaysrg vfrrdahkse vahrfkdlge enfkalvlia faqylqqcpf
61   edhvklvnev tefaktcvad esaencdksl htlfgdklct vatlretyge madccakqep
121  ernecflqhk ddnpnlprlv rpevdvmcta fhdneetflk kylyeiarrh pyfyapellf
181  fakrykaaft eccqaadkaa cllpkldelr degkassakq rlkcaslqkf gerafkawav
241  arlsqrfpka efaevsklvt dltkvhtecc hgdllecadd radlakyice nqdsisskik
301  eccekpllek shciaevend empadlpsla adfveskdvc knyaeakdvf lgmflyeyar
361  rhpdysvvll lrlaktyett lekccaaadp hecyakvfde fkplveepqn likqncelfe
421  qlgeykfqna llvrytkkvp qvstptlvev srnlgkvgsk cckhpeakrm pcaedylsvv
481  lnqlcvlhek tpvsdrvtkc cteslvnrrp cfsalevdet yvpkefnaet ftfhadictl
541  sekergikkg talvelvkhk pkatkeqlka vmddfaafve kcckaddket cfaeegkklv
601  aasqaalgl
```

By "ALB polynucleotide" is meant a polynucleotide encoding a ALB polypeptide or fragment thereof. An exemplary AFP polynucleotide sequence is provided at NCBI Ref: NM_000477.5. The sequence provided at NCBI Ref: NM_000477.5 is reproduced below:

(SEQ ID NO: 4)

```
   1 agtatattag tgctaatttc cctccgtttg tcctagcttt tctcttctgt caaccccaca
  61 cgcctttggc acaatgaagt gggtaacctt tatttccctt ctttttctct ttagctcggc
 121 ttattccagg ggtgtgtttc gtcgagatgc acacaagagt gaggttgctc atcggtttaa
 181 agatttggga gaagaaaatt tcaaagcctt ggtgttgatt gcctttgctc agtatcttca
 241 gcagtgtcca tttgaagatc atgtaaaatt agtgaatgaa gtaactgaat ttgcaaaaac
 301 atgtgttgct gatgagtcag ctgaaaattg tgacaaatca cttcataccc tttttggaga
 361 caaattatgc acagttgcaa ctcttcgtga aacctatggt gaaatggctg actgctgtgc
 421 aaaacaagaa cctgagagaa atgaatgctt cttgcaacac aaagatgaca acccaaacct
 481 cccccgattg gtgagaccag aggttgatgt gatgtgcact gcttttcatg acaatgaaga
 541 gacatttttg aaaaaatact tatatgaaat tgccagaaga catccttact tttatgcccc
 601 ggaactcctt ttctttgcta aaaggtataa agctgctttt acagaatgtt gccaagctgc
 661 tgataaagct gcctgcctgt tgccaaagct cgatgaactt cgggatgaag ggaaggcttc
 721 gtctgccaaa cagagactca agtgtgccag tctccaaaaa tttggagaaa gagctttcaa
 781 agcatgggca gtagctcgcc tgagccagag atttcccaaa gctgagtttg cagaagtttc
 841 caagttagtg acagatctta ccaaagtcca cacggaatgc tgccatggag atctgcttga
 901 atgtgctgat gacagggcgg accttgccaa gtatatctgt gaaaatcaag attcgatctc
 961 cagtaaactg aaggaatgct gtgaaaaacc tctgttggaa aaatcccact gcattgccga
1021 agtggaaaat gatgagatgc ctgctgactt gccttcatta gctgctgatt ttgttgaaag
1081 taaggatgtt tgcaaaaact atgctgaggc aaaggatgtc ttcctgggca tgtttttgta
1141 tgaatatgca agaaggcatc ctgattactc tgtcgtgctg ctgctgagac ttgccaagac
1201 atatgaaacc actctagaga agtgctgtgc cgctgcagat cctcatgaat gctatgccaa
1261 agtgttcgat gaatttaaac ctcttgtgga agagcctcag aatttaatca aacaaaattg
1321 tgagcttttt gagcagcttg gagagtacaa attccagaat gcgctattag ttcgttacac
1381 caagaaagta ccccaagtgt caactccaac tcttgtagag gtctcaagaa acctaggaaa
```

-continued

```
1441 agtgggcagc aaatgttgta aacatcctga agcaaaaaga atgccctgtg cagaagacta
1501 tctatccgtg gtcctgaacc agttatgtgt gttgcatgag aaaacgccag taagtgacag
1561 agtcaccaaa tgctgcacag aatccttggt gaacaggcga ccatgctttt cagctctgga
1621 agtcgatgaa acatacgttc ccaaagagtt taatgctgaa acattcacct tccatgcaga
1681 tatatgcaca ctttctgaga aggagagaca aatcaagaaa caaactgcac ttgttgagct
1741 cgtgaaacac aagcccaagg caacaaaaga gcaactgaaa gctgttatgg atgatttcgc
1801 agcttttgta gagaagtgct gcaaggctga cgataaggag acctgctttg ccgaggaggg
1861 taaaaaactt gttgctgcaa gtcaagctgc cttaggctta taacatcaca tttaaaagca
1921 tctcagccta ccatgagaat aagagaaaga aaatgaagat caaaagctta ttcatctgtt
1981 tttcttttc gttggtgtaa agccaacacc ctgtctaaaa aacataaatt tctttaatca
2041 ttttgcctct tttctctgtg cttcaattaa taaaaaatgg aaagaatcta atagagtggt
2101 acagcactgt tatttttcaa agatgtgttg ctatcctgaa aattctgtag gttctgtgga
2161 agttccagtg ttctctctta ttccacttcg gtagaggatt tctagtttct tgtgggctaa
2221 ttaaataaat cattaatact cttctaaaaa aaaaaaaaaa aaaa
```

By “agent” is meant any small molecule chemical compound, antibody, nucleic acid molecule, or polypeptide, or fragments thereof.

By “ameliorate” is meant decrease, suppress, attenuate, diminish, arrest, or stabilize the development or progression of a disease.

By “altered” is meant an increase or decrease. An increase is any positive change, e.g., by at least about 5%, 10%, or 20%; by at least about 25%, 50%, 75%, or even by 100%, 200%, 300% or more. A decrease is a negative change, e.g., a decrease by at least about 5%, 10%, or 20%; by at least about 25%, 50%, 75%; or even an increase by 100%, 200%, 300% or more.

In this disclosure, “comprises,” “comprising,” “containing” and “having” and the like can have the meaning ascribed to them in U.S. Patent law and can mean “includes,” “including,” and the like; “consisting essentially of” or “consists essentially” likewise has the meaning ascribed in U.S. Patent law and the term is open-ended, allowing for the presence of more than that which is recited so long as basic or novel characteristics of that which is recited is not changed by the presence of more than that which is recited, but excludes prior art embodiments.

By “CDX2 polypeptide” is meant a protein or fragment thereof having at least 85% amino acid sequence identity to the sequence provided at NCBI Accession No. NP_001256.3 and having transcription factor activity. The amino acid sequence provided at NCBI Accession No. NP_001256.3 is shown below:

```
                                                          (SEQ ID NO: 5)
  1 myvsylldkd vsmypssvrh sgglnlapqn fvsppqypdy ggyhvaaaaa aaanldsaqs
 61 pgpswpaayg aplredwngy apggaaaaan avahglnggs paaamgyssp adyhphhhph
121 hhphhpaaap scasgllgtl npgppgpaat aaaeqlspgg qrrnlcewmr kpaqqslgsq
181 vktrtkdkyr vvytdhqrle lekefhysry itirrkaela atlglserqv kiwfqnrrak
241 erkinkkklq qqqqqqppqp pppppqppqp qpgplrsvpe plspvsslqa sysgsvpgvl
301 gptggvinpt vtq
```

By “CDX2 polynucleotide” is meant a polynucleotide encoding a CDX2 polypeptide or fragment thereof. An exemplary CDX2 polynucleotide sequence is provided at NCBI Ref: NM_001265.4. The sequence provided at NCBI Ref: NM_001265.4 is reproduced below:

```
                                                          (SEQ ID NO: 6)
  1 ctccaaccat tggtgtctgt gtcattacta atagagtctt gtaaacactc gttaatcacg
 61 gaaggccgcc ggcctggggc tccgcacgcc agcctgtggc gggtcttccc cgcctctgca
121 gcctagtggg aaggaggtgg gaggaaagaa ggaagaaagg gagggaggga ggaggcaggc
181 cagagggagg gaccgcctcg gaggcagaag agccgcgagg agccagcgga gcaccgcggg
241 ctggggcgca gccacccgcc gctcctcgag tcccctcgcc cctttccctt cgtgcccccc
```

-continued

```
301  ggcagcctcc agcgtcggtc cccaggcagc atggtgaggt ctgctcccgg accctcgcca
361  ccatgtacgt gagctacctc ctggacaagg acgtgagcat gtaccctagc tccgtgcgcc
421  actctggcgg cctcaacctg gcgccgcaga acttcgtcag ccccccgcag tacccggact
481  acggcggtta ccacgtggcg gccgcagctg cagcggcagc gaacttggac agcgcgcagt
541  ccccgggggcc atcctggccg gcagcgtatg gcgccccact ccgggaggac tggaatggct
601  acgcgcccgg aggcgccgcg gccgccgcca acgccgtggc tcacggcctc aacggtggct
661  ccccggccgc agccatgggc tacagcagcc ccgcagacta ccatccgcac caccacccgc
721  atcaccaccc gcaccacccg gccgccgcgc cttcctgcgc ttctgggctg ctgcaaacgc
781  tcaaccccgg ccctcctggg cccgccgcca ccgctgccgc cgagcagctg tctcccggcg
841  gccagcggcg gaacctgtgc gagtggatgc ggaagccggc gcagcagtcc ctcggcagcc
901  aagtgaaaac caggacgaaa gacaaatatc gagtggtgta cacggaccac cagcggctgg
961  agctggagaa ggagtttcac tacagtcgct acatcaccat ccggaggaaa gccgagctag
1021 ccgccacgct ggggctctct gagaggcagg ttaaaatctg gtttcagaac cgcagagcaa
1081 aggagaggaa aatcaacaag aagaagttgc agcagcaaca gcagcagcag ccaccacagc
1141 cgcctccgcc gccaccacag cctccccagc ctcagccagg tcctctgaga agtgtcccag
1201 agcccttgag tccggtgtct tccctgcaag cctcagtgtc tggctctgtc cctggggttc
1261 tggggccaac tgggggggtg ctaaacccca ccgtcaccca gtgacccacc gggttctgca
1321 gcggcagagc aattccaggc tgagccatga ggagcgtgga ctctgctaga ctcctcagga
1381 gagacccctc ccctcccacc cacagccata gacctacaga cctggctctc agaggaaaaa
1441 tgggagccag gagtaagaca agtgggattt ggggcctcaa gaaatatact ctcccagatt
1501 tttacttttt cccatctggc tttttctgcc actgaggaga cagaaagcct ccgctgggct
1561 tcattccgga ctggcagaag cattgcctgg actgaccaca ccaaccaggc cttcatcctc
1621 ctccccagct cttctcttcc tagatctgca ggctgcacct ctggctagag ccgaggggag
1681 agagggactc aagggaaagg caagcttgag gccaagatgg ctgctgcctg ctcatggccc
1741 tcggaggtcc agctgggcct cctgcctccg ggcaggcaag gtttacactg cggaagccaa
1801 aggcagctaa gatagaaagc tggactgacc aaagactgca gaaccccccag gtggcctgcg
1861 tctttttttct cttcccttcc cagaccagga aaggcttggc tggtgtatgc acagggtgtg
1921 gtatgagggg gtggttattg gactccaggc ctgaccaggg ggcccgaaca gggacttgtt
1981 tagagagcct gtcaccagag cttctctggg ctgaatgtat gtcagtgcta taaatgccag
2041 agccaacctg gacttcctgt cattttcaca atcttggggc tgatgaagaa gggggtgggg
2101 ggagtttgtg ttgttgttgc tgctgtttgg gttgttggtc tgtgtaacat ccaagccaga
2161 gtttttaaag ccttctggat ccatgggggg agaagtgata tggtgaaggg aagtggggag
2221 tatttgaaca cagttgaatt ttttctaaaa agaaaaagag ataaatgagc tttccagatt
2281 tcagattctg tatttatctt cagattttgt ctgcaactat tttttatttt ttaaagaaat
2341 gaaatatctt caaaaaaaaa aaaaaaaaaa
```

By "CYP3A7 polypeptide" or "cytochrome P450" is meant a protein or fragment thereof having at least 85% amino acid sequence identity to the sequence provided at NCBI Accession No. NP_000756.3 and having monooxygenase activity. The amino acid sequence provided at NCBI Accession No. NP_000756.3 is shown below:

```
                                                     (SEQ ID NO: 7)
  1  mdlipnlave twlllavsli llylygtrth glfkklgipg ptplpflgna lsfrkgywtf

 61  dmecykkyrk vwgiydcqqp mlaitdpdmi ktvlvkecys vftnrrpfgp vgfmknaisi

121  aedeewkrir sllsptftsg klkemvpiia qygdvlvrnl rreaetgkpv tlkhvfgays

181  mdvitstsfg vsidslnnpq dpfventkkl lrfnpldpfv lsikvfpflt pilealnitv

241  fprkvisflt ksvkqikegr lketqkhrvd flqlmidsqn skdsethkal sdlelmaqsi

301  ififagyett ssvlsfiiye lathpdvqqk vqkeidtvlp nkapptydtv lqleyldmvv

361  netlrlfpva mrlervckkd veingmfipk gvvvmipsyv lhhdpkywte pekflperfs

421  kknkdnidpy iytpfgsgpr ncigmrfalv nmklalvrvl qnfsfkpcke tqiplklrfg

481  gllltekpiv lkaesrdetv sga
```

By "CYP3A7 polynucleotide" is meant a polynucleotide encoding a CYP3A7 polypeptide or fragment thereof. An exemplary AFP polynucleotide sequence is provided at NCBI Ref: NM_000765.4. The sequence provided at NCBI Ref: NM_000765.4 is reproduced below:

```
                                                      (SEQ ID NO: 8)
   1 aatcactgct gtgcagggca ggaaagctcc acacacacag cccagcaaac agcagcacgc

  61 tgctgaaaaa aagactcaga ggagagagat aaggaaggaa agtagtgatg gatctcatcc

 121 caaacttggc cgtggaaacc tggcttctcc tggctgtcag cctgatactc ctctatctat

 181 atggaacccg tacacatgga ctttttaaga agcttggaat tccagggccc acacctctgc

 241 ctttttgggg aaatgctttg tccttccgta agggctattg gacgtttgac atggaatgtt

 301 ataaaaagta tagaaaagtc tggggtattt atgactgtca acagcctatg ctggctatca

 361 cagatcccga catgatcaaa acagtgctag tgaaagaatg ttattctgtc ttcacaaacc

 421 ggaggccttt cgggccagtg ggatttatga aaaatgccat ctctatagct gaggatgaag

 481 aatggaagag aatacgatca ttgctgtctc caacattcac cagcggaaaa ctcaaggaga

 541 tggtccctat cattgcccag tatggagatg tgttggtgag aaatctgagg cgggaagcag

 601 agacaggcaa gcctgtcacc ttgaaacacg tctttggggc ctacagcatg gatgtgatca

 661 ctagcacatc atttggagtg agcatcgact ctctcaacaa tccacaagac ccctttgtgg

 721 aaaacaccaa gaagctttta agatttaatc cattagatcc attcgttctc tcaataaaag

 781 tctttccatt ccttacccca attcttgaag cattaaatat cactgtgttt ccaagaaaag

 841 ttataagttt tctaacaaaa tctgtaaaac agataaaaga aggtcgcctc aaagagacac

 901 aaaagcaccg agtggatttc cttcagctga tgattgactc tcagaattca aaagactctg

 961 agacccacaa agctctgtct gatctggagc tcatggccca atcaattatc tttatttttg

1021 ctggctatga aaccacgagc agtgttctct ccttcattat atatgaactg gccactcacc

1081 ctgatgtcca gcagaaagtg cagaaggaaa ttgatacagt tttacccaat aaggcaccac

1141 ccacctatga tactgtgcta cagttggagt atcttgacat ggtggtgaat gaaacactca

1201 gattattccc agttgctatg agacttgaga gggtctgcaa aaaagatgtt gaaatcaatg

1261 ggatgtttat tcccaaaggg gtggtggtga tgattccaag ctatgttctt catcatgacc

1321 caaagtactg gacagagcct gagaagttcc tccctgaaag gttcagtaaa aagaacaagg

1381 acaacataga tccttacata tacacaccct ttggaagtgg acccagaaac tgcattggca
```

-continued

```
1441 tgaggtttgc tctcgtgaac atgaaacttg ctctagtcag agtccttcag aacttctcct
1501 tcaaaccttg taaagaaaca cagatccccc tgaaattacg ctttggagga cttcttctaa
1561 cagaaaaacc cattgttcta aaggctgagt caagggatga gaccgtaagt ggagcctgat
1621 ttccctaagg acttctggtt tgctctttaa gaaagctgtg ccccagaaca ccagagacct
1681 caaattactt tacaaataga accctgaaat gaagacgggc ttcatccaat gtgctgcata
1741 aataatcagg gattctgtac gtgcattgtg ctctctcatg gtctgtatag agtgttatac
1801 ttggtaatat agaggagatg accaaatcag tgctggggaa gtagatttgg cttctctgct
1861 tctcatagga ctatctccac cacccccagt tagcaccatt aactcctcct gagctctgat
1921 aacataatta acatttctca ataatttcaa ccacaatcat taataaaaat aggaattatt
1981 ttgatggctc taacagtgac atttatatca tgtgttatat ctgtagtatt ctatagtaag
2041 ctttatatta agcaaatcaa taaaaacctc tttacaaaag taaaaaaaaa aaaaaaaaa
```

"Detect" refers to identifying the presence, absence or amount of the analyte to be detected.

By "detectable label" is meant a composition that when linked to a molecule of interest renders the latter detectable, via spectroscopic, photochemical, biochemical, immunochemical, or chemical means. For example, useful labels include radioactive isotopes, magnetic beads, metallic beads, colloidal particles, fluorescent dyes, electron-dense reagents, enzymes (for example, as commonly used in an ELISA), biotin, digoxigenin, or haptens.

"Differentiation" refers to the developmental process of lineage commitment. Differentiation can be assayed by measuring an increase in one or more cell specific markers relative to their expression in a corresponding undifferentiated control cell. A "lineage" refers to a pathway of cellular development, in which precursor or "progenitor" cells undergo progressive physiological changes to become a specified cell type having a characteristic function. In some embodiments, the cell type is a beta cell. In some embodiments, the cell type is an alpha cell, delta cell, or duct cell. In some other embodiments, the cell type is a hepatocyte. In still other embodiments, the cell type is a cardiomyocyte. In some embodiments, the cell type is a intestinal cell. Differentiation occurs in stages, whereby cells gradually become more specified until they reach full maturity, which is also referred to as "terminal differentiation." A "terminally differentiated cell" is a cell that has committed to a specific lineage, and has reached the end stage of differentiation (i.e., a cell that has fully matured). In some embodiments, an induced pluripotent stem cell (iPSC) is differentiated into a beta-like cell, an alpha-like cell, a delta-like cell, or a duct-like cell. In some other embodiments, an induced pluripotent stem cell (iPSC) is differentiated into a hepatocyte, cardiomyocyte, or intestinal cell.

A "de-differentiated cell" is a cell in which the process of differentiation has been, at least to some degree, reversed. De-differentiation can be assayed, for example, by identifying a reduction in the expression of one or more cell specific markers relative to their expression in a corresponding control cell. Alternatively, de-differentiation can be assayed by measuring an increase in one or more markers typically expressed in an embryonic stem cell, a pluripotent or multi-potent cell type, or expressed at an earlier stage of development. In some embodiments, the de-differentiated cell is an induced pluripotent stem cell (iPSC). In certain embodiments, the de-differentiated cell is a human induced pluripotent stem cell (iPSC).

By "disease" is meant any condition or disorder that damages or interferes with the normal function of a cell, tissue, or organ. Examples of diseases include type 1 diabetes, type 2 diabetes, and pancreatic cancer.

By "effective amount" is meant the amount of a therapeutic agent or organoid required to ameliorate the symptoms of a disease in a subject relative to an untreated subject. The effective amount of a therapeutic used to practice the present invention for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount. In some embodiments, the therapeutic organoid is a pancreatic islet organoid. In some other embodiments, an effective amount of a pancreatic islet organoid is administered to a subject having type 1 or type 2 diabetes.

By "ESRRG polypeptide" is meant a protein or fragment thereof having at least 85% amino acid sequence identity to the sequence provided at NCBI Accession No. NP_001230448.1 and having nuclear hormone receptor activity. The amino acid sequence provided at NCBI Accession No. NP_001230448.1 is shown below:

```
                                                      (SEQ ID NO: 9)
  1 msnkdrhids scssfiktep sspasltdsv nhhspggssd asgsysstmn ghqngldspp
 61 lypsapilgg sgpvrklydd csstivedpq tkceymlnsm pkrlclvcgd iasgyhygva
121 sceackaffk rtiqgnieys cpatneceit krrrkscqac rfmkclkvgm lkegvrldrv
181 rggrqkykrr idaenspyln pqlvqpakkp ynkivshllv aepekiyamp dptvpdsdik
241 altticdlad relvviigwa khipgfstls ladqmsllqs awmeililgv vyrslsfede
```

-continued

```
301 lvyaddyimd edqsklagll dlnnailqlv kkyksmklek eefvtlkaia lansdsmhie

361 dveavqklqd vlhealqdye agqhmedprr agkmlmtlpl lrgtstkavq hfyniklegk

421 vpmhklflem leakv
```

By “ESRRG polynucleotide” is meant a polynucleotide encoding a ESRRG polypeptide or fragment thereof. An exemplary ESRRG polynucleotide sequence is provided at NCBI Ref: NM_001243519.1. The sequence provided at NCBI Ref: NM_001243519.1 is reproduced below:

```
                                                   (SEQ ID NO: 10)
   1 aagctccaat cggggcttta agtccttgat taggagagtg tgagagcttt ggtcccaact

  61 ggctgtgcct ataggcttgt cactaggaga acatttgtgt taattgcact gtgctctgtc

 121 aaggaaactt tgatttatag ctggggtgca caaataatgg ttgccggtcg cacatggatt

 181 cggtagaact ttgccttcct gaatcttttt ccctgcacta cgaggaagag tagacttgaa

 241 tgagacctgc ctcatcagtc atgggatcat agtgtcacag atggaaaagc aactatcagc

 301 tgaattgtac tgaactacac acttggctaa ttcatcttat tgctctacac atctaaagga

 361 aggctcattc tgttcttgga gtctagacag catcaggagt tgggctcagt gaacaaaact

 421 ttaatgtcta gagcatttat gagggtttta atgattggaa aatctatcct gagaatgtgg

 481 tcaccatatg tgacagcctt gctttctatc ttgtcttcag tttctggggc ttctctgcag

 541 aatgtcaaac aaagatcgac acattgattc cagctgttcg tccttcatca agacggaacc

 601 ttccagccca gcctccctga cggacagcgt caaccaccac agccctggtg gctcttcaga

 661 cgccagtggg agctacagtt caaccatgaa tggccatcag aacggacttg actcgccacc

 721 tctctaccct tctgctccta tcctgggagg tagtgggcct gtcaggaaac tgtatgatga

 781 ctgctccagc accattgttg aagatcccca gaccaagtgt gaatacatgc tcaactcgat

 841 gcccaagaga ctgtgtttag tgtgtggtga catcgcttct gggtaccact atggggtagc

 901 atcatgtgaa gcctgcaagg cattcttcaa gaggacaatt caaggcaata tagaatacag

 961 ctgccctgcc acgaatgaat gtgaaatcac aaagcgcaga cgtaaatcct gccaggcttg

1021 ccgcttcatg aagtgtttaa aagtgggcat gctgaaagaa ggggtgcgtc ttgacagagt

1081 acgtggaggt cggcagaagt acaagcgcag gatagatgcg gagaacagcc catacctgaa

1141 ccctcagctg gttcagccag ccaaaaagcc atataacaag attgtctcac atttgttggt

1201 ggctgaaccg gagaagatct atgccatgcc tgaccctact gtccccgaca gtgacatcaa

1261 agccctcact acactgtgtg acttggccga ccgagagttg gtggttatca ttggatgggc

1321 gaagcatatt ccaggcttct ccacgctgtc cctggcggac cagatgagcc ttctgcagag

1381 tgcttggatg gaaattttga tccttggtgt cgtataccgg tctctttcgt ttgaggatga

1441 acttgtctat gcagacgatt atataatgga cgaagaccag tccaaattag caggccttct

1501 tgatctaaat aatgctatcc tgcagctggt aaagaaatac aagagcatga agctggaaaa

1561 agaagaattt gtcaccctca aagctatagc tcttgctaat tcagactcca tgcacataga

1621 agatgttgaa gccgttcaga agcttcagga tgtcttacat gaagcgctgc aggattatga

1681 agctggccag cacatggaag accctcgtcg agctggcaag atgctgatga cactgccact

1741 cctgaggcag acctctacca aggccgtgca gcatttctac aacatcaaac tagaaggcaa

1801 agtcccaatg cacaaacttt ttttggaaat gttggaggcc aaggtctgac taaaagctcc

1861 ctgggccttc ccatccttca tgttgaaaaa gggaaaataa acccaagagt gatgtcgaag
```

-continued 1921 aaacttagag tttagttaac aacatcaaaa atcaacagac tgcactgata atttagcagc 1981 aagactatga agcagctttc agattcctcc ataggttcct gatgagtttc tttctacttt 2041 ctccatcatc ttctttcctc tttcttccca catttctctt tctctttatt ttttctcctt 2101 ttcttctttc acctccctta tttctttgct tctttcattc ctagttccca ttctccttta 2161 ttttcttccc gtctgcctgc cttctttctt ttctttacct actctcattc ctctcttttc 2221 tcatccttcc cctttttttct aaatttgaaa tagctttagt ttaaaaaaaa atcctccctt 2281 ccccctttcc tttccctttc tttcctttt ccctttcctt ttccctttcc tttcctttcc 2341 tcttgacctt ctttccatct ttctttttct tccttctgct gctgaacttt taaaagaggt 2401 ctctaactga agagagatgg aagccagccc tgccaaagga tggagatcca taatatggat 2461 gccagtgaac ttattgtgaa ccatactgtc cccaatgact aaggaatcaa agagagagaa 2521 ccaacgttcc taaaagtaca gtgcaacata tacaaattga ctgagtgcag tattagattt 2581 catgggagca gcctctaatt agacaactta agcaacgttg catcggctgc ttcttatcat 2641 tgcttttcca tctagatcag ttacagccat ttgattcctt aattgttttt tcaagtcttc 2701 caggtatttg ttagtttagc tactatgtaa ctttttcagg gaatagttta agctttattc 2761 attcatgcaa tactaaagag aaataagaat actgcaattt tgtgctggct ttgaacaatt 2821 acgaacaata atgaaggaca aatgaatcct gaaggaagat ttttaaaaat gttttgtttc 2881 ttcttacaaa tggagatttt tttgtaccag ctttaccact tttcagccat ttattaatat 2941 gggaatttaa cttactcaag caatagttga agggaaggtg catattatca cggatgcaat 3001 ttatgttgtg tgccagtctg gtcccaaaca tcaatttctt aacatgagct ccagtttacc 3061 taaatgttca ctgacacaaa ggatgagatt acacctacag tgactctgag tagtcacata 3121 tataagcact gcacatgaga tatagatccg tagaattgtc aggagtgcac ctctctactt 3181 gggaggtaca attgccatat gatttctagc tgccatggtg gttaggaatg tgatactgcc 3241 tgtttgcaaa gtcacagacc ttgcctcaga aggagctgtg agccagtatt catttaagag 3301 gcaataaggc aaatgccaga attaaaaaaa aaaatcatca aagacagaaa atgcctgacc 3361 aaattctaaa acctaatcca tataagttta ttcatttagg aatgttcgtt taaattaatc 3421 tgcagttttt accaagagct aagccaatat atgtgctttt caaccagtat tgtcacagca 3481 tgaaagtcaa gtcaggttcc agactgttaa gaggtgtaat ctaatgaaga aatcaattag 3541 atgccccgaa atctacagtc gctgaataac caataaacag taacctccat caaatgctat 3601 accaatggac cagtgttagt agctgctccc tgtattatgt gaacagtctt attctatgta 3661 cacagatgta attaaaattg taatcctaac aaacaaaaga aatgtagttc agcttttcaa 3721 tgtttcatgt ttgctgtgct tttctgaatt ttatgttgca ttcaaagact gttgtcttgt 3781 tcttgtggtg tttggattct tgtggtgtgt gcttttagac acagggtaga attagagaca 3841 atattggatg tacaattcct caggagacta cagtagtata ttctattcct taccagtaat 3901 aaggttcttc ctaataataa ttaagagatt gaaactccaa acaagtattc attatgaaca 3961 gatacacatc aaaatcataa taatattttc aaaacaagga ataatttctc taatggttta 4021 ttatagaata ccaatgtata gcttagaaat aaaactttga atatttcaag aatatagata 4081 agtctaattt ttaaatgctg tatatatggc tttcactcaa tcatctctca gatgttgtta 4141 ttaactcgct ctgtgttgtt gcaaaacttt ttggtgcaga ttcgtttcca aaactattgc 4201 tactttgtgt gctttaaaca aaataccttg ggttgatgaa acatcaaccc agtgctagga 4261 atactgtgta tctatcatta gctatatggg actatattgt agattgtggt ttctcagtag 4321 agaagtgact gtagtgtgat tctagataaa tcatcattag caattcattc agatggtcaa -continued

```
4381 taacttgaaa tttatagctg tgataggagt tcagaaattg gcacatccct ttaaaaataa
4441 caacagaaaa tacaactcct gggaaaaaag gtgctgattc tataagatta tttatatatg
4501 taagtgttta aaaagattat tttccagaaa gtttgtgcag ggtttaagtt gctactattc
4561 aactacacta tatataaata aaatatatac aatatataca ttgttttcac tgtatcacat
4621 taaagtactt gggcttcaga agtaagagcc aaccaactga aaacctgaga tggagatatg
4681 ttcaaagaat gagatacaat tttttagttt tcagtttaag taactctcag cattacaaaa
4741 gagtaagtat ctcacaaata ggaaataaaa ctaaaacgtg gatttaaaaa gaactgcacg
4801 ggctttaggg taaatgctca tcttaaacct cactagaggg aagtcttctc aagtttcaag
4861 caagaccatt tacttaatgt gaagttttgg aaagttataa aggtgtatgt tttagccata
4921 tgattttaat tttaattttg cttcttttag gttcgttctt atttaaagca atatgattgt
4981 gtgactcctt gtagttacac ttgtgtttca atcagatcag attgttgtat ttattccact
5041 attttgcatt taaatgataa cataaaagat ataaaaaatt taaaactgct atttttctta
5101 tagaagagaa aatgggtgtt ggtgattgta ttttaattat ttaagcgtct ctgtttacct
5161 gcctaggaaa acattttatg gcagtcttat gtgcaaagat cgtaaaagga caaaaaattt
5221 aaactgctta taataatcca ggagttgcat tatagccagt agtaaaaata ataataataa
5281 taataaaacc atgtctatag ctgtagatgg gcttcacatc tgtaaagcaa tcaattgtat
5341 atttttgtga tgtgtaccat actgtgtgct ccagcaaatg tccatttgtg taaatgtatt
5401 tattttatat tgtatatatt gttaaatgca aaaaggagat atgattctgt aactccaatc
5461 agttcagatg tgtaactcaa attattatgc ctttcaggat gatggtagag caatattaaa
5521 caagcttcca cttttgactg ctaaaaaaaa aaaaaaaaa
```

As used herein, “endocrine” refers to secretion of an agent (e.g., a hormone) into a bloodstream. “Exocrine” refers to secretion of an agent into an epithelial surface by way of a duct.

By “fragment” is meant a portion of a polypeptide or nucleic acid molecule. This portion contains at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

By “FOXA2 polypeptide” is meant a protein or fragment thereof having at least 85% amino acid sequence identity to the sequence provided at NCBI Accession No. NP_068556.2 and having transcription factor activity. The amino acid sequence provided at NCBI Accession No. NP_068556.2 is shown below:

```
                                                    (SEQ ID NO: 11)
  1 mhsassmlga vkmeghepsd wssyyaepeg yssvsnmnag lgmngmntym smsaaamgsg
 61 sgnmsagsmn mssyvgagms pslagmspga gamagmggsa gaagvagmgp hlspslsplg
121 gqaagamggl apyanmnsms pmygqaglsr ardpktyrrs ythakppysy islitmaigq
181 spnkmltlse iyqwimdlfp fyrqnqqrwq nsirhslsfn dcflkvprsp dkpgkgsfwt
241 lhpdsgnmfe ngcylrrqkr fkcekqlalk eaagaagsgk kaaagagasq aqlgeaagpa
301 setpagtesp hssaspcqeh krgglgelkg tpaaalsppe papspgqqqq aaahllgpph
361 hpglppeahl kpehhyafnh pfsinnlmss eqqhhhshhh hqphkmdlka yeqvmhypgy
421 gspmpgslam gpvtnktgld asplaadtsy yqgvysrpim nss
```

By "FOXA2 polynucleotide" is meant a polynucleotide encoding a FOXA2 polypeptide or fragment thereof. An exemplary FOXA2 polynucleotide sequence is provided at NCBI Ref: NM_021784.4. The sequence provided at NCBI Ref: NM_021784.4 is reproduced below:

```
                                                   (SEQ ID NO: 12)
   1 cccgcccact tccaactacc gcctccggcc tgcccaggga gagagaggga gtggagccca

  61 gggagaggga gcgcgagaga gggagggagg aggggacggt gctttggctg actttttttt

 121 aaaagagggt gggggtgggg ggtgattgct ggtcgtttgt tgtggctgtt aaattttaaa

 181 ctgccatgca ctcggcttcc agtatgctgg gagcggtgaa gatggaaggg cacgagccgt

 241 ccgactggag cagctactat gcagagcccg agggctactc ctccgtgagc aacatgaacg

 301 ccggcctggg gatgaacggc atgaacacgt acatgagcat gtcggcggcc gccatgggca

 361 gcggctcggg caacatgagc gcgggctcca tgaacatgtc gtcgtacgtg ggcgctggca

 421 tgagcccgtc cctggcgggg atgtcccccg gcgcgggcgc catggcgggc atgggcggct

 481 cggccggggc ggccggcgtg gcgggcatgg ggccgcactt gagtcccagc ctgagcccgc

 541 tcggggggca ggcggccggg gccatgggcg gcctggcccc ctacgccaac atgaactcca

 601 tgagccccat gtacgggcag gcgggcctga gccgcgcccg cgaccccaag acctacaggc

 661 gcagctacac gcacgcaaag ccgccctact cgtacatctc gctcatcacc atggccatcc

 721 agcagagccc caacaagatg ctgacgctga gcgagatcta ccagtggatc atggacctct

 781 tccccttcta ccggcagaac cagcagcgct ggcagaactc catccgccac tcgctctcct

 841 tcaacgactg tttcctgaag gtgccccgct cgcccgacaa gcccggcaag ggctccttct

 901 ggaccctgca ccctgactcg ggcaacatgt tcgagaacgg ctgctacctg cgccgccaga

 961 agcgcttcaa gtgcgagaag cagctggcgc tgaaggaggc cgcaggcgcc gccggcagcg

1021 gcaagaaggc ggccgccgga gcccaggcct cacaggctca actcggggag gccgccgggc

1081 cggcctccga gactccggcg ggcaccgagt cgcctcactc gagcgcctcc ccgtgccagg

1141 agcacaagcg agggggcctg ggagagctga aggggacgcc ggctgcggcg ctgagccccc

1201 cagagccggc gccctctccc gggcagcagc agcaggccgc ggcccacctg ctgggcccgc

1261 cccaccaccc gggcctgccg cctgaggccc acctgaagcc ggaacaccac tacgccttca

1321 accacccgtt ctccatcaac aacctcatgt cctcggagca gcagcaccac cacagccacc

1381 accaccacca accccacaaa atggacctca aggcctacga acaggtgatg cactaccccg

1441 gctacggttc ccccatgcct ggcagcttgg ccatgggccc ggtcacgaac aaaacgggcc

1501 tggacgcctc gcccctggcc gcagatacct cctactacca gggggtgtac tcccggccca

1561 ttatgaactc ctcttaagaa gacgacggct tcaggcccgg ctaactctgg caccccggat

1621 cgaggacaag tgagagagca agtgggggtc gagactttgg ggagacggtg ttgcagagac

1681 gcaagggaga agaaatccat aacaccccca ccccaacacc cccaagacag cagtcttctt

1741 cacccgctgc agccgttccg tcccaaacag agggccacac agataccccca cgttctatat

1801 aaggaggaaa acgggaaaga atataaagtt aaaaaaaagc ctccggtttc cactactgtg

1861 tagactcctg cttcttcaag cacctgcaga ttctgatttt tttgttgttg ttgttctcct

1921 ccattgctgt tgttgcaggg aagtcttact taaaaaaaaa aaaaaatttt gtgagtgact

1981 cggtgtaaaa ccatgtagtt ttaacagaac cagagggttg tactattgtt taaaaacagg

2041 aaaaaaaata atgtaagggt ctgttgtaaa tgaccaagaa aaagaaaaaa aaagcattcc

2101 caatcttgac acggtgaaat ccaggtctcg ggtccgatta atttatggtt tctgcgtgct

2161 ttatttatgg cttataaatg tgtattctgg ctgcaagggc cagagttcca caaatctata
```

-continued 2221 ttaaagtgtt atacccggtt ttatcccttg aatcttttct tccagatttt tcttttcttt 2281 acttggctta caaaatatac aggcttggaa attatttcaa gaaggaggga gggataccct 2341 gtctggttgc aggttgtatt ttattttggc ccagggagtg ttgctgtttt cccaacattt 2401 tattaataaa attttcagac ataaaaaa By "GATA6 polypeptide" is meant a protein or fragment thereof having at least 85% amino acid sequence identity to the sequence provided at NCBI Accession No. NP_005248.2 and having transcription factor activity. The amino acid sequence provided at NCBI Accession No. NP_005248.2 is shown below:

(SEQ ID NO: 13)

1 maltdggwcl pkrfgaagad asdsrafpar epstppspis ssssscsrgg ergpggasnc 61 gtpqldteaa agpparslll ssyashpfga phgpsapgva gpggnlsswe dlllftdldq 121 aataskllws srgaklspfa peqpeemyqt laalssqgpa aydgapggfv hsaaaaaaaa 181 aaasspvyvp ttrvgsmlpg lpyhlqgsgs gpanhaggag ahpgwpqasa dsppygsggg 241 aagggaagpg gagsaaahvs arfpyspspp mangaarepg gyaaagsgga ggvsgggssl 301 aamggrepqy sslsaarpln gtyhhhhhhh hhhpspyspy vgapltpawp agpfetpvlh 361 slqsragapl pvprgpsadl ledlsesrec vncgsiqtpl wrrdgtghyl cnacglyskm 421 nglsrplikp qkrvpssrrl glscanchtt tttlwrrnae gepvcnacgl ymklhgvprp 481 lamkkegiqt rkrkpknink sktcsgnsnn sipmtptsts snsddcsknt spttqptasg 541 agapvmtgag estnpensel kysgqdglyi gvslaspaev tssvrpdswc alala By "GATA6 polynucleotide" is meant a polynucleotide encoding a GATA6 polypeptide or fragment thereof. An exemplary KCNK3 polynucleotide sequence is provided at NCBI Ref: NM_005257.5. The sequence provided at NCBI Ref: NM_005257.5 is reproduced below:

(SEQ ID NO: 14)

1 agttccgacc cacagcctgg caccccttcgg cgagcgctgt ttgtttaggg ctcggtgagt 61 ccaatcagga gcccaggctg cagttttccg gcagagcagt aagaggcgcc tcctctctcc 121 tttttattca ccagcagcgc ggcgcagacc ccggactcgc gctcgcccgc tggcgccctc 181 ggcttctctc cgcgcctggg agcaccctcc gccgcggccg ttctccatgc gcagcgcccg 241 cccgaggagc tagacgtcag cttggagcgg cgccggaccg tggatggcct tgactgacgg 301 cggctggtgc ttgccgaagc gcttcggggc cgcgggtgcg gacgccagcg actccagagc 361 ctttccagcg cgggagccct ccacgccgcc ttccccccatc tcttcctcgt cctcctcctg 421 ctcccggggc ggagagcggg gccccggcgg cgccagcaac tgcgggacgc ctcagctcga 481 cacggaggcg gcggccggac ccccggcccg ctcgctgctg ctcagttcct acgcttcgca 541 tcccttcggg gctccccacg gaccttcggc gcctggggtc gcgggccccg ggggcaacct 601 gtcgagctgg gaggacttgc tgctgttcac tgacctcgac caagccgcga ccgccagcaa 661 gctgctgtgg tccagccgcg gcgccaagct gagccccttc gcacccgagc agccggagga 721 gatgtaccag accctcgccg ctctctccag ccagggtccg gccgcctacg acggcgcgcc 781 cggcggcttc gtgcactctg cggccgcggc ggcagcagcc gcggcggcgg ccagctcccc 841 ggtctacgtg cccaccaccc gcgtgggttc catgctgccc ggcctaccgt accacctgca 901 ggggtcgggc agtgggccag ccaaccacgc gggcggcgcg ggcgcgcacc ccggctggcc 961 tcaggcctcg gccgacagcc ctccatacgg cagcggaggc ggcgcggctg gcggcggggc -continued 1021 cgcggggcct ggcggcgctg gctcagccgc ggcgcacgtc tcggcgcgct tcccctactc 1081 tcccagcccg cccatggcca acggcgccgc gcgggagccg ggaggctacg cggcggcggg 1141 cagtgggggc gcgggaggcg tgagcggcgg cggcagtagc ctggcggcca tgggcggccg 1201 cgagccccag tacagctcgc tgtcggccgc gcggccgctg aacgggacgt accaccacca 1261 ccaccaccac caccaccacc atccgagccc ctactcgccc tacgtggggg cgccactgac 1321 gcctgcctgg cccgccggac ccttcgagac ccggtgctg cacagcctgc agagccgcgc 1381 cggagccccg ctcccggtgc cccggggtcc cagtgcagac ctgctggagg acctgtccga 1441 gagccgcgag tgcgtgaact gcggctccat ccagacgccg ctgtggcggc gggacggcac 1501 cggccactac ctgtgcaacg cctgcgggct ctacagcaag atgaacggcc tcagccggcc 1561 cctcatcaag ccgcagaagc gcgtgccttc atcacggcgg cttggattgt cctgtgccaa 1621 ctgtcacacc acaactacca ccttatggcg cagaaacgcc gagggtgaac ccgtgtgcaa 1681 tgcttgtgga ctctacatga aactccatgg ggtgcccaga ccacttgcta tgaaaaaaga 1741 gggaattcaa accaggaaac gaaaacctaa gaacataaat aaatcaaaga cttgctctgg 1801 taatagcaat aattccattc ccatgactcc aacttccacc tcttctaact cagatgattg 1861 cagcaaaaat acttccccca caacacaacc tacagcctca ggggcgggtg ccccggtgat 1921 gactggtgcg ggagagagca ccaatcccga gaacagcgag ctcaagtatt cgggtcaaga 1981 tgggctctac ataggcgtca gtctcgcctc gccggccgaa gtcacgtcct ccgtgcgacc 2041 ggattcctgg tgcgccctgg ccctggcctg agcccacgcc gccaggaggc agggagggct 2101 ccgccgcggg cctcactcca ctcgtgtctg cttttgtgca gcggtccaga cagtggcgac 2161 tgcgctgaca gaacgtgatt ctcgtgcctt tattttgaaa gagatgtttt tcccaagagg 2221 cttgctgaaa gagtgagaga agatggaagg gaagggccag tgcaactggg cgcttgggcc 2281 actccagcca gcccgcctcc ggggcggacc ctgctccact tccagaagcc aggactagga 2341 cctgggcctt gcctgctatg gaatattgag agagattttt taaaaaagat tttgcatttt 2401 gtccaaaatc atgtgcttct tctgatcaat tttggttgtt ccagaatttc ttcatacctt 2461 ttccacatcc agatttcatg tgcgttcatg gagaagatca cttgaggcca tttggtacac 2521 atctctggag gctgagtcgg ttcatgaggt ctcttatcaa aaatattact cagtttgcaa 2581 gactgcattg taactttaac atacactgtg actgacgttt ctcaaagttc atattgtgtg 2641 gctgatctga agtcagtcgg aatttgtaaa cagggtagca aacaagatat ttttcttcca 2701 tgtatacaat aatttttttta aaaagtgcaa tttgcgttgc agcaatcagt gttaaatcat 2761 ttgcataaga tttaacagca ttttttataa tgaatgtaaa cattttaact taatggtact 2821 taaaataatt taaaagaaaa atgttaactt agacattctt atgcttcttt tacaactaca 2881 tcccatttta tatttccaat tgttaaagaa aaatatttca agaacaaatc ttctctcagg 2941 aaaattgcct ttctctattt gttaagaatt tttatacaag aacaccaata taccccccttt 3001 attttactgt ggaatatgtg ctggaaaaat tgcaacaaca ctttactacc taacggatag 3061 catttgtaaa tactctaggt atctgtaaac actctgatga agtctgtata gtgtgactaa 3121 cccacaggca ggttggttta cattaatttt tttttgaa tgggatgtcc tatggaaacc 3181 tatttcacca gagttttaaa aataaaaagg gtattgtttt gtcttctgta cagtgagttc 3241 cttccctttt caaagctttc tttttatgct gtatgtgact atagatattc atataaaaca 3301 agtgcacgtg aagtttgcaa aatgctttaa ggccttcctt tcaaagcata gtccttttgg 3361 agccgttttg taccttttat accttggctt atttgaagtt gacacatggg gttagttact 3421 actctccatg tgcattgggg acagtttta taagtgggaa ggactcagta ttattatatt -continued

```
3481 tgagatgata agcattttgt ttgggaacaa tgcttaaaaa tattccagaa agttcagatt

3541 ttttttcttt gtgaatgaaa tatattctgg cccacgaaca gggcgatttc ctttcagttt

3601 tttccttttg caacgtgcct tgaagtctca aagctcacct gaggttgcag acgttacccc

3661 caacagaaga taggtagaaa tgattccagt ggcctctttg tattttcttc attgttgagt

3721 agatttcagg aaatcaggag gtgtttcaca atacagaatg atggccttta actgtgaaaa

3781 aaaaa
```

By "gellan gum" is meant a polysaccharide having a straight chain with a repeating unit that has any one of the following molecular structures:

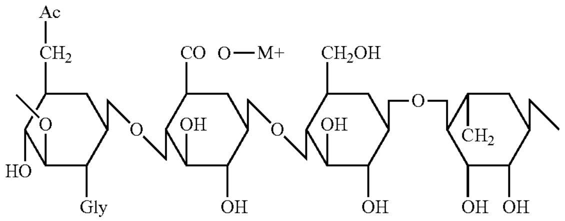

Gellan gum - high acyl form

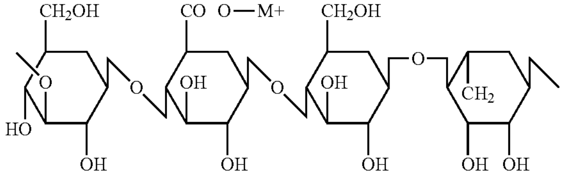

Gellan gum - low acyl form

In the foregoing structures, "Ac" refers to an acetate group and "Gly" refers to a glycerate group and "M+" is a monovalent cation. In some embodiments, the gellan gum is KELCOGEL® gellan gum.

"Hybridization" means hydrogen bonding, which may be Watson-Crick, Hoogsteen or reversed Hoogsteen hydrogen bonding, between complementary nucleobases. For example, adenine and thymine are complementary nucleobases that pair through the formation of hydrogen bonds.

By "immunosuppressive agent" or "immunosuppressant" is meant an agent that inhibits or prevents an immune reaction, such as rejection, of a transplanted organ or organoid in a subject. Examples of immunosuppressants include, but are not limited to, basilizimab, antithymocyte globulin, alemtuzumab, prednisone, azathioprine, mycophenolate, cyclosporine, sirolimus, methotrexate, interferon, and tacrolimus.

By "induced pluripotent stem cell" or "iPSC" is meant a differentiated somatic cell that acquires pluripotency by the exogenous expression of one or more transcription factors in the cell. An "iPSC-derived cell" is a cell derived from an induced pluripotent stem cell. An "iPSC-derived beta-like cell," "iPSC-derived alpha-like cell," "iPSC-derived delta-like cell," or "iPSC-derived duct-like cell" is a cell derived from an induced pluripotent stem cell and has characteristics of a beta cell, alpha cell, delta cell, or duct cell, respectively.

The terms "isolated," "purified," or "biologically pure" refer to material that is free to varying degrees from components which normally accompany it as found in its native state. "Isolate" denotes a degree of separation from original source or surroundings. "Purify" denotes a degree of separation that is higher than isolation. A "purified" or "biologically pure" protein is sufficiently free of other materials such that any impurities do not materially affect the biological properties of the protein or cause other adverse consequences. That is, a nucleic acid or peptide of this invention is purified if it is substantially free of cellular material, viral material, or culture medium when produced by recombinant DNA techniques, or chemical precursors or other chemicals when chemically synthesized. Purity and homogeneity are typically determined using analytical chemistry techniques, for example, polyacrylamide gel electrophoresis or high performance liquid chromatography. The term "purified" can denote that a nucleic acid or protein gives rise to essentially one band in an electrophoretic gel. For a protein that can be subjected to modifications, for example, phosphorylation or glycosylation, different modifications may give rise to different isolated proteins, which can be separately purified.

By "isolated polynucleotide" is meant a nucleic acid (e.g., a DNA) that is free of the genes which, in the naturally-occurring genome of the organism from which the nucleic acid molecule of the invention is derived, flank the gene. The term therefore includes, for example, a recombinant DNA that is incorporated into a vector; into an autonomously replicating plasmid or virus; or into the genomic DNA of a prokaryote or eukaryote; or that exists as a separate molecule (for example, a cDNA or a genomic or cDNA fragment produced by PCR or restriction endonuclease digestion) independent of other sequences. In addition, the term includes an RNA molecule that is transcribed from a DNA molecule, as well as a recombinant DNA that is part of a hybrid gene encoding additional polypeptide sequence.

By an "isolated polypeptide" is meant a polypeptide of the invention that has been separated from components that naturally accompany it. Typically, the polypeptide is isolated when it is at least 60%, by weight, free from the proteins and naturally-occurring organic molecules with which it is naturally associated. The preparation can be at least 75%, at least 90%, and at least 99%, by weight, a polypeptide of the invention. An isolated polypeptide of the invention may be obtained, for example, by extraction from a natural source, by expression of a recombinant nucleic acid encoding such a polypeptide; or by chemically synthesizing the protein. Purity can be measured by any appropriate method, for example, column chromatography, polyacrylamide gel electrophoresis, or by HPLC analysis.

By "KCNK3 polypeptide" is meant a protein or fragment thereof having at least 85% amino acid sequence identity to the sequence provided at NCBI Accession No. NP_002237.1 and having potassium channel activity. The amino acid sequence provided at NCBI Accession No. NP_002237.1 is shown below:

(SEQ ID NO: 15)
```
  1 mkrqnvrtla livctftyll vgaavfdale sepelierqr lelrqqelra rynlsqggye
 61 elervvlrlk phkagvqwrf agsfyfaitv ittigyghaa pstdggkvfc mfyallgipl
121 tlvmfqslge rintlvryll hrakkglgmr radvsmanmv ligffscist lcigaaafsh
181 yehwtffqay yycfitltti gfgdyvalqk dgalgtqpqy vafsfvyilt gltvigafln
241 lvvlrfmtmn aedekrdaeh ralltrngqa gggggggsah ttdtasstaa aggggfrnvy
301 aevlhfqsmc sclwyksrek lqysipmiip rdlstsdtcv eqshsspggg grysdtpsrr
361 clcsgaprsa issystglhs lstfrglmkr rssv
```

By "KCNK3 polynucleotide" is meant a polynucleotide encoding a KCNK3 polypeptide or fragment thereof. An exemplary KCNK3 polynucleotide sequence is provided at NCBI Ref: NM_002246.2. The sequence provided at NCBI Ref: NM_002246.2 is reproduced below:

(SEQ ID NO: 16)
```
   1 ggcggcggcg gcggcggcgg ccccgggcgc tgagcgggtg cccggcgcgg agagcggcga
  61 gcgcagccat gccccaggcc gcctccgggg cagcagcagc ggcggccggg gccgaggcgc
 121 gggccggggg cgccgggggg ccggcggcgg cccgggcggg acgatgaagc ggcagaacgt
 181 gcgcacgctg gcgctcatcg tgtgcacctt cacctacctg ctggtgggcg ccgcggtctt
 241 cgacgcgctg gagtcggagc ccgagctgat cgagcggcag cggctggagc tgcggcagca
 301 ggagctgcgg gcgcgctaca acctcagcca gggcggctac gaggagctgg agcgcgtcgt
 361 gctgcgcctc aagccgcaca aggccggcgt gcagtggcgc ttcgccggct ccttctactt
 421 cgccatcacc gtcatcacca ccatcggcta cgggcacgcg gcacccagca cggatggcgg
 481 caaggtgttc tgcatgttct acgcgctgct gggcatcccg ctcacgctcg tcatgttcca
 541 gagcctgggc gagcgcatca acaccttggt gaggtacctg ctgcaccgcg ccaagaaggg
 601 gctgggcatg cggcgcgccg acgtgtccat ggccaacatg gtgctcatcg gcttcttctc
 661 gtgcatcagc acgctgtgca tcggcgccgc cgccttctcc cactacgagc actggacctt
 721 cttccaggcc tactactact gcttcatcac cctcaccacc atcggcttcg gcgactacgt
 781 ggcgctgcag aaggaccagg ccctgcagac gcagccgcag tacgtggcct tcagcttcgt
 841 ctacatcctt acgggcctca cggtcatcgg cgccttcctc aacctcgtgg tgctgcgctt
 901 catgaccatg aacgccgagg acgagaagcg cgacgccgag caccgcgcgc tgctcacgcg
 961 caacgggcag gcgggcggcg gcggaggggg tggcagcgcg cacactacgg acaccgcctc
1021 atccacggcg gcagcgggcg gcggcggctt ccgcaacgtc tacgcggagg tgctgcactt
1081 ccagtccatg tgctcgtgcc tgtggtacaa gagccgcgag aagctgcagt actccatccc
1141 catgatcatc ccgcgggacc tctccacgtc cgacacgtgc gtggagcaga gccactcgtc
1201 gccgggaggg ggcggccgct acagcgacac gccctcgcga cgctgcctgt gcagcggggc
1261 gccacgctcc gccatcagct cggtgtccac gggtctgcac agcctgtcca ccttccgcgg
1321 cctcatgaag cgcaggagct ccgtgtgact gccccgaggg gcctggagca cctgggggcg
1381 cgggcggggg acccctgctg ggaggccagg agactgcccc tgctgccttc tgcccagtgg
1441 gaccccgcac aacatccctc accactctcc cccagcaccc ccatctccga ctgtgcctgc
1501 ttgcaccagc cggcaggagg ccgggctctg aggacccctg gggcccccat cggagccctg
1561 caaattccga gaaatgtgaa acttggtggg gtcagggagg aaaggcagaa gctgggagcc
1621 tcccttccct ttgaaaatct aagaagctcc cagtcctcag agaccctgct ggtacccaga
```

-continued 1681 cccccacctt cggaggggac ttcatgttcc gtgtacgttt gcatctctat ttatacctct
1741 gtcctgctag gtctcccacc ttcccttggt tccaaaagcc agggtgtcta tgtccaagtc
1801 accccctactc agccccactc cccttcctca tccccagctg tgtctcccaa cctcccttcg
1861 tgttgttttg catggctttg cagttatgga gaaagtggaa acccagcagt ccctaaagct
1921 ggtccccaga aagcaggaca gaaagaagga gggacaggca ggcagcagga ggggcgagct
1981 gggaggcagg aggcagcggc ctgtcagtct gcagaatggt cgcactggag gttcaagcta
2041 actggcctcc agccacattc tcatagcagg taggacttca gccttccaga cactgccctt
2101 agaatctgga acagaagact tcagactcac cataattgct gataattacc cactcttaaa
2161 tttgtcgagt gatttttagc ctctgaaaac tctatgctgg ccactgattc ctttgagtct
2221 cacaaaaccc tacttaggtc atcagggcag gagttctcac tcccatttta cagatgagaa
2281 tactgaggcc tggacaggtg aagtgaccag agagcaaaag gcaaaggggt gggggctggg
2341 tgcagtggct cacacctgta ttcccaacac ttttggaggc tgaggttgga ggattgcttg
2401 agcccaggaa tttgagacca gcctaggtga catagtgaga ccccatctct acaaaaaata
2461 aaaaattaac caggtgtggt ggcacgtgcc tgggagtccc agcgacttgg gaggctgagg
2521 tgggaggatt gtttgagcct gggaggtcga ggctgtagtg agccctgatt gcaccactgt
2581 actccagcct gggtgacagg gcaagaccct gtctcaaaaa aaaaaaaaaa aatggcaaag
2641 ggagacaaga gcccagcctg cttgttgcta gccaaagtgt tctttccttc cagcttggcc
2701 tgctcttaaa agcaaagctc ctgcagtgta catcctggca ttgtgtggct acctgggttt
2761 taaaccagaa tcagaagtcc cggatcagag ggcactgctg aggttcagcc tcttctcttc
2821 ttggccagga ggcagcagct ctgaatgggc ccctgaggct gcacaggggc ctttgtcact
2881 ggggcgcatg cttacaaaca gtgcagttct tgggaccgag gtaagcaggg ctgggtctca
2941 tggcagaaag gccaggatct ggggctctag gaatttggga attgggcaga gtggccaaga
3001 aagctggcag gcatatccta tgggacatca cacctggcac cattgtcatt gttggtgcct
3061 gtgtcccaag tagctagtga taagctgagg ctgcagcaag aaacaccctt cccaggtggg
3121 ggagtttgga ccagaggtgc cctctgccca ccacacctgc aacccagaag cccagatgga
3181 acgcagctga cgaaggtgat gcttgaggct cacttttggg gccccacagc tggagccggt
3241 ataatgactg ggacaacatc aaggggtgga tgaggggcct ctcctcccgc aacactgcct
3301 tcccatgctg ttcccctgcc agctccttaa cactgccgac caaggccagc cctggcattc
3361 agggaaattg gagggcagca cccgtagggt ggccagcctc aggccccacc ccagctgtgt
3421 cctctagtct ctggggaccc ctggggggaa gaagtctacc ctgcttgtga gtcccgtctc
3481 agtgtggagg aactggctgc acgtgggacc tgaaggtgcc ctctgtgttt atgttggggg
3541 tggggggca gtgctggctg cctctgtcct gtgtgtgacc ctgccctcga agggtcctgt
3601 cctgtcagtc ccgagggagc cacaaccaaa gctgcggaga gaaggtgggg aagggtgcag
3661 aatggccgtg gggcacagcg tggcagactg ttcagtctct gctgggtctt tcctagggac
3721 ctggaaggcc agtgttgctt ccccctcact ccctttcact gcaggcagcc tctctgcttc
3781 cccaatgcct tatgcctggg cacactgcca cagaatatgc aatatgtgtg ggtgaccatg
3841 ccctcacgac cacaccccca ccccgggcag cccccggact ccaaaggtcg tggctgccac
3901 agcctccctc agctcttcct gcctatctgt cttcacactg agaatggcgc ccaataaatg
3961 ctatccacgg agaccagg By "KCNQ1 polypeptide" is meant a protein or fragment thereof having at least 85% amino acid sequence identity to the sequence provided at NCBI Accession No. NP_000209.2 (isoform 1) or NP_861463.1 (isoform 2) and having potassium channel activity. The amino acid sequence provided at NCBI Accession No. NP_000209.2 is shown below:

```
                                                   (SEQ ID NO: 17)
  1 maaasspprа erkrwgwgrl pgarrgsagl akkcpfslel aeggpaggal yapiapgapg

 61 pappaspaap aappvasdlg prppvsldpr vsiystrrpv larthvqgry ynflerptgw

121 kcfvyhfavf livlvclifs vlstieqyaa latgtlfwme ivlvvffgte yvvrlwsagc

181 rskyvglwgr lrfarkpisi idlivvvasm vvlcvgskgq vfatsairgi rflqilrmlh

241 vdrqggtwrl lgsvvfihrq elittlyigf lglifssyfv ylaekdavne sgrvefgsya

301 dalwwgvvtv ttigygdkvp qtwvgktias cfsvfaisff alpagilgsg falkvqqkqr

361 qkhfnrqipa aasliqtawr cyaaenpdss twkiyirkap rshtllspsp kpkksvvvkk

421 kkfkldkdng vtpgekmltv phitcdppee rrldhfsvdg ydssvrkspt llevsmphfm

481 rtnsfaedld legetlltpi thisqlrehh ratikvirrm qyfvakkkfq qarkpydvrd

541 vieqysqghl nlmvrikelq rrldqsigkp slfisvseks kdrgsntiga rlnrvedkvt

601 qldqrlalit dmlhqllslh ggstpgsggp preggahitq pcgsggsvdp elflpsntlp

661 tyeqltvprr gpdegs
```

By "KCNQ1 polynucleotide" is meant a polynucleotide encoding a KCNQ1 polypeptide or fragment thereof. An exemplary KCNQ1 polynucleotide sequence is provided at NCBI Ref: NM_000218.2. The sequence provided at NCBI Ref: NM_000218.2 is reproduced below:

```
                                                       (SEQ ID NO: 18)
   1 gcggcggggc tggcagcagt ggctgcccgc actgcgcccg ggcgctcgcc ttcgctgcag

  61 ctcccggtgc cgccgctcgg gccggccccc cggcaggccc tcctcgttat ggccgcggcc

 121 tcctccccgc ccagggccga gaggaagcgc tggggttggg gccgcctgcc aggcgcccgg

 181 cggggcagcg cgggcctggc caagaagtgc cccttctcgc tggagctggc ggagggcggc

 241 ccggcgggcg gcgcgctcta cgcgcccatc gcgcccggcg ccccaggtcc cgcgccccct

 301 gcgtccccgg ccgcgcccgc cgcgccccca gttgcctccg accttggccc gcggccgccg

 361 gtgagcctag acccgcgcgt ctccatctac agcacgcgcc gcccggtgtt ggcgcgcacc

 421 cacgtccagg gccgcgtcta caacttcctc gagcgtccca ccggctggaa atgcttcgtt

 481 taccacttcg ccgtcttcct catcgtcctg gtctgcctca tcttcagcgt gctgtccacc

 541 atcgagcagt atgccgccct ggccacgggg actctcttct ggatggagat cgtgctggtg

 601 gtgttcttcg ggacggagta cgtggtccgc ctctggtccg ccggctgccg cagcaagtac

 661 gtgggcctct gggggcggct gcgctttgcc cggaagccca tttccatcat cgacctcatc

 721 gtggtcgtgg cctccatggt ggtcctctgc gtgggctcca aggggcaggt gtttgccacg

 781 tcggccatca ggggcatccg cttcctgcag atcctgagga tgctacacgt cgaccgccag

 841 ggaggcacct ggaggctcct gggctccgtg gtcttcatcc accgccagga gctgataacc

 901 accctgtaca tcggcttcct gggcctcatc ttctcctcgt actttgtgta cctggctgag

 961 aaggacgcgg tgaacgagtc aggccgcgtg gagttcggca gctacgcaga tgcgctgtgg

1021 tgggggtgg tcacagtcac caccatcggc tatggggaca aggtgcccca gacgtgggtc

1081 gggaagacca tcgcctcctg cttctctgtc tttgccatct ccttctttgc gctcccagcg
```

-continued

```
1141 gggattcttg gctcggggtt tgccctgaag gtgcagcaga agcagaggca gaagcacttc
1201 aaccggcaga tcccggcggc agcctcactc attcagaccg catggaggtg ctatgctgcc
1261 gagaaccccg actcctccac ctggaagatc tacatccgga aggccccccg gagccacact
1321 ctgctgtcac ccagccccaa acccaagaag tctgtggtgg taaagaaaaa aaagttcaag
1381 ctggacaaag acaatggggt gactcctgga gagaagatgc tcacagtccc ccatatcacg
1441 tgcgaccccc cagaagagcg gcggctggac cacttctctg tcgacggcta tgacagttct
1501 gtaaggaaga gcccaacact gctggaagtg agcatgcccc atttcatgag aaccaacagc
1561 ttcgccgagg acctggacct ggaaggggag actctgctga cacccatcac ccacatctca
1621 cagctgcggg aacaccatcg ggccaccatt aaggtcattc gacgcatgca gtactttgtg
1681 gccaagaaga aattccagca agcgcggaag ccttacgatg tgcgggacgt cattgagcag
1741 tactcgcagg gccacctcaa cctcatggtg cgcatcaagg agctgcagag gaggctggac
1801 cagtccattg ggaagccctc actgttcatc tccgtctcag aaaagagcaa ggatcgcggc
1861 agcaacacga tcggcgcccg cctgaaccga gtagaagaca aggtgacgca gctggaccag
1921 aggctggcac tcatcaccga catgcttcac cagctgctct ccttgcacgg tggcagcacc
1981 cccggcagcg gcggcccccc cagagagggc ggggcccaca tcacccagcc ctgcggcagt
2041 ggcggctccg tcgaccctga gctcttcctg cccagcaaca ccctgcccac ctacgagcag
2101 ctgaccgtgc ccaggagggg ccccgatgag ggtcctgag gaggggatgg ggctggggga
2161 tgggcctgag tgagagggga ggccaagagt ggccccacct ggccctctct gaaggaggcc
2221 acctcctaaa aggcccagag agaagagccc cactctcaga ggccccaata ccccatggac
2281 catgctgtct ggcacagcct gcacttgggg gctcagcaag gccacctctt cctggccggt
2341 gtgggggccc cgtctcaggt ctgagttgtt accccaagcg ccctggcccc cacatggtga
2401 tgttgacatc actggcatgg tggttgggac ccagtggcag ggcacagggc ctggcccatg
2461 tatggccagg aagtagcaca ggctgagtgc aggcccaccc tgcttggccc agggggcttc
2521 ctgaggggag acagagcaac ccctggaccc cagcctcaaa tccaggaccc tgccaggcac
2581 aggcagggca ggaccagccc acgctgacta cagggccgcc ggcaataaaa gcccaggagc
2641 ccatttggag ggcctgggcc tggctccctc actctcagga aatgctgacc catgggcagg
2701 agactgtgga gactgctcct gagcccccag cttccagcag gagggacagt ctcaccattt
2761 ccccagggca cgtggttgag tgggggggaac gcccacttcc ctgggttaga ctgccagctc
2821 ttcctagctg gagaggagcc ctgcctctcc gcccctgagc ccactgtgcg tggggctccc
2881 gcctccaacc cctcgcccag tcccagcagc cagccaaaca cacagaaggg gactgccacc
2941 tccccttgcc agctgctgag ccgcagagaa gtgacggttc ctacacagga caggggttcc
3001 ttctgggcat tacatcgcat agaaatcaat aatttgtggt gatttggatc tgtgttttaa
3061 tgagtttcac agtgtgattt tgattattaa ttgtgcaagc ttttcctaat aaacgtggag
3121 aatcacaggc tgggctgggc actgctctca ccttggttcc tggggcatcc atggggtctc
3181 tcacagacag gacccctgca gttcccctgg aagcagtgcc caggtggctg tggaatagga
3241 acgctaaaaa aaaaaaaaaa aa
```

By "LGR5 polypeptide" is meant a protein or fragment thereof having at least 85% amino acid sequence identity to the sequence provided at NCBI Accession No. NP_003658.1 (isoform 1), NP_001264155.1 (isoform 2), or NP_001264156.1 (isoform 3) and having transmembrane signaling receptor activity or G-protein coupled receptor activity. The amino acid sequence provided at NCBI Accession No. NP_003658.1 is shown below:

(SEQ ID NO: 19)
1 mdtsrlgvll slpvllqlat ggssprsgvl lrgcpthchc epdgrmllrv dcsdlglsel 61 psnlsvftsy ldlsmnnisq llpnplpslr fleelrlagn altyipkgaf tglyslkvlm 121 lqnnqlrhvp tealqnlrsl qslrldanhi syvppscfsg lhslrhlwld dnalteipvq 181 afrslsalqa mtlalnkihh ipdyafgnls slvvlhlhnn rihslgkkcf dglhsletld 241 lnynnldefp tairtlsnlk elgfhsnnir sipekafvgn pslitihfyd npiqfvgrsa 301 fghlpelrtl tlngasqite fpdltgtanl esltltgaqi sslpqtvcnq lpnlqvldls 361 ynlledlpsf svcqklqkid lrhneiyeik vdtfqqllsl rslnlawnki aiihpnafst 421 lpslikldls snllssfpit glhglthlkl tgnhalqsli ssenfpelkv iempyayqcc 481 afgvcenayk isnqwnkgdn ssmddlhkkd agmfqaqder dledflldfe edlkalhsvq 541 cspspgpfkp cehlldgwli rigvwtiavl altcnalvts tvfrsplyis piklligvia 601 avnmltgvss avlagvdaft fgsfarhgaw wengvgchvi gflsifases svflltlaal 661 ergfsvkysa kfetkapfss lkviillcal laltmaavpl lggskygasp lclplpfgep 721 stmgymvali llnslcflmm tiaytklycn ldkgdleniw dcsmvkhial llftncilnc 781 pvaflsfssl inltfispev ikfillvvvp lpaclnplly ilfnphfked lvslrkqtyv 841 wtrskhpslm sinsddvekq scdstqalvt ftsssitydl ppssvpspay pvteschlss 901 vafvpcl By "LGR5 polynucleotide" is meant a polynucleotide encoding a LGR5 polypeptide or fragment thereof. An exemplary LGR5 polynucleotide sequence is provided at NCBI Ref: NM_003667.3. The sequence provided at NCBI Ref: NM_003667.3 is reproduced below:

(SEQ ID NO: 20)
1 aaaaaacgag cgtgcaagca gagatgctgc tccacaccgc tcaggccgcg agcagcagca 61 aggcgcaccg ccactgtcgc cgctgcagcc agggctgctc cgaaggccgg cgtggcggca 121 accggcacct ctgtccccgc cgcgcttctc ctcgccgccc acgccgtggg gtcaggaacg 181 cggcgtctgg cgctgcagac gcccgctgag ttgcagaagc ccacggagcg gcgcccggcg 241 cgccacggcc cgtagcagtc cggtgctgct ctccgcccgc gtccggctcg tggcccccta 301 cttcgggcac catggacacc tcccggctcg gtgtgctcct gtccttgcct gtgctgctgc 361 agctggcgac cgggggcagc tctcccaggt ctggtgtgtt gctgaggggc tgccccacac 421 actgtcattg cgagcccgac ggcaggatgt tgctcagggt ggactgctcc gacctggggc 481 tctcggagct gccttccaac ctcagcgtct tcacctccta cctagacctc agtatgaaca 541 acatcagtca gctgctcccg aatcccctgc ccagtctccg cttcctggag gagttacgtc 601 ttgcgggaaa cgctctgaca tacattccca agggagcatt cactggcctt tacagtctta 661 aagttcttat gctgcagaat aatcagctaa gacacgtacc cacagaagct ctgcagaatt 721 tgcgaagcct tcaatccctg cgtctggatg ctaaccacat cagctatgtg cccccaagct 781 gtttcagtgg cctgcattcc ctgaggcacc tgtggctgga tgacaatgcg ttaacagaaa 841 tccccgtcca ggcttttaga agtttatcgg cattgcaagc catgaccttg gccctgaaca 901 aaatacacca cataccagac tatgcctttg gaaacctctc cagcttggta gttctacatc 961 tccataacaa tagaatccac tccctgggaa agaaatgctt tgatgggctc cacagcctag 1021 agactttaga tttaaattac aataaccttg atgaattccc cactgcaatt aggacactct 1081 ccaaccttaa agaactagga tttcatagca acaatatcag gtcgatacct gagaaagcat -continued 1141 ttgtaggcaa cccttctctt attacaatac atttctatga caatcccatc cagtttgttg
1201 ggagatctgc ttttcaacat ttacctgaac taagaacact gactctgaat ggtgcctcac
1261 aaataactga atttcctgat ttaactggaa ctgcaaacct ggagagtctg actttaactg
1321 gagcacagat ctcatctctt cctcaaaccg tctgcaatca gttacctaat ctccaagtgc
1381 tagatctgtc ttacaaccta ttagaagatt tacccagttt ttcagtctgc caaaagcttc
1441 agaaaattga cctaagacat aatgaaatct acgaaattaa agttgacact ttccagcagt
1501 tgcttagcct ccgatcgctg aatttggctt ggaacaaaat tgctattatt caccccaatg
1561 cattttccac tttgccatcc ctaataaagc tggacctatc gtccaacctc ctgtcgtctt
1621 ttcctataac tgggttacat ggtttaactc acttaaaatt aacaggaaat catgccttac
1681 agagcttgat atcatctgaa aactttccag aactcaaggt tatagaaatg ccttatgctt
1741 accagtgctg tgcatttgga gtgtgtgaga atgcctataa gatttctaat caatggaata
1801 aaggtgacaa cagcagtatg gacgaccttc ataagaaaga tgctggaatg tttcaggctc
1861 aagatgaacg tgaccttgaa gatttcctgc ttgactttga ggaagacctg aaagcccttc
1921 attcagtgca gtgttcacct tccccaggcc ccttcaaacc ctgtgaacac ctgcttgatg
1981 gctggctgat cagaattgga gtgtggacca tagcagttct ggcacttact tgtaatgctt
2041 tggtgacttc aacagttttc agatcccctc tgtacatttc ccccattaaa ctgttaattg
2101 gggtcatcgc agcagtgaac atgctcacgg gagtctccag tgccgtgctg gctggtgtgg
2161 atgcgttcac ttttggcagc tttgcacgac atggtgcctg gtgggagaat ggggttggtt
2221 gccatgtcat tggttttttg tccatttttg cttcagaatc atctgttttc ctgcttactc
2281 tggcagccct ggagcgtggg ttctctgtga aatattctgc aaaatttgaa acgaaagctc
2341 cattttctag cctgaaagta atcattttgc tctgtgccct gctggccttg accatggccg
2401 cagttcccct gctgggtggc agcaagtatg gcgcctcccc tctctgcctg cctttgcctt
2461 ttggggagcc cagcaccatg ggctacatgg tcgctctcat cttgctcaat tccctttgct
2521 tcctcatgat gaccattgcc tacaccaagc tctactgcaa tttggacaag ggagacctgg
2581 agaatatttg ggactgctct atggtaaaac acattgccct gttgctcttc accaactgca
2641 tcctaaactg ccctgtggct ttcttgtcct tctcctcttt aataaacctt acatttatca
2701 gtcctgaagt aattaagttt atccttctgg tggtagtccc acttcctgca tgtctcaatc
2761 cccttctcta catcttgttc aatcctcact ttaaggagga tctggtgagc ctgagaaagc
2821 aaacctacgt ctggacaaga tcaaaacacc caagcttgat gtcaattaac tctgatgatg
2881 tcgaaaaaca gtcctgtgac tcaactcaag ccttggtaac ctttaccagc tccagcatca
2941 cttatgacct gcctcccagt tccgtgccat caccagctta tccagtgact gagagctgcc
3001 atctttcctc tgtggcattt gtcccatgtc tctaattaat atgtgaagga aaatgttttc
3061 aaaggttgag aacctgaaaa tgtgagattg agtatatcag agcagtaatt aataagaaga
3121 gctgaggtga aactcggttt aaaaaccaaa aaagaatctc tcagttagta agaaaaggct
3181 gaaaacctct tgatacttga gagtgaatat aagtctaaat gctgctttgt ataatttgtt
3241 cagctaaggg atagatcgat cacactattt aagtgagccc agatcaaaaa agcagattga
3301 aattttcttt agaaaagatt ctccatgatt tgaattgcat tctctttaaa ctcaccaatg
3361 taatcatttt gggaggaggg agaacccact tgctttccaa atgggtttat ttaaacccac
3421 aaactcaaga ggttgttggg ggaattagga aaataagggt tttcaatgac ctacattgct
3481 aggtagaggc tgtgatccat gggatttcat tctaatgacc atgtgaagat gtttgagtcc
3541 tcctttgcct ttcctcagaa agaatccttc taaggcacaa atcccttaga tggataatgt -continued

```
3601 aaggtattgt taactcactc atattgagat catttttaga gataccaggt tttatgtatc
3661 agcactagat ggttccaccc tcatgggata aaactgctta caagtatttt gaaagaaaaa
3721 ctgaccaaaa ttcttaaatt gttactaagg caatcatgca caggtgacgt atgtcttatc
3781 tgatttgttt ttaactcctt ggtgcccaaa gctcagaagg gaattccact gccagcaatg
3841 aacatacctg gaaaagaaag taagcaatct gggatttttt ttctgggtta gtaaagaatt
3901 tttgcaataa gttttatcag ttgattcaaa ctgatgtgca tcttaatgat caaatgtgca
3961 cattacataa attaagtcca ctgatacaac ttcttacaca tgtatctcta gtagctctgg
4021 caaacccaat atctgacacc actttggact caagagactc agtaacgtat tatcctgttt
4081 atttagcttg gttttagctg tgttctctct ggataaccca cttgatgtta ggaacattac
4141 ttctctgctt attccatatt aatactgtgt taggtatttt aagaagcaag ttattaaata
4201 agaaaagtca aagtattaat tcttaccttc tattatccta tattagcttc aatacatcca
4261 aaccaaatgg ctgttaggta gatttatttt tatataagca tgtttatttt gatcagatgt
4321 tttaacttgg atttgaaaaa atacatttat gagatgtttt ataagatgtg taaatataga
4381 actgtattta ttactatagt aaaggttcag taacattaag gaccatgata atgataataa
4441 accttgtaca gtggcatatt ctttgattta tattgtgttt ctctgcccat tttctttaaa
4501 ttcattaact gtatatatgt aaatatatag tacttgtaaa tagattccaa atttgctttt
4561 ctattgggta aaaaataaat ttgtaataaa atgtgtgact atgaaacaaa aaaaaaaaaa
4621 aaaaa
```

By “LDHA polypeptide” or “lactate dehydrogenase A polypeptide” is meant a protein or fragment thereof having at least 85% amino acid sequence identity to the sequence provided at NCBI Accession No. NP_005557.1 (isoform 1), NP_001128711.1 (isoform 2), NP_001158886.1 (isoform 3), NP_001158887.1 (isoform 4), or NP_001158888.1 (isoform 5) and having dehydrogenase activity. The amino acid sequence provided at NCBI Accession No. NP_005557.1 is shown below:

```
                                                    (SEQ ID NO: 21)
  1 matlkdqliy nllkeeqtpq nkitvvgvga vgmacaisil mkdladelal vdviedklkg
 61 emmdlqhgsl flrtpkivsg kdynvtansk lviitagarq qegesrlnlv qrnvnifkfi
121 ipnvvkyspn ckllivsnpv diltyvawki sgfpknrvig sgcnldsarf rylmgerlgv
181 hplschgwvl gehgdssvpv wsgmnvagvs lktlhpdlgt dkdkeqwkev hkqvvesaye
241 viklkgytsw aiglsvadla esimknlrrv hpvstmikgl ygikddvfls vpcilgqngi
301 sdlvkvtlts eeearlkksa dtlwgiqkel qf
```

By “LDHA polynucleotide” or “lactate dehydrogenase A polynucleotide” is meant a polynucleotide encoding a LDHA polypeptide or fragment thereof. An exemplary LDHA polynucleotide sequence is provided at NCBI Ref: NM_005566.3. The sequence provided at NCBI Ref: NM_005566.3 is reproduced below:

```
                                                    (SEQ ID NO: 22)
  1 gtctgccggt cggttgtctg gctgcgcgcg ccacccgggc ctctccagtg ccccgcctgg
 61 ctcggcatcc acccccagcc cgactcacac gtgggttccc gcacgtccgc cggccccccc
121 cgctgacgtc agcatagctg ttccacttaa ggcccctccc gcgcccagct cagagtgctg
181 cagccgctgc cgccgattcc ggatctcatt gccacgcgcc cccgacgacc gcccgacgtg
241 cattcccgat tccttttggt tccaagtcca atatggcaac tctaaaggat cagctgattt
```

-continued 301 ataatcttct aaaggaagaa cagacccccc agaataagat tacagttgtt ggggttggtg 361 ctgttggcat ggcctgtgcc atcagtatct taatgaagga cttggcagat gaacttgctc 421 ttgttgatgt catcgaagac aaattgaagg gagagatgat ggatctccaa catggcagcc 481 ttttccttag aacaccaaag attgtctctg gcaaagacta taatgtaact gcaaactcca 541 agctggtcat tatcacggct ggggcacgtc agcaagaggg agaaagccgt cttaatttgg 601 tccagcgtaa cgtgaacatc tttaaattca tcattcctaa tgttgtaaaa tacagcccga 661 actgcaagtt gcttattgtt tcaaatccag tggatatctt gacctacgtg gcttggaaga 721 taagtggttt tcccaaaaac cgtgttattg gaagcggttg caatctggat tcagcccgat 781 tccgttacct aatgggggaa aggctgggag ttcacccatt aagctgtcat gggtgggtcc 841 ttggggaaca tggagattcc agtgtgcctg tatggagtgg aatgaatgtt gctggtgtct 901 ctctgaagac tctgcaccca gatttaggga ctgataaaga taaggaacag tggaaagagg 961 ttcacaagca ggtggttgag agtgcttatg aggtgatcaa actcaaaggc tacacatcct 1021 gggctattgg actctctgta gcagatttgg cagagagtat aatgaagaat cttaggcggg 1081 tgcacccagt ttccaccatg attaagggtc tttacggaat aaaggatgat gtcttcctta 1141 gtgttccttg cattttggga cagaatggaa tctcagacct tgtgaaggtg actctgactt 1201 ctgaggaaga ggcccgtttg aagaagagtg cagatacact tgggggggatc caaaaggagc 1261 tgcaatttta aagtcttctg atgtcatatc atttcactgt ctaggctaca acaggattct 1321 aggtggaggt tgtgcatgtt gtccttttta tctgatctgt gattaaagca gtaatatttt 1381 aagatggact gggaaaaaca tcaactcctg aagttagaaa taagaatggt ttgtaaaatc 1441 cacagctata tcctgatgct ggatggtatt aatcttgtgt agtcttcaac tggttagtgt 1501 gaaatagttc tgccacctct gacgcaccac tgccaatgct gtacgtactg catttgcccc 1561 ttgagccagg tggatgttta ccgtgtgtta tataacttcc tggctccttc actgaacatg 1621 cctagtccaa catttttcc cagtgagtca catcctggga tccagtgtat aaatccaata 1681 tcatgtcttg tgcataattc ttccaaagga tcttattttg tgaactatat cagtagtgta 1741 cattaccata taatgtaaaa agatctacat acaaacaatg caaccaacta tccaagtgtt 1801 ataccaacta aaacccccaa taaaccttga acagtgacta ctttggttaa ttcattatat 1861 taagatataa agtcataaag ctgctagtta ttatattaat ttggaaatat taggctattc 1921 ttgggcaacc ctgcaacgat tttttctaac agggatatta ttgactaata gcagaggatg 1981 taatagtcaa ctgagttgta ttggtaccac ttccattgta agtcccaaag tattatatat 2041 ttgataataa tgctaatcat aattggaaag taacattcta tatgtaaatg taaaatttat 2101 ttgccaactg aatataggca atgatagtgt gtcactatag ggaacacaga tttttgagat 2161 cttgtcctct ggaagctggt aacaattaaa aacaatctta aggcagggaa aaaaaaaaaa 2221 aaaaaa By "MAFA polypeptide" is meant a protein or fragment thereof having at least 85% amino acid sequence identity to the sequence provided at NCBI Accession No. NP_963883.2 and having transcription factor activity. The amino acid sequence provided at NCBI Accession No. NP_963883.2 is shown below:

(SEQ ID NO: 23)

1 maaelamgae lpssplaiey vndfdlmkfe vkkeppeaer fchrlppgsl sstplstpcs 61 svpsspsfca pspgtggggg agggggssqa ggapgppsgg pgavggtsgk paledlywms 121 gyqhhlnpea lnltpedave aligsghhga hhgahhpaaa aayeafrgpg faggggaddm -continued

```
181   gaghhhgahh aahhhhaahh hhhhhhhhgg aghgggaghh vrleerfsdd qlvsmsvrel

241   nrqlrgfske evirlkqkrr tlknrgyaqs crfkrvqqrh ilesekcqlq sqveqlklev

301   grlakerdly kekyeklagr ggpgsaggag fprepsppqa gpggakgtad ffl
```

By "MAFA polynucleotide" is meant a polynucleotide encoding a MAFA polypeptide or fragment thereof. An exemplary MAFA polynucleotide sequence is provided at NCBI Ref: NM_201589.3. The sequence provided at NCBI Ref: NM_201589.3 is reproduced below:

(SEQ ID NO: 24)

```
1     gcgcggccgg gcgcgggccc cgggcgatgg ccgcggagct ggcgatgggc gccgagctgc

61    ccagcagccc gctggccatc gagtacgtca acgacttcga cctgatgaag ttcgaggtga

121   agaaggagcc tcccgaggcc gagcgcttct gccaccgcct gccgccaggc tcgctgtcct

181   cgacgccgct cagcacgccc tgctcctccg tgccctcctc gcccagcttc tgcgcgccca

241   gcccgggcac cggcggcggc ggcggcgcgg ggggcggcgg cggctcgtct caggccgggg

301   gcgcccccgg gccgccgagc gggggccccg gcgccgtcgg gggcacctcg gggaagccgg

361   cgctggagga tctgtactgg atgagcggct accagcatca cctcaacccc gaggcgctca

421   acctgacgcc cgaggacgcg gtggaggcgc tcatcggcag cggccaccac ggcgcgcacc

481   acggcgcgca ccacccggcg gccgccgcag cctacgaggc tttccgcggc ccgggcttcg

541   cgggcggcgg cggagcggac gacatgggcg ccggccacca ccacggcgcg caccacgccg

601   cccaccatca ccacgccgcc caccaccacc accaccacca ccaccaccat ggcggcgcgg

661   gacacggcgg tggcgcgggc caccacgtgc gcctggagga gcgcttctcc gacgaccagc

721   tggtgtccat gtcggtgcgc gagctgaacc ggcagctccg cggcttcagc aaggaggagg

781   tcatccggct caagcagaag cggcgcacgc tcaagaaccg cggctacgcg cagtcctgcc

841   gcttcaagcg ggtgcagcag cggcacattc tggagagcga gaagtgccaa ctccagagcc

901   aggtggagca gctgaagctg gaggtggggc gcctggccaa agagcgggac ctgtacaagg

961   agaaatacga gaagctggcg ggccggggcg gccccgggag cgcgggcggg gccggtttcc

1021  cgcgggagcc ttcgccgccg caggccggtc ccggcggggc caagggcacg gccgacttct

1081  tcctgtaggc gccggacccc gagcccgcgc cgccgtcgcc ggggacaagt tcgcgcaggc

1141  ctctcggggc ctcggctcgg actccgcggt acaggacgtg gacaccaggc ccggcccggc

1201  cgtgctggcc ccggtgccaa gtctgcgggc gcggggctgg aggccccttc gctcccggtc

1261  cccgttcgcg cgcgtcggcc cgggtcgccg tcctgaggtt gagcggagaa cggtgatttc

1321  taaggaaact tgagccaggt ctaacttctt tccaagcgtc cgcttgtaca tacgttgaac

1381  gtggttctcc gttcccacct tcgccctgcc agcctagagg gaccgcgctg ccgtcccttc

1441  ccgggtggcc cctgcctgcc cccgccctcc ttcgttctct tctcagcctc cctttccttg

1501  cctttttaa cttcccctcc ccgttttaaa atcggtctta ttttcgaagt atttataatt

1561  attatgcttg gtgattagaa aagaaaacct tggaggaagc cccttctttc cccagccggg

1621  gtccgccctc agtcgcgagt cacagcatga gtcgctcgcc aggaggggcc cggcccctgc

1681  ctgccccctc cccgcttgcc cccgaccctg ctaccggcgt tccttggagg tcgaagccag

1741  ggacgtcacc cgtgctgtgt ccaggcctgc tgtcctacta tgctcaaccg ggggtggggg

1801  gagggggggtg agtcctgtgc tcagtcgggt gggggctggc ccggatcccg agctgctgtc

1861  tctctatgca ccagaacata tctgtaactc ctggggaaat acatcttgtt ttaaccttca

1921  agagaagtga aagaaaaaag taatgcacag tatttctagc agaaaatttt ttttttaag
```

-continued

```
1981  aggaggcttg ggccagagcc ttctggcatg gggcgggtgg agaaagtgtt tttattttaa
2041  tttaaattgt gtttcgtttt gtttgtggaa tctttcttta atgcttcgtc gctctttgga
2101  ctagccggga gagagggcga ggaggcgggt gctccaggcc ctgtaggctg ggccaggcgc
2161  ctgggggatc tgcccgtttt cggaggccct caggggccat cagtgggatt ccagccgctc
2221  cacacccctc ccctgagcac tcggagtgga aggcgcgccg actcgttgaa agttttgttg
2281  tgtagttggt tttcgttgag ttcttttttc atttgctacg aaactgagaa aaagaaaaaa
2341  atacacaaaa taaatctgtt cagatccaag tca
```

As used herein, a "marker" is meant any protein or polynucleotide having an alteration in expression level or activity that is associated with a disease or disorder or that is associated with a particular cell type. In some embodiments, a marker for a beta cell is Pdx1, MafA, Pax4, Pax6, NeuroD1, Nkx6-1, Gata6, or Foxa2. In some embodiments, a marker for a hepatocyte is AFP, ALB, or Cyp3a7. In some other embodiments, a marker for a cardiomyocyte is hMlc2a, hNkx2-5, alphaMHC or KCNQ1. In still other embodiments, a marker for a small intestine cell is CDX2, Muc2, or Lgr5.

By "alphaMHC polypeptide" or "myosin heavy chain (MHC) alpha polypeptide" is meant a protein or fragment thereof having at least 85% amino acid sequence identity to the sequence provided at NCBI Accession No. NP_002462.2 and having actin binding activity. The amino acid sequence provided at NCBI Accession No. NP_002462.2 is shown below:

(SEQ ID NO: 25)

```
1     mtdaqmadfg aaaqylrkse kerleaqtrp fdirtecfvp ddkeefvkak ilsreggkvi
61    aetengktvt vkedqvlqqn ppkfdkiedm amltflhepa vlfnlkerya awmiytysgl
121   fcvtvnpykw lpvynaevva ayrgkkrsea pphifsisdn ayqymltdre nqsilitges
181   gagktvntkr viqyfasiaa igdrgkkdna nankgtledq iiqanpalea fgnaktvrnd
241   nssrfgkfir ihfgatgkla sadietylle ksrvifqlka ernyhifyqi lsnkkpelld
301   mllvtnnpyd yafvsqgevs vasiddseel matdsafdvl gftseekagv ykltgaimhy
361   gnmkfkqkqr eeqaepdgte dadksaylmg lnsadllkgl chprvkvgne yvtkggsvgq
421   vyysigalak avyekmfnwm vtrinatlet kqprgyfigv ldiagfeifd fnsfeqlcin
481   ftneklqqff nhhmfvleqe eykkegiewt fidfgmdlqa cidliekpmg imsileeecm
541   fpkatdmtfk aklydnhlgk snnfqkprni kgkqeahfsl ihyagtvdyn ilgwleknkd
601   pinetvvaly qksslklmat lfssyatadt gdsgkskggk kkgssfqtvs alhrenlnkl
661   mtnlrtthph fvrciipner kapgvmdnpl vmhqlrongv legiricrkg fpnrilygdf
721   rqryrilnpv aipegqfids rkgteklls ldidhnqykf ghtkvffkag llglleemrd
781   erlsriitrm gagargqlmr iefkkiverr dallviqwni rafmgvknwp wmklyfkikp
841   llksaeteke matmkeefgr iketleksea rrkeleekmv sllgekndlq lqvgaegdnl
901   ndaeercdql iknkiqleak vkemnerled eeemnaelta kkrkledecs elkkdiddle
961   ltlakvekek hatenkvknl teemagldei iakltkekka lqeahqqald dlqveedkvn
1021  slskskvkle qqvddlegsl egekkvrmdl erakrklegd lkltqesimd lendklqlee
1081  klkkkefdin qqnskiedeq vlalqlqkkl kenqarieel eeeleaerta rakveklrsd
1141  lsreleeise rleeaggats vqiemnkkre aefqkmrrdl eeatlqheat aaalrkkhad
1201  svaelgeqid nlqrvkqkle keksefklel ddvtsnmeqi ikakanlekv srtledqane
1261  yrvkleeaqr slndfttqra klqtengela rqleekeali sqltrgklsy tqqmedlkrq
1321  leeegkakna lahalqsarh dcdllregye eeteakaelq rvlskansev aqwrtkyetd
1381  aiqrteelee akkklaqrlq daeeaveavn akcsslektk hrlgneiedl mvdversnaa
```

-continued

```
1441   aaaldkkqrn fdkilaewkq kyeesqsele ssqkearsls telfklknay eeslehletf

1501   krenknlqee isdlteqlge ggknvhelek vrkqlevekl elqsaleeae asleheegki

1561   lraglefnqi kaeierklae kdeemeqakr nhqrvvdslq tsldaetrsr nevlrvkkkm

1621   egdlnemeiq lshanrmaae aqkqvkslqs llkdtgiqld davranddlk eniaiverrn

1681   nllqaeleel ravveqters rklaeqelie tservqllhs qntslinqkk kmesdltqlq

1741   seveeavqec rnaeekakka itdaammaee lkkeqdtsah lermkknmeq tikdlqhrld

1801   eaeqialkgg kkqlqklear vrelegelea eqkrnaesvk gmrkserrik eltyqteedk

1861   knllrlqdlv dklqlkvkay krqaeeaeeq antnlskfrk vqheldeaee radiaesqvn

1921   klraksrdig akqkmhdee
```

By “alphaMHC polynucleotide” is meant a polynucleotide encoding a alphaMHC polypeptide or fragment thereof. An exemplary alphaMHC polynucleotide sequence is provided at NCBI Ref: NM_002471.3. The sequence provided at NCBI Ref: NM_002471.3 is reproduced below:

```
                                                      (SEQ ID NO: 26)
   1   agatagagag actcctgcgg cccagattct tcaggattct ccgtgaaggg ataaccaggg

  61   gaagcaccaa gatgaccgat gcccagatgg ctgactttgg ggcagcggcc cagtacctcc

 121   gcaagtcaga gaaggagcgt ctagaggccc agacccggcc ctttgacatt cgcactgagt

 181   gcttcgtgcc cgatgacaag gaagagtttg tcaaagccaa gattttgtcc cgggagggag

 241   gcaaggtcat tgctgaaacc gagaatggga agacggtgac tgtgaaggag gaccaggtgt

 301   tgcagcagaa cccacccaag ttcgacaaga ttgaggacat ggccatgctg accttcctgc

 361   acgagcccgc ggtgcttttc aacctcaagg agcgctacgc ggcctggatg atatatacct

 421   actcgggcct cttctgtgtc actgtcaacc cctacaagtg gctgccggtg tacaatgccg

 481   aggtggtggc cgcctaccgg ggcaagaaga ggagtgaggc cccgccccac atcttctcca

 541   tctccgacaa cgcctatcag tacatgctga cagatcggga gaaccagtcc atcctcatca

 601   cgggagaatc cggggcgggg aagactgtga acaccaagcg tgtcatccag tactttgcca

 661   gcattgcagc cataggtgac cgtggcaaga aggacaatgc caatgcgaac aagggcaccc

 721   tggaggacca gatcatccag gccaaccccg ctctggaggc cttcggcaat gccaagactg

 781   tccggaacga caactcctcc cgctttggga aattcattag gatccacttt ggggccactg

 841   gaaagctggc ttctgcagac atagagacct acctgctgga gaagtcccgg gtgatcttcc

 901   agctgaaagc tgagagaaac taccacatct tctaccagat tctgtccaac aagaagccgg

 961   agttgctgga catgctgctg gtcaccaaca atccctacga ctacgccttc gtgtctcagg

1021   gagaggtgtc cgtggcctcc attgatgact ccgaggagct catggccacc gatagtgcct

1081   ttgacgtgct gggcttcact tcagaggaga aagctggcgt ctacaagctg acgggagcca

1141   tcatgcacta cgggaacatg aagttcaagc agaagcagcg ggaggagcag gcggagccag

1201   acggcaccga agatgctgac aagtcggcct acctcatggg gctgaactca gctgacctgc

1261   tcaaggggct gtgccaccct cgggtgaaag tgggcaacga gtatgtcacc aaggggcaga

1321   gcgtgcagca ggtgtactac tccatcgggg ctctggccaa ggcagtgtat gagaagatgt

1381   tcaactggat ggtgacgcgc atcaacgcca ccctggagac caagcagcca cgccagtact

1441   tcataggagt cctggacatc gctggcttcg agatcttcga cttcaacagc tttgagcagc

1501   tctgcatcaa cttcaccaac gagaagctgc agcagttctt caaccaccac atgttcgtgc

1561   tggagcagga ggagtacaag aaggagggca ttgagtggac attcattgac tttggcatgg
```

-continued

```
1621  acctgcaggc ctgcattgac ctcatcgaga agcccatggg catcatgtcc atcctggagg
1681  aggagtgcat gttccccaag gccactgaca tgaccttcaa ggccaagctg tacgacaacc
1741  acctgggcaa gtccaacaat ttccagaagc cacgcaacat caaggggaag caggaagccc
1801  acttctccct gatccactac gccggcactg tggactacaa catcctgggc tggctggaaa
1861  aaaacaagga tcctctcaac gagactgttg tggccctgta ccagaagtcc tccctcaagc
1921  tcatggccac tctcttctcc tcctacgcaa ctgccgatac tggggacagt ggtaaaagca
1981  aaggaggcaa gaaaaagggc tcatccttcc agacggtgtc ggctctccac cgggaaaatc
2041  tcaacaagct aatgaccaac ctgaggacca cccatcctca ctttgtgcgt tgcatcatcc
2101  ccaatgagcg gaaggctcca ggggtgatgg acaacccccct ggtcatgcac cagctgcgct
2161  gcaatggcgt gctggagggc atccgcatct gcaggaaggg cttccccaac cgcatcctct
2221  acggggactt ccggcagagg tatcgcatcc tgaacccagt ggccatccct gagggacagt
2281  tcattgatag caggaagggg acagagaagc tgctcagctc tctggacatt gatcacaacc
2341  agtacaagtt tggccacacc aaggtgttct tcaaggcagg gctgcttggg ctgctggagg
2401  agatgcggga tgagaggctg agccgcatca tcacgcgcat gcaggcccaa gcccggggcc
2461  agctcatgcg cattgagttc aagaagatag tggaacgcag ggatgccctg ctggtaatcc
2521  agtggaacat tcgggccttc atgggggtca agaattggcc ctggatgaag ctctacttca
2581  agatcaagcc gctgctgaag agcgcagaga cggagaagga gatggccacc atgaaggaag
2641  agttcgggcg catcaaagag acgctggaga agtccgaggc tcgccgcaag gagctggagg
2701  agaagatggt gtccctgctg caggagaaga atgacctgca gctccaagtg caggcggaac
2761  aagacaacct caatgatgct gaggagcgct gcgaccagct gatcaaaaac aagattcagc
2821  tggaggccaa agtaaaggag atgaatgaga ggctggagga tgaggaggag atgaacgcgg
2881  agctcactgc caagaagcgc aagctggaag acgagtgctc agagctcaag aaggacattg
2941  atgacctgga gctgacactg gccaaggtgg agaaggagaa gcatgcaaca gagaacaagg
3001  tgaagaacct aacagaggag atggctgggc tggatgaaat catcgctaag ctgaccaagg
3061  agaagaaagc tctacaagag gcccatcagc aggccctgga tgaccttcag gttgaggaag
3121  acaaggtcaa cagcctgtcc aagtctaagg tcaagctgga gcagcaggtg gatgatctgg
3181  agggatccct agagcaagag aagaaggtgc gcatggacct ggagcgagca aagcggaaac
3241  tggagggcga cctgaagctg acccaggaga gcatcatgga cctggaaaat gataaactgc
3301  agctggaaga aaagcttaag aagaaggagt ttgacattaa tcagcagaac agtaagattg
3361  aggatgagca ggtgctggcc cttcaactac agaagaaact gaaggaaaac caggcacgca
3421  tcgaggagct ggaggaggag ctggaggccg agcgcaccgc cagggctaag gtggagaagc
3481  tgcgctcaga cctgtctcgg gagctggagg agatcagcga gcggctggaa gaggccggcg
3541  gggccacgtc cgtgcagatc gagatgaaca agaagcgcga ggccgagttc cagaagatgc
3601  ggcgggacct ggaggaggcc acgctgcagc acgaggccac tgccgcggcc ctgcgcaaga
3661  agcacgccga cagcgtggcc gagctgggcg agcagatcga caacctgcag cgggtgaagc
3721  agaagctgga gaaggagaag agcgagttca agctggagct ggatgacgtc acctccaaca
3781  tggagcagat catcaaggcc aaggcaaacc tggagaaagt gtctcggacg ctggaggacc
3841  aggccaatga gtaccgcgtg aagctagaag aggcccaacg ctccctcaat gatttcacca
3901  cccagcgagc caagctgcag accgagaatg gagagttggc ccggcagcta gaggaaaagg
3961  aggcgctaat ctcgcagctg acccggggga agctctctta tacccagcaa atggaggacc
```

-continued

```
4021 tcaaaaggca gctggaggag gagggcaagg cgaagaacgc cctggcccat gcactgcagt
4081 cggcccggca tgactgcgac ctgctgcggg agcagtacga ggaggagaca gaggccaagg
4141 ccgagctgca gcgcgtcctg tccaaggcca actcggaggt ggcccagtgg aggaccaagt
4201 atgagacgga cgccattcag cggactgagg agctcgaaga ggccaaaaag aagctggccc
4261 agcggctgca ggatgccgag gaggccgtgg aggctgttaa tgccaagtgc tcctcactgg
4321 agaagaccaa gcaccggcta cagaatgaga tagaggactt gatggtggac gtagagcgct
4381 ccaatgctgc tgctgcagcc ctggacaaga agcagagaaa ctttgacaag atcctggccg
4441 agtggaagca gaagtatgag gagtcgcagt ctgagctgga gtcctcacag aaggaggctc
4501 gctccctcag cacagagctc ttcaagctca agaacgccta cgaggagtcc ctggagcacc
4561 tagagacctt caagcgggag aacaagaacc ttcaggagga aatctcggac cttactgagc
4621 agctaggaga aggaggaaag aatgtgcatg agctggagaa ggtccgcaaa cagctggagg
4681 tggagaagct ggagctgcag tcagccctgg aggaggcaga ggcctccctg gagcacgagg
4741 agggcaagat cctccgggcc cagctagagt tcaaccagat caaggcagag atcgagcgga
4801 agctggcaga gaaggacgag gagatggaac aggccaagcg caaccaccag cgggtggtgg
4861 actcgctgca gacctccctg gatgcagaga cacgcagccg caacgaggtc ctgagggtga
4921 agaagaagat ggaaggagac ctcaatgaga tggagatcca gctcagccac gccaaccgca
4981 tggctgccga ggcccagaag caagtcaaga gcctccagag cttgctgaag gacacccaga
5041 tccagctgga cgatgcggtc cgtgccaacg acgacctgaa ggagaacatc gccatcgtgg
5101 agcggcgcaa caacctgctg caggctgagc tggaggagct gcgtgccgtg gtggagcaga
5161 cagagcggtc ccggaagctg gcggagcagg agctgattga gaccagcgag cgggtgcagc
5221 tgctgcattc ccagaacacc agcctcatca accagaagaa gaagatggag tcggatctga
5281 cccagctcca gtcggaagtg gaggaggcag tgcaggagtg cagaaacgcc gaggagaagg
5341 ccaagaaggc catcacggat gccgccatga tggcagagga gctgaagaag gagcaggaca
5401 ccagcgccca cctggagcgc atgaagaaga acatggagca gaccattaag gacctgcagc
5461 accggctgga cgaggccgag cagatcgccc tcaagggagg caagaagcag ctgcagaagc
5521 tggaagcgcg ggtgcgggag ctggagggtg agctggaggc cgagcagaag cgcaacgcag
5581 agtcggtgaa gggcatgagg aagagcgagc ggcgcatcaa ggagctcacc taccagacag
5641 aggaagacaa aaagaacctg ctgcggctac aggacctggt ggacaagctg caactgaagg
5701 tcaaggccta caagcgccag gccgaggagg cggaggagca agccaacacc aacctgtcca
5761 agttccgcaa ggtgcagcat gagctggatg aggcagagga gcgggcggac atcgctgagt
5821 cccaggtcaa caagcttcga gccaagagcc gtgacattgg tgccaagcaa aaaatgcacg
5881 atgaggagtg acactgcctc gggaacctca ctcttgccaa cctgtaataa atatgagtgc
5941 c
```

By "MLC2A polypeptide" or "human MLSC2A (hMLC2A) polypeptide" is meant a protein or fragment thereof having at least 85% amino acid sequence identity to the sequence provided at NCBI Accession No. NP_067046.1 and having calcium binding activity. The amino acid sequence provided at NCBI Accession No. NP_067046.1 is shown below:

```
                                                          (SEQ ID NO: 27)
  1  masrkagtrg kvaatkqaqr gssnvfsmfe qaqiqefkea fscidqnrdg iickadlret

 61  ysqlgkvsvp eeeldamlqe gkgpinftvf ltlfgeklng tdpeeailsa frmfdpsgkg

121  vvnkdefkql lltqadkfsp aeveqmfalt pmdlagnidy kslcyiithg dekee
```

By "MLC2A polynucleotide" is meant a polynucleotide encoding a MLC2A polypeptide or fragment thereof. An exemplary MLC2A polynucleotide sequence is provided at NCBI Ref: NM_021223.2. The sequence provided at NCBI Ref: NM_021223.2 is reproduced below:

```
                                                          (SEQ ID NO: 28)
  1  tctgcagaga gaatggccag caggaaggcg gggacccggg gcaaggtggc agccaccaag

 61  caggcccaac gtggttcttc caacgtcttt tccatgtttg aacaagccca gatacaggag

121  ttcaaagaag ccttcagctg tatcgaccag aatcgtgatg gcatcatctg caaggcagac

181  ctgagggaga cctactccca gctggggaag gtgagtgtcc cagaggagga gctggacgcc

241  atgctgcaag agggcaaggg ccccatcaac ttcaccgtct tcctcacgct ctttggggag

301  aagctcaatg ggacagaccc cgaggaagcc atcctgagtg ccttccgcat gtttgacccc

361  agcggcaaag gggtggtgaa caaggatgag ttcaagcagc ttctcctgac ccaggcagac

421  aagttctctc cagctgaggt ggagcagatg ttcgccctga cacccatgga cctggcgggg

481  aacatcgact acaagtcact gtgctacatc atcacccatg gagacgagaa agaggaatga

541  ggggcagggc caggcccacg ggggggcacc tcaataaact ctgttgcaaa attggaaaaa

601  aaaaaaaaaa aaaaaaaaa
```

By "MUC2 polypeptide" is meant a protein or fragment thereof having at least 85% amino acid sequence identity to the sequence provided at NCBI Accession No. NP_002448.3 and having and having a biological activity of a MUC2 polypeptide. Exemplary biological activities of a MUC2 polypeptide include polymerization into a gel and coating of epithelia of the intestines and other mucus membrane-containing organs. The amino acid sequence provided at NCBI Accession No. NP_002448.3 is shown below:

```
                                                            (SEQ ID NO: 29)
  1   mglplarlaa vclalslagg selqtegrtr nhghnvcstw gnfhyktfdg dvfrfpgpcd

 61   ynfasdcrgs ykefavhlkr gpgqaeapag vesilltikd dtiyltrhla vlngavvstp

121   hyspglliek sdaytkvysr agltlmwnre dalmleldtk frnhtcglcg dynglqsyse

181   flsdgvlfsp lefgnmqkin qpdvvcedpe eevapascse hraecerllt aeafadcgdl

241   vplepylrac qqdrcrcpgg dtcvcstvae fsrqcshagg rpgnwrtatl cpktcpgnlv

301   ylesgspcmd tcshlevssl ceehrmdgcf cpegtvyddi gdsgcvpvsq chcrlhghly

361   tpgqeitndc eqcvcnagrw vckdlpcpgt caleggshit tfdgktytfh gdcyyvlakg

421   dhndsyallg elapcgstdk qtclktvvll adkkknvvvf ksdgsvllne lqvnlphvta

481   sfsvfrpssy himvsmaigv rlqvglapvm qlfvtldgas qgqvgglogn fnglegddfk
```

-continued

```
541   tasglveatg agfantwkaq stchdkldwl ddpcslnies anyaehwcsl lkktetpfgr
601   chsavdpaey ykrckydtcn cqnnedclca alssyaract akgvmlwgwr ehvcnkdvgs
661   cpnsqvflyn lttcqqtcrs lseadshcle gfapvdgcgc pdhtfldekg rcvplakcsc
721   yhrglyleag dvvvrqeerc vcrdgrlhcr qirligqsct apkihmdcsn ltalatskpr
781   alscqtlaag yyhtecvsgc vcpdglmddg rggcvvekec pcvhnndlys sgakikvdcn
841   tctckrgrwv ctqavchgtc siygsghyit fdgkyydfdg hcsyvavgdy cgqnsslgsf
901   siitenvpcg ttgvtcskai kifmgrtelk ledkhrvviq rdeghhvayt trevgqylvv
961   esstgiiviw dkrttvfikl apsykgtvcg lcgnfdhrsn ndfttrdhmv vsseldfgns
1021  wkeaptcpdv stnpepcsln phrrswaekq csilkssvfs ichskvdpkp fyeacvhdsc
1081  scdtggdcec fcsavasyaq ectkegacvf wrtpdlcpif cdyynpphec ewhyepcgnr
1141  sfetcrting ihsnisysyl egcyprcpkd rpiyeedlkk cvtadkcgcy vedthyppga
1201  svpteetcks cvctnssqvv crpeegkiln qtqdgafcyw eicgpngtve khfnicsitt
1261  rpstlttftt itlpttpttf ttttttttpt sstvlsttpk lcclwsdwin edhpssgsdd
1321  gdretfdgvc gapediecrs vkdphlsleq lgqkvqcdvs vgficknedq fgngpfglcy
1381  dykirvnccw pmdkcittps pptttpsppp tstttlpptt tpspptttt tppptttpsp
1441  pitttttppp tttpsppist tttppptttp sppttttpspp tttpspptttt tttppptttp
1501  spptttpitp pastttlppt ttpspptttt ttppptttps pptttpitpp tstttlpptt
1561  tpsppptttt tppptttpsp pttttpsppt ittttppptt tpspptttt tppptttpsp
1621  ptttpitppt stttlpptttt pspppttttt ppptttpspp ttttpsppit ttttppptttt
1681  psspitttps ppttttmttps ptttpsspit ttttpsstttt psppttmtt pspttpspp
1741  tttmttlppt ttsspltttp lppsitpptf spfstttptt pcvplcnwtg wldsgkpnfh
1801  kpggdtelig dvcgpgwaan iscratmypd vpigglgqtv vcdvsvglic knedqkpggv
1861  ipmafclnye invqccecvt qpttmttttt enptppttttp ittttttvtpt ptptgtqtpt
1921  ttpitttttv tptptptgtq tptttpittt ttvtptptpt gtqtptttpi tttttvtptp
1981  tptgtqtptt tpitttttvt ptptptgtqt ptttpitttt tvtptptptg tqtptttpit
2041  ttttvtptpt ptgtqtpttt pittttttvtp tptptgtqtp tttpittttt vtptptptgt
2101  qtptttpitt tttvtptptp tgtqtptttp itttttvtpt ptptgtqtpt ttpitttttv
2161  tptptptgtq tptttpittt ttvtptptpt gtqtptttpi tttttvtptp tptgtqtptt
2221  tpitttttvt ptptptgtqt ptttpitttt tvtptptptg tqtptttpit ttttvtptpt
2281  ptgtqtpttt pitttttvtp tptptgtqtp tttpittttt vtptptptgt qtptttpitt
2341  tttvtptptp tgtqtptttp itttttvtpt ptptgtqtpt ttpitttttv tptptptgtq
2401  tptttpittt ttvtptptpt gtqtptttpi tttttvtptp tptgtqtptt tpitttttvt
2461  ptptptgtqt ptttpitttt tvtptptptg tqtptttpit ttttvtptpt ptgtqtpttt
2521  pitttttvtp tptptgtqtp tttpittttt vtptptptgt qtptttpitt tttvtptptp
2581  tgtqtptttp itttttvtpt ptptgtqtpt ttpitttttv tptptptgtq tptttpittt
2641  ttvtptptpt gtqtptttpi tttttvtptp tptgtqtptt tpitttttvt ptptptgtqt
2701  ptttpitttt tvtptptptg tqtptttpit ttttvtptpt ptgtqtpttt pitttttvtp
2761  tptptgtqtp tttpittttt vtptptptgt qtptttpitt tttvtptptp tgtqtptttp
2821  itttttvtpt ptptgtqtpt ttpitttttv tptptptgtq tptttpittt ttvtptptpt
2881  gtqtptttpi tttttvtptp tptgtqtptt tpitttttvt ptptptgtqt ptttpitttt
2941  tvtptptptg tqtptttpit ttttvtptpt ptgtqtpttt pitttttvtp tptptgtqtp
```

-continued 3001 tttpittttt vtptptptgt qtptttpitt tttvtptptp tgtqtptttp itttttvtpt
3061 ptptgtqtpt ttpitttttv tptptptgtq tptttpittt ttvtptptpt gtqtptttpi
3121 tttttvtptp tptgtqtptt tpitttttvt ptptptgtqt ptttpitttt tvtptptptg
3181 tqtptttpit ttttvtptpt ptgtqtpttt pitttttvtp tptptgtqtp tttpittttt
3241 vtptptptgt qtptttpitt tttvtptptp tgtqtptttp itttttvtpt ptptgtqtpt
3301 ttpitttttv tptptptgtq tptttpittt ttvtptptpt gtqtptttpi tttttvtptp
3361 tptgtqtptt tpitttttvt ptptptgtqt ptttpitttt tvtptptptg tqtptttpit
3421 ttttvtptpt ptgtqtpttt pitttttvtp tptptgtqtp tttpittttt vtptptptgt
3481 qtptttpitt tttvtptptp tgtqtptttp itttttvtpt ptptgtqtpt ttpitttttv
3541 tptptptgtq tptttpittt ttvtptptpt gtqtptttpi tttttvtptp tptgtqtptt
3601 tpitttttvt ptptptgtqt ptttpitttt tvtptptptg tqtptttpit ttttvtptpt
3661 ptgtqtpttt pitttttvtp tptptgtqtp tttpittttt vtptptptgt qtptttpitt
3721 tttvtptptp tgtqtptttp itttttvtpt ptptgtqtpt ttpitttttv tptptptgtq
3781 tptttpittt ttvtptptpt gtqtptttpi tttttvtptp tptgtqtptt tpitttttvt
3841 ptptptgtqt ptttpitttt tvtptptptg tqtptttpit ttttvtptpt ptgtqtpttt
3901 pitttttvtp tptptgtqtp tttpittttt vtptptptgt qtptttpitt tttvtptptp
3961 tgtqtptttp itttttvtpt ptptgtqtpt ttpitttttv tptptptgtq tptttpittt
4021 ttvtptptpt gtqtptttpi tttttvtptp tptgtqtptt tpitttttvt ptptptgtqt
4081 ptttpitttt tvtptptptg tqtptttpit ttttvtptpt ptgtqtpttt pitttttvtp
4141 tptptgtqtp tttpittttt vtptptptgt qtptttpitt tttvtptptp tgtqtgppth
4201 tstapiaelt tsnpppesst pqtsrstssp ltesttllst lppaiemtst appstptapt
4261 ttsgghtlsp ppstttsppg tptrgtttgs ssaptpstvq ttttsawtpt ptplstpsii
4321 rttglrpyps svliccvind tyyapgeevy ngtygdtcyf vncslsctle fynwscpstp
4381 sptptpskst ptpskpsstp skptpgtkpp ecpdfdpprq enetwwlcdc fmatckynnt
4441 veivkvecep ppmptcsngl qpvrvedpdg ccwhwecdcy ctgwgdphyv tfdglyysyq
4501 gnctyvlvee ispsvdnfgv yidnyhcdpn dkvscprtli vrhetqevli ktvhmmpmqv
4561 qvgvnrgava lpykkyglev yqsginyvvd ipelgvlvsy nglsfsvrlp yhrfgnntkg
4621 qcgtctntts ddcilpsgei vsnceaaadq wlvndpskph cphsssttkr pavtvpgggk
4681 ttphkdctps ploglikdsl faqchalvpp qhyydacvfd scfmpgssle caslqayaal
4741 caqqnicldw rnhthgaclv ecpshreyqa cgpaeeptck ssssqqnntv lvegcfcpeg
4801 tmnyapgfdv cvktcgcvgp dnvprefgeh fefdckncvc leggsgiicq pkrcsqkpvt
4861 hcvedgtyla tevnpadtcc nitvckcnts lckekpsvcp lgfevkskmv pgrccpfywc
4921 eskgvcvhgn aeyqpgspvy sskcqdcvct dkvdnntlln viacthvpcn tscspgfelm
4981 eapgecckkc eqthciikrp dnqhvilkpg dfksdpknnc tffscvkihn qlissysnit
5041 cpnfdasici pgsitfmpng ccktctprne trvpcstvpv ttevsyagct ktvlmnhcsg
5101 scgtfvmysa kaqaldhscs cckeektsqr evvlscpngg slthtythie scqcqdtvcg
5161 lptgtsrrar rsprhlgsg By "MUC2 polynucleotide" is meant a polynucleotide encoding a MUC2 polypeptide or fragment thereof. An exemplary MUC2 polynucleotide sequence is provided at NCBI Ref: NM_002457.3. The sequence provided at NCBI Ref: NM_002457.3 is reproduced below:

```
                                                      (SEQ ID NO: 30)
   1  caacccacac cgcccctgcc agccaccatg gggctgccac tagcccgcct ggcggctgtg

  61  tgcctggccc tgtctttggc agggggctcg gagctccaga cagagggcag aacccgaaac

 121  cacggccaca acgtctgcag cacctggggc aacttccact acaagacctt cgacggggac

 181  gtcttccgct tccccggccc ctgcgactac aacttcgcct ccgactgccg aggctcctac

 241  aaggaatttg ctgtgcacct gaagcggggt ccgggccagg ctgaggcccc cgccggggtg

 301  gagtccatcc tgctgaccat caaggatgac accatctacc tcacccgcca cctggctgtg

 361  cttaacgggg ccgtggtcag caccccgcac tacagccccg ggctgctcat tgagaagagc

 421  gatgcctaca ccaaagtcta ctcccgcgcc ggcctcaccc tcatgtggaa ccgggaggat

 481  gcactcatgc tggagctgga cactaagttc cggaaccaca cctgtggcct ctgcggggac

 541  tacaacggcc tgcagagcta ttcagaattc ctctctgacg gcgtgctctt cagtcccctg

 601  gagtttggga acatgcagaa gatcaaccag cccgatgtgg tgtgtgagga tcccgaggag

 661  gaggtggccc ccgcatcctg ctccgagcac cgcgccgagt gtgagaggct gctgaccgcc

 721  gaggccttcg cggactgtca ggacctggtg ccgctggagc cgtatctgcg cgcctgccag

 781  caggaccgct gccggtgccc gggcggtgac acctgcgtct gcagcaccgt ggccgagttc

 841  tcccgccagt gctcccacgc cggcggccgg cccgggaact ggaggaccgc cacgctctgc

 901  cccaagacct gccccgggaa cctggtgtac ctggagagcg gctcgccctg catggacacc

 961  tgctcacacc tggaggtgag cagcctgtgc gaggagcacc gcatggacgg ctgtttctgc

1021  ccagaaggca ccgtatatga cgacatcggg gacagtggct gcgttcctgt gagccagtgc

1081  cactgcaggc tgcacggaca cctgtacaca ccgggccagg agatcaccaa tgactgcgag

1141  cagtgtgtct gtaacgctgg ccgctgggtg tgcaaagacc tgccctgccc cggcacctgt

1201  gccctggaag gcggctccca catcaccacc ttcgatggga agacgtacac cttccacggg

1261  gactgctact atgtcctggc caagggtgac cacaacgatt cctacgctct cctgggcgag

1321  ctggccccct gtggctccac agacaagcag acctgcctga agacggtggt gctgctggct

1381  gacaagaaga agaatgtggt ggtcttcaag tccgatggca gtgtactgct caacgagctg

1441  caggtgaacc tgccccacgt gaccgcgagc ttctctgtct tccgcccgtc ttcctaccac

1501  atcatggtga gcatggccat tggcgtccgg ctgcaggtgc agctggcccc agtcatgcaa

1561  ctctttgtga cactggacca ggcctcccag gggcaggtgc agggcctctg cgggaacttc

1621  aacggcctgg aaggtgacga cttcaagacg gccagcgggc tggtggaggc cacgggggcc

1681  ggctttgcca acacctggaa ggcacagtca acctgccatg acaagctgga ctggttggac

1741  gatccctgct ccctgaacat cgagagcgcc aactacgccg agcactggtg ctccctcctg

1801  aagaagacag agacccccctt tggcaggtgc cactcggctg tggaccctgc tgagtattac

1861  aagaggtgca aatatgacac gtgtaactgt cagaacaatg aggactgcct gtgcgccgcc

1921  ctgtcctcct acgcgcgcgc ctgcaccgcc aagggcgtca tgctgtgggg ctggcgggag

1981  catgtctgca acaaggatgt gggctcctgc cccaactcgc aggtcttcct gtacaacctg

2041  accacctgcc agcagacctg ccgctccctc tccgaggccg acagccactg tctcgagggc

2101  tttgcgcctg tggacggctg cggctgccct gaccacacct tcctggacga gaagggccgc

2161  tgcgtacccc tggccaagtg ctcctgttac caccgcggtc tctacctgga ggcgggggac
```

-continued

```
2221  gtggtcgtca ggcaggaaga acgatgtgtg tgccgggatg ggcggctgca ctgtaggcag
2281  atccggctga tcggccagag ctgcacggcc ccaaagatcc acatggactg cagcaacctg
2341  actgcactgg ccacctcgaa gccccgagcc ctcagctgcc agacgctggc cgccggctat
2401  taccacacag agtgtgtcag tggctgtgtg tgccccgacg ggctgatgga tgacggccgg
2461  ggtggctgcg tggtggagaa ggaatgccct tgcgtccata acaacgacct gtattcttcc
2521  ggcgccaaga tcaaggtgga ctgcaatacc tgcacctgca agagaggacg ctgggtgtgc
2581  acccaggctg tgtgccatgg cacctgctcc atttacggga gtggccacta catcaccttt
2641  gacgggaagt actacgactt tgacggacac tgctcctacg tggctgttca ggactactgc
2701  ggccagaact cctcactggg ctcattcagc atcatcaccg agaacgtccc ctgtggcact
2761  acgggcgtca cctgctccaa ggccatcaag atcttcatgg ggaggacgga gctgaagttg
2821  gaagacaagc accgtgtggt gatccagcgt gatgagggtc accacgtggc ctacaccacg
2881  cgggaggtgg gccagtacct ggtggtggag tccagcacgg gcatcatcgt catctgggac
2941  aagaggacca ccgtgttcat caagctggct ccctcctaca agggcaccgt gtgtggcctg
3001  tgtgggaact ttgaccaccg ctccaacaac gacttcacca cgcgggacca catggtggtg
3061  agcagcgagc tggacttcgg gaacagctgg aaggaggccc ccacctgccc agatgtgagc
3121  accaaccccg agccctgcag cctgaacccg caccgccgct cctgggccga gaagcagtgc
3181  agcatcctca aagcagcgt gttcagcatc tgccacagca aggtggaccc caagcccttc
3241  tacgaggcct gtgtgcacga ctcgtgctcc tgtgacacgg gtggggactg tgagtgcttc
3301  tgctctgccg tggcctccta cgcccaggag tgtaccaaag agggggcctg cgtgttctgg
3361  aggacgccgg acctgtgccc catattctgc gactactaca accctccgca tgagtgtgag
3421  tggcactatg agccatgtgg gaaccggagc ttcgagacct gcaggaccat caatggcatc
3481  cactccaaca tctccgtgtc ctacctggag ggctgctacc cccggtgccc caaggacagg
3541  cccatctatg aggaggatct gaagaagtgt gtcactgcag acaagtgtgg ctgctatgtc
3601  gaggacaccc actacccacc tggagcatcg gttcccaccg aggagacctg caagtcctgc
3661  gtgtgtacca actcctccca agtcgtctgc aggccggagg aaggaaagat tcttaaccag
3721  acccaggatg gcgccttctg ctactgggag atctgtggcc ccaacgggac ggtggagaag
3781  cacttcaaca tctgttccat tacgacacgc ccgtccaccc tgaccacctt caccaccatc
3841  accctcccca ccacccccac caccttcacc actaccacca ccaccaccac cccgacctcc
3901  agcacagttt tatcaacaac tccgaagctg tgctgcctct ggtctgactg gatcaatgag
3961  gaccacccca gcagtggcag cgacgacggt gaccgagaaa catttgatgg ggtctgcggg
4021  gcccctgagg acatcgagtg caggtcggtc aaggatcccc acctcagctt ggagcagcta
4081  ggccagaagg tgcagtgtga tgtctctgtt gggttcattt gcaagaatga agaccagttt
4141  ggaaatggac catttggact gtgttacgac tacaagatac gtgtcaattg ttgctggccc
4201  atggataagt gtatcaccac tcccagccct ccaactacca ctcccagccc tccaccaacc
4261  agcacgacca cccttccacc aaccaccacc cccagccctc caaccaccac cacaaccacc
4321  cctccaccaa ccaccacccc cagccctcca ataaccacca cgaccacccc tccaccaacc
4381  accactccca gccctccaat aagcaccaca accacccctc caccaaccac cactcccagc
4441  cctccaacca ccactcccag ccctccaacc accactccca gccctccaac aaccaccaca
4501  accacccctc caccaaccac cactcccagc cctccaacga ctacgcccat cactccacca
4561  gccagcacta ccacccttcc accaaccacc actcccagcc ctccaacaac caccacaacc
```

-continued

```
4621  acccctccac caaccaccac tcccagtcct ccaacgacta cgcccatcac tccaccaacc
4681  agcactacta cccttccacc aaccaccact cccagccctc caccaaccac cacaaccacc
4741  cctccaccaa ccaccactcc cagccctcca acaaccacca ctcccagtcc tccaacaatc
4801  accacaacca cccctccacc aaccaccact cccagccctc caacaacgac cacaaccacc
4861  cctccaccaa ccaccactcc cagccctcca acgactacac ccatcactcc accaaccagc
4921  actaccaccc ttccaccaac caccactccc agccctccac caaccaccac aaccacccct
4981  ccaccaacca ccactcccag ccctccaaca accaccactc ccagccctcc aataaccacc
5041  acaaccaccc ctccaccaac caccactccc agctctccaa taaccaccac tcccagccct
5101  ccaacaacca ccatgaccac cccttcacca accaccaccc ccagctctcc aataaccacc
5161  acaaccaccc cttcctcaac taccactccc agccctccac caaccaccat gaccacccct
5221  tcaccaacca ccactcccag ccctccaaca accaccatga ccacccttcc accaaccacc
5281  acttccagcc ctctaacaac tactcctcta cctccatcaa taactcctcc tacattttca
5341  ccattctcaa cgacaacccc tactacccca tgcgtgcctc tctgcaattg gactggctgg
5401  ctggattctg gaaaacccaa ctttcacaaa ccaggtggag acacagaatt gattggagac
5461  gtctgtggac caggctgggc agctaacatc tcttgcagag ccaccatgta tcctgatgtt
5521  cccattggac agcttggaca aacagtggtg tgtgatgtct ctgtggggct gatatgcaaa
5581  aatgaagacc aaaagccagg tggggtcatc cctatggcct tctgcctcaa ctacgagatc
5641  aacgttcagt gctgtgagtg tgtcacccaa cccaccacca tgacaaccac caccacagag
5701  aacccaactc cgccaaccac gacacccatc accaccacca ctacggtgac ccccaacccca
5761  acacccaccg gcacacagac ccccaaccacg acacccatca ccaccaccac tacggtgacc
5821  ccaaccccaa cacccaccgg cacacagacc ccaaccacga cacccatcac caccaccact
5881  acggtgaccc caaccccaac acccaccggc acacagaccc caaccacgac acccatcacc
5941  accaccacta cggtgacccc aaccccaaca cccaccggca cacagacccc aaccacgaca
6001  cccatcacca ccaccactac ggtgacccca accccaacac ccaccggcac acagacccca
6061  accacgacac ccatcaccac caccactacg gtgaccccaa ccccaacacc caccggcaca
6121  cagaccccaa ccacgacacc catcaccacc accactacgg tgaccccaac cccaacaccc
6181  accggcacac agaccccaac cacgacaccc atcaccacca ccactacggt gaccccaacc
6241  ccaacaccca ccggcacaca gaccccaacc acgacaccca tcaccaccac cactacggtg
6301  accccaaccc caacacccac cggcacacag accccaacca cgacacccat caccaccacc
6361  actacggtga ccccaacccc aacacccacc ggcacacaga ccccaaccac gacacccatc
6421  accaccacca ctacggtgac cccaacccca acacccaccg gcacacagac cccaaccacg
6481  acacccatca ccaccaccac tacggtgacc ccaaccccaa cacccaccgg cacacagacc
6541  ccaaccacga cacccatcac caccaccact acggtgaccc caaccccaac acccaccggc
6601  acacagaccc caaccacgac acccatcacc accaccacta cggtgacccc aaccccaaca
6661  cccaccggca cacagacccc aaccacgaca cccatcacca ccaccactac ggtgacccca
6721  accccaacac ccaccggcac acagacccca accacgacac ccatcaccac caccactacg
6781  gtgaccccaa ccccaacacc caccggcaca cagaccccaa ccacgacacc catcaccacc
6841  accactacgg tgaccccaac cccaacaccc accggcacac agaccccaac cacgacaccc
6901  atcaccacca ccactacggt gaccccaacc ccaacaccca ccggcacaca gaccccaacc
6961  acgacaccca tcaccaccac cactacggtg accccaaccc caacacccac cggcacacag
7021  accccaacca cgacacccat caccaccacc actacggtga ccccaacccc aacacccacc
```

-continued 7081 ggcacacaga ccccaaccac gacacccatc accaccacca ctacggtgac cccaacccca 7141 acacccaccg gcacacagac cccaaccacg acacccatca ccaccaccac tacggtgacc 7201 ccaaccccaa cacccaccgg cacacagacc ccaaccacga cacccatcac caccaccact 7261 acggtgaccc caaccccaac acccaccggc acacagaccc caaccacgac acccatcacc 7321 accaccacta cggtgacccc aaccccaaca cccaccggca cacagacccc aaccacgaca 7381 cccatcacca ccaccactac ggtgacccca accccaacac ccaccggcac acagacccca 7441 accacgacac ccatcaccac caccactacg gtgaccccaa ccccaacacc caccggcaca 7501 cagaccccaa ccacgacacc catcaccacc accactacgg tgaccccaac cccaacaccc 7561 accggcacac agaccccaac cacgacaccc atcaccacca ccactacggt gaccccaacc 7621 ccaacaccca ccggcacaca gaccccaacc acgacaccca tcaccaccac cactacggtg 7681 accccaaccc caacacccac cggcacacag accccaacca cgacacccat caccaccacc 7741 actacggtga ccccaacccc aacacccacc ggcacacaga ccccaaccac gacacccatc 7801 accaccacca ctacggtgac cccaacccca acacccaccg gcacacagac cccaaccacg 7861 acacccatca ccaccaccac tacggtgacc ccaaccccaa cacccaccgg cacacagacc 7921 ccaaccacga cacccatcac caccaccact acggtgaccc caaccccaac acccaccggc 7981 acacagaccc caaccacgac acccatcacc accaccacta cggtgacccc aaccccaaca 8041 cccaccggca cacagacccc aaccacgaca cccatcacca ccaccactac ggtgacccca 8101 accccaacac ccaccggcac acagacccca accacgacac ccatcaccac caccactacg 8161 gtgaccccaa ccccaacacc caccggcaca cagaccccaa ccacgacacc catcaccacc 8221 accactacgg tgaccccaac cccaacaccc accggcacac agaccccaac cacgacaccc 8281 atcaccacca ccactacggt gaccccaacc ccaacaccca ccggcacaca gaccccaacc 8341 acgacaccca tcaccaccac cactacggtg accccaaccc caacacccac cggcacacag 8401 accccaacca cgacacccat caccaccacc actacggtga ccccaacccc aacacccacc 8461 ggcacacaga ccccaaccac gacacccatc accaccacca ctacggtgac cccaacccca 8521 acacccaccg gcacacagac cccaaccacg acacccatca ccaccaccac tacggtgacc 8581 ccaaccccaa cacccaccgg cacacagacc ccaaccacga cacccatcac caccaccact 8641 acggtgaccc caaccccaac acccaccggc acacagaccc caaccacgac acccatcacc 8701 accaccacta cggtgacccc aaccccaaca cccaccggca cacagacccc aaccacgaca 8761 cccatcacca ccaccactac ggtgacccca accccaacac ccaccggcac acagacccca 8821 accacgacac ccatcaccac caccactacg gtgaccccaa ccccaacacc caccggcaca 8881 cagaccccaa ccacgacacc catcaccacc accactacgg tgaccccaac cccaacaccc 8941 accggcacac agaccccaac cacgacaccc atcaccacca ccactacggt gaccccaacc 9001 ccaacaccca ccggcacaca gaccccaacc acgacaccca tcaccaccac cactacggtg 9061 accccaaccc caacacccac cggcacacag accccaacca cgacacccat caccaccacc 9121 actacggtga ccccaacccc aacacccacc ggcacacaga ccccaaccac gacacccatc 9181 accaccacca ctacggtgac cccaacccca acacccaccg gcacacagac cccaaccacg 9241 acacccatca ccaccaccac tacggtgacc ccaaccccaa cacccaccgg cacacagacc 9301 ccaaccacga cacccatcac caccaccact acggtgaccc caaccccaac acccaccggc 9361 acacagaccc caaccacgac acccatcacc accaccacta cggtgacccc aaccccaaca 9421 cccaccggca cacagacccc aaccacgaca cccatcacca ccaccactac ggtgacccca -continued

```
9481  accccaacac ccaccggcac acagacccca accacgacac ccatcaccac caccactacg

9541  gtgaccccaa ccccaacacc caccggcaca cagaccccaa ccacgacacc catcaccacc

9601  accactacgg tgaccccaac cccaacaccc accggcacac agaccccaac cacgacaccc

9661  atcaccacca ccactacggt gaccccaacc ccaacaccca ccggcacaca gaccccaacc

9721  acgacaccca tcaccaccac cactacggtg accccaaccc caacacccac cggcacacag

9781  accccaacca cgacacccat caccaccacc actacggtga ccccaacccc aacacccacc

9841  ggcacacaga ccccaaccac gacacccatc accaccacca ctacggtgac cccaacccca

9901  acacccaccg gcacacagac cccaaccacg acacccatca ccaccaccac tacggtgacc

9961  ccaaccccaa cacccaccgg cacacagacc ccaaccacga cacccatcac caccaccact

10021 acggtgaccc caaccccaac acccaccggc acacagaccc caaccacgac acccatcacc

10081 accaccacta cggtgacccc aaccccaaca cccaccggca cacagacccc aaccacgaca

10141 cccatcacca ccaccactac ggtgacccca accccaacac ccaccggcac acagacccca

10201 accacgacac ccatcaccac caccactacg gtgaccccaa ccccaacacc caccggcaca

10261 cagaccccaa ccacgacacc catcaccacc accactacgg tgaccccaac cccaacaccc

10321 accggcacac agaccccaac cacgacaccc atcaccacca ccactacggt gaccccaacc

10381 ccaacaccca ccggcacaca gaccccaacc acgacaccca tcaccaccac cactacggtg

10441 accccaaccc caacacccac cggcacacag accccaacca cgacacccat caccaccacc

10501 actacggtga ccccaacccc aacacccacc ggcacacaga ccccaaccac gacacccatc

10561 accaccacca ctacggtgac cccaacccca acacccaccg gcacacagac cccaaccacg

10621 acacccatca ccaccaccac tacggtgacc ccaaccccaa cacccaccgg cacacagacc

10681 ccaaccacga cacccatcac caccaccact acggtgaccc caaccccaac acccaccggc

10741 acacagaccc caaccacgac acccatcacc accaccacta cggtgacccc aaccccaaca

10801 cccaccggca cacagacccc aaccacgaca cccatcacca ccaccactac ggtgacccca

10861 accccaacac ccaccggcac acagacccca accacgacac ccatcaccac caccactacg

10921 gtgaccccaa ccccaacacc caccggcaca cagaccccaa ccacgacacc catcaccacc

10981 accactacgg tgaccccaac cccaacaccc accggcacac agaccccaac cacgacaccc

11041 atcaccacca ccactacggt gaccccaacc ccaacaccca ccggcacaca gaccccaacc

11101 acgacaccca tcaccaccac cactacggtg accccaaccc caacacccac cggcacacag

11161 accccaacca cgacacccat caccaccacc actacggtga ccccaacccc aacacccacc

11221 ggcacacaga ccccaaccac gacacccatc accaccacca ctacggtgac cccaacccca

11281 acacccaccg gcacacagac cccaaccacg acacccatca ccaccaccac tacggtgacc

11341 ccaaccccaa cacccaccgg cacacagacc ccaaccacga cacccatcac caccaccact

11401 acggtgaccc caaccccaac acccaccggc acacagaccc caaccacgac acccatcacc

11461 accaccacta cggtgacccc aaccccaaca cccaccggca cacagacccc aaccacgaca

11521 cccatcacca ccaccactac ggtgacccca accccaacac ccaccggcac acagacccca

11581 accacgacac ccatcaccac caccactacg gtgaccccaa ccccaacacc caccggcaca

11641 cagaccccaa ccacgacacc catcaccacc accactacgg tgaccccaac cccaacaccc

11701 accggcacac agaccccaac cacgacaccc atcaccacca ccactacggt gaccccaacc

11761 ccaacaccca ccggcacaca gaccccaacc acgacaccca tcaccaccac cactacggtg

11821 accccaaccc caacacccac cggcacacag accccaacca cgacacccat caccaccacc

11881 actacggtga ccccaacccc aacacccacc ggcacacaga ccccaaccac gacacccatc
```

-continued

```
11941  accaccacca ctacggtgac cccaacccca acacccaccg gcacacagac cccaaccacg
12001  acacccatca ccaccaccac tacggtgacc ccaaccccaa cacccaccgg cacacagacc
12061  ccaaccacga cacccatcac caccaccact acggtgaccc caaccccaac acccaccggc
12121  acacagaccc caaccacgac acccatcacc accaccacta cggtgacccc aaccccaaca
12181  cccaccggca cacagacccc aaccacgaca cccatcacca ccaccactac ggtgacccca
12241  accccaacac ccaccggcac acagacccca accacgacac ccatcaccac caccactacg
12301  gtgaccccaa ccccaacacc caccggcaca cagaccccaa ccacgacacc catcaccacc
12361  accactacgg tgaccccaac cccaacaccc accggcacac agaccccaac cacgacaccc
12421  atcaccacca ccactacggt gaccccaacc ccaacaccca ccggcacaca gaccccaacc
12481  acgacaccca tcaccaccac cactacggtg accccaaccc caacacccac cggcacacag
12541  accccaacca cgacacccat caccaccacc actacggtga ccccaacccc aacacccacc
12601  ggcacacaga ccgggccccc cacccacaca agcacagcac cgattgctga gttgaccaca
12661  tccaatcctc cgcctgagtc ctcaacccct cagacctctc ggtccacctc ttcccctctc
12721  acggagtcaa ccacccttct gagtacccta ccacctgcca ttgagatgac cagcacggcc
12781  ccaccctcca cacccacggc acccacgacc acgagcggag gccacacact gtctccaccg
12841  cccagcacca ccacgtcccc tccaggcacc cccactcgcg gtaccacgac tgggtcatct
12901  tcagccccca cccccagcac tgtgcagacg accaccacca gtgcctggac ccccacgccg
12961  accccactct ccacacccag catcatcagg accacaggcc tgaggcccta cccttcctct
13021  gtgcttatct gctgtgtcct gaacgacacc tactacgcac caggtgagga ggtgtacaac
13081  ggcacatacg gagacacctg ttatttcgtc aactgctcac tgagctgtac gttggagttc
13141  tataactggt cctgcccatc cacgccctcc ccaacaccca cgccctccaa gtcgacgccc
13201  acgccttcca agccatcgtc cacgccctcc aagccgacgc ccggcaccaa gcccccccgag
13261  tgcccagact ttgatcctcc cagacaggag aacgagactt ggtggctgtg cgactgcttc
13321  atggccacgt gcaagtacaa caacacggtg gagatcgtga aggtggagtg tgagccgccg
13381  cccatgccca cctgctccaa cggcctccaa cccgtgcgcg tcgaggaccc cgacggctgc
13441  tgctggcact gggagtgcga ctgctactgc acgggctggg gcgacccgca ctatgtcacc
13501  ttcgacggac tctactacag ctaccagggc aactgcacct acgtgctggt ggaggagatc
13561  agcccctccg tggacaactt cggagtttac atcgacaact accactgcga tcccaacgac
13621  aaggtgtcct gcccccgcac cctcatcgtg cgccacgaga cccaggaggt gctgatcaag
13681  accgtgcata tgatgcccat gcaggtgcag gtgcaggtga acaggcaggc ggtggcactg
13741  ccctacaaga agtacgggct ggaggtgtac cagtctggca tcaactacgt ggtggacatc
13801  cccgagctgg gtgtcctcgt ctcctacaat ggcctgtcct tctccgtcag gctgccctac
13861  caccggtttg gcaacaacac caagggccag tgtggcacct gcaccaacac cacctccgac
13921  gactgcattc tgcccagcgg ggagatcgtc tccaactgtg aggctgcggc tgaccagtgg
13981  ctggtgaacg acccctccaa gccacactgc ccccacagca gctccacgac caagcgcccg
14041  gccgtcactg tgcccggggg cggtaaaacg accccacaca aggactgcac cccatctccc
14101  ctctgccagc tcatcaagga cagcctgttt gcccagtgcc acgcactggt gcccccgcag
14161  cactactacg atgcctgcgt gttcgacagc tgcttcatgc cgggctcgag cctggagtgc
14221  gccagtctgc aggcctacgc agccctctgt gcccagcaga acatctgcct cgactggcgg
14281  aaccacacgc atggggcctg cttggtggag tgcccatctc acagggagta ccaggcctgt
```

-continued

```
14341 ggccctgcag aagagcccac gtgcaaatcc agctcctccc agcagaacaa cacagtcctg
14401 gtggaaggct gcttctgtcc tgagggcacc atgaactacg ctcctggctt tgatgtctgc
14461 gtgaagacct gcggctgtgt gggacctgac aatgtgccca gagagtttgg ggagcacttc
14521 gagttcgact gcaagaactg tgtctgcctg gagggtggaa gtggcatcat ctgccaaccc
14581 aagaggtgca gccagaagcc cgttacccac tgcgtggaag acggcaccta cctcgccacg
14641 gaggtcaacc ctgccgacac ctgctgcaac attaccgtct gcaagtgcaa caccagcctg
14701 tgcaaagaga agccctccgt gtgcccgctg ggattcgaag tgaagagcaa gatggtgcct
14761 ggaaggtgct gtcctttcta ctggtgtgag tccaaggggg tgtgtgttca cgggaatgct
14821 gagtaccagc ccggttctcc agtttattcc tccaagtgcc aggactgcgt gtgcacggac
14881 aaggtggaca acaacaccct gctcaacgtc atcgcctgca cccacgtgcc ctgcaacacc
14941 tcctgcagcc ctggcttcga actcatggag gcccccgggg agtgctgtaa gaagtgtgaa
15001 cagacgcact gtatcatcaa acggcccgac aaccagcacg tcatcctgaa gcccggggac
15061 ttcaagagcg acccgaagaa caactgcaca ttcttcagct gcgtgaagat ccacaaccag
15121 ctcatctcgt ccgtctccaa catcacctgc cccaactttg atgccagcat ttgcatcccg
15181 ggctccatca cattcatgcc caatggatgc tgcaagacct gcacccctcg caatgagacc
15241 agggtgccct gctccaccgt ccccgtcacc acggaggttt cgtacgccgg ctgcaccaag
15301 accgtcctca tgaatcattg ctccgggtcc tgcgggacat ttgtcatgta ctcggccaag
15361 gcccaggccc tggaccacag ctgctcctgc tgcaaagagg agaaaaccag ccagcgtgag
15421 gtggtcctga gctgccccaa tggcggctcg ctgacacaca cctacaccca catcgagagc
15481 tgccagtgcc aggacaccgt ctgcgggctc cccaccggca cctcccgccg ggcccggcgc
15541 tcccctaggc atctggggag cgggtgagcg gggtgggcac agccccctc actgccctcg
15601 acagctttac ctccccccgga ccctctgagc ctcctaagct cggcttcctc tcttcagata
15661 tttattgtct gagtctttgt tcagtccttg ctttccaata ataaactcag gggacatgc
```

By “NKX2-5 polypeptide” or “human NKX2-5 (hNKX2-5) polypeptide” is meant a protein or fragment thereof having at least 85% amino acid sequence identity to the sequence provided at NCBI Accession No. NP_004378.1 (isoform 1), NP_001159647.1 (isoform 2), or NP_001159648.1 (isoform 3) and having transcription factor activity. The amino acid sequence provided at NCBI Accession No. NP_004378.1 is shown below:

```
                                                    (SEQ ID NO: 31)
  1 mfpspaltpt pfsvkdilnl eqqqrslaaa gelsarleat lapsscmlaa fkpeayagpe
 61 aaapglpelr aelgrapspa kcasafpaap afypraysdp dpakdpraek kelcalqkav
121 elekteadna erprarrrrk prvlfsqaqv yelerrfkgq rylsaperdq lasvlkltst
181 qvkiwfqnrr ykckrqrqdq tlelvglppp ppppparriav pvlvrdgkpc lgdsapyapa
241 ygvglnpygy naypaypgyg gaacspgysc taaypagpsp agpataaann nfvnfgvgdl
301 navqspgipq snsgvstlhg iraw
```

By “NKX2-5 polynucleotide” is meant a polynucleotide encoding a NKX2-5 polypeptide or fragment thereof. An exemplary NKX2-5 polynucleotide sequence is provided at NCBI Ref: NM_004387.3. The sequence provided at NCBI Ref: NM_004387.3 is reproduced below:

```
                                                    (SEQ ID NO: 32)
  1 gctcctgtca tcgaggcccc tggcccaatg gcaggctgag tccccctcct ctggcctggt
 61 cccgcctctc ctgccccttg tgctcagcgc tacctgctgc ccggacacat ccagagctgg
```

-continued

```
 121  ccgacgggtg cgcgggcggg cggcggcacc atgcagggaa gctgccaggg gccgtgggca
 181  gcgccgcttt ctgccgccca cctggcgctg tgagactggc gctgccacca tgttccccag
 241  ccctgctctc acgcccacgc ccttctcagt caaagacatc ctaaacctgg aacagcagca
 301  gcgcagcctg gctgccgccg gagagctctc tgcccgcctg gaggcgaccc tggcgccctc
 361  ctcctgcatg ctggccgcct tcaagccaga ggcctacgct gggcccgagg cggctgcgcc
 421  gggcctccca gagctgcgcg cagagctggg ccgcgcgcct tcaccggcca agtgtgcgtc
 481  tgcctttccc gccgcccccg ccttctatcc acgtgcctac agcgaccccg acccagccaa
 541  ggaccctaga gccgaaaaga aagagctgtg cgcgctgcag aaggcggtgg agctggagaa
 601  gacagaggcg gacaacgcgg agcggccccg ggcgcgacgg cggaggaagc cgcgcgtgct
 661  cttctcgcag gcgcaggtct atgagctgga gcggcgcttc aagcagcagc ggtacctgtc
 721  ggcccccgaa cgcgaccagc tggccagcgt gctgaaactc acgtccacgc aggtcaagat
 781  ctggttccag aaccggcgct acaagtgcaa gcggcagcgg caggaccaga ctctggagct
 841  ggtggggctg cccccgccgc cgccgccgcc tgcccgcagg atcgcggtgc cagtgctggt
 901  gcgcgatggc aagccatgcc taggggactc ggcgccctac gcgcctgcct acggcgtggg
 961  cctcaatccc tacggttata acgcctaccc cgcctatccg ggttacggcg gcgcggcctg
1021  cagccctggc tacagctgca ctgccgctta ccccgccggg ccttccccag cgcagccggc
1081  cactgccgcc gccaacaaca acttcgtgaa cttcggcgtc ggggacttga atgcggttca
1141  gagccccggg attccgcaga gcaactcggg agtgtccacg ctgcatggta tccgagcctg
1201  gtagggaagg gacccgcgtg gcgcgaccct gaccgatccc acctcaacag ctccctgact
1261  ctcgggggga gaaggggctc ccaacatgac cctgagtccc ctggattttg cattcactcc
1321  tgcggagacc taggaacttt ttctgtccca cgcgcgtttg ttcttgcgca cgggagagtt
1381  tgtggcggcg attatgcagc gtgcaatgag tgatcctgca gcctggtgtc ttagctgtcc
1441  ccccaggagt gccctccgag agtccatggg cacccccggt tggaactggg actgagctcg
1501  ggcacgcagg gcctgagatc tggccgccca ttccgcgagc cagggccggg cgcccgggcc
1561  tttgctatct cgccgtcgcc cgcccacgca cccacccgta tttatgtttt tacctattgc
1621  tgtaagaaat gacgatcccc ttcccattaa agagagtgcg ttgaccccg
```

By "NEUROD1 polypeptide" is meant a protein or fragment thereof having at least 85% amino acid sequence identity to the sequence provided at NCBI Accession No. NP_002491.2 and having transcription factor activity. The amino acid sequence provided at NCBI Accession No. NP_002491.2 is shown below:

(SEQ ID NO: 33)

```
  1  mtksysesgl mgepqpqgpp swtdeclssq deeheadkke ddleamnaee dslrnggeee
 61  dededleeee eeeeedddqk pkrrgpkkkk mtkarlerfk lrrmkanare rnrmhglnaa
121  ldnlrkvvpc ysktqklski etlrlaknyi walseilrsg kspdlvsfvq tlckglsgpt
181  tnlvagclql nprtflpeqn qdmpphlpta sasfpvhpys yqspglpspp ygtmdsshvf
241  hvkppphays aalepffesp ltdctspsfd gplspplsin gnfsfkheps aefeknyaft
301  mhypaatlag aqshgsifsg taaprceipi dnimsfdshs hhervmsaql naifhd
```

By "NEUROD1 polynucleotide" is meant a polynucleotide encoding a NEUROD1 polypeptide or fragment thereof. An exemplary NEUROD1 polynucleotide sequence is provided at NCBI Ref: NM_002500.4. The sequence provided at NCBI Ref: NM_002500.4 is reproduced below:

(SEQ ID NO: 34)

```
   1 ggggaggagg ggagaacggg gagcgcacag cctggacgcg tgcgcaggcg tcaggcgcat
  61 agacctgcta gcccctcagc tagcggcccc gcccgcgctt agcatcacta actgggctat
 121 ataacctgag cgcccgcgcg gccacgacac gaggaattcg cccacgcagg aggcgcggcg
 181 tccggaggcc ccagggttat gagactatca ctgctcagga cctactaaca acaaaggaaa
 241 tcgaaacatg accaaatcgt acagcgagag tgggctgatg ggcgagcctc agccccaagg
 301 tcctccaagc tggacagacg agtgtctcag ttctcaggac gaggagcacg aggcagacaa
 361 gaaggaggac gacctcgaag ccatgaacgc agaggaggac tcactgagga acgggggaga
 421 ggaggaggac gaagatgagg acctggaaga ggaggaagaa gaggaagagg aggatgacga
 481 tcaaaagccc aagagacgcg gccccaaaaa gaagaagatg actaaggctc gcctggagcg
 541 ttttaaattg agacgcatga aggctaacgc ccgggagcgg aaccgcatgc acggactgaa
 601 cgcggcgcta gacaacctgc gcaaggtggt gccttgctat tctaagacgc agaagctgtc
 661 caaaatcgag actctgcgct tggccaagaa ctacatctgg gctctgtcgg agatcctgcg
 721 ctcaggcaaa agcccagacc tggtctcctt cgttcagacg ctttgcaagg gcttatccca
 781 acccaccacc aacctggttg cgggctgcct gcaactcaat cctcggactt ttctgcctga
 841 gcagaaccag gacatgcccc cccacctgcc gacggccagc gcttccttcc ctgtacaccc
 901 ctactcctac cagtcgcctg ggctgcccag tccgccttac ggtaccatgg acagctccca
 961 tgtcttccac gttaagcctc cgccgcacgc ctacagcgca gcgctggagc ccttctttga
1021 aagccctctg actgattgca ccagcccttc ctttgatgga cccctcagcc cgccgctcag
1081 catcaatggc aacttctctt tcaaacacga accgtccgcc gagtttgaga aaaattatgc
1141 ctttaccatg cactatcctg cagcgacact ggcaggggcc caaagccacg gatcaatctt
1201 ctcaggcacc gctgcccctc gctgcgagat ccccatagac aatattatgt ccttcgatag
1261 ccattcacat catgagcgag tcatgagtgc ccagctcaat gccatatttc atgattagag
1321 gcacgccagt ttcaccattt ccgggaaacg aacccactgt gcttacagtg actgtcgtgt
1381 ttacaaaagg cagccctttg ggtactactg ctgcaaagtg caaatactcc aagcttcaag
1441 tgatatatgt atttattgtc attactgcct ttggaagaaa caggggatca aagttcctgt
1501 tcaccttatg tattattttc tatagctctt ctatttaaaa aataaaaaaa tacagtaaag
1561 tttaaaaaat acaccacgaa tttggtgtgg ctgtattcag atcgtattaa ttatctgatc
1621 gggataacaa aatcacaagc aataattagg atctatgcaa tttttaaact agtaatgggc
1681 caattaaaat atatataaat atatattttt caaccagcat tttactactt gttacctttc
1741 ccatgctgaa ttattttgtt gtgattttgt acagaatttt taatgacttt ttataatgtg
1801 gatttcctat tttaaaacca tgcagcttca tcaattttta tacatatcag aaaagtagaa
1861 ttatatctaa tttatacaaa ataatttaac taatttaaac cagcagaaaa gtgcttagaa
1921 agttattgtg ttgccttagc acttctttcc tctccaattg taaaaaaaaa aaaaaaaaaa
1981 aaaaaaaaaa aaaaattgca caatttgagc aattcatttc actttaaagt ctttccgtct
2041 ccctaaaata aaaaccagaa tcataatttt caagagaaga aaaaattaag agatacattc
2101 cctatcaaaa catatcaatt caacacatta cttgcacaag cttgtatata catattataa
2161 ataaatgcca acataccctt ctttaaatca aaagctgctt gactatcaca tacaatttgc
```

-continued

```
2221  actgttactt tttagtcttt tactcctttg cattccatga ttttacagag aatctgaagc
2281  tattgatgtt tccagaaaat ataaatgcat gattttatac atagtcacaa aaatggtggt
2341  ttgtcatata ttcatgtaat aaatctgagc ctaaatctaa tcaggttgtt aatgttggga
2401  tttatatcta tagtagtcaa ttagtacagt agcttaaata aattcaaacc atttaattca
2461  taattagaac aatagctatt gcatgtaaaa tgcagtccag aataagtgct gtttgagatg
2521  tgatgctggt accactggaa tcgatctgta ctgtaatttt gtttgtaatc ctgtatatta
2581  tggtgtaatg cacaatttag aaaacattca tccagttgca ataaaatagt attgaaagtg
2641  agagcaattg ttgcatttct tcttaaaggg attctgtttt tatttttggg gaaagtagtt
2701  gctttttgc tgagttaaaa aatactaaac actatatgta gaataaaaga aaagaaaaaa
2761  gtttaccttg gcatatgctc ttgtctgttt atcttgcaca gggagtcacc agttctatgt
2821  agataatgaa aagacctaac tgatatttca ttatttggaa tatgggactg gacggcagta
2881  caaacagtgt gttttttct ttgttttaag tggcttagcc tttaggtttt ttatttccat
2941  ttttaaaaat gattgttaca tgttttcttc tatttctttt tttaaaaggt ggattttaat
3001  aa
```

By "NKX6-1 polypeptide" is meant a protein or fragment thereof having at least 85% amino acid sequence identity to the sequence provided at NCBI Accession No. NP_006159.2 and having transcription factor activity. The amino acid sequence provided at NCBI Accession No. NP_006159.2 is shown below:

```
                                                      (SEQ ID NO: 35)
  1  mlavgamegt rqsafllssp plaalhsmae mktplypaay pplpagppss sssssssssp
 61  spplgthnpg glkppatggl sslgsppqql saatphgind ilsrpsmpva sgaalpsasp
121  sgsssssssss asassasaaa aaaaaaaaaa sspagllagl prfsslsppp pppglyfsps
181  aaavaavgry pkplaelpgr tpifwpgvmq sppwrdarla ctphqgsill dkdgkrkhtr
241  ptfsgqqifa lektfeqtky lagperarla yslgmtesqv kvwfqnrrtk wrkkhaaema
301  takkkqdset erlkgasene eedddynkpl dpnsddekit qllkkhksss gggggllha
361  sepesss
```

By "NKX6-1 polynucleotide" is meant a polynucleotide encoding a NKX6-1 polypeptide or fragment thereof. An exemplary NKX6-1 polynucleotide sequence is provided at NCBI Ref: NM_006168.2. The sequence provided at NCBI Ref: NM_006168.2 is reproduced below:

```
                                                        (SEQ ID NO: 36)
  1   cgtgggatgt tagcggtggg ggcaatggag ggcacccggc agagcgcatt cctgctcagc
 61   agccctcccc tggccgccct gcacagcatg gccgagatga agaccccgct gtaccctgcc
121   gcgtatcccc cgctgcctgc cggcccccc tcctcctcgt cctcgtcgtc gtcctcctcg
181   tcgccctccc cgcctctggg cacccacaac ccaggcggcc tgaagccccc ggccacgggg
241   gggctctcat ccctcggcag cccccgcag cagctctcgg ccgccacccc acacggcatc
301   aacgatatcc tgagccggcc ctccatgccc gtggcctcgg gggccgccct gccctccgcc
361   tcgccctccg gttcctcctc ctcctcttcc tcgtccgcct ctgcctcctc cgcctctgcc
421   gccgccgcgg ctgctgccgc ggccgcagcc gccgcctcat ccccggcggg gctgctggcc
481   ggactgccac gctttagcag cctgagcccg ccgccgccgc cgcccgggct ctacttcagc
541   cccagcgccg cggccgtggc cgccgtgggc cggtacccca agccgctggc tgagctgcct
```

-continued

```
601  ggccggacgc ccatcttctg gcccggagtg atgcagagcc cgccctggag ggacgcacgc
661  ctggcctgta cccctcatca aggatccatt ttgttggaca aagacgggaa gagaaaacac
721  acgagaccca ctttttccgg acagcagatc ttcgccctgg agaagacttt cgaacaaaca
781  aaatacttgg cggggcccga gagggctcgt ttggcctatt cgttggggat gacagagagt
841  caggtcaagg tctggttcca gaaccgccgg accaagtgga ggaagaagca cgctgccgag
901  atggccacgg ccaagaagaa gcaggactcg gagacagagc gcctcaaggg ggcctcggag
961  aacgaggaag aggacgacga ctacaataag cctctggatc ccaactcgga cgacgagaaa
1021 atcacgcagc tgttgaagaa gcacaagtcc agcagcggcg gcggcggcgg cctcctactg
1081 cacgcgtccg agccggagag ctcatcctga acgccg
```

By "NDUFA4 polypeptide" is meant a protein or fragment thereof having at least 85% amino acid sequence identity to the sequence provided at NCBI Accession No. NP_002480.1 and having NADH dehydrogenase activity and oxidoreductase activity. The amino acid sequence provided at NCBI Accession No. NP_002480.1 is shown below:

```
                                                        (SEQ ID NO: 37)
  1  maaelamgae lpssplaiey vndfdlmkfe vkkeppeaer fchrlppgsl sstplstpcs
 61  svpsspsfca pspgtggggg aggggggssqa ggapgppsgg pgavggtsgk paledlywms
121  gyqhhlnpea lnltpedave aligsghhga hhgahhpaaa aayeafrgpg faggggaddm
181  gaghhhgahh aahhhhaahh hhhhhhhhgg aghgggaghh vrleerfsdd qlvsmsvrel
241  nrqlrgfske evirlkqkrr tlknrgyaqs crfkrvqqrh ilesekcqlq sqveqlklev
301  grlakerdly kekyeklagr ggpgsaggag fprepsppqa gpggakgtad ffl
```

By "NDUFA4 polynucleotide" is meant a polynucleotide encoding a NDUFA4 polypeptide or fragment thereof. An exemplary NDUFA4 polynucleotide sequence is provided at NCBI Ref: NM_002489.3. The sequence provided at NCBI Ref: NM_002489.3 is reproduced below:

```
                                                        (SEQ ID NO: 38)
  1  gggtccttca ggtaggaggt cctgggtgac tttggaagtc cgtagtgtct cattgcagat
 61  aatttttagc ttagggcctg gtggctaggt cggttctctc ctttccagtc ggagacctct
121  gccgcaaaca tgctccgcca gatcatcggt caggccaaga agcatccgag cttgatcccc
181  ctctttgtat ttattggaac tggagctact ggagcaacac tgtatctctt gcgtctggca
241  ttgttcaatc cagatgtttg ttgggacaga aataacccag agccctggaa caaactgggt
301  cccaatgatc aatacaagtt ctactcagtg aatgtggatt acagcaagct gaagaaggaa
361  cgtccagatt tctaaatgaa atgtttcact ataacgctgc tttagaatga aggtcttcca
421  gaagccacat ccgcacaatt ttccacttaa ccaggaaata tttctcctct aaatgcatga
481  aatcatgttg gagatctcta ttgtaatctc tattggagat tacaatgatt aaatcaataa
541  ataactgaaa cttgatatgt gtcacttttt tatgctgaaa gtatgctctg aactttagag
601  tataggaaat taactattag aatttaaaga atttcttgaa tttctgtagt ttgaaaatac
661  gactttaagc tgctttagta aaacacttcc attttgtgta tagactgttg gtaacttcac
721  tagagcatac ataacaactg gaactggaaa ttatacaaaa gtaaattggg aaggatactc
781  cagcatctga cactggcaaa atggaaacct ttgagtttct cttactggct gttgaagtgt
841  gtgcagtttt taacaatggt ttttacttgg catctctttg ttgtgatttt caaggttata
901  agttgctttg gtcctaggat tgaagttgaa atctgagttt atcagtgcta accatggtgc
961  tagtagtcaa gagatcttga gaattttggc tgctgagtct tggtgcaggg tgcaggtttt
```

-continued

```
1021  cttttctttt ttcttttttt tttttttgag atagtctctg tcacccaggc tggagtgcag
1081  tggtacaaac atggatcact gcagcctcta cctcccgggc ttaagtgatc ctcctgcctc
1141  agcccctaag tagccgggac tacaggtatg tgccaccatg cccagttaat ttttgtaatt
1201  tttttagag acagggtttt gccatgttgc ccaggctggt ctcaaactct tgagctcaag
1261  cgatccattc tcctcagcct cccagggtgc tgggattaca ggcgtgagcc attgcgctta
1321  gccatggtgc aggttttcaa aggccaggaa gtatattcat aattttaaga tggggaatat
1381  agcaagtttt cacataggtg tgtgtaagtc atcacatcat agaaacttga ggaattcagt
1441  gacattaatt ttggattttc atacgtaagt atacaattaa atgtttacag ggtagtagaa
1501  gcacatttta aatgtcagga actgaactaa gtatttgaat tacgtggatt atctcaaaaa
1561  ttttgaaatt gttaaacgag ttgaattact tgaattcatt ctgttagtca aatggtggat
1621  atttacaccc atgtagtttt gaatttagag tgtgtagagt gttttcagtt accagactcc
1681  atgcttttac ctcctatgtg tcaggtataa tttgaacctc taagaacagg gtttctcaac
1741  cttgccactg ttgactattt ctgaaagaca gtttggttta gcagaccatc ccatgcgctt
1801  tagcttgttt agtagctaac ttgggctctg ccactacaga caaaaagcac tctttccctc
1861  caattcccac aggctatgag aagaatggag acattaccaa atgtccattg gtgggcaaaa
1921  ttgcttcatt cctacctctg ttgagaatta ctctagatcc tttggcacaa attacctcaa
1981  agtttaaaat tgtgtaaaca aacagtgtgt catgtaattg aaaaacatta agcaactcca
2041  aataaatgct acattaag
```

As used herein, "obtaining" as in "obtaining an agent" includes synthesizing, purchasing, or otherwise acquiring the agent.

By "organ" is meant a collection of cells that perform a biological function. In one embodiment, an organ includes, but is not limited to, bladder, brain, nervous tissue, glial tissue, esophagus, fallopian tube, heart, pancreas, intestines, gallbladder, kidney, liver, lung, ovaries, prostate, spinal cord, spleen, stomach, testes, thymus, thyroid, trachea, urogenital tract, ureter, urethra, uterus, breast, skeletal muscle, skin, bone, and cartilage. The biological function of an organ can be assayed using standard methods known to the skilled artisan.

By "organoid" is meant an in vitro generated body that mimics organ structure and function. "Organoid" and "mini organ" are used interchangeably herein. A "pancreatic islet organoid" is an in vitro generated cell cluster that mimics structure and function of a pancreatic islet. Exemplary functions of a pancreatic islet include, without limitation, glucose-stimulated insulin secretion (GSIS), potassium chloride (KCl)-stimulated insulin secretion, GLP-1 stimulated insulin secretion, somatostatin secretion, or glucagon secretion. "Pancreatic islet organoid" and "mini pancreatic islet" are used interchangeably herein. A "pancreatic organoid" is an in vitro generated body that mimics structure and function of a pancreas. Exemplary functions of a pancreas include, without limitation, endocrine secretion of hormones, such as glucose and glucagon, that regulate glucose metabolism and blood glucose concentration, and exocrine secretion of digestive enzymes that help break down carbohydrates, proteins, and lipids. "Pancreatic organoid" and "mini pancreas" are used interchangeably herein.

By "PAX4 polypeptide" is meant a protein or fragment thereof having at least 85% amino acid sequence identity to the sequence provided at NCBI Accession No. NP_006184.2 and having transcription factor activity. The amino acid sequence provided at NCBI Accession No. NP_006184.2 is shown below:

```
                                                          (SEQ ID NO: 39)
  1  mnqlgglfvn grplpldtrq qivrlavsgm rpcdisrilk vsngcvskil gryyrtgvle
 61  pkgiggskpr latppvvari aqlkgecpal faweiqrqlc aeglctqdkt psvssinrvl
121  ralqedqglp ctrlrspavl apavltphsg setprgthpg tghrnrtifs psqaealeke
181  fqrgqypdsv argklatats lpedtvrvwf snrrakwrrq eklkwemqlp gasqgltvpr
241  vapgiisaqq spgsvptaal paleplgpsc yqlcwatape rclsdtppka clkpcwghlp
301  pqpnsldsgl lclpcpsshc hlaslsgsqa llwpgcplly gle
```

By "PAX4 polynucleotide" is meant a polynucleotide encoding a PAX4 polypeptide or fragment thereof. An exemplary PAX4 polynucleotide sequence is provided at NCBI Ref: NM_006193.2. The sequence provided at NCBI Ref: NM_006193.2 is reproduced below:

(SEQ ID NO: 40)

```
1    caaagactca cccgtgagcc agctctcaaa gaaagcagct tgcgttgaca gcctgggggc
61   agcaaggatg cagtctccca ggagaggatg cactcggtgg tgggaagcca ggctggaggg
121  gcctgagtga ccctctccac aggcgggcag ggcagtggga gaggtggtgt gtggatacct
181  ctgtctcacg cccagggatc agcagcatga accagcttgg ggggctcttt gtgaatggcc
241  ggcccctgcc tctggatacc cggcagcaga ttgtgcggct agcagtcagt ggaatgcggc
301  cctgtgacat ctcacggatc cttaaggtat ctaatggctg tgtgagcaag atcctagggc
361  gttactaccg cacaggtgtc ttggagccaa agggcattgg gggaagcaag ccacggctgg
421  ctacaccccc tgtggtggct cgaattgccc agctgaaggg tgagtgtcca gccctctttg
481  cctgggaaat ccaacgccag ctttgtgctg aagggctttg cacccaggac aagactccca
541  gtgtctcctc catcaaccga gtcctgcggg cattacagga ggaccaggga ctaccgtgca
601  cacggctcag gtcaccagct gttttggctc cagctgtcct cactccccat agtggctctg
661  agactccccg gggtacccac ccagggaccg gccaccggaa tcggactatc ttctccccaa
721  gccaagcaga ggcactggag aaagagttcc agcgtgggca gtatcctgat tcagtggccc
781  gtggaaagct ggctactgcc acctctctgc ctgaggacac ggtgagggtc tggttttcca
841  acagaagagc caaatggcgt cggcaagaga agctcaagtg ggaaatgcag ctgccaggtg
901  cttcccaggg gctgactgta ccaagggttg ccccaggaat catctctgca cagcagtccc
961  ctggcagtgt gcccacagca gccctgcctg ccctggaacc actgggtccc tcctgctatc
1021 agctgtgctg ggcaacagca ccagaaaggt gtctgagtga caccccacct aaagcctgtc
1081 tcaagccctg ctggggccac ttgcccccac agccgaattc cctggactca ggactgcttt
1141 gccttccttg cccttcctcc cactgtcacc tggccagtct tagtggctct caggccctgc
1201 tctggcctgg ctgcccacta ctgtatggct tggaatgagg caggagtggg aaggagatgg
1261 catagagaag atctaatacc atcctgccca ttgtccttac cgtcctgccc atacagactg
1321 tggctccttc ctccttcctg tgattgctcc ctcctgtgtg gacgttgcct ggccctgcct
1381 cgatgcctct ctggcgcatc acctgattgg aggggctggt aaagcaacac ccacccactt
1441 ctcacactag ccttaagagg cctccactca gcagtaataa aagctgtttt tattagcagt
1501 agttctgttg tccatcatgt tttccctatg agcaccccta tgcccactct aatattcaac
1561 aattatagac aatttgccct atcatttatt tacatctatg tatctaccat ctaatctatg
1621 catgtatgta ggcaatacat gtatctaaac aatgtatttg tcaatgcatc aatttaccta
1681 ctctatgtat gcatctatat gtgtattatg tatgcgtgca tgcgtgcgcg cacacacaca
1741 cacacacaca cacactgaca ttatatcatg gcattttatt cctaaatctt ccagcatgca
1801 tccccaaaaa acaagaaact tgtcttacat aatcacaata atatatccac atctaagaaa
1861 atttactgta acttcttaat ctaagaaaat tatgtatttt tgtcatatgt attttgtcat
1921 atgtattttg tatttgcata tgtattttgt atttgcatat gtatttttgt catagcagca
1981 aacagagtga aatgccattt ttcatattct
```

By "PAX6 polypeptide" is meant a protein or fragment thereof having at least 85% amino acid sequence identity to the sequence provided at NCBI Accession No. NP_001297090.1 and having transcription factor activity. The amino acid sequence provided at NCBI Accession No. NP_001297090.1 is shown below:

(SEQ ID NO: 41)

```
1    mgadgmydkl rmlngqtgsw gtrpgwypgt svpgqptqdg cqqqegggen tnsissnged
61   sdeaqmrlql krklqrnrts ftqeqieale keferthypd vfarerlaak idlpeariqv
```

-continued

```
121  wfsnrrakwr reeklrnqrr qasntpship isssfstsvy qpipqpttpv ssftsgsmlg

181  rtdtaltnty salppmpsft mannlpmqpp vpsqtssysc mlptspsvng rsydtytpph

241  mqthmnsqpm gtsgttstgl ispgvsvpvq vpgsepdmsq ywprlq
```

By "PAX6 polynucleotide" is meant a polynucleotide encoding a PAX6 polypeptide or fragment thereof. An exemplary PAX6 polynucleotide sequence is provided at NCBI Ref: NM_001310161.1. The sequence provided at NCBI Ref: NM_001310161.1 is reproduced below:

```
                                                    (SEQ ID NO: 42)
   1 cttttcaatt agccttccat gcatgatccg gagcgacttc cgcctatttc cagaaattaa

  61 gctcaaactt gacgtgcagc tagttttatt ttaaagacaa atgtcagaga ggctcatcat

 121 attttccccc ctcttctata tttggagctt atttattgct aagaagctca ggctcctggc

 181 gtcaatttat cagtaggctc caaggagaag agaggagagg agaggagagc tgaacaggga

 241 gccacgtctt ttcctgggag ggctgctatc taagtcgggg ctgcaggtca cagcggagtg

 301 aatcagctcg gtggtgtctt tgtcaacggg cggccactgc cggactccac ccggcagaag

 361 attgtagagc tagctcacag cggggcccgg ccgtgcgaca tttcccgaat tctgcagacc

 421 catgcagatg caaaagtcca agtgctggac aatcaaaacg tgtccaacgg atgtgtgagt

 481 aaaattctgg gcaggtatta cgagactggc tccatcagac ccagggcaat cggtggtagt

 541 aaaccgagag tagcgactcc agaagttgta agcaaaatag cccagtataa gcgggagtgc

 601 ccgtccatct ttgcttggga aatccgagac agattactgt ccgagggggt ctgtaccaac

 661 gataacatac caagcgtgtc atcaataaac agagttcttc gcaacctggc tagcgaaaag

 721 caacagatgg gcgcagacgg catgtatgat aaactaagga tgttgaacgg gcagaccgga

 781 agctggggca cccgccctgg ttggtatccg gggacttcgg tgccagggca acctacgcaa

 841 gatggctgcc agcaacagga aggaggggga gagaatacca actccatcag ttccaacgga

 901 gaagattcag atgaggctca aatgcgactt cagctgaagc ggaagctgca aagaaataga

 961 acatccttta cccaagagca aattgaggcc ctggagaaag agtttgagag aacccattat

1021 ccagatgtgt ttgcccgaga aagactagca gccaaaatag atctacctga agcaagaata

1081 caggtatggt tttctaatcg aagggccaaa tggagaagag aagaaaaact gaggaatcag

1141 agaagacagg ccagcaacac acctagtcat attcctatca gcagtagttt cagcaccagt

1201 gtctaccaac caattccaca acccaccaca ccggtttcct ccttcacatc tggctccatg

1261 ttgggccgaa cagacacagc cctcacaaac acctacagcg ctctgccgcc tatgcccagc

1321 ttcaccatgg caaataacct gcctatgcaa cccccagtcc ccagccagac ctcctcatac

1381 tcctgcatgc tgcccaccag cccttcggtg aatgggcgga gttatgatac ctacaccccc

1441 ccacatatgc agacacacat gaacagtcag ccaatgggca cctcgggcac cacttcaaca

1501 ggactcattt cccctggtgt gtcagttcca gttcaagttc ccggaagtga acctgatatg

1561 tctcaatact ggccaagatt acagtaaaaa aaaaaaaaaa aaaaaaaagg aaaggaaata

1621 ttgtgttaat tcagtcagtg actatgggga cacaacagtt gagctttcag gaaagaaaga

1681 aaaatggctg ttagagccgc ttcagttcta caattgtgtc ctgtattgta ccactgggga

1741 aggaatggac ttgaaacaag gacctttgta tacagaaggc acgatatcag ttggaacaaa

1801 tcttcatttt ggtatccaaa cttttattca ttttggtgta ttatttgtaa atgggcattt

1861 gtatgttata atgaaaaaaa gaacaatgta gactggatgg atgtttgatc tgtgttggtc

1921 atgaagttgt tttttttttt tttaaaaaga aaaccatgat caacaagctt tgccacgaat
```

-continued 1981 ttaagagttt tatcaagata tatcgaatac ttctacccat ctgttcatag tttatggact
2041 gatgttccaa gtttgtatca ttcctttgca tataattaaa cctggaacaa catgcactag
2101 atttatgtca gaaatatctg ttggttttcc aaaggttgtt aacagatgaa gtttatgtgc
2161 aaaaaagggt aagatataaa ttcaaggaag aaaaaaagtt gatagctaaa aggtagagtg
2221 tgtcttcgat ataatccaat ttgttttatg tcaaaatgta agtatttgtc ttccctagaa
2281 atcctcagaa tgatttctat aataaagtta atttcattta tatttgacaa gaatatagat
2341 gttttataca cattttcatg caatcatacg tttctttttt ggccagcaaa agttaattgt
2401 tcttagatat agttgtatta ctgttcacgg tccaatcatt ttgtgcatct agagttcatt
2461 cctaatcaat taaaagtgct tgcaagagtt ttaaacttaa gtgttttgaa gttgttcaca
2521 actacatatc aaaattaacc attgttgatt gtaaaaaacc atgccaaagc ctttgtattt
2581 cctttattat acagttttct ttttaacctt atagtgtggt gttacaaatt ttatttccat
2641 gttagatcaa cattctaaac caatggttac tttcacacac actctgtttt acatcctgat
2701 gatccttaaa aaataatcct tatagatacc ataaatcaaa aacgtgttag aaaaaaattc
2761 cacttacagc agggtgtaga tctgtgccca tttataccca caacatatat acaaaatggt
2821 aacatttccc agttagccat ttaattctaa agctcaaagt ctagaaataa tttaaaaatg
2881 caacaagcga ttagctagga attgtttttt gaattaggac tggcattttc aatctgggca
2941 gatttccatt gtcagcctat ttcaacaatg atttcactga agtatattca aaagtagatt
3001 tcttaaagga gactttctga aagctgttgc ctttttcaaa taggccctct cccttttctg
3061 tctccctccc ctttgcacaa gaggcatcat ttcccattga accactacag ctgttcccat
3121 ttgaatcttg ctttctgtgc ggttgtggat ggttggaggg tggagggggg atgttgcatg
3181 tcaaggaata atgagcacag acacatcaac agacaacaac aaagcagact gtgactggcc
3241 ggtgggaatt aaaggccttc agtcattggc agcttaagcc aaacattccc aaatctatga
3301 agcagggccc attgttggtc agttgttatt tgcaatgaag cacagttctg atcatgttta
3361 aagtggaggc acgcagggca ggagtgcttg agcccaagca aaggatggaa aaaaataagc
3421 ctttgttggg taaaaaagga ctgtctgaga ctttcatttg ttctgtgcaa catataagtc
3481 aatacagata agtcttcctc tgcaaacttc actaaaaagc ctgggggttc tggcagtcta
3541 gattaaaatg cttgcacatg cagaaacctc tggggacaaa gacacacttc cactgaatta
3601 tactctgctt taaaaaaatc cccaaaagca aatgatcaga aatgtagaaa ttaatggaag
3661 gatttaaaca tgaccttctc gttcaatatc tactgttttt tagttaagga attacttgtg
3721 aacagataat tgagattcat tgctccggca tgaaatatac taataatttt attccaccag
3781 agttgctgca catttggaga caccttccta agttgcagtt tttgtatgtg tgcatgtagt
3841 tttgttcagt gtcagcctgc actgcacagc agcacatttc tgcaggggag tgagcacaca
3901 tacgcactgt tggtacaatt gccggtgcag acatttctac ctcctgacat tttgcagcct
3961 acattccctg agggctgtgt gctgagggaa ctgtcagaga agggctatgt gggagtgcat
4021 gccacagctg ctggctggct tacttcttcc ttctcgctgg ctgtaatttc caccacggtc
4081 aggcagccag ttccggccca cggttctgtt gtgtagacag cagagacttt ggagacccgg
4141 atgtcgcacg ccaggtgcaa gaggtgggaa tgggagaaaa ggagtgacgt gggagcggag
4201 ggtctgtatg tgtgcacttg ggcacgtata tgtgtgctct gaaggtcagg attgccaggg
4261 caaagtagca cagtctggta tagtctgaag aagcggctgc tcagctgcag aagccctctg
4321 gtccggcagg atgggaacgg ctgccttgcc ttctgcccac accctaggga catgagctgt -continued 4381 ccttccaaac agagctccag gcactctctt ggggacagca tggcaggctc tgtgtggtag
4441 cagtgcctgg gagttggcct tttactcatt gttgaaataa tttttgttta ttatttattt
4501 aacgatacat atatttatat atttatcaat ggggtatctg cagggatgtt ttgacaccat
4561 cttccaggat ggagattatt tgtgaagact tcagtagaat cccaggacta aacgtctaaa
4621 ttttttctcc aaacttgact gacttgggaa aaccaggtga atagaataag agctgaatgt
4681 tttaagtaat aaacgttcaa actgctctaa gtaaaaaaat gcattttact gcaatgaatt
4741 tctagaatat ttttccccca aagctatgcc tcctaaccct taaatggtga acaactggtt
4801 tcttgctaca gctcactgcc atttcttctt actatcatca ctaggtttcc taagattcac
4861 tcatacagta ttatttgaag attcagcttt gttctgtgaa tgtcatctta ggattgtgtc
4921 tatattcttt tgcttatttc tttttactct gggcctctca tactagtaag attttaaaaa
4981 gccttttctt ctctgtatgt ttggctcacc aaggcgaaat atatattctt ctctttttca
5041 tttctcaaga ataaacctca tctgcttttt tgtttttctg tgttttggct tggtactgaa
5101 tgactcaact gctcggtttt aaagttcaaa gtgtaagtac ttagggttag tactgcttat
5161 ttcaataatg ttgacggtga ctatctttgg aaagcagtaa catgctgtct tagaaatgac
5221 attaataatg ggcttaaaca aatgaatagg ggggtccccc cactctcctt ttgtatgcct
5281 atgtgtgtct gatttgttaa aagatggaca gggaattgat tgcagagtgt cgcttccttc
5341 taaagtagtt ttattttgtc tactgttagt atttaaagat cctggaggtg gacataagga
5401 ataaatggaa gagaaaagta gatattgtat ggtggctact aaaaggaaat tcaaaaagtc
5461 ttagaacccg agcacctgag caaactgcag tagtcaaaat atttatctca tgttaaagaa
5521 aggcaaatct agtgtaagaa atgagtacca tatagggttt tgaagttcat atactagaaa
5581 cacttaaaag atatcatttc agatattacg tttggcattg ttcttaagta tttatatctt
5641 tgagtcaagc tgataattaa aaaaaatctg ttaatggagt gtatatttca taatgtatca
5701 aaatggtgtc tatacctaag gtagcattat tgaagagaga tatgtttatg tagtaagtta
5761 ttaacataat gagtaacaaa taatgtttcc agaagaaagg aaaacacatt ttcagagtgc
5821 gtttttatca gaggaagaca aaaatacaca cccctctcca gtagcttatt tttacaaagc
5881 cggcccagtg aattagaaaa acaaagcact tggatatgat ttttggaaag cccaggtaca
5941 cttattattc aaaatgcact tttactgagt ttgaaaagtt tcttttatat ttaaaataag
6001 ggttcaaata tgcatattca atttttatag tagttatcta tttgcaaagc atatattaac
6061 tagtaattgg ctgttaattt tatagacatg gtagccaggg aagtatatca atgacctatt
6121 aagtattttg acaagcaatt tacatatctg atgacctcgt atctcttttt cagcaagtca
6181 aatgctatgt aattgttcca ttgtgtgttg tataaaatga atcaacacgg taagaaaaag
6241 gttagagtta ttaaaataat aaactgacta aaatactcat ttgaatttat tcagaatgtt
6301 cataatgctt tcaaaggaca tagcagagct tttgtggagt atccgcacaa cattatttat
6361 tatctatgga ctaaatcaat tttttgaagt tgctttaaaa tttaaaagca cctttgctta
6421 atataaagcc ctttaatttt aactgacaga tcaattctga aactttattt tgaaaagaaa
6481 atggggaaga atctgtgtct ttagaattaa aagaaatgaa aaaaataaac ccgacattct
6541 aaaaaaatag aataagaaac ctgatttttta gtactaatga aatagcgggt gacaaaatag
6601 ttgtcttttt gattttgatc acaaaaaata aactggtagt gacaggatat gatggagaga
6661 tttgacatcc tggcaaatca ctgtcattga ttcaattatt ctaattctga ataaaagctg
6721 tatacagtaa aa By "PDX1 polypeptide" is meant a protein or fragment thereof having at least 85% amino acid sequence identity to the sequence provided at NCBI Accession No. NP_000200.1 and having transcription factor activity. The amino acid sequence provided at NCBI Accession No. NP_000200.1 is shown below:

(SEQ ID NO: 43)

```
  1 mngeeqyyaa tqlykdpcaf qrgpapefsa sppaclymgr qpppppphpf pgalgaleqg

 61 sppdispyev ppladdpava hlhhhlpaql alphppagpf pegaepgvle epnrvqlpfp

121 wmkstkahaw kgqwaggaya aepeenkrtr taytraqlle lekeflfnky isrprrvela

181 vmlnlterhi kiwfqnrrmk wkkeedkkrg ggtavggggv aepeqdcavt sgeellalpp

241 ppppggavpp aapvaaregr lppglsaspq pssvaprrpq epr
```

By "PDX1 polynucleotide" is meant a polynucleotide encoding a PDX1 polypeptide or fragment thereof. An exemplary PDX1 polynucleotide sequence is provided at NCBI Ref: NM_000209.3. The sequence provided at NCBI Ref: NM_000209.3 is reproduced below:

(SEQ ID NO: 44)

```
   1 gggtggcgcc gggagtggga acgccacaca gtgccaaatc cccggctcca gctcccgact

  61 cccggctccc ggctcccggc tcccggtgcc caatcccggg ccgcagccat gaacggcgag

 121 gagcagtact acgcggccac gcagctttac aaggacccat gcgcgttcca gcgaggcccg

 181 gcgccggagt tcagcgccag ccccccctgcg tgcctgtaca tgggccgcca gccccccgccg

 241 ccgccgccgc acccgttccc tggcgccctg ggcgcgctgg agcagggcag ccccccggac

 301 atctccccgt acgaggtgcc cccccctcgcc gacgaccccg cggtggcgca ccttcaccac

 361 cacctcccgg ctcagctcgc gctcccccac ccgcccgccg ggcccttccc ggagggagcc

 421 gagccgggcg tcctggagga gcccaaccgc gtccagctgc ctttcccatg gatgaagtct

 481 accaaagctc acgcgtggaa aggccagtgg gcaggcggcg cctacgctgc ggagccggag

 541 gagaacaagc ggacgcgcac ggcctacacg cgcgcacagc tgctagagct ggagaaggag

 601 ttcctattca acaagtacat ctcacggccg cgccgggtgg agctggctgt catgttgaac

 661 ttgaccgaga gacacatcaa gatctggttc caaaaccgcc gcatgaagtg gaaaaaggag

 721 gaggacaaga agcgcggcgg cgggacagct gtcgggggtg gcggggtcgc ggagcctgag

 781 caggactgcg ccgtgacctc cggcgaggag cttctggcgc tgccgccgcc gccgcccccc

 841 ggaggtgctg tgccgcccgc tgccccccgtt gccgcccgag agggccgcct gccgcctggc

 901 cttagcgcgt cgccacagcc ctccagcgtc gcgcctcggc ggccgcagga accacgatga

 961 gaggcaggag ctgctcctgg ctgaggggct tcaaccactc gccgaggagg agcagagggc

1021 ctaggaggac cccgggcgtg gaccacccgc cctggcagtt gaatggggcg gcaattgcgg

1081 ggcccacctt agaccgaagg ggaaaacccg ctctctcagg cgcatgtgcc agttggggcc

1141 ccgcgggtag atgccggcag gccttccgga agaaaaagag ccattggttt ttgtagtatt

1201 ggggccctct tttagtgata ctggattggc gttgtttgtg gctgttgcgc acatccctgc

1261 cctcctacag cactccacct tgggacctgt ttagagaagc cggctcttca aagacaatgg

1321 aaactgtacc atacacattg gaaggctccc taacacacac agcggggaag ctgggccgag

1381 taccttaatc tgccataaag ccattcttac tcgggcgacc cctttaagtt tagaaataat

1441 tgaaaggaaa tgtttgagtt ttcaaagatc ccgtgaaatt gatgccagtg gaatacagtg

1501 agtcctcctc ttcctcctcc tcctcttccc cctcccctttc ctcctcctcc tcttcttttc

1561 cctcctcttc ctcttcctcc tgctctcctt tcctcccccct cctcttttcc ctcctcttcc

1621 tcttcctcct gctctccttt cctccccctc ctctttctcc tcctcctcct cttcttcccc
```

-continued

```
1681  ctcctctccc tcctcctctt cttccccctc ctctccctcc tcctcttctt ctccctcctc
1741  ttcctcttcc tcctcttcca cgtgctctcc tttcctcccc ctcctcttgc tccccttctt
1801  ccccgtcctc ttcctcctcc tcctcttctt ctccctcctc ttcctcctcc tctttcttcc
1861  tgacctcttt ctttctcctc ctcctccttc tacctcccct tctcatccct cctcttcctc
1921  ttctctagct gcacacttca ctactgcaca tcttataact tgcacccctt tcttctgagg
1981  aagagaacat cttgcaaggc agggcgagca gcggcagggc tggcttagga gcagtgcaag
2041  agtccctgtg ctccagttcc acactgctgg cagggaaggc aaggggggac gggcctggat
2101  ctgggggtga gggagaaaga tggacccctg ggtgaccact aaaccaaaga tattcggaac
2161  tttctattta ggatgtggac gtaattcctg ttccgaggta gaggctgtgc tgaagacaag
2221  cacagtggcc tggtgcgcct tggaaaccaa caactattca cgagccagta tgaccttcac
2281  atctttagaa attatgaaaa cgtatgtgat tggagggttt ggaaaaccag ttatcttatt
2341  taacatttta aaaattacct aacagttatt tacaaacagg tctgtgcatc ccaggtctgt
2401  cttcttttca aggtctgggc cttgtgctcg ggttatgttt gtgggaaatg cttaataaat
2461  actgataata tgggaagaga tgaaaactga ttctcctcac tttgtttcaa acctttctgg
2521  cagtgggatg attcgaattc acttttaaaa ttaaattagc gtgttttgtt ttg
```

By “PTF1 polypeptide” is meant a protein or fragment thereof having at least 85% amino acid sequence identity to the sequence provided at NCBI Accession No. NP_835455.1 and having transcription factor activity. The amino acid sequence provided at NCBI Accession No. NP_835455.1 is shown below:

```
                                                          (SEQ ID NO: 45)
  1  mdavllehfp ggldafpssy fdeddfftdq ssrdpledgd elladeqaev eflshqlhey
 61  cyrdgaclll qpappaapla lappssgglg epddgggggy ccetgappgg fpyspgspps
121  claypcagaa vlspgarlrg lsgaaaaaar rrrrvrseae lqqlrqaanv rerrrmqsin
181  dafeglrshi ptlpyekrls kvdtlrlaig yinflselvq adlplrggga ggcggpgggg
241  rlggdspgsq aqkviichrg trspspsdpd yglpplaghs lswtdekqlk eqniirtakv
301  wtpedprkln skssfnnien eppfefvs
```

By “PTF1 polynucleotide” is meant a polynucleotide encoding a PTF1 polypeptide or fragment thereof. An exemplary PTF1 polynucleotide sequence is provided at NCBI Ref: NM_178161.2. The sequence provided at NCBI Ref: NM_178161.2 is reproduced below:

```
                                                          (SEQ ID NO: 46)
  1  atggacgcgg tgttgctgga gcacttcccc gggggcctag acgcctttcc ttcttcgtac
 61  ttcgacgagg acgacttctt caccgaccag tcttcacggg accccctgga ggacggcgat
121  gagctgctgg cggacgagca ggccgaggtg gagttcctta gccaccagct ccacgagtac
181  tgctaccgcg acggggcgtg cctgctgctg cagcccgcgc ccccggccgc cccgctagcg
241  ctcgccccgc cgtcctcggg gggcctcggt gagccagacg acggcggcgg cggcggctac
301  tgctgcgaga cgggggcgcc cccaggcggc ttcccctact cgcccggctc gccgccctcg
361  tgcctggcct acccgtgcgc cggggcggca gtactgtctc ccggggcgcg gctgcgcggc
421  ctgagcggag cggcggctgc ggcggcgcgg cgccggcggc gggtgcgctc cgaggcggag
481  ctgcagcagc tgcggcaggc ggccaacgtg cgcgagcggc ggcgcatgca gtccatcaac
541  gacgccttcg aggggctgcg ctcgcacatc cccacgctgc cctacgagaa gcgcctctcc
```

-continued

```
 601  aaggtggaca cgctgcgcct ggccatcggc tacatcaact tcctcagcga gctcgtgcag
 661  gccgacctgc ccttgcgcgg cggtggcgcg ggcggctgcg gggggccggg cggcggcggg
 721  cgcctgggcg gggacagccc gggcagccag gcccagaagg tcatcatctg ccatcggggc
 781  acccggtccc cctcccccag cgaccctgat tatggcctcc ctcccctagc aggacactct
 841  ctctcatgga ctgatgaaaa acaactcaag gaacaaaata ttatccgaac agccaaagtc
 901  tggaccccag aggaccccag aaaactcaac agcaaatctt ccttcaacaa catagaaaac
 961  gaaccaccat ttgagtttgt gtcctgagaa gtcccagact cggctgaaga tctgattatg
1021  tctctgtgca tattgtacat gtaaatatct ataatgtaaa tgtaatttaa gaatcaaatt
1081  tttcgaatgg caatcaactg tttattattt atctatttat tatcctgttg agttgatgaa
1141  atagatgatt tctttttaaa tatataattt atataactta tcctgatttt ctgaaaatat
1201  gcaatagcct atgattttcc tgaactctgt gttgttggga gaactctggc cagaaaacgt
1261  cctgcttatt tattgccaga tatggtttat ttctaagcgt tgtcaataaa tgctatttac
1321  accttttcct gaaaaaaaa
```

By "Wnt3a polynucleotide" is meant a polynucleotide encoding a Wnt3a polypeptide or a fragment thereof, or a polynucleotide having at least 85% sequence identity to the human Wnt3a polynucleotide sequence. An exemplary human Wnt3a polynucleotide sequence is provided at NCBI GenBank Accession No. AB060284.1. The polynucleotide sequence provided at NCBI GenBank Accession No. AB060284.1 is reproduced below:

```
                                                          (SEQ ID NO: 47)
   1  cggcgatggc cccactcgga tacttcttac tcctctgcag cctgaagcag gctctgggca
  61  gctacccgat ctggtggtcg ctggctgttg ggccacagta ttcctccctg ggctcgcagc
 121  ccatcctgtg tgccagcatc ccgggcctgg tccccaagca gctccgcttc tgcaggaact
 181  acgtggagat catgcccagc gtggccgagg gcatcaagat tggcatccag gagtgccagc
 241  accagttccg cggccgccgg tggaactgca ccaccgtcca cgacagcctg gccatcttcg
 301  ggcccgtgct ggacaaagct accagggagt cggcctttgt ccacgccatt gcctcagccg
 361  gtgtggcctt tgcagtgaca cgctcatgtg cagaaggcac ggccgccatc tgtggctgca
 421  gcagccgcca ccagggctca ccaggcaagg gctggaagtg ggtggctgt agcgaggaca
 481  tcgagtttgg tgggatggtg tctcgggagt tcgccgacgc ccgggagaac cggccagatg
 541  cccgctcagc catgaaccgc cacaacaacg aggctgggcg ccaggccatc gccagccaca
 601  tgcacctcaa gtgcaagtgc cacgggctgt cgggcagctg cgaggtgaag acatgctggt
 661  ggtcgcaacc cgacttccgc gccatcggtg acttcctcaa ggacaagtac gacagcgcct
 721  cggagatggt ggtggagaag caccgggagt cccgcggctg ggtggagacc ctgcggccgc
 781  gctacaccta cttcaaggtg cccacggagc gcgacctggt ctactacgag gcctcgccca
 841  acttctgcga gcccaaccct gagacgggct ccttcggcac gcgcgaccgc acctgcaacg
 901  tcagctcgca cggcatcgac ggctgcgacc tgctgtgctg cggccgcggc cacaacgcgc
 961  gagcggagcg gcgccgggag aagtgccgct gcgtgttcca ctggtgctgc tacgtcagct
1021  gccaggagtg cacgcgcgtc tacgacgtgc acacctgcaa gtaggcaccg gccgcggctc
1081  cccctggacg gggcgggccc tgcctgaggg tgggcttttc cctgggtgga gcaggactcc
1141  cacctaaacg gggcagtact cctccctggg ggcgggactc ctccctgggg gtggggctcc
1201  tacctggggg cagaactcct acctgaaggc agggctcctc cctggagcta gtgtctcctc
1261  tctggtggct gggctgctcc tgaatgaggc ggagctccag gatggggagg ggctctgcgt
1321  tggcttctcc ctggggacgg ggctcccctg gacagaggcg gggctacaga ttgggcgggg
```

-continued

```
1381  cttctcttgg gtgggacagg gcttctcctg cgggggcgag gcccctccca gtaagggcgt

1441  ggctctgggt gggcggggca ctaggtaggc ttctacctgc aggcggggct cctcctgaag

1501  gaggcggggc tctaggatgg ggcacggctc tggggtaggc tgctccctga gggcg
```

By "Wnt3a polypeptide" is meant a Wnt3a polypeptide or a fragment thereof, or a polypeptide having at least 85% sequence identity to the human Wnt3a polypeptide sequence. An exemplary human Wnt3a polypeptide sequence is provided at NCBI GenBank: AAI03924.1. The sequence provided at GenBank: AAI03924.1 is reproduced below:

```
                                                    (SEQ ID NO: 48)
  1   maplgyflll cslkqalgsy piwwslavgp qysslgsqpi lcasipglvp kqlrfcrnyv

 61   eimpsvaegi kigiqecqhq frgrrwnctt vhdslaifgp vldkatresa fvhaiasagv

121   afavtrscae gtaaicgcss rhqgspgkgw kwggcsedie fggmvsrefa darenrpdar

181   samnrhnnea grqaiashmh lkckchglsg scevktcwws qpdfraigdf lkdkydsase

241   mvvekhresr gwvetlrpry tyfkvpterd lvyyeaspnf cepnpetgsf gtrdrtcnvs

301   shgidgcdll ccgrghnara errrekcrcv fhwccyvscq ectrvydvht cknpgsragn

361   sahqpphpqp pvrfhpplrr agkvp
```

By "Wnt4 polynucleotide" is meant a polynucleotide encoding Wnt4 polypeptide or a fragment thereof, or a polynucleotide having at least 85% sequence identity to the human Wnt4 polynucleotide sequence. An exemplary human Wnt4 polynucleotide sequence is provided at NCBI GenBank Accession No. AY009398.1. Accession number NCBI Ref NG 008974.1 is a reference standard Wnt4a polynucleotide sequence. The polynucleotide sequence provided at NCBI GenBank Accession No. AY009398.1 is reproduced below:

```
                                                    (SEQ ID NO: 49)
   1  atgagtcccc gctcgtgcct gcgttcgctg cgcctcctcg tcttcgccgt cttctcagcc

  61  gccgcgagca actggctgta cctggccaag ctgtcgtcgg tggggagcat ctcagaggag

 121  gagacgtgcg agaaactcaa gggcctgatc cagaggcagg tgcagatgtg caagcggaac

 181  ctggaagtca tggactcggt gcgccgcggt gcccagctgg ccattgagga gtgccagtac

 241  cagttccgga accggcgctg gaactgctcc acactcgact ccttgcccgt cttcggcaag

 301  gtggtgacgc aagggattcg ggaggcggcc ttggtgtacg ccatctcttc ggcaggtgtg

 361  gcctttgcag tgacgcgggc gtgcagcagt ggggagctgg agaagtgcgg ctgtgacagg

 421  acagtgcatg gggtcagccc acagggcttc cagtggtcag gatgctctga caacatcgcc

 481  tacggtgtgg ccttctcaca gtcgtttgtg gatgtgcggg agagaagcaa gggggcctcg

 541  tccagcagag ccctcatgaa cctccacaac aatgaggccg gcaggaaggc catcctgaca

 601  cacatgcggg tggaatgcaa gtgccacggg gtgtcaggct cctgtgaggt aaagacgtgc

 661  tggcgagccg tgccgccctt ccgccaggtg ggtcacgcac tgaaggagaa gtttgatggt

 721  gccactgagg tggagccacg ccgcgtgggc tcctccaggg cactggtgcc acgcaacgca

 781  cagttcaagc cgcacacaga tgaggacttg gtgtacttgg agcctagccc cgacttctgt

 841  gagcaggaca tgcgcagcgg cgtgctgggc acgaggggcc gcacatgcaa caagacgtcc

 901  aaggccatcg acggctgtga gctgctgtgc tgtggccgcg gcttccacac ggcgcaggtg

 961  gagctggctg aacgctgcag ctgcaaattc cactggtgct gcttcgtcaa gtgccggcag

1021  tgccagcggc tcgtggagtt gcacacgtgc cgatga
```

By "Wnt4 polypeptide" is meant a Wnt4 polypeptide or a fragment thereof, or a polypeptide having at least 85% sequence identity to the human Wnt4 polypeptide sequence. An exemplary human Wnt4 polypeptide sequence is provided at NCBI GenBank Accession No.: AAG38658.1. The sequence provided at GenBank Accession No.: AAG38658.1 is reproduced below:

```
                                                  (SEQ ID NO: 50)
  1    msprsclrsl rllvfavfsa aasnwlylak lssvgsisee etceklkgli qrqvqmckrn

 61    levmdsvrrg aqlaieecqy qfrnrrwncs tldslpvfgk vvtqgireaa lvyaissagv

121    afavtracss gelekcgcdr tvhgvspqgf qwsgcsdnia ygvafsqsfv dvrerskgas

181    ssralmnlhn neagrkailt hmrveckchg vsgscevktc wravppfrqv ghalkekfdg

241    ateveprrvg ssralvprna qfkphtdedl vylepspdfc eqdmrsgvlg trgrtcnkts

301    kaidgcellc cgrgfhtaqv elaercsckf hwccfvkcrq cqrlvelhtc r
```

By "Wnt5a polynucleotide" is meant a polynucleotide encoding Wnt5a polypeptide or a fragment thereof, or a polynucleotide having at least 85% sequence identity to the human Wnt5a polynucleotide sequence. An exemplary polynucleotide sequence coding for human Wnt5a is provided at NCBI Ref: GenBank NM_003392, a reference standard sequence. Nucleotides 658-1800 of the Wnt5a genomic sequence having 6194 nucleotides codes for a human Wnt5a polypeptide. The polynucleotide sequence of the human Wnt5a coding sequence provided at bases 658-1800 of NCBI Ref: GenBank NM_003392 is reproduced below:

```
                                                      (SEQ ID NO: 51)
 658    atg

 661    aagaagtcca ttggaatatt aagcccagga gttgctttgg ggatggctgg aagtgcaatg

 721    tcttccaagt tcttcctagt ggctttggcc atatttttct ccttcgccca ggttgtaatt

 781    gaagccaatt cttggtggtc gctaggtatg aataaccctg ttcagatgtc agaagtatat

 841    attataggag cacagcctct ctgcagccaa ctggcaggac tttctcaagg acagaagaaa

 901    ctgtgccact tgtatcagga ccacatgcag tacatcggag aaggcgcgaa gacaggcatc

 961    aaagaatgcc agtatcaatt ccgacatcga aggtggaact gcagcactgt ggataacacc

1021    tctgtttttg gcagggtgat gcagataggc agccgcgaga cggccttcac atacgcggtg

1081    agcgcagcag gggtggtgaa cgccatgagc cgggcgtgcc gcgagggcga gctgtccacc

1141    tgcggctgca gccgcgccgc gcgccccaag gacctgccgc gggactggct ctggggcggc

1201    tgcggcgaca acatcgacta tggctaccgc tttgccaagg agttcgtgga cgcccgcgag

1261    cgggagcgca tccacgccaa gggctcctac gagagtgctc gcatcctcat gaacctgcac

1321    aacaacgagg ccggccgcag gacggtgtac aacctggctg atgtggcctg caagtgccat

1381    ggggtgtccg gctcatgtag cctgaagaca tgctggctgc agctggcaga cttccgcaag

1441    gtgggtgatg ccctgaagga gaagtacgac agcgcggcgg ccatgcggct caacagccgg

1501    ggcaagttgg tacaggtcaa cagccgcttc aactcgccca ccacacaaga cctggtctac

1561    atcgacccca gccctgacta ctgcgtgcgc aatgagagca ccggctcgct gggcacgcag

1621    ggccgcctgt gcaacaagac gtcggagggc atggatggct gcgagctcat gtgctgcggc

1681    cgtggctacg accagttcaa gaccgtgcag acggagcgct gccactgcaa gttccactgg

1741    tgctgctacg tcaagtgcaa gaagtgcacg gagatcgtgg accagtttgt gtgcaagtag
```

By "Wnt5a polypeptide" is meant a Wnt5a polypeptide or a fragment thereof, or a polypeptide having at least 85% sequence identity to the human Wnt5a polypeptide sequence. An exemplary human Wnt5a (isoform 1) polypeptide sequence is provided at UniProtKB Identifier: P41221-1. The sequence provided at UniProtKB Identifier: P41221-1 is reproduced below:

```
                                                   (SEQ ID NO: 52)
  1    mkksigilsp gvalgmagsa msskfflval aiffsfaqvv ieanswwslg

 51    mnnpvqmsev yiigaqplcs qlaglsqgqk klchlyqdhm qyigegaktg

101    ikecqyqfrh rrwncstvdn tsvfgrvmqi gsretaftya vsaagvvnam

151    sracregels tcgcsraarp kdlprdwlwg gcgdnidygy rfakefvdar

201    ererihakgs yesarilmnl hnneagrrtv ynladvackc hgvsgscslk

251    tcwlqladfr kvgdalkeky dsaaamrlns rgklvqvnsr fnspttqdlv

301    yidpspdycv rnestgslgt qgrlcnktse gmdgcelmcc grgydqfktv

351    qterchckfh wccyvkckkc teivdqfvck
```

By "progenitor cell" is meant a cell that a multipotent stem cell that is capable of generating (e.g., by differentiation or division) an endothelial cell. A progenitor cell that is capable of generating an endothelial cell may express this capability when grown under appropriate in vitro or in vivo conditions, such as those described herein.

By "progeny" is meant a cell derived from a multipotent stem cell of the invention. Progeny include without limitation progenitor cells, differentiated cells, and terminally differentiated cells.

By "derived from" is meant the process of obtaining a progeny cell.

By "reduces" is meant a negative alteration of at least 10%, 25%, 50%, 75%, or 100%.

By "reference" or "control" is meant a standard condition. For example, an untreated cell, tissue, or organ that is used as a reference.

A "reference sequence" is a defined sequence used as a basis for sequence comparison. A reference sequence may be a subset of or the entirety of a specified sequence; for example, a segment of a full-length cDNA or gene sequence, or the complete cDNA or gene sequence. For polypeptides, the length of the reference polypeptide sequence will generally be at least about 16 amino acids, at least about 20 amino acids, or at least about 25 amino acids. The length of the reference polypeptide sequence can be about 35 amino acids, about 50 amino acids, or about 100 amino acids. For nucleic acids, the length of the reference nucleic acid sequence will generally be at least about 50 nucleotides, at least about 60 nucleotides, or at least about 75 nucleotides. The length of the reference nucleic acid sequence can be about 100 nucleotides, about 300 nucleotides or any integer thereabout or therebetween.

A "somatic" cell refers to a cell that is obtained from a tissue of a subject. Such subjects are at a post-natal stage of development (e.g., adult, infant, child). In contrast, an "embryonic cell" or "embryonic stem cell" is derived from an embryo at a pre-natal stage of development.

By "specifically binds" is meant a compound or antibody that recognizes and binds a polypeptide of the invention, but which does not substantially recognize and bind other molecules in a sample, for example, a biological sample, which naturally includes a polypeptide of the invention.

Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. Nucleic acid molecules useful in the methods of the invention include any nucleic acid molecule that encodes a polypeptide of the invention or a fragment thereof. Such nucleic acid molecules need not be 100% identical with an endogenous nucleic acid sequence, but will typically exhibit substantial identity. Polynucleotides having "substantial identity" to an endogenous sequence are typically capable of hybridizing with at least one strand of a double-stranded nucleic acid molecule. By "hybridize" is meant pair to form a double-stranded molecule between complementary polynucleotide sequences (e.g., a gene described herein), or portions thereof, under various conditions of stringency. (See, e.g., Wahl, G. M. and S. L. Berger (1987) Methods Enzymol. 152:399; Kimmel, A. R. (1987) Methods Enzymol. 152:507).

For example, stringent salt concentration will ordinarily be less than about 750 mM NaCl and 75 mM trisodium citrate, less than about 500 mM NaCl and 50 mM trisodium citrate, or less than about 250 mM NaCl and 25 mM trisodium citrate. Low stringency hybridization can be obtained in the absence of organic solvent, e.g., formamide, while high stringency hybridization can be obtained in the presence of at least about 35% formamide, or at least about 50% formamide. Stringent temperature conditions will ordinarily include temperatures of at least about 30° C., at least about 37° C., and at least about 42° C. Varying additional parameters, such as hybridization time, the concentration of detergent, e.g., sodium dodecyl sulfate (SDS), and the inclusion or exclusion of carrier DNA, are well known to those skilled in the art. Various levels of stringency are accomplished by combining these various conditions as needed. In one embodiment, hybridization will occur at 30° C. in 750 mM NaCl, 75 mM trisodium citrate, and 1% SDS. In another embodiment, hybridization will occur at 37° C. in 500 mM NaCl, 50 mM trisodium citrate, 1% SDS, 35% formamide, and 100 μg/ml denatured salmon sperm DNA (ssDNA). In yet another embodiment, hybridization will occur at 42° C. in 250 mM NaCl, 25 mM trisodium citrate, 1% SDS, 50% formamide, and 200 μg/ml ssDNA. Useful variations on these conditions will be readily apparent to those skilled in the art.

For most applications, washing steps that follow hybridization will also vary in stringency. Wash stringency conditions can be defined by salt concentration and by temperature. As above, wash stringency can be increased by decreasing salt concentration or by increasing temperature. For example, stringent salt concentration for the wash steps will be less than about 30 mM NaCl and 3 mM trisodium citrate, or less than about 15 mM NaCl and 1.5 mM trisodium citrate. Stringent temperature conditions for the wash steps will ordinarily include a temperature of at least about 25° C., at least about 42° C., and at least about 68° C. In one embodiment, wash steps will occur at 25° C. in 30 mM NaCl, 3 mM trisodium citrate, and 0.1% SDS. In another embodiment, wash steps will occur at 42 C in 15 mM NaCl, 1.5 mM trisodium citrate, and 0.1% SDS. In yet another embodiment, wash steps will occur at 68° C. in 15 mM NaCl, 1.5 mM trisodium citrate, and 0.1% SDS. Additional variations on these conditions will be readily apparent to those skilled in the art. Hybridization techniques are well known to those skilled in the art and are described, for example, in Benton and Davis (Science 196:180, 1977); Grunstein and Hogness (Proc. Natl. Acad. Sci., USA 72:3961, 1975); Ausubel et al. (Current Protocols in Molecular Biology, Wiley Interscience, New York, 2001); Berger and Kimmel (Guide to Molecular Cloning Techniques, 1987, Academic Press, New York); and Sambrook et al., Molecular Cloning: A Laboratory Manual, Cold Spring Harbor Laboratory Press, New York.

By "substantially identical" is meant a polypeptide or nucleic acid molecule exhibiting at least 50% identity to a reference amino acid sequence (for example, any one of the amino acid sequences described herein) or nucleic acid sequence (for example, any one of the nucleic acid sequences described herein). Such a sequence is at least 60%, at least 80%, at least 85%, at least 90%, at least 95% or even at least 99% identical at the amino acid level or nucleic acid to the sequence used for comparison.

Sequence identity is typically measured using sequence analysis software (for example, Sequence Analysis Software Package of the Genetics Computer Group, University of Wisconsin Biotechnology Center, 1710 University Avenue, Madison, Wis. 53705, BLAST, BESTFIT, GAP, or PILEUP/PRETTYBOX programs). Such software matches identical or similar sequences by assigning degrees of homology to various substitutions, deletions, and/or other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine. In an exemplary approach to determining the degree of identity, a BLAST program may be used, with a probability score between $e^{-3}$ and $e^{-100}$ indicating a closely related sequence.

The term "self renewal" as used herein refers to the process by which a stem cell divides to generate one (asymmetric division) or two (symmetric division) daughter cells with development potentials that are indistinguishable from those of the mother cell. Self renewal involves both proliferation and the maintenance of an undifferentiated state.

The term "stem cell" is meant a pluripotent cell or multipotent stem cell having the capacity to self-renew and to differentiate into multiple cell lineages.

By "subject" is meant a mammal, including, but not limited to, a human or non-human mammal, such as a bovine, equine, canine, ovine, rodent, or feline.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

By "tissue" is meant a collection of cells having a similar morphology and function. As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

By "vascularized" is meant having a blood vessel. In some embodiments, the pancreatic islet organoid or pancreatic organoid is vascularized.

Unless specifically stated or obvious from context, as used herein, the term "or" is understood to be inclusive. Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

BRIEF DESCRIPTION OF THE DRAWINGS

FIG. 2 compares the appearance of human iPSC-derived pancreatic progenitors (PPs. Day 15-day 19), human umbilical vein endothelial cells (HUVEC), and hADSCs cultured on plates (2D) with those cultured in the 3 dimensional matrigel (Matrigel® system for 24 hours in PP cell differentiation media, endothelial cell growth media, and hADSC growth media, respectively. FIGS. 2D and 2D-1 to 2D-4 show transcriptional changes occurring in hADSCs during 48 hours of culture in Matrigel, depicted as a heatmap. Statistically different changes in gene expression were determined by RNA-Seq analyses of cells after the indicated time in Matrigel. Biological pathways altered during culture in Matrigel were identified using DAVID software.

FIG. 3A is a schematic showing the generation of a stably-expressed insulin reporter in the rat beta cell line INS-1 cells, where luciferase expression is under the control of the proinsulin promoter. FIG. 3B is a plot showing luciferase activity induced in the INS-1 reporter cells in response to treatment with 3 mM glucose (G3), 20 mM glucose (G20), 20 mM glucose (G20) plus 100 nM Exendin-4 (Ex-4), or 20 mM potassium chloride (KCl). FIG. 3C is an image showing a single mouse islet in one well of a 96-well plate. The mouse islet cells were infected with the proinsulin-luciferase lentivirus reporter construct 2 days before assaying. FIG. 3D is a set of plots showing the luciferase activity from individual mouse islets infected with the proinsulin luciferase reporter in response to 3 mM glucose (G3 mM) and 20 mM glucose (G20 mM) (left), and the average of the individual assays (right). FIG. 3E is an image showing a single human islet in one well of a 96-well plate. The human islet cells were infected with the proinsulin-luciferase lentivirus reporter construct 2 days before assaying. FIG. 3F is a set of plots showing the luciferase activity from individual human islets infected with the proinsulin luciferase reporter in response to 3 mM glucose (G3 mM) and 20 mM glucose (G20 mM) (left), and the average of the individual assays (right). FIGS. 3D and 3F show that glucose-stimulated insulin secretion (GSIS) can be measured from single mouse and human islets, respectively, after the infection with the lentiviral luciferase reporter.

FIGS. 4A-4I are plots, images, graphs and a schematic showing generation of functional, vascularized human pancreatic islets in a dish. FIG. 4A is a schematic showing a scheme for the generation of functional, vascularized human pancreatic islets in Gellan gum. FIG. 4B shows human islet-like mini organs. Top panels show insulin positive cells (green fluorescent protein expression driven by the insulin promoter (left)) and phase contrast images (left) of islet-like organoids grown in 3D Gellan gum suspensions (bottom panel). Electron microscopy images reveal insulin granules in the β-like cells and lipid droplets in the hADSCs. FIG. 4C shows that human islet-like-mini organs generated by methods described herein are morphologically identical to human islets. FIG. 4D and FIG. 4E show relative expression of genes associated with β cell determination (FIG. 4D), and mitochondrial function (FIG. 4E), as measured by qPCR. Islet-like cell clusters (derived from pancreatic progenitors cultured in gellan gum, day 35) and islet-like organoids (derived from pancreatic progenitors co-cultured with HUVECs and hADSCs in gellan gum) were FACS stored into insulin expressing (GFP positive) and non-expressing (GFP negative) cells prior to analysis, and compared with gene expression in human islets. FIG. 4F shows glucose-stimulated insulin secretion, measured by the fold change in c-peptide secretion 30 minutes after exposure to 20 mM glucose, in selected islet-like organoid preparations prepared in 3D gellan gum cultures and human islets. FIG. 4G shows that human islet-like mini organs generated by the methods described herein can develop functional vascularization. Human islet-like organoids were transferred to matrigel and grown in the presence of endothelial growth media. Cells expressing insulin are visualized as green fluorescence. Top panels are fluorescent images of cells showing HUVEC cell outgrowth 24 and 48 hours after stimulation by endothelial cell growth medium (ECM). The bottom panel is a schematic summarizing the experiment and the finding. FIG. 4H shows a graph illustrating that human islet-like mini organs generated by the methods described herein can regulate blood glucose in a known mouse model of type 1 diabetes, NODSCID. In this mouse model, the SCID (Severe Combined Immune Deficiency) mutation has been transferred onto a diabetes-susceptible Non-Obese Diabetic (NOD) background. The multiple immunological defects in this mouse model provide a system for reconstituting the animal with human hematopoietic cells. The graph in FIG. 4H shows the blood glucose levels in NODSCID mice treated with streptozotocin (STZ) (180 mg/kg) to induce type 1 diabetes after transplantation into the kidney capsule of hiPSC-derived human islet-like organoids (n=1000), (dotted line with squares); human islets (n=1000), (dashed line); or mock treatment (solid line with white circles). FIG. 4I shows a bar graph illustrating that human islet-like mini organs ("human islets organoids") generated by the methods described herein are able to secrete insulin postprandially. The graph of FIG. 4I shows the serum levels of human c-peptide (pmol/L) in NODSCID mice 4 weeks after the transplantations described in FIG. 4H under random fed (left bar), 8 hour fasted (middle bar), and refed (right bar) conditions. Human c-peptide levels provide a measure of insulin secretion from the transplants that is distinct from endogenous murine insulin.

FIG. 5A is a schematic describing the generation of hiPSCs stably incorporating dual reporters for insulin expression (GFP) and insulin secretion (luciferase). FIG. 5B is a bar graph showing the increased expression of human insulin during the differentiation of hiPSCs incorporating the dual reporters. FIG. 5C is a bar graph comparing the glucose stimulated insulin secretion (GSIS) from human islet-like organoids generated using the methods described herein with human islets. GSIS, as measured using secreted luciferase, in single islet-like organoids or human islets in response to 3 mM and 20 mM glucose. Arrows indicate functional organoids capable of increasing insulin secretion in response to a glucose challenge. FIG. 5D is a bar graph comparing the insulin secretion of independent batches of islet-like organoids, prepared as described herein, to mouse islets as a negative control. Insulin secretion was measured in response to 3 mM glucose (G3 mM), 20 mM glucose (G20 mM), 20 mM glucose (G20 mM) and Exendin-4 (Ex4), or 20 mM potassium chloride (KC120 mM) after 133 days in culture. Response was measured as secreted luciferase activity from pooled organoids (100 organoids/sample). FIG. 5E shows intracellular luciferase activity as a measure of intracellular insulin (100 organoids/sample).

FIG. 6A is a schematic showing generation of functional human mini organs including human islets, pancreas, liver, heart, and intestine. FIGS. 6B-6C show the generation of a human heart organoid. FIG. 6B (top) provides a schematic illustrating the protocol for differentiation of a human pluripotent stem cell (hPSC) into a cardiomyocyte (when cultured in 2D) or into a mini heart (when co-cultured with hADSCs and HUVECs in 3D). FIG. 6B (bottom left) provides a plot showing relative expression of cardiomyocyte-specific genes human MLC2a (hMLC2a), human Nkx2-5 (hNkx2-5), alpha myosin heavy chain (alphaMHC), and KCNQ1 before (day 0) and at day 18 of the differentiation protocol, with and without the PPARδ agonist GW501516. At the bottom right of FIG. 6B is a videomicrograph showing beating of the hiPSC-derived cardiomyocytes. FIG. 6C shows an image of a human mini heart-like organoid generated by culturing the hiPSC-derived cardiomyocytes with hADSC and HUVEC, as described in the schematic above. FIGS. 6D-6F show generation of a human liver organoid. FIG. 6D (top) provides a schematic illustrating the protocol for differentiation of a human pluripotent stem cell (hPSC) into hepatocytes. FIG. 6D (bottom left) provides a plot showing relative expression of hepatocyte-specific genes AFP, ALB, and Cyp3a7, during the differentiation of 6 independent preparations. At the bottom right of FIG. 6D is a micrograph showing hiPSC-derived hepatocytes. FIG. 6E is a set of microcrographs showing hiPSC-derived hepatocytes. Top panels show expression of Cyp7a1 (Cyp7a1-GFP reporter, left) and SREBP1c (SREBP1c-GFP reporter, right) in hiPSC-derived hepatocytes indicating functional maturation. The bottom panels show hiPSC-derived hepatocytes cultured with (right) or without (left) phosphatidic acid (PA) overnight. Higher magnification images shown in the bottom left reveal the accumulation of lipid droplets in the hepatocytes treated with phosphatidic acid. FIG. 6F shows a human mini liver-like organoid generated by culturing the hiPSC-derived hepatocytes with hADSCs and HUVECs in the gellan gum 3D culture system. FIG. 6G (top) provides a schematic illustrating the protocol for differentiation of human pluripotent stem cells (hPSCs) into intestinal organoids when co-cultured with hADSCs and HUVECs in the gellan gum 3D culture system. The lower images shows budding of the human intestinal organoid cultures, consistent with crypt-like structures and indicating functional organoids. FIG. 6H (top) provides a schematic illustrating the protocol for differentiation of human pluripotent stem cells (hPSCs) into a mini pancreas when co-cultured with hADSCs and HUVECs in the gellan gum 3D culture system. The middle panels show images of insulin positive β cells, marked by the expression of green fluorescent protein driven by the insulin promoter, and the equivalent light microscopy image of pancreatic organoids. Exocrine cells are the remaining unlabeled cells. The bottom panels show an image of a single pancreatic organoid in a 96 well plate.

FIG. 8A shows a scheme for screening potential drugs for use in human type 2 diabetes or human pancreatic cancer tumorigenesis in a dish. Organoid cultures are exposed to appropriate stress (e.g. high levels of free fatty acids (FFAs), high glucose levels, or relevant cytokines) to induce disease-like phenotypes prior to screening drug libraries for compounds that reverse or diminish disease indications. FIG. 8B shows approaches to evaluate potential drug candidates for type 2 diabetes and human pancreatic cancer tumorigenesis/metastasis in mice. Mice transplanted with individual (e.g. pancreas) or combinations of human organoids (e.g., pancreas and liver) are exposed to appropriate disease-inducing stressors (e.g. high fat/high cholesterol (HF/HC) diet) prior to treatment with potential disease altering drug candidates.

FIG. 10A is a schematic describing the protocol to generate islet-like organoids by culturing in 3D in gellan gum. FIG. 10B is a series of images recording the growth and differentiation of hPSCs into pancreatic lineages in 3D Gellan gum cultures, as described herein. Insulin expression is indicated by the green fluorescence seen at day 21. FIG. 10C is a heatmap representation of changes in gene expression during the differentiation of hiPSCs into islet-like organoids. FIG. 10D is a set of bar graphs reporting the changes in relative expression of the pluripotency marker Nanog, the endocrine hormones insulin, somatostatin, and glucagon, and the β cell lineage marker Nkx6-1 in hiPSCs and two stem cell lines (HuES8 and H1ES) during differentiation as described in the methods herein. Gene expression was measured by qPCR.

FIG. 11A is a heatmap depiction of gene expression changes in hADSCs during the spontaneous self-organization that occurs in 3D culture. Genes that are induced in the WNT5a pathway are listed. FIG. 11B is a graph showing the relative levels of several individual WNT proteins in hADSC 3D culture over time, identifying the WNT5a protein as the predominant protein expressed.

FIG. 12A shows bar graphs comparing the expression of Fltp and Esrrg genes in iPSC-derived islet organoids (day 21, generated without co-culture with hADSCs or HUVECs) after treatment with PBS, WNT3a (500 ng/ml), WNT4 (100 ng/ml), or WNT5a (400 ng/ml) for 5 days. FIG. 12B is a bar graph showing the induction of Esrrg gene expression in hiPSC-derived islet organoids, generated in the absence of supporting hADSC or HUVECs, in response to increasing doses of WNT4 (0, 10, 25, 50, 100, 200 ng/ml) and WNT5a (0, 25, 50, 100, 200, 400 ng/ml). FIG. 12C is a bar graph showing the induction of mitochondrial genes involved in oxidative phosphorylation (Cox7a2, Ndufa1, Ndufa7), lactate dehydrogenase (Ldha) and Fltp (a Wnt/planar cell polarity (PCP) effector and reporter gene) in hiPSC-derived islet organoids, generated in the absence of supporting hADSC or HUVECs, in response to increasing doses of WNT4 (0, 10, 25, 50, 100, 200 ng/ml) and WNT5a (0, 25, 50, 100, 200, 400 ng/ml). FIG. 12D shows fluorescent images showing mitochondrial (Mitotracker; Mito-Red) and insulin (Insulin-GFP) levels in hiPSC-derived islet organoids (day 27) after 8 days treatment with PBS or WNT4 (100 ng/ml). FIG. 12E shows fluorescent images of FACS analysis of hiPSC-derived islet organoids (day 27) after 8 days treatment with PBS or WNT4 (100 ng/ml). FIGS. 12F, 12G, and 12H show a set of bar graphs illustrating the results of FACS analyses of hiPSC-derived islet organoids (day 27) after 8 days treatment with PBS, WNT4 (100 ng/ml), WNT5a (400 ng/ml), control fibroblast conditioned media (50%), or WNT5a secreting fibroblast conditioned media (50%). The WNT proteins used were recombinant human (rh) proteins.

DETAILED DESCRIPTION OF THE INVENTION

The invention features compositions and methods that are useful for generating scalable, functional, vascularized organoids in vitro, particularly human pancreatic or pancreatic islet organoids. The invention is based, at least in part, on the discovery that culturing iPSC-derived beta-like cells with human adipose-derived stem cells (hADSC) and human umbilical vein endothelial cells (Huvec) in a three-dimensional matrix containing gellan gum generated functional pancreatic and pancreatic islet organoids.

The organoids generated were vascularized and exhibited functional properties, such as glucose-stimulated insulin secretion (GSIS). Islet transplantation is known as the best therapy for curing insulin deficient diabetes such as type 1 and late stage of type 2 diabetes. Recent studies have shown the possibility of generating glucose responsive insulin producing beta-like cells from human Pluripotent Stem Cells (PSCs), however the generation of functional, vascularized pancreatic islets from PSCs capable of secreting insulin, glucagon and somatostatin in response to nutrients has not been previously achieved.

Studies described herein demonstrate that using the self-organizing function of human adipose-derived stem cells (hADSC), HUVEC, and human iPSC-derived beta-like cells allows for the in vitro generation of glucose-responsive insulin secreting islet-like organoids with the ability to form functional vasculature. Studies herein further demonstrate the successful scaling of islet-like organoids production through the use of Gellan gum based 3D culture systems. Using a Gaussia luciferase reporter to measure insulin secretion, the functional heterogeneity in hiPSC-derived islet-like organoids was characterized. Without intending to be bound by theory, results herein suggest that the novel human islet-like organoids may offer a therapeutic treatment for diabetes, as well as offer a platform for drug screening, genome editing, and the modeling of organogenesis and pathogenesis of diabetes.

Pancreas

Figure 9:
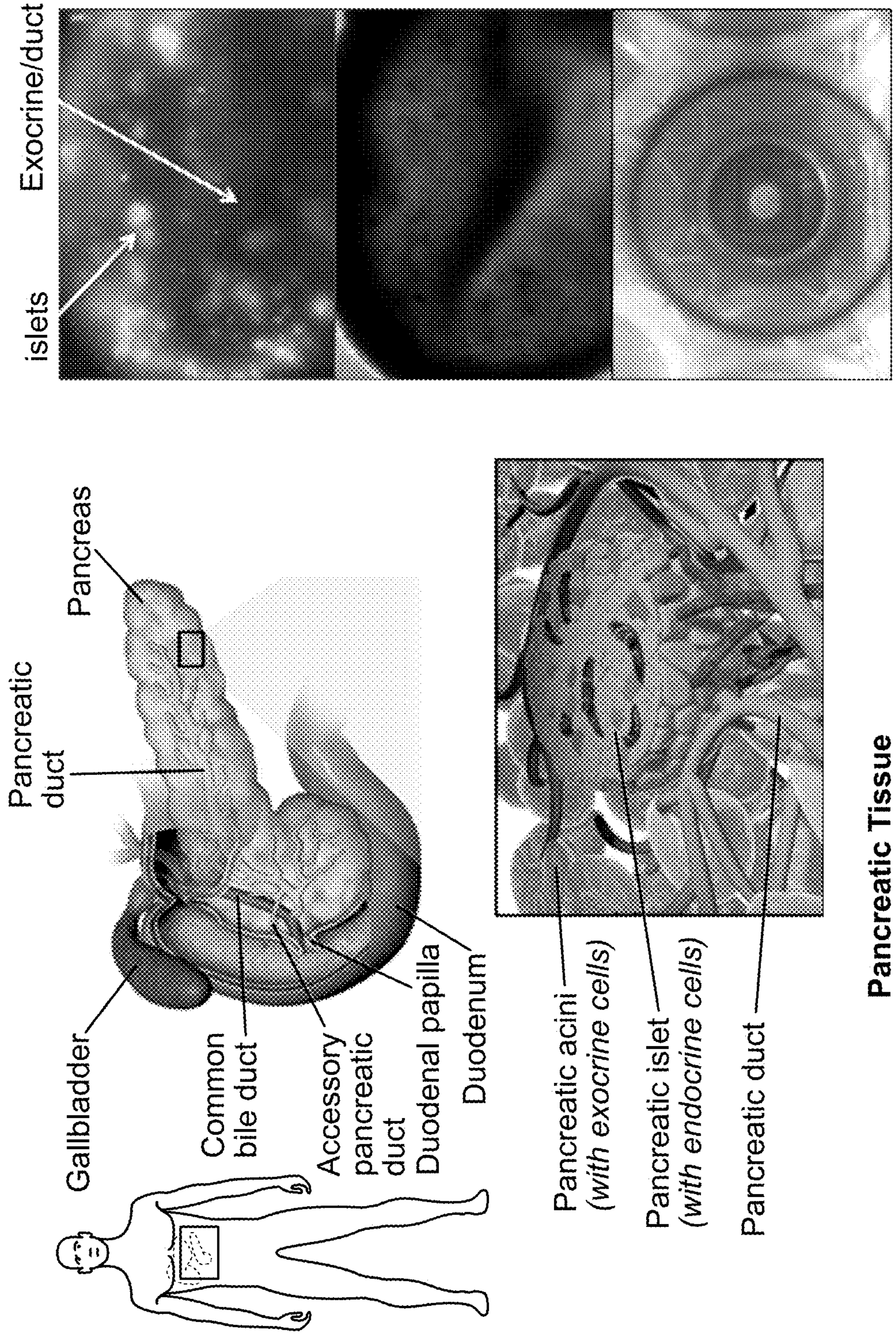
FIG. 9 is a set of schematics and images showing a structure of a pancreas and pancreatic tissue and images of a pancreatic islet-like organoid and pancreatic organoid generated herein. The schematics on the left of FIG. 9 depict the anatomy and structure of a pancreas (top) and pancreatic islets (bottom). The image on the top-right corner of FIG. 9 shows an iPSC-derived pancreatic organoid with pancreatic islets (as marked by green fluorescent protein expression driven by the insulin promoter) and an exocrine/duct component as indicated. The image in the middle-right of FIG. 9 shows the corresponding light microscopy image of the fluorescent image above. The image on the bottom-right corner of FIG. 9 shows a single pancreatic islet organoid.

In some aspects, the invention provides a pancreatic organoid or a pancreatic islet organoid. The pancreas is an organ that lies in the abdomen and has endocrine and exocrine functions. FIG. 9 provides schematics showing the structure of the pancreas. The portion of the pancreas having an endocrine role are cell clusters called "pancreatic islets" (also known as islets of Langerhans). Pancreatic endocrine secretions include hormones that regulate glucose metabolism and blood glucose concentration. Four main cell types are present in the islets: alpha cells which secrete glucagon (a hormone that increases blood glucose concentration); beta cells which secrete insulin (a hormone that decreases blood glucose concentration); delta cells, which secrete somatostatin (a hormone that regulates alpha and beta cells), and gamma cells which secrete pancreatic polypeptide.

The portion of the pancreas that has an exocrine role is referred to as the exocrine component. The exocrine pancreatic secretions contain digestive enzymes that pass into the small intestine and help break down carbohydrates, proteins, and lipids. The exocrine component has ducts arranged in clusters called pancreatic acini. Pancreatic exocrine secretions are secreted into the lumen of the acinus, which accumulate and drain into the pancreatic duct and duodenum.

Pancreatic islet organoids and pancreatic organoids of the invention mimic the structure of a pancreatic islet and a pancreas, respectively. In some embodiments, the pancreatic islet organoid or pancreatic organoid of the invention contains any one or more of the following cells: an iPSC-derived beta-like cell, an iPSC-derived alpha-like cell, an iPSC derived delta-like cell, and an iPSC-derived duct-like cell. In some embodiments, the pancreatic organoid of the invention contains an iPSC-derived exocrine component. In some embodiments, the iPSC is a human iPSC (hiPSC). Human embryonic stem cells and human induced pluripotent stem cells are commercially available (e.g., from WiCell, which provides iPS(IMR-90)-1, iPS(IMR-90)-4 and iPS(Foreskin)-1). Human induced pluripotent stem cells can also be generated using methods known in the art from a variety of somatic cell types (Yu, J., K. Hu, et al. (2009). "Human induced pluripotent stem cells free of vector and transgene sequences." Science 324(5928): 797-801).

Pancreatic islet organoids and pancreatic organoids of the invention also exhibit function(s) of a pancreatic islet and a pancreas. In certain embodiments, the pancreatic islet organoid or pancreatic organoid exhibits any one or more of the following functions: glucose-stimulated insulin secretion (GSIS), KCl-stimulated insulin secretion, GLP-1 stimulated insulin secretion, somatostatin secretion, and glucagon secretion. In some embodiments, the pancreatic islet or pancreatic organoid expresses any one or more of the transcription factors Pdx1, MafA, Pax4, Pax6, NeuroD1, Nkx6-1, Gata6, and Foxa2.

Generation of Pancreatic and Pancreatic Islet Organoids

In some other aspects, the invention features methods of generating a pancreatic or pancreatic islet organoid. Recent studies have shown that while it was possible to generate glucose responsive insulin producing beta-like cells, efforts to generate pancreatic islets which are capable of secreting insulin, glucagon and somatostatin in response to nutrients, as well as efforts to obtain vascularization from stem cells, have not succeeded. Described herein are results demonstrating that using the self-organizing function of human Adipose-derived stem cells (hADSC), human umbilical vein endothelial cells (HUVEC), and human iPSC-derived beta-like cells, glucose responsive insulin secreting islet-like organoids capable of functional vascularization are successfully generated in vitro. Further, islet-like organoid generation methods were successfully scaled up using gellan gum based 3D culture systems. The functional heterogeneity in hiPSC-derived human islet-like organoids was also investigated using a Gaussia luciferase reporter to measure insulin secretion.

Generation of functional human organs provides new therapeutic strategies in drug-screening, disease modeling and inhibiting or preventing end point organ failure. Efficient stepwise differentiation methods from human embryonic stem cells (hESC) and human induced pluripotent stem cells (hiPSC) to insulin producing β-like cells were demonstrated previously. D'Amour et al and Kroon E et al reported the efficient differentiation of hESCs into insulin producing cells which, after 4 to 5 months in vivo maturation, are able to secrete insulin in response to glucose (D'Amour et al., 2006, Nature biotechnology 24, 1392-1401; Kroon et al., 2008, Nature biotechnology 26, 443-452). Recently, Rezania et al. and Pagliuca et al. reported differentiation methods that induced formation of mature human beta-like cells in vitro in that they expressed terminal β-cells marker, MAFA and Nkx6-1 and exhibited partial functionality (e.g., insulin secretion) (Rezania et al., 2014, Nature Biotechnology November; 32(11):1121-33; Pagliuca et al., 2014, Cell 159, 428-439). However, in contrast to cadaveric human islets, those beta-like cells required in vivo functional maturation for a few months, and lacked the functionality provided by the other pancreatic islet cell types, such as glycemic control by α-cells (glucagon secrete) and δ-cells (somatostatin secretion). Further, the beta-like cells lacked both a mesenchyme and vascularized endothelial cells, which human islets naturally have. These crucial differences between hPSCs derived beta-like cells and human islets may compromise the ability of hPSCs based therapies to treat insulin dependent diabetes (such as type 1 or late stage type 2 diabetes).

Previously, it was identified that a metabolic transition occurs during the neonatal to adult maturation of β-cells in which the orphan nuclear receptor Estrogen-related receptor γ (ERRγ) regulates an increase in oxidative metabolism required for fully functional β cells. Consistent with this result, human iPSC-derived β like cells expressing insulin, MAFA, and Nkx6-1 can be metabolically matured through the overexpression of ERRγ to increase their oxidative metabolism and thereby enhance their glucose stimulated insulin secretion (GSIS) functionality. These results indicated that in addition to the expression of lineage determination factors such as PDX1, MAFA, Nkx6-1, and insulin, further cellular signaling which mature the β-cells' metabolism is required to generate fully functional β-cells.

During early pancreas organogenesis, newly specified pancreatic cells originate from the foregut endodermal sheet and form a pancreatic bud, a condensed tissue mass that is soon vascularized. A similar progression has been observed in liver organogenesis as well. Such large-scale morphogenetic changes depend on the exquisite orchestration of signals between endodermal epithelial, mesenchymal, and endothelial progenitors before blood perfusion. Takebe et al, successfully generated hepatic organ buds by culturing hepatic endoderm cells with endothelial and mesenchymal linages which rapidly vascularized and functional matured in vivo (Takebe et al., 2013, Nature 499, 481-484).

Previous work did not reveal the possibility of generating in vitro other organoid tissue types, such as pancreas organoids, which were mature, functional, and vascularized. Further, previous work showed a lack of scalability because the organoids were generated using MATRIGEL® matrix, which is not efficient to use for scaled-up production.

Described herein are studies demonstrating successful large-scale generation of human islet-like organoids which are capable of secreting insulin and which are vascularized, as seen in human islets. It is demonstrated herein that (1) human adipose derived stem cells (hADSCs) have a self-organizing capacity; (2) late stage pancreatic progenitors are capable of forming an islet-like cluster when co-cultured with HUVECs and hADSCs with comparable efficiency to beta-like cells; (3) human islet-like organoids had improved expression of lineage determination factors as well as metabolic regulatory genes including ERRγ; (4) islet insulin secretion assays, measured using a Gaussia Luciferase pro-insulin system, revealed that human islet-like organoids contain functional cells capable of secreting insulin in response to glucose; (5) human islet-like organoids exhibited vascularization; (6) human islet-like organoids derived from hiPSC by the method described herein recaptured human islet organogenesis and pathogenesis of type 1 and type 2 diabetes in a dish; (7) human islet-like organoids derived from hiPSC by the method described herein offered a new replaceable resource for human islet transplantation to treat type 1 and type 2 diabetes; and (8) human islet-like organoids transplanted into an STZ-induced NODSCID mouse model of type 1 diabetes ameliorated type 1 diabetes in the recipient animals. (FIGS. 4H and 4I).

Figure 11A:
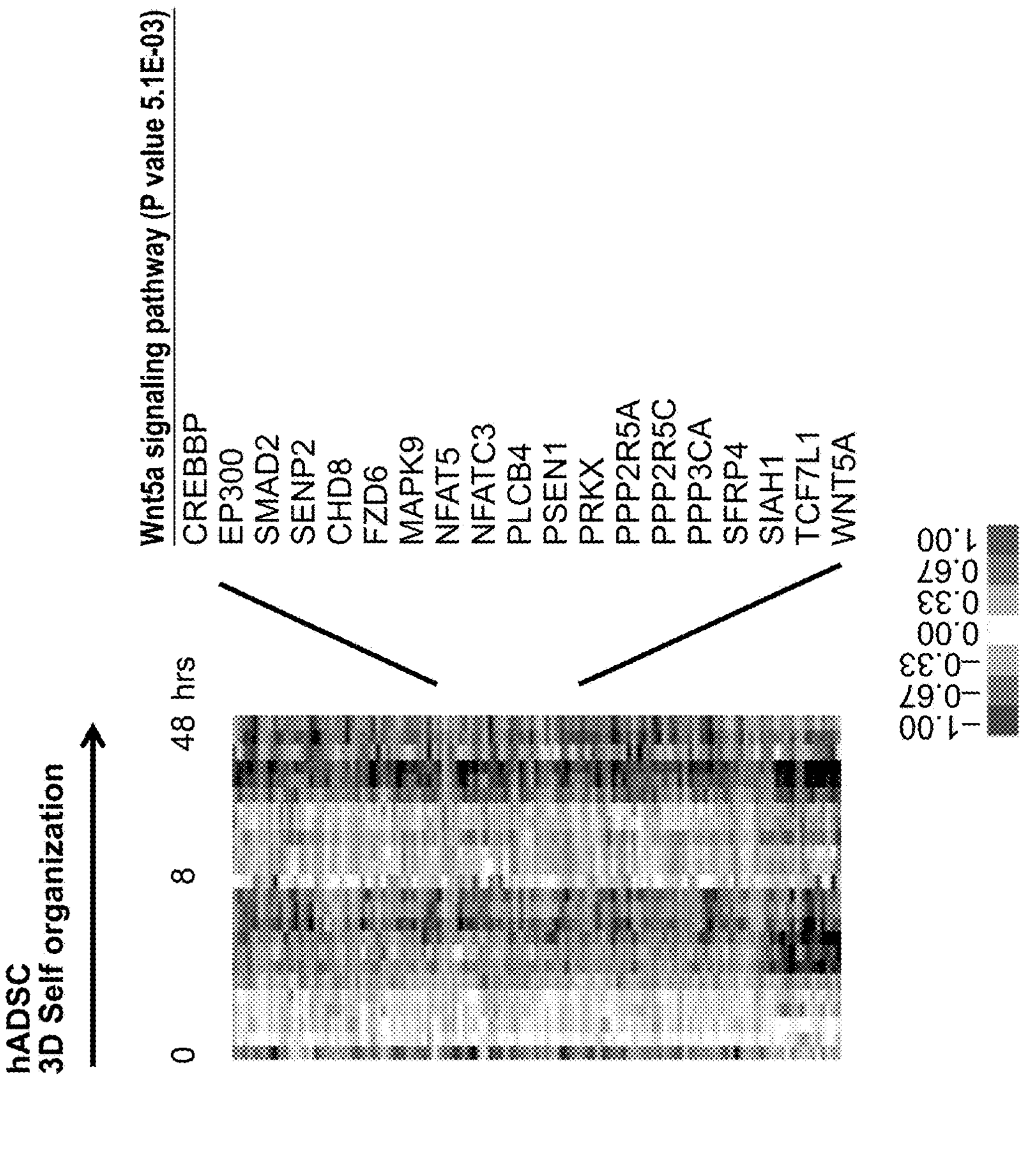
FIGS. 11A and 11B show a heatmap and graph illustrating the role of WNT proteins in the hADSCs in 3D culture.
Figure 11B:
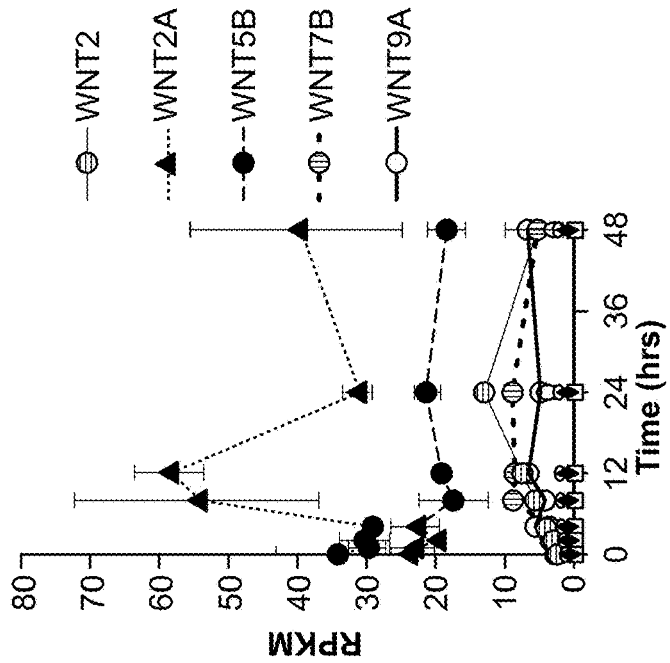
Figure 12B:
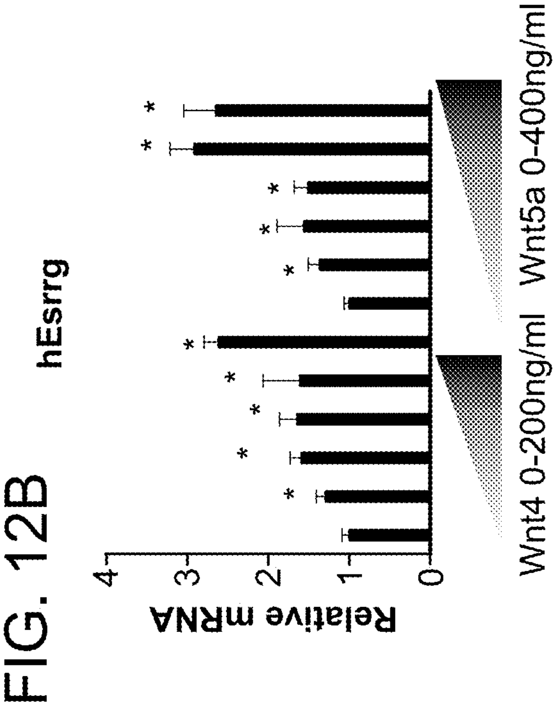
FIGS. 12A-12H show a set of bar graphs and images illustrating the role of WNT proteins in the metabolic maturation of iPSC-derived islet organoids.
Figure 12A:
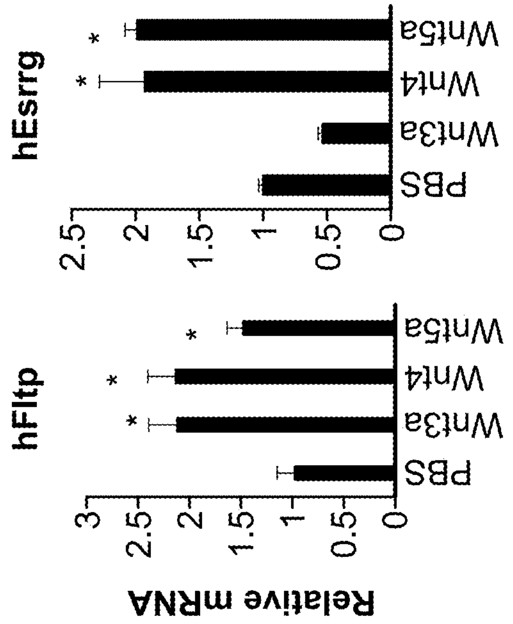
Figure 12C:
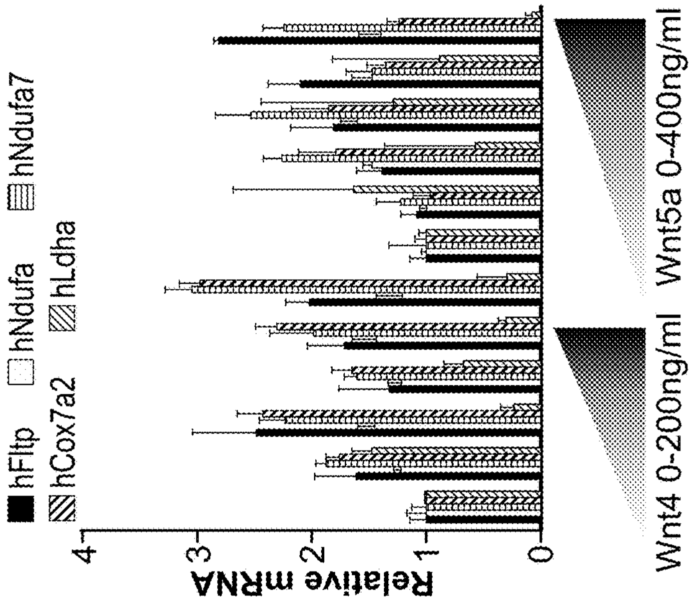
Figure 12D:
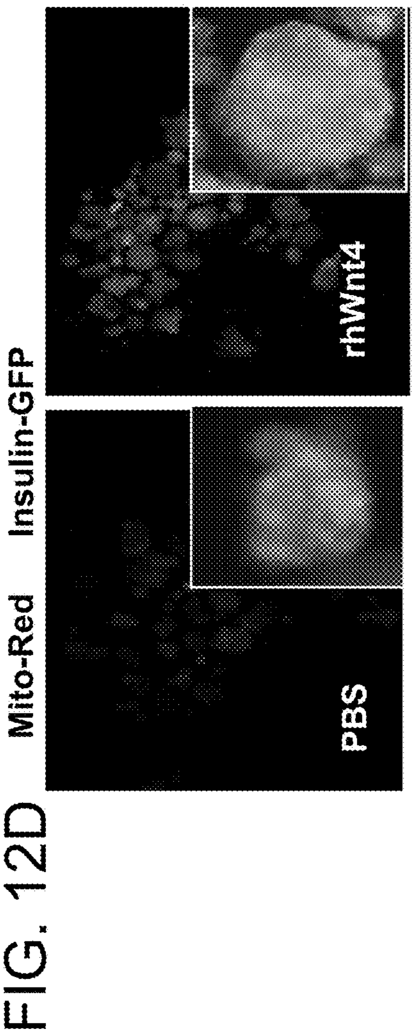
Figure 12E:
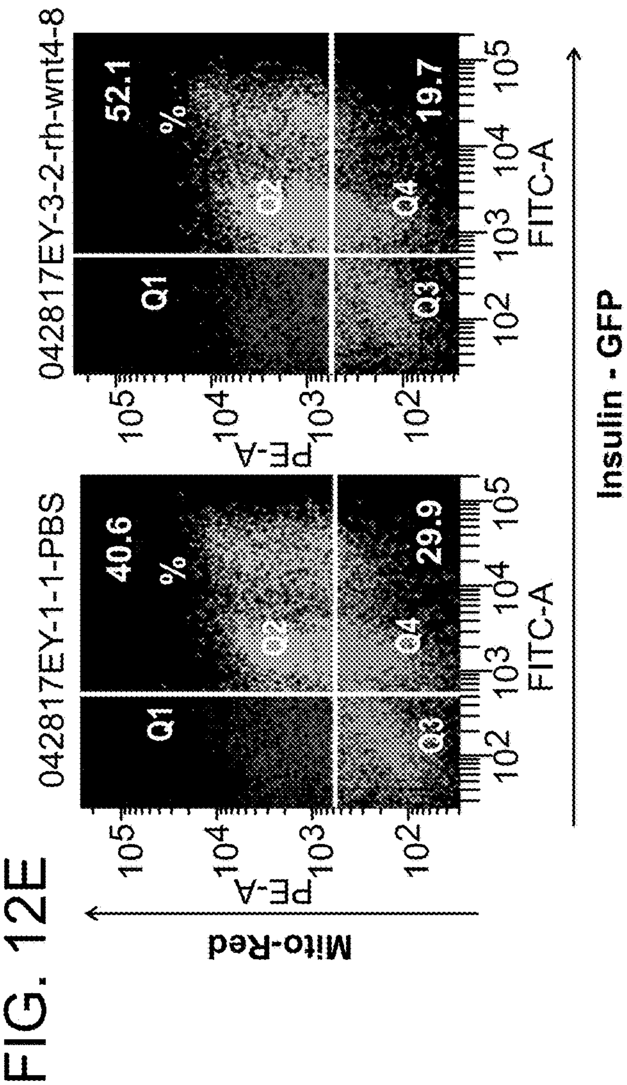
Figure 12F:
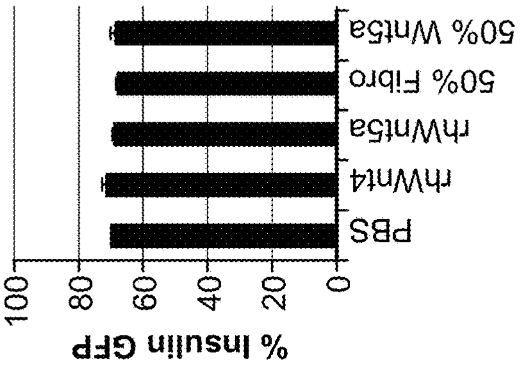
Figure 12G:
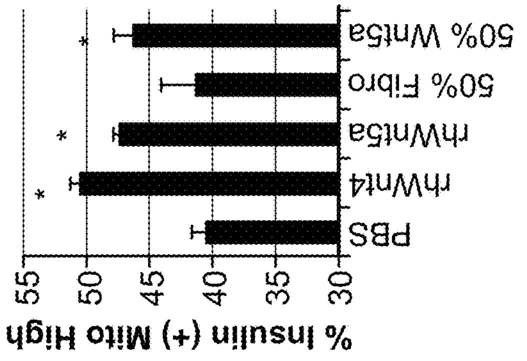
Figure 12H:
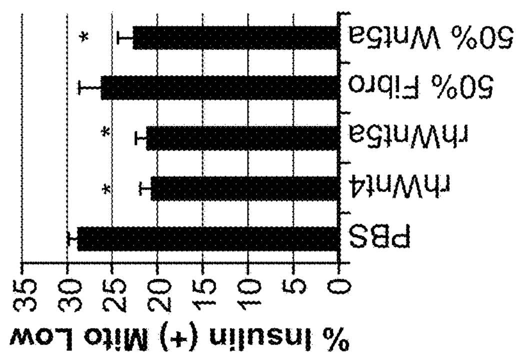
Figure 13:
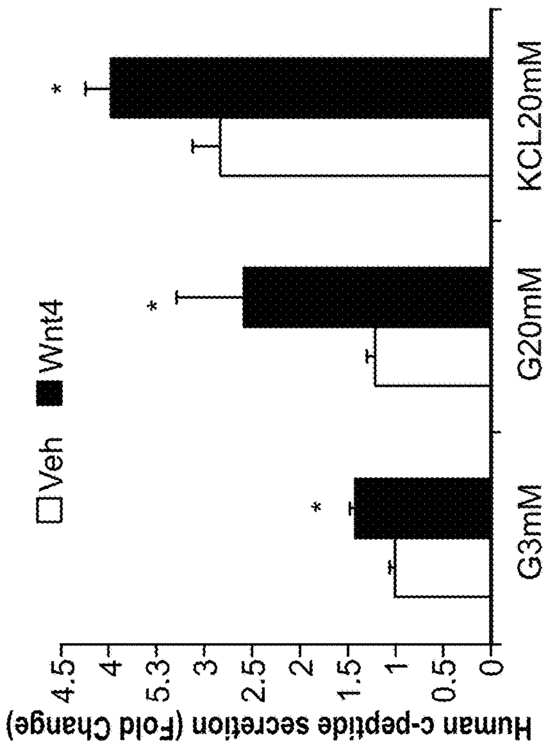
FIG. 13 shows a bar graph demonstrating a role for WNT4 in the functional maturation of hiPSC-derived islet organoids. Human iPSC (hiPSC)-derived islet organoids (day 22) were treated with PBS (Vehicle, "Veh") or WNT4 (100 ng/ml) for 12 days, and the secretion of human c-peptide was measured in response to low glucose βmM, "G3 mM"), high glucose (20 mM, "G20 mM"), or high KCl levels (20 mM, "KCL20 mM").

Also described herein are studies in which the role of certain Wnt (also "WNT" herein) proteins was assessed in developing human islet-like organoids which are capable of secreting insulin and which are vascularized, as seen in human islets. The WNT gene family consists of structurally related genes that encode secreted signaling proteins, which have been implicated in oncogenesis and in several developmental processes, including regulation of cell fate and patterning during embryogenesis. Wnt proteins comprise a major family of signaling molecules that orchestrate and influence a variety of cell biological and developmental processes. Wnt proteins undergo a complex set of posttranslational modifications involving several highly specialized processing enzymes. Upon release from the cell, the Wnt proteins interact with a number of molecules in the extracellular environment, such as glycans, protein-binding partners (e.g., WIF, Sfrp) and cell surface receptors. (Willert, K. et al., 2012, Cold Spring Harbor, *Perspectives in Biology,* 2012). It is demonstrated herein that (1) Wnt5a is the predominant Wnt protein that induces the self-organization of hADSCs (FIGS. 11A and 11B); (2) Wnt5a, as well as Wnt4, activate the ERRγ-mitochondrial metabolic pathway (FIGS. 12A-12H); (3) Wnt4 is sufficient to induce in vitro functional maturation of hiPSC-derived islet-like organoids in the absence of additional cell types such as hADSC and HUVECs (FIG. 13).

Methods of Treatment

Islet transplantation is a therapy for treating insulin deficient diabetes such as type 1 and late stage type 2 diabetes. Thus, in another aspect, the present invention provides methods of treating a pancreatic disease such as type 1 or type 2 diabetes comprising administering a pancreatic or pancreatic islet organoid of the invention to a subject (e.g., a mammal such as a human) by transplantation. One embodiment is a method of treating a subject suffering from or susceptible to a pancreatic disease (e.g., type 1 diabetes) or disorder or symptom thereof. The method includes the step of transplanting a pancreatic or pancreatic islet organoid of the invention to the mammal sufficient to treat the disease or disorder or symptom thereof, under conditions such that the disease or disorder is treated.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

The therapeutic methods of the invention (which include prophylactic treatment) in general comprise administration (in particular, transplantation) of an effective amount of a pancreatic or pancreatic islet organoid to a subject (e.g., animal, human) in need thereof, including a mammal, particularly a human. The administration of the pancreatic or pancreatic islet organoid may be by any suitable means that results in an amount of the organoid that, combined with other components, is effective in ameliorating, reducing, or stabilizing a pancreatic disease such as type 1 or type 2 diabetes.

In some aspects, the subject is further administered an immunosuppressant. The immunosuppressant can be administered to the subject before, during, or after the subject is administered (e.g., transplanted) with the organoid. The immunosuppressive agent can be an agent that inhibits or prevents rejection (e.g., acute rejection) of the transplanted organoid upon transplantation, or an agent that maintains immunosuppression after the transplantation. Immunosuppressants include, but are not limited to, basilizimab, antithymocyte globulin, alemtuzumab, prednisone, azathioprine, mycophenolate, cyclosporine, sirolimus, and tacrolimus.

In some embodiments, at least about 100,000, at least about 200,000, at least about 300,000, at least about 400,000, at least about 500,000, at least about 600,000, at least about 700,000, at least about 800,000, at least about 900,000 or at least about 1 million pancreatic islet organoids are transplanted into the subject. In some embodiments, islets of the subject are removed prior to transplanting the organoids of the invention. In some other embodiments, pancreatic islet organoids are transplanted into a subject by injection into the upper abdomen of the subjects. In some embodiments, the pancreatic islet organoids are injected into the liver. The pancreatic islet organoids can be injected into the subject using a catheter. In some other embodiments, the pancreatic organoid or pancreatic islet organoid is administered to the subject by surgery. In another embodiment, pancreatic islet organoids are transplanted onto the omentum. For omentum transplantation, a layering technique can be used in which the islet organoid (or cells thereof) are combined with autologous plasma and are laparoscopically layered onto the omentum. A solution (20 ml) containing recombinant thrombin (1000 U/ml) is next layered over the islet organoid, followed by another layer of autologous plasma to produce a biodegradable biologic scaffold that can survive and function in the patient for at least a year (See, e.g., Baidal, D. et al., 2017, *N. Engl. J. Med.,* 376:19). In another embodiment, hydrogel biomaterials that mitigate an immune response by the recipient can be used for islet organoid transplantation. (See, e.g., Vegas, A. et al., 2016, *Nature Biotechnology,* 34:345-352).

To further reduce an immune reaction to the transplanted organoid in the subject, the organoid can be encapsulated in a hydrogel and then transplanted in the subject. Such methods of transplantation are further described in Vegas et al., Nature Medicine 2016, doi:10.1038/nm.4030; Vegas et al., Nature Biotechnology 2016, doi:10.1038/nbt.3462. In some embodiments, the hydrogel contains an alginate or alginate derivative (e.g., triazole-thiomorpholine dioxide). Various modifications of alginate hydrogels that substantially reduce inflammatory or fibrotic effects of alginate hydrogels have also been identified (Vegas et al., Nature Biotechnology 2016, doi:10.1038/nbt.3462). Thus, in some other embodiments, the hydrogel contains a chemical modification that reduces an inflammatory effect of the transplanted organoid in the subject.

Screening Assays

Pancreatic islet organoids and pancreatic organoids of the invention can be useful for modeling diseases of the pancreas in vitro or in vivo. Such pancreas disease models can be used to identify drugs that are useful for treatment of a pancreatic disease. Thus, in some aspects, the invention provides methods for identifying modulators, i.e., candidate or test compounds or agents (e.g., proteins, peptides, peptidomimetics, peptoids, polynucleotides, small molecules or other drugs) that are useful for the treatment of a pancreatic disease, particularly type 2 diabetes and/or pancreatic cancer. In one embodiment, the agent modulates an activity of an organoid of the invention.

The test agents of the present invention can be obtained singly or using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. (1994) et al., J. Med. Chem. 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) Anticancer Drug Des. 12:145).

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994) J. Med. Chem. 37:2678; Cho et al. (1993) Science 261:1303; Carrell et al. (1994) Angew. Chem. Int. Ed. Engl. 33:2059; Carell et al (1994) Angew. Chem. Int. Ed. Engl. 33:2061; and Gallop et al. (1994) J. Med. Chem. 37:1233.

Libraries of compounds may be presented in solution (e.g., Houghten (1992), Biotechniques 13:412-421), or on beads (Lam (1991), Nature 354:82-84), chips (Fodor (1993) Nature 364:555-556), bacteria (Ladner, U.S. Pat. No. 5,223,409), spores (Ladner U.S. Pat. No. 5,223,409), plasmids (Cull et al. (1992) Proc Natl Acad Sci USA 89:1865-1869) or on phage (Scott and Smith (1990) Science 249:386-390; Devlin (1990) Science 249:404-406; Cwirla et al. (1990) Proc. Natl. Acad. Sci. 87:6378-6382; Felici (1991) J. Mol. Biol. 222:301-310; Ladner supra.).

Chemical compounds to be used as test agents (i.e., potential inhibitor, antagonist, agonist) can be obtained from commercial sources or can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock (1989) Comprehensive Organic Transformations, VCH Publishers; T. W. Greene and P. G. M. Wuts, Protective Groups in Organic Synthesis, 2nd ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

Combinations of substituents and variables in compounds envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., transport, storage, assaying, therapeutic administration to a subject).

The compounds described herein can contain one or more asymmetric centers and thus occur as racemates and racemic mixtures, single enantiomers, individual diastereomers and diastereomeric mixtures. All such isomeric forms of these compounds are expressly included in the present invention. The compounds described herein can also be represented in multiple tautomeric forms, all of which are included herein. The compounds can also occur in cis- or trans- or E- or Z-double bond isomeric forms. All such isomeric forms of such compounds are expressly included in the present invention.

Test agents of the invention can also be peptides (e.g., growth factors, cytokines, receptor ligands) or polynucleotides encoding such peptides.

Screening methods of the invention identify agents that increase or decrease a biological activity of pancreatic islet organoids and pancreatic organoids of the invention. In some embodiments, a pancreatic disease, such as type 2 diabetes or pancreatic cancer, is induced or mimicked in the pancreatic islet organoid or pancreatic organoid. Type 2 diabetes in the pancreatic islet or pancreatic organoid can be induced, for example, by contacting the organoid with free fatty acids (FFAs), glucose, and cytokines (in particular, high levels of glucose and/or high levels of FFAs). In one embodiment, a pancreatic organoid is co-cultured with pancreatic cancer cells, stellate cells and immune cells to create a human pancreatic cancer microenvironment in vitro.

In some embodiments, the organoid is contacted with a candidate agent, and an effect of the candidate agent on a biological activity, function, or event is assayed. In some embodiments, the candidate agent is a drug approved by the Food and Drug Administration (FDA). For example, biological activities of a pancreatic islet organoid or pancreatic organoid assayed in the screening methods of the invention include insulin secretion (e.g., glucose-stimulated insulin secretion (GSIS)), beta cell apoptosis, LDHA activity, K(ATP) channel activity, mitochondrial function, level or activity of NDUFA4, ESRRG, KCNK3, or MAFA polypeptide or polynucleotide, cell death, cell growth, and metastasis. In some embodiments, the agent increases GSIS.

In some other embodiments, an organoid of the invention (e.g., pancreatic islet organoid or pancreatic organoid) is transplanted into a host to model pancreatic disease, such as type 2 diabetes or pancreatic cancer, in vivo. Methods of transplanting an organ or organoid are known in the art. The host can be any non-human mammal, such as a rat or mouse.

To reduce an immune reaction to the transplanted organoid in the host after, the organoid can be encapsulated in a hydrogel and then transplanted in the host. Such methods of transplantation are further described in Vegas et al., Nature Medicine 2016, doi:10.1038/nm.4030; Vegas et al., Nature Biotechnology 2016, doi:10.1038/nbt.3462. In some embodiments, the hydrogel contains an alginate or alginate derivative (e.g., triazole-thiomorpholine dioxide). Various modifications of alginate hydrogels that substantially reduce inflammatory or fibrotic effects of alginate hydrogels have also been identified (Vegas et al., Nature Biotechnology 2016, doi:10.1038/nbt.3462). Thus, in some other embodiments, the hydrogel contains a chemical modification that reduces an inflammatory effect of the transplanted organoid in the host.

In some embodiments, a pancreatic organoid and liver organoid are co-transplanted in the host. The liver is a major target organ for metastasis of pancreatic cancer. In mice in vivo endothelial cells in the mini pancreas and in the mini liver are connected to each other and create a pancreas-liver vasculature network for pancreatic cancer metastasis. Therefore, a host co-transplanted with a pancreatic organoid and liver organoid can be useful for studies of human pancreatic cancer metastasis into human liver.

In some embodiments, the host transplanted with an organoid of the invention is administered an environmental stress (e.g., administered a high fat/high glucose diet or administered pancreatic cancer cells) to induce or mimic a pancreatic disease in the host. In some other embodiments, the host is transplanted with a pancreatic islet or pancreatic organoid and/or a liver organoid where a disease (e.g., type 2 diabetes or pancreatic cancer) has been induced.

In some embodiments, the host is administered with a candidate agent. In certain embodiments, the candidate agent is a drug approved by the Food and Drug Administration (FDA). In some embodiments, an effect of the candidate agent on a host phenotype (such as biological activity or function associated with the pancreas, or activities associated with a disease) is assayed. Exemplary biological activities include insulin secretion (e.g., glucose-stimulated insulin secretion (GSIS)), beta cell apoptosis, LDHA activity, K(ATP) channel activity, mitochondrial function, level or activity of NDUFA4, ESRRG, or MAFA polypeptide or polynucleotide, cell death, cell growth, and metastasis. In some embodiments, the agent increases GSIS.

In any one of the embodiments herein, the effect of the candidate agent (i.e., ability to modulate a pancreatic activity or function) is measured relative to a reference. The reference can be, for example, an untreated pancreatic islet organoid or pancreatic organoid. In some embodiments, the reference is a host transplanted with an organoid of the invention, where the host is not administered with a candidate agent.

Agents useful in the methods of the invention can also be detected by identifying an increase in expression of a desirable marker (e.g., MAFA as a beta cell fate marker). The level of expression can be measured in a number of ways, including, but not limited to: measuring the mRNA encoded by the genetic markers; measuring the amount of protein encoded by the genetic markers; or measuring the activity of the protein encoded by the genetic markers.

The level of mRNA corresponding to a marker can be determined both by in situ and by in vitro formats. The isolated mRNA can be used in hybridization or amplification assays that include, but are not limited to, Southern or Northern analyses, polymerase chain reaction analyses and probe arrays. In one format, mRNA (or cDNA) is immobilized on a surface and contacted with the probes, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array described below. A skilled artisan can adapt known mRNA detection methods for use in detecting the level of mRNA encoded by the markers described herein.

The level of mRNA in a sample can be evaluated with nucleic acid amplification, e.g., by rtPCR (Mullis (1987) U.S. Pat. No. 4,683,202), ligase chain reaction (Barany (1991) Proc. Natl. Acad. Sci. USA 88:189-193), self-sustained sequence replication (Guatelli et al. (1990) Proc. Natl. Acad. Sci. USA 87:1874-1878), transcriptional amplification system (Kwoh et al. (1989) Proc. Natl. Acad. Sci. USA 86:1173-1177), Q-Beta Replicase (Lizardi et al. (1988) Bio/Technology 6:1197), rolling circle replication (Lizardi et al., U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

The practice of the present invention employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", second edition (Sambrook, 1989); "Oligonucleotide Synthesis" (Gait, 1984); "Animal Cell Culture" (Freshney, 1987); "Methods in Enzymology" "Handbook of Experimental Immunology" (Weir, 1996); "Gene Transfer Vectors for Mammalian Cells" (Miller and Calos, 1987); "Current Protocols in Molecular Biology" (Ausubel, 1987); "PCR: The Polymerase Chain Reaction", (Mullis, 1994); "Current Protocols in Immunology" (Coligan, 1991). These techniques are applicable to the production of the polynucleotides and polypeptides of the invention, and, as such, may be considered in making and practicing the invention. Particularly useful techniques for particular embodiments will be discussed in the sections that follow.

The following examples are put forth so as to provide those of ordinary skill in the art with a complete disclosure and description of how to make and use the assay, screening, and therapeutic methods of the invention, and are not intended to limit the scope of what the inventors regard as their invention.

EXAMPLES

Figure 1:
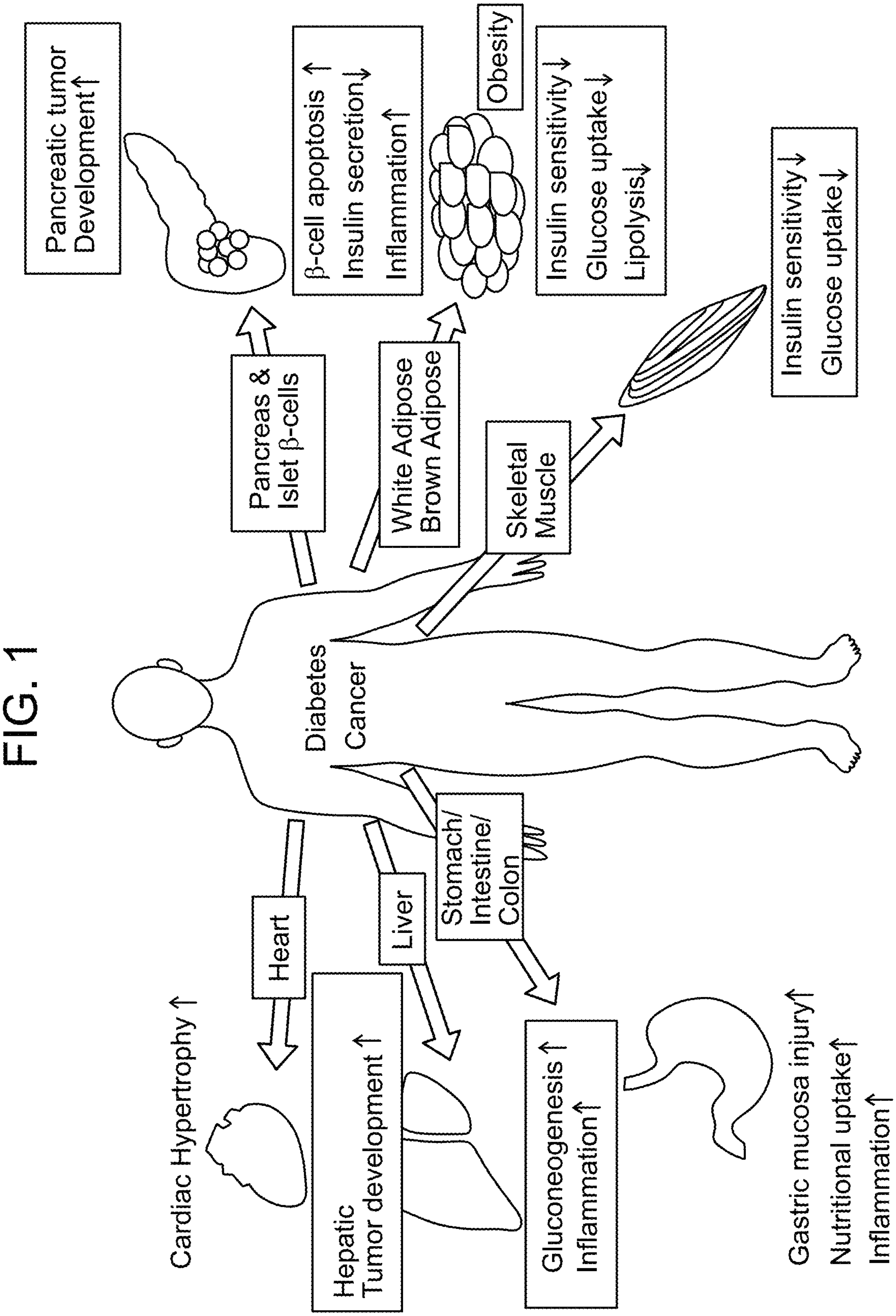
FIG. 1 is a schematic showing the various symptoms of human disease that can be modeled in a dish. Generation of functional human organs provides new therapeutic strategies in drug-screening and disease modeling. Described herein is a novel technique to generate 3D human mini-organs in a dish. Using this technique, human type 2 diabetes can be modeled in a dish to find effective drugs in genetic, patients or environmental specific diseases such as human type 2 diabetes.

Example 1: Generation and Characterization of Pancreatic and Pancreatic Islet Organoids Although an animal disease model can yield insight into the pathogenesis of diseases, drugs identified from screens using animal models often fail to be adopted in human patients. Generation of functional human organoids provides a new therapeutic strategy in drug-screening and disease modeling (FIG. 1). Described herein is a novel technique to generate 3D human "mini-organs" or organoids in a dish. Using this technique, diseases such as human type 2 diabetes can be modeled in a dish to find effective drugs in genetic, patient or environmental specific diseases such as human type 2 diabetes.

Developing Gellan Gum Based 3D Culture System for β-Like Cells Differentiation

Figure 10A:
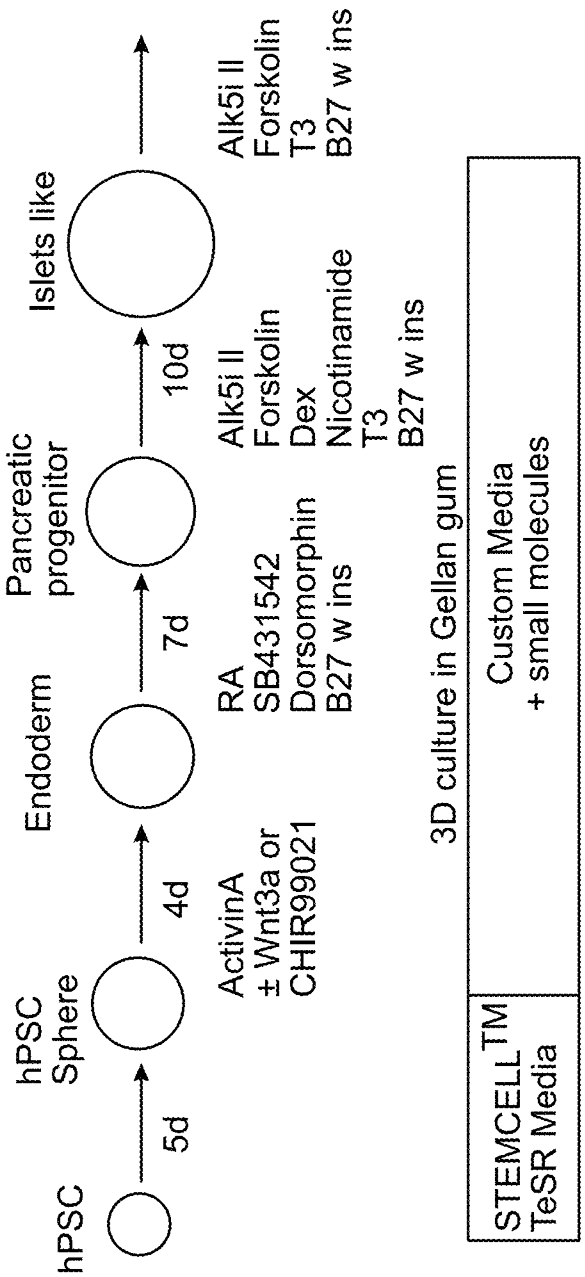
FIGS. 10A-10D is a set of schematics, images, heatmaps, and bar graphs summarizing the generation of islet-like organoids from PSCs.
Figure 10B:
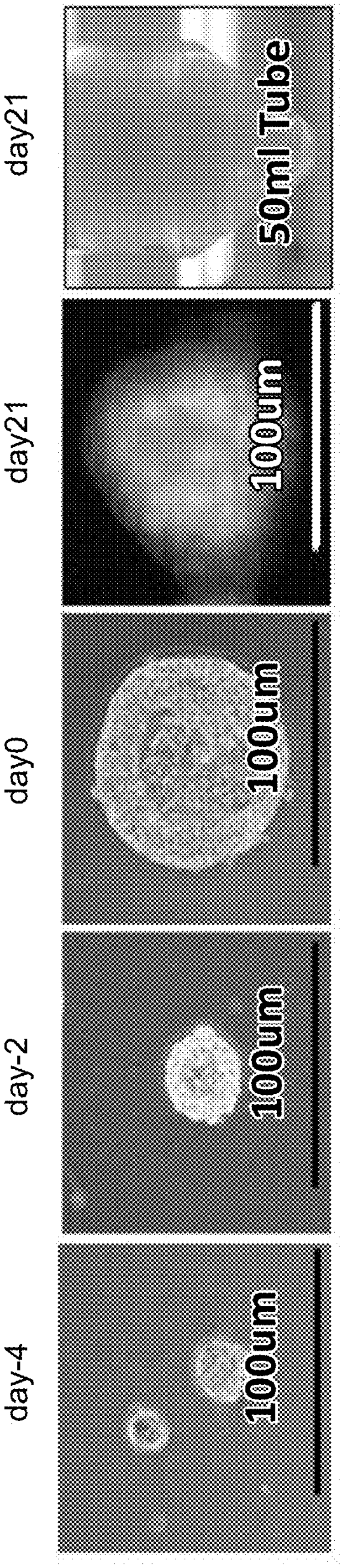
Figure 10C:
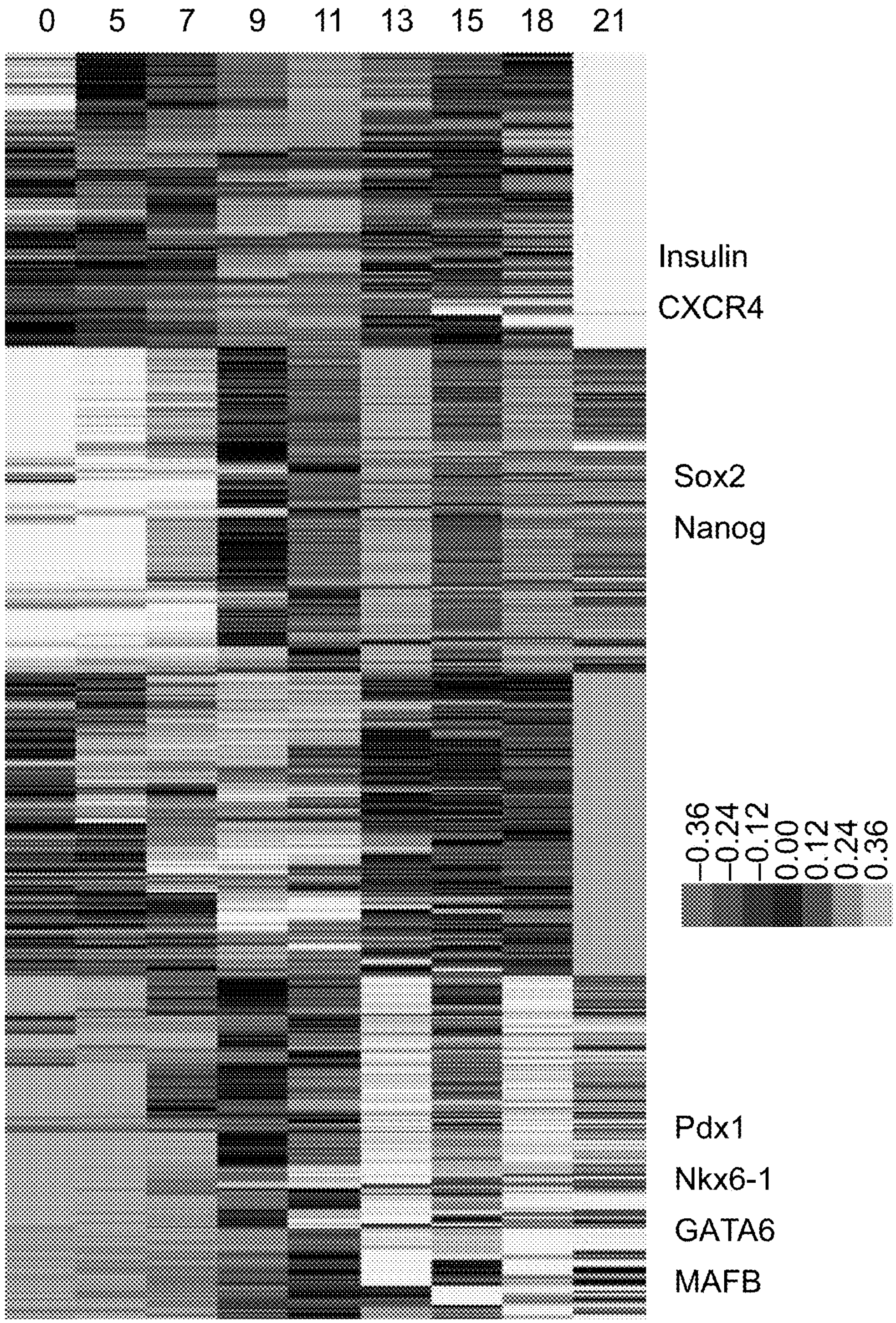
Figure 10D:
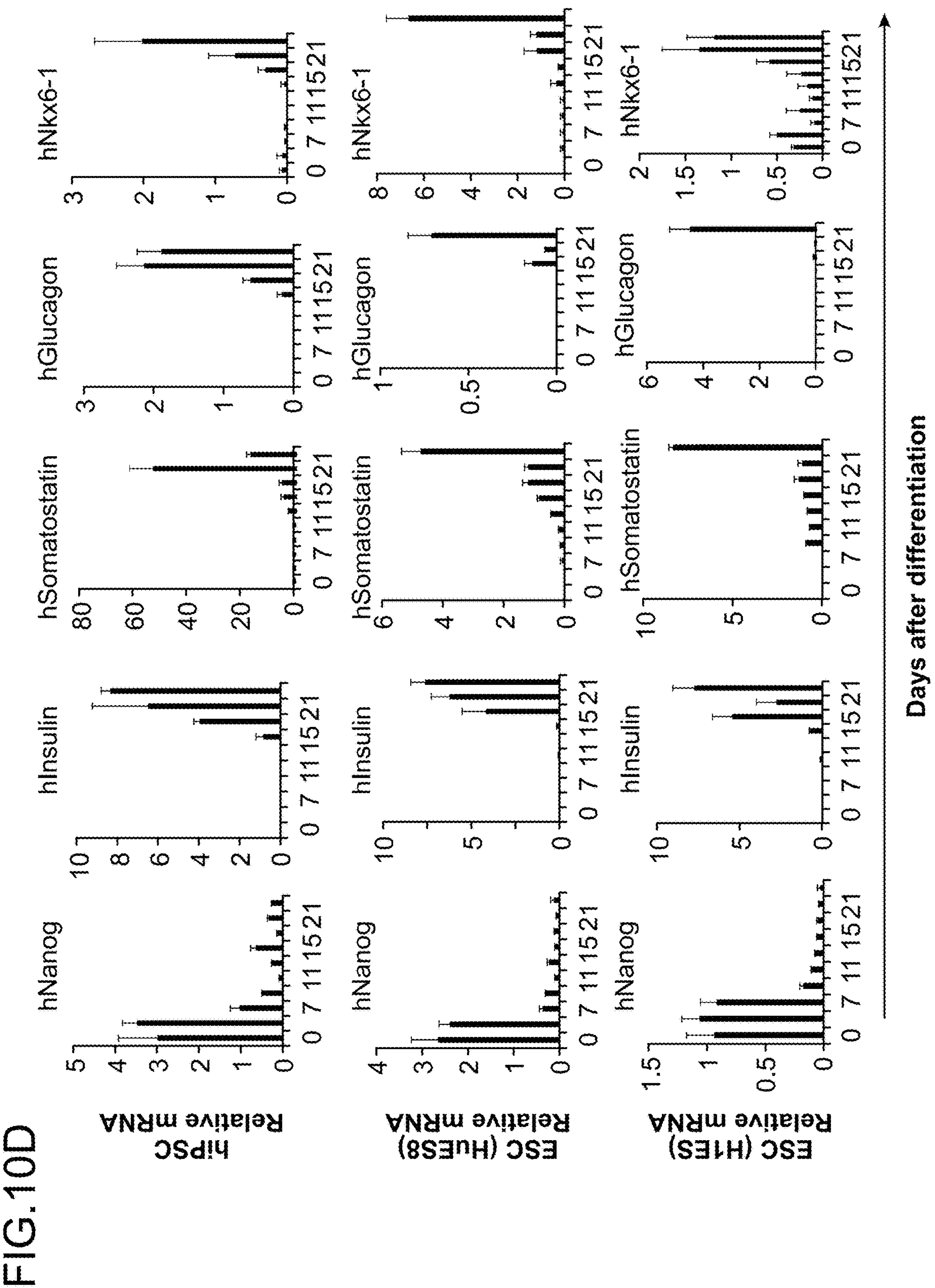

It is known that 3 dimensional (3D) culture systems contribute to facilitating self-organization and integration of cells. Therefore, MATRIGEL® matrix containing extracellular matrix components such as collagen and fibronectin is often used as the basement of a 3D culture system. However, MATRIGEL® matrix-based 3D culture systems are not ideal for large-scale human organoid generation because of their cost and difficulties in scale up. Described herein are Gellan-gum based 3D culture systems and methods for β-like cell differentiation, which are cost effective and easily scalable. Using a fully chemically-defined stepwise differentiation protocol (FIG. 10A) human pluripotent cells (hPSCs) are differentiated into insulin producing islet-like spherical cell clusters with high efficiency and reproducibility in Gellan-gum based 3D culture systems (FIG. 10B). Single dissociated pluripotent stem cells (PSCs) successfully formed into spheres within 5 days in Gellan gum containing STEMCELL™ TeSR™ media. Fifteen (15) to 21 days after differentiation in Gellan gum-containing Custom TeSR™ with defined small molecule stimulation, insulin positive GFP clusters were observed (FIG. 10B). Global transcriptome analysis by RNA-seq revealed the stepwise differentiation of hiPSCs into insulin positive cells expressing β cell lineage specific marker genes including Pdx1, Nkx6-1, GATA6 and MAFB (FIG. 10C). The differentiation of hiPSCs, as well as the human ESC lines HuES8 and H1ES, into islet-like cell clusters was further confirmed by the progressive loss of the pluripotent marker Nanog, the induction of the β cell specific marker Nkx6-1, and the progressive induction of the endocrine hormones insulin, somatostatin and glucagon, as determined by qPCR (FIG. 10D). These results demonstrate that the Gellan-gum based 3D culture systems is suitable for the generation of large-scale islet-like organoids from hPSCs.

Generation of Scalable, Human Islet-Like Organoids In Vitro

β-like cells derived from human embryonic stem cells (hESC) or human induced pluripotent stem cells (hiPSC) have limited functionality and lack the morphological and functional feature of human islets. Previous studies revealed that co-culturing hiPSC derived hepatocyte with human umbilical vein endothelial cells (HUVECs) and human bone marrow-derived mesenchymal stem cells (hMSC) generates self-organized 3D liver-bud spheres in matrigel (Takebe et al., 2013, Nature 499, 481-484). This study found that the liver "organoids" had superior expression of lineage determinant factors compared to the differentiation of isolated hepatocytes and that these organoids rapidly vascularized and functionally matured in vivo.

Figure 2A:
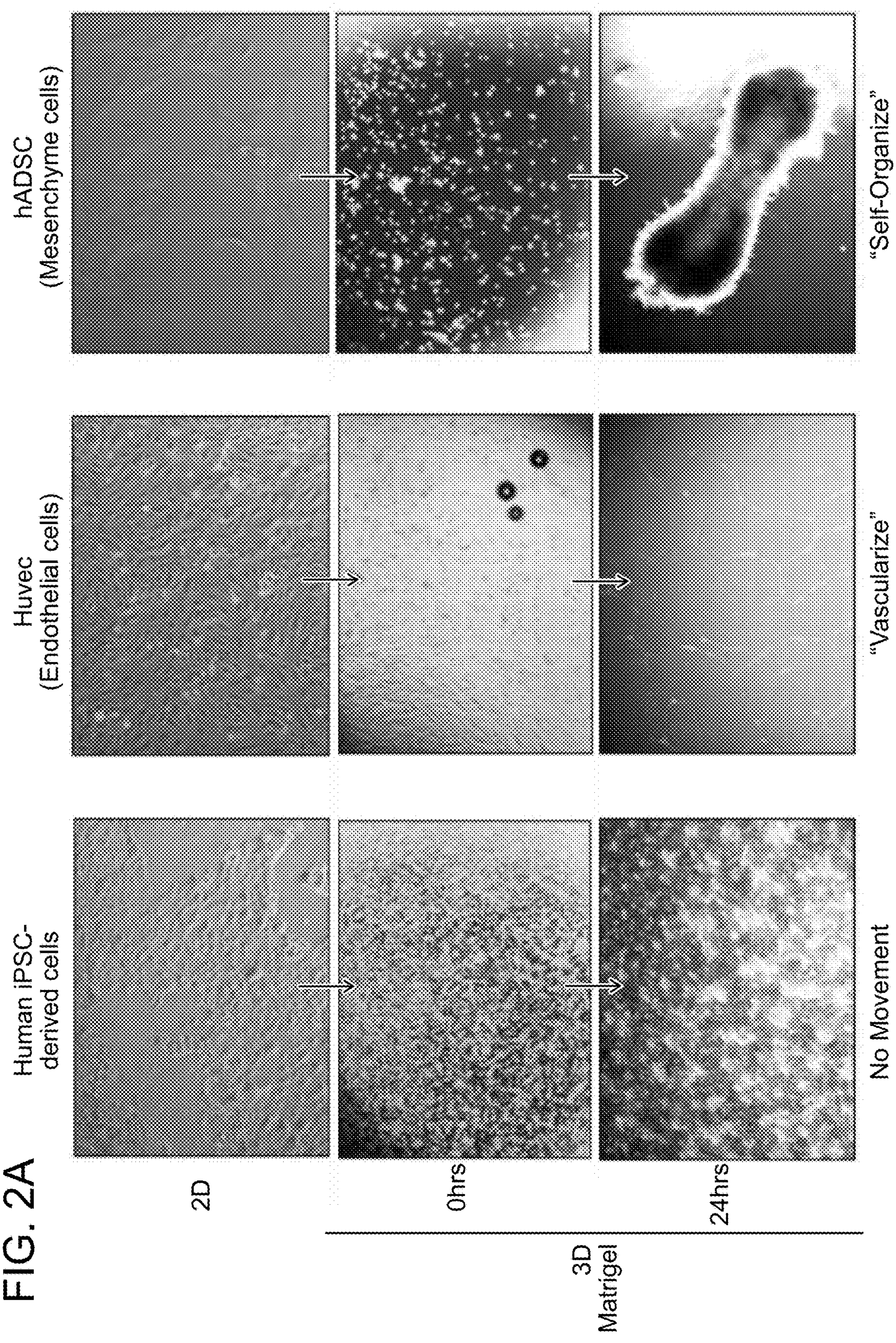
FIG. 2A is a set of micrographs showing the utility of human adipose-derived stem cells (hADSC) in organogenesis. In studies described herein, human adipose-derived stem cells were found to be a novel resource for generation of self-organized organoids (organ bud).

Studies herein found that hiPSC-derived pancreatic progenitor cells (hiPSC-PP) generated using a 2D differentiation protocol (Yoshihara et al, Cell Metab. 23, 622-634) did not self-organize in 3D MATRIGEL® matrix (FIG. 2A). In contrast, HUVEC cells rapidly formed a vasculature-like structure while human adipocyte-derived stem cells (hADSCs) self-organized in 3D MATRIGEL® matrix (FIG. 2A).

Figure 2B:
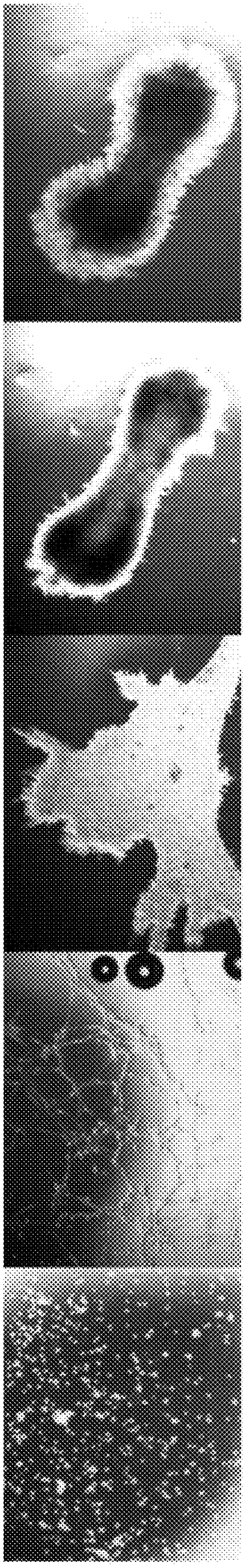
FIG. 2B is a set of micrographs demonstrating the ability of ADSCs to progressively self-organize when cultured in Matrigel.
Figure 2C:
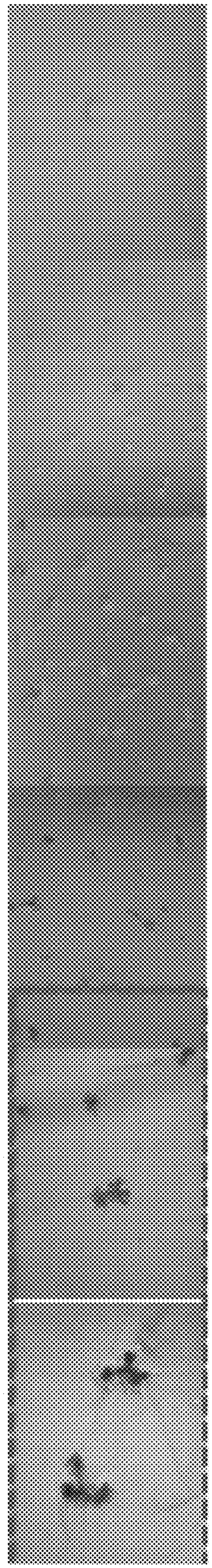
FIG. 2C is a set of images of hADSCs, seeded at the indicated density, that demonstrate the minimum number of cells required for sphere formation when grown in Matrigel.
Figures 1, 2D:
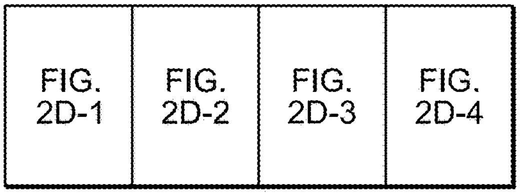
Figure 2D:
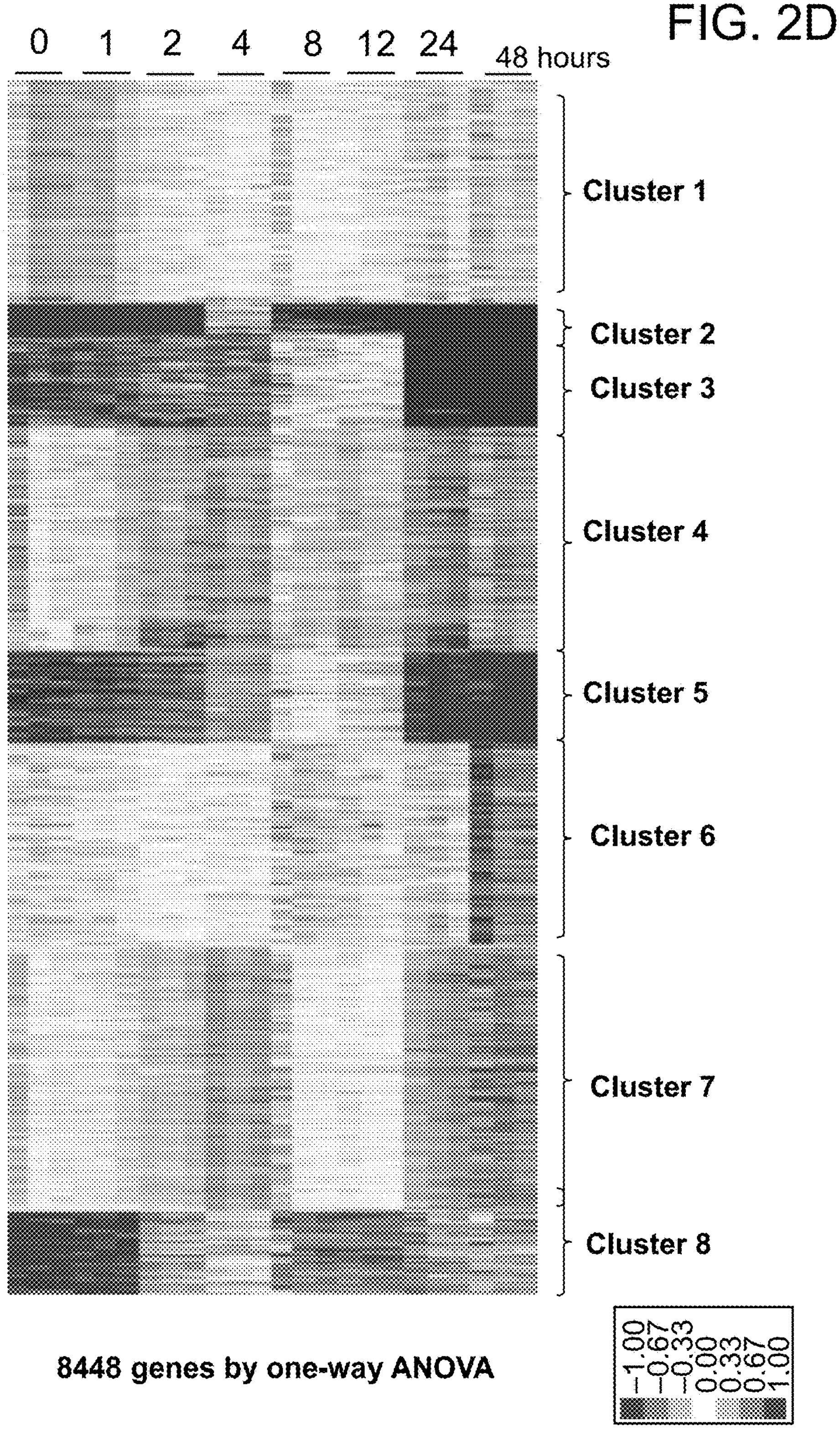

In MATRIGEL® matrix, dispersed hADSC cells projected processes within 4 hours, formed a cloth-like wrapper within 12 hours, and adopted a sphere-like formation within 24 to 48 hours (FIG. 2B). Furthermore, a minimum cell density for self-organization was identified (i.e., ~10,000-20,000 cells in 300 µl of MATRIGEL® matrix in ~2 cm$^2$ well (FIG. 2C). RNA-seq analysis identified dynamic transcriptional changes during hADSC 3D self-organization, suggesting that the ability to self-organize under 3D culture conditions is an inherent feature of naïve hADSCs (FIG. 2D). These results identify the mesenchymal hADSC as a resource for generating self-organizing organoids.

Figure 2E:
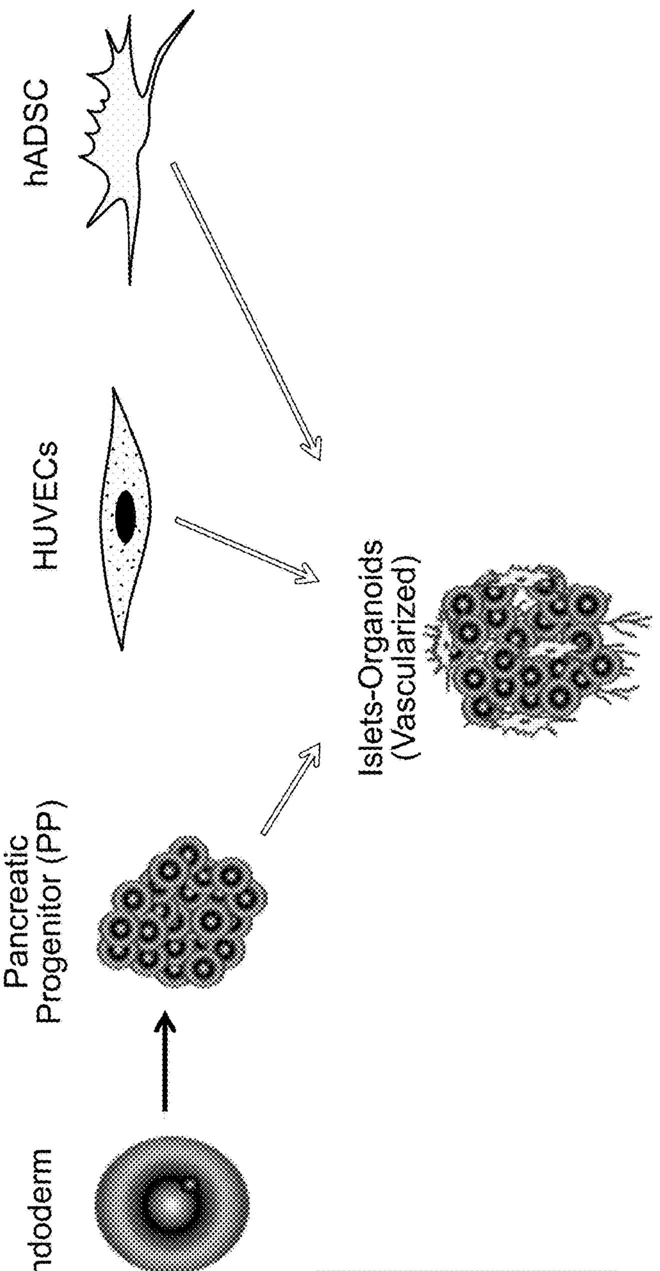
FIG. 2E is a schematic describing the generation of human islet-like organoids by culturing in Matrigel.
Figure 2F:
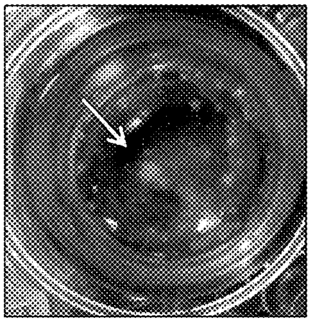
FIG. 2F is an image of human islet-like organoids in a single well of a 24 well plate.
Figure 2G:
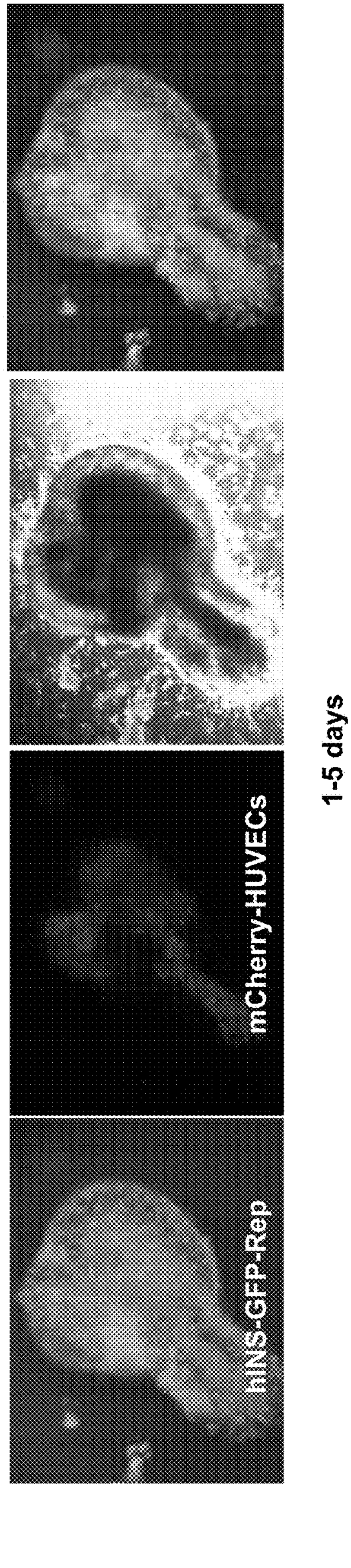
FIG. 2G is a set of images of a human islet-like organoid generated by co-culturing hiPSC-derived pancreatic progenitors, HUVECs, and hADSCs for 1-5 days in Matrigel. GFP is used to indicate human insulin expression (green, $1^{st}$ panel), mCherry to label HUVEC cells (red, $2^{nd}$ panel), brightfield image ($3^{rd}$ panel), and an overlay of GFP and mCherry images ($4^{th}$ panel).
Figure 3B:
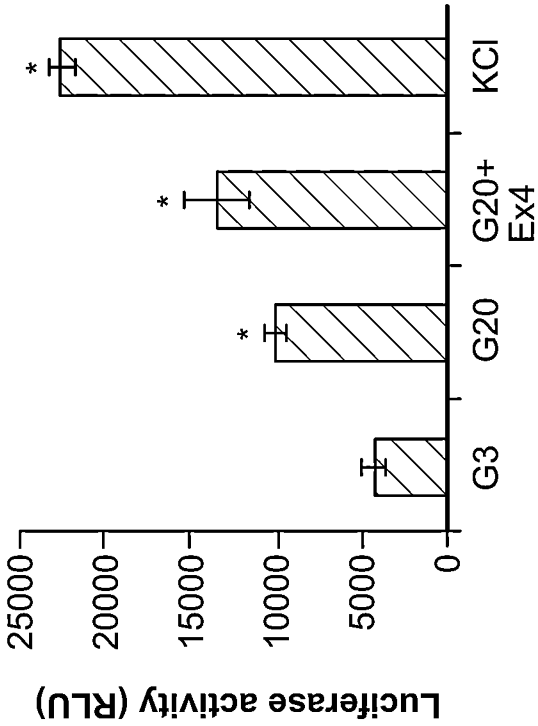
FIGS. 3A-3F are plots, images, and a schematic showing characterization of insulin secretion of INS-1 cells, mouse islets, and human islets using a proinsulin luciferase reporter system as a quantitative insulin secretion assay.
Figure 3A:
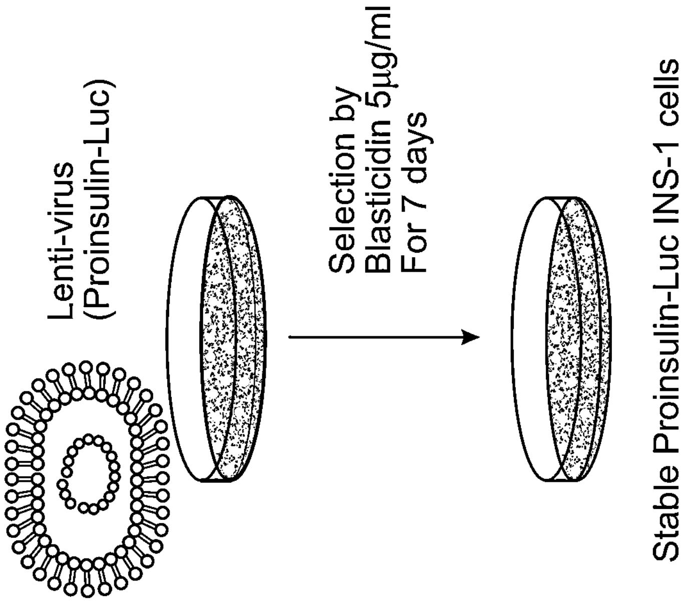
Figure 3C:
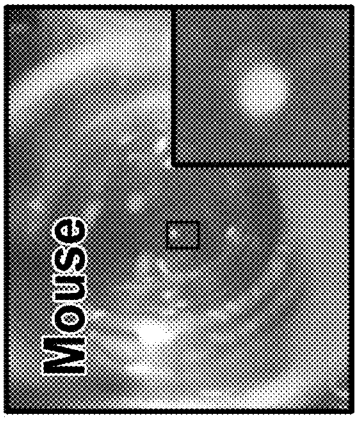
Figure 3D:
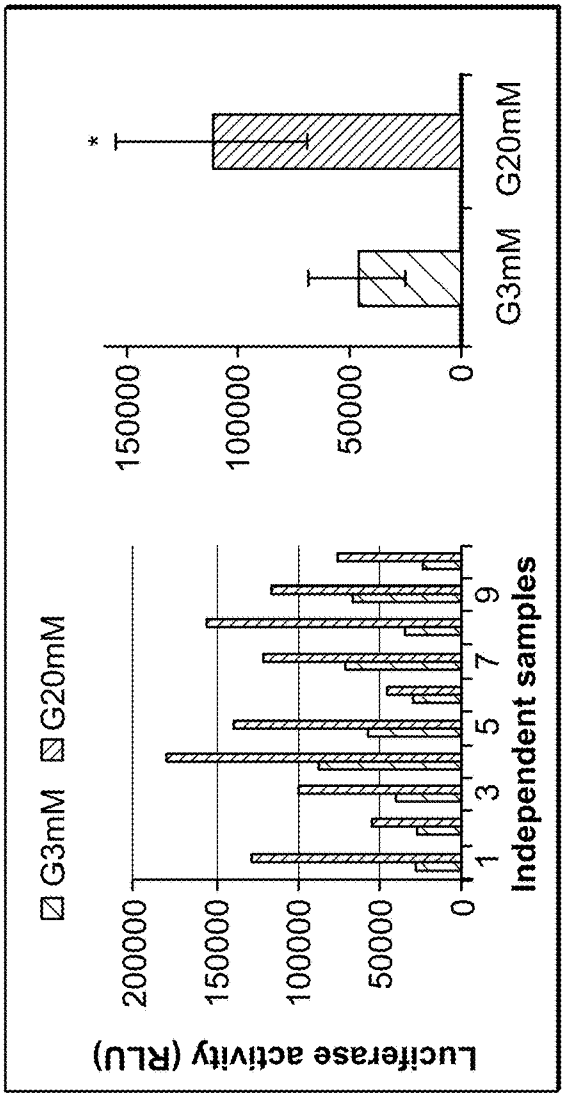
Figure 3E:
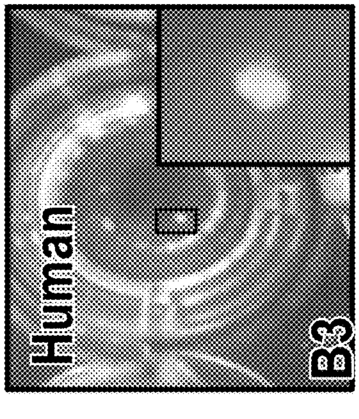
Figure 3F:
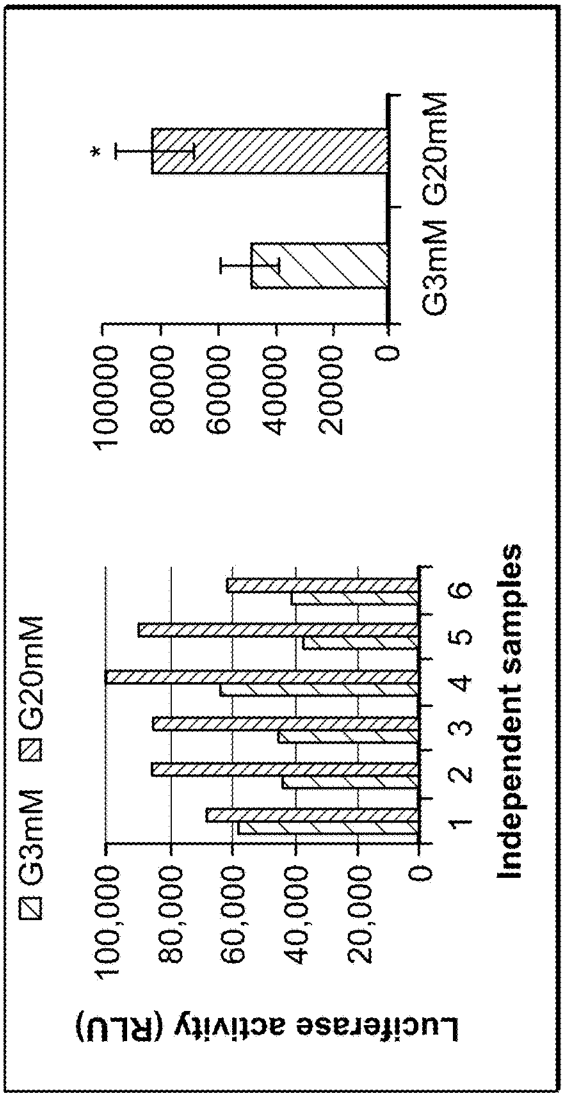

To explore pancreatic organogenesis, hiPSC-PP ($1\times10^6$ cells) cells were co-cultured with HUVECs ($7\times10^5$ cells) and hADSCs ($1-2\times10^5$ cells) (FIG. 2E) in Matrigel matrix. This co-culture yielded macroscopically visible 3D cell clusters 48 hours after seeding (FIG. 2F). Furthermore, insulin expression, based on the expression of a GFP reporter, was detected 5 days after seeding and increased with time in culture in the human islet-like organoids. In addition, HUVECs-based endothelial cells are integrated inside the organoids as shown by fluorescence-labeled (mCherry) HUVECs (FIG. 2G).

The limitations of MATRIGEL® matrix for organoid production include high cost, difficult organoid recovery, scaling restrictions, and batch to batch variabilities.

Figure 4A:
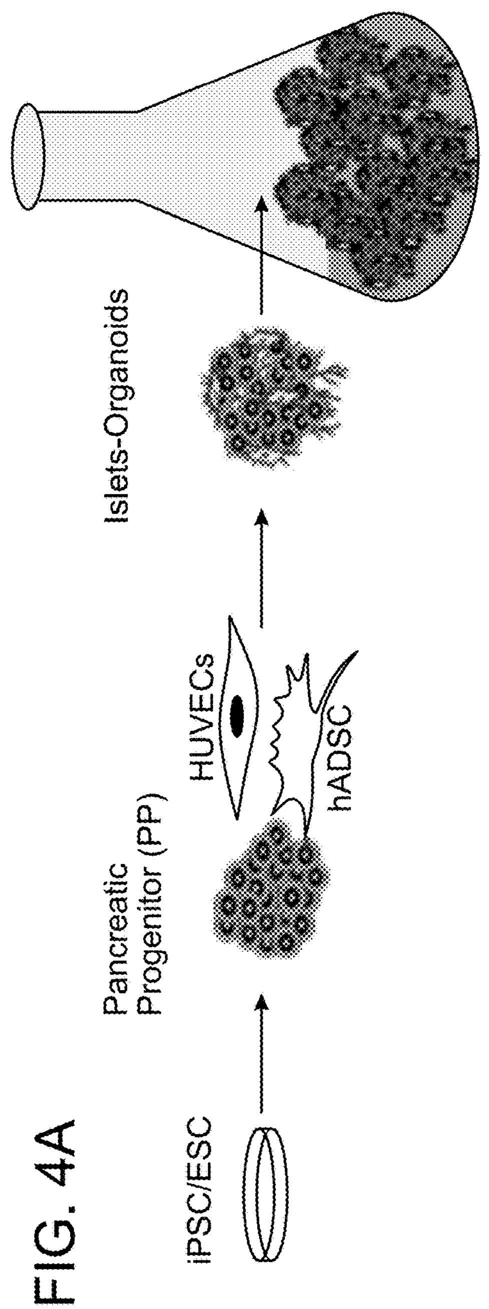
Figure 4B:
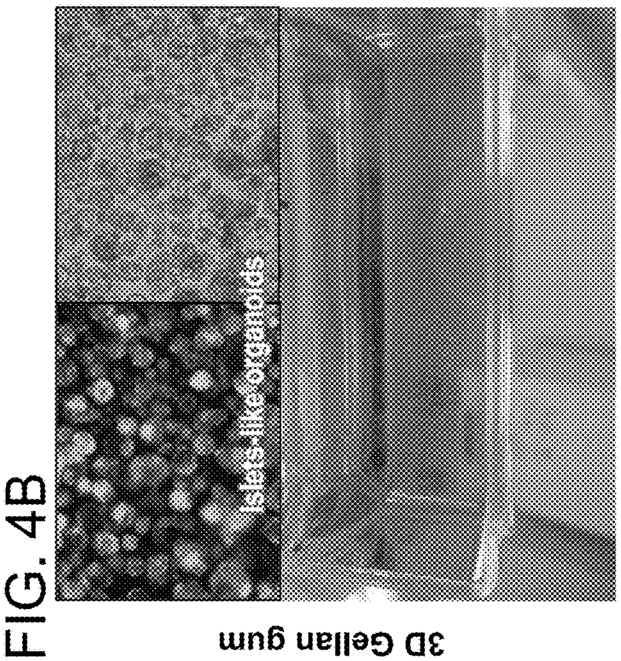
Figure 4B:
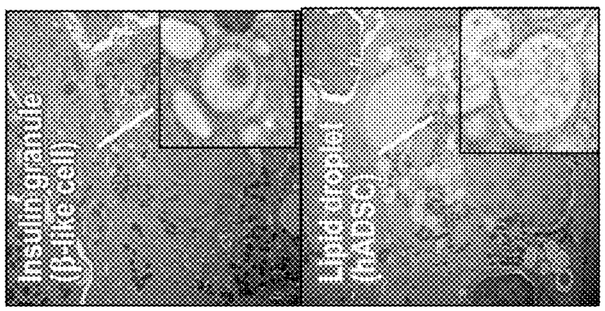
Figure 4C:
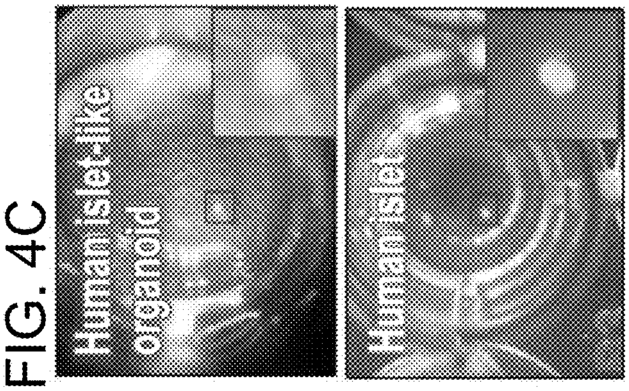
Figure 4D:
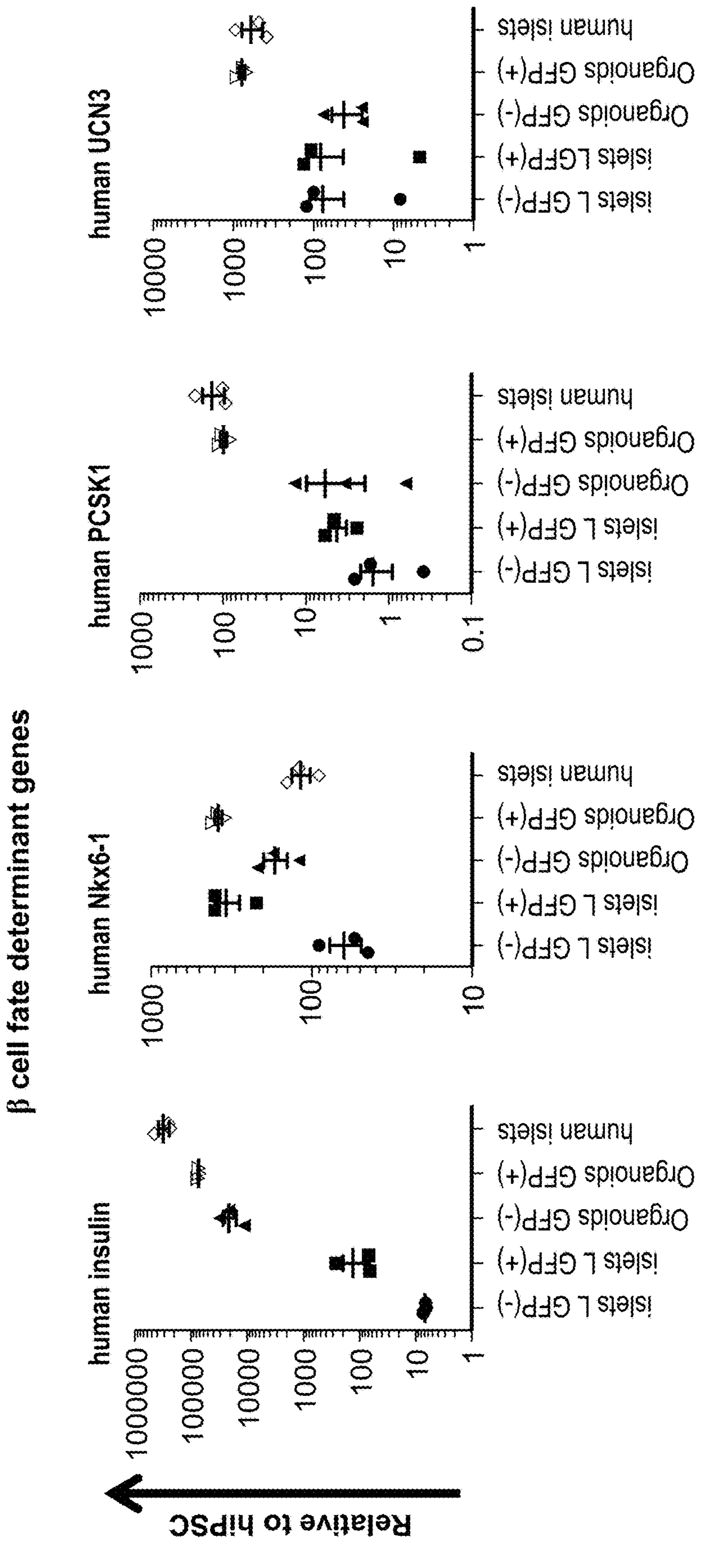
Figure 4E:
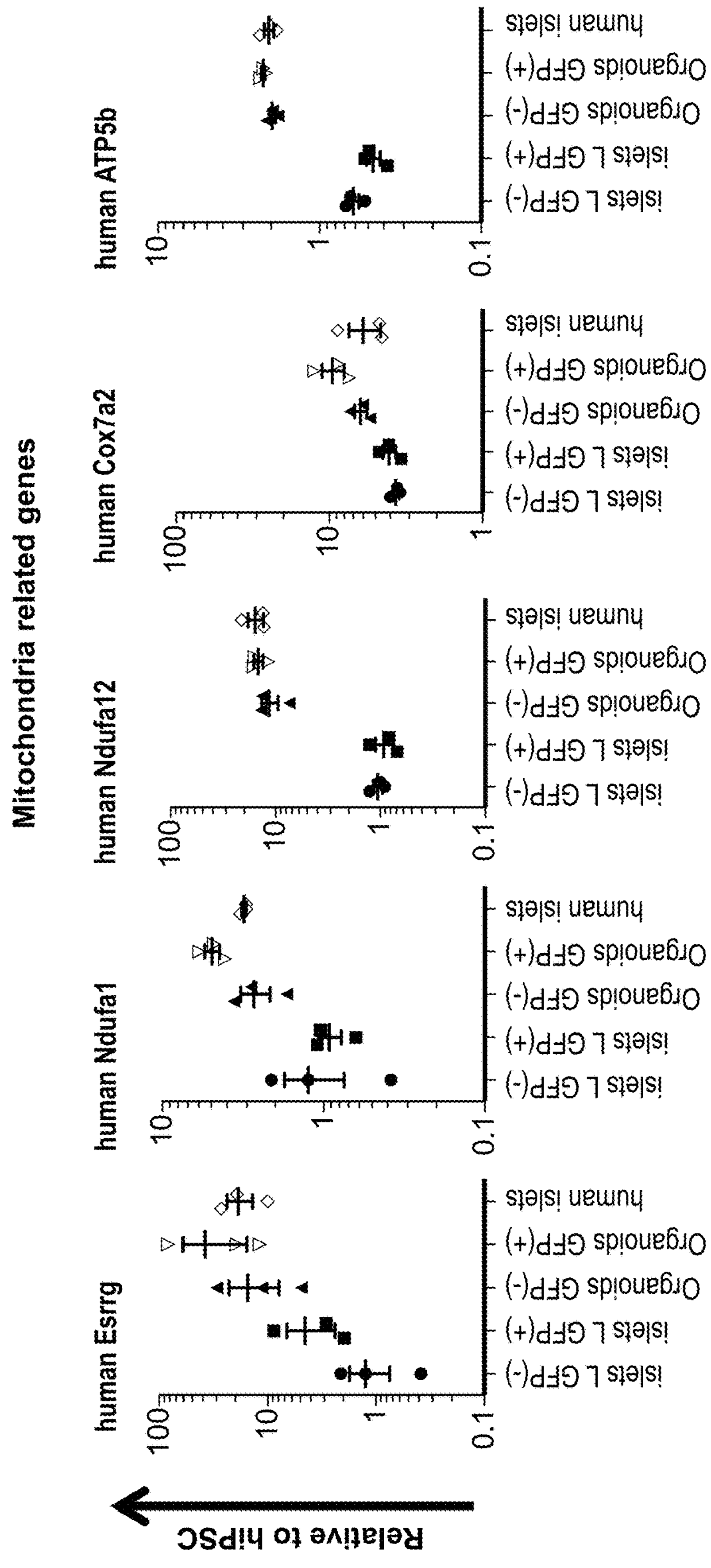
Figure 4F:
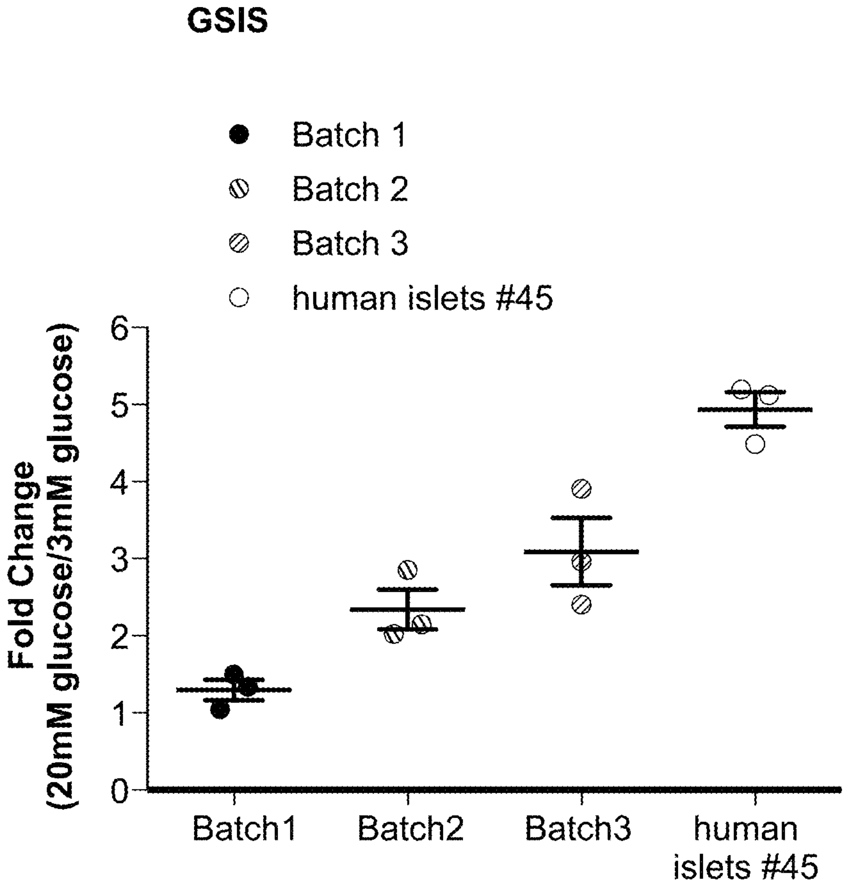
Figure 4I:
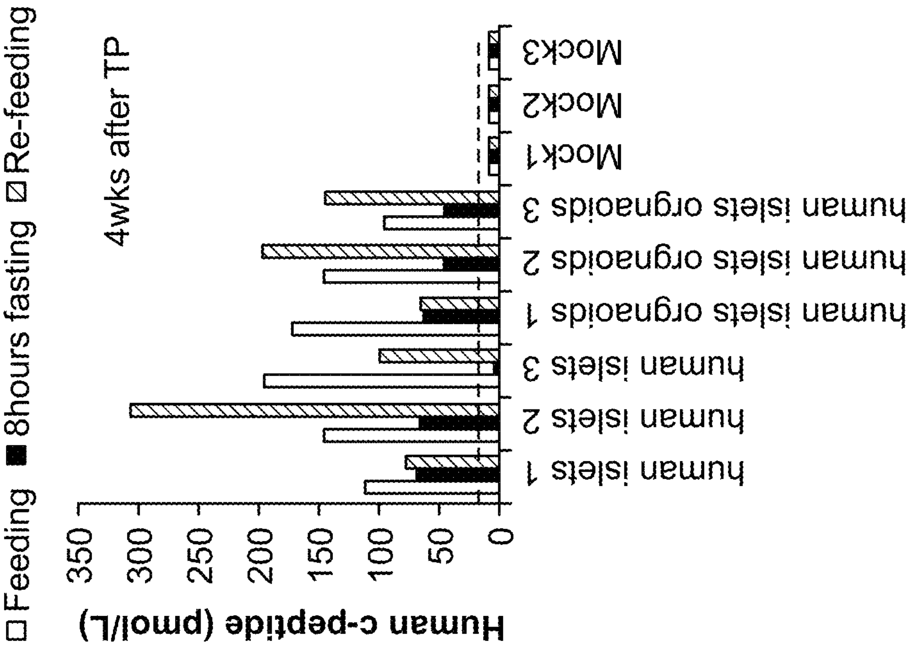
Figure 4H:
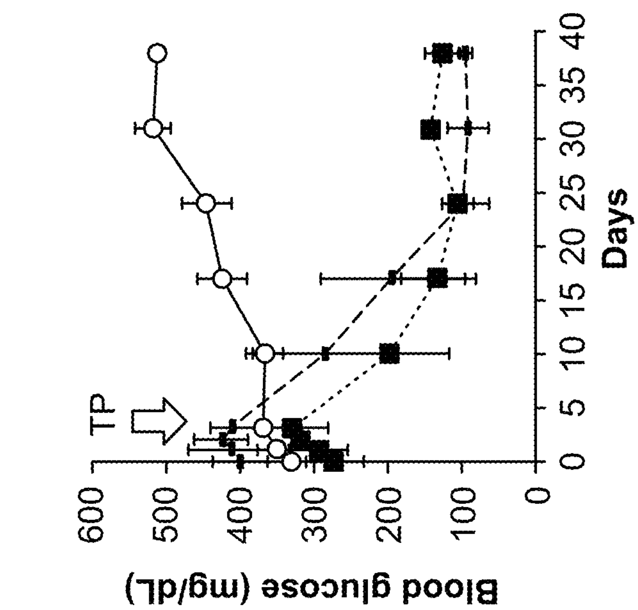

Described herein are methods to generate morphologically identical human islet-like organoids using gellan gum based 3D cultures (FIGS. 4A-4G). FIG. 4A shows a scheme for generation of functional, vascularized human pancreatic islets in as dish. Human induced pluripotent stem cells derived—pancreatic progenitors (hiPSC-PPs) ($1\times10^8$ cells) were cultivated with a stromal cell population such as human umbilical vein endothelial cells (HUVECs) ($2-7\times10^6$ cells) and human adipose-derived stem cells (hADSCs) ($2-7\times10^6$) in 50 ml of gellan gum based 3D culture media (FIG. 4B). FIG. 4B shows that hiPSC-PP rapidly formed isle-like sphere formation with HUVECs and hADSCs within 5 days after seeding into the gellan gum based 3D culture media. Human islets like mini-organs expressed human insulin GFP reporter in 5 days after seeding with gradually enhancing GFP intensity. Co-culturing hiPSC-PP, hADSCs, and HUVECs according to this method, generated human islet-like organoids with high reproducibility that were morphologically similar to human islets (FIG. 4C). In addition, the generated human islet-like organoids contained insulin granules in β-like cells (FIG. 4B). Genes expression analyses revealed increased expression of β cell fate determinant genes (Insulin, Nkx6-1, PCSK1 and UCN3) and mitochondrial related metabolic genes (Esrrg, Ndufa1, Ndufa 12, Cox7a2. Atp5b) in the insulin expressing cell population (GFP enriched (GFP+)) in islet-like organoids compared to those prepared without hADSC and HUVEC co-culture (FIGS. 4D & 4E). Glucose-stimulated human c-peptide secretion assay revealed that islet-like organoids generated by this method are able to secrete human c-peptide in response to high (20 mM) glucose (FIG. 4F).

An in vitro functional vascularization test was then performed. FIG. 4G shows in vitro functional vascularization tests performed. Islet-like mini organs generated in gellan gum were transferred to MATRIGEL® matrix and cultured in endothelial growth media (EGM). Green fluorescence indicates expression of insulin genes. Within 24 hours to 48 hours after stimulation by EGM, the outgrowth of HUVEC cells was observed, indicating that human islet-like organoids generated by the method described herein possessed the ability to form vascular structures.

Establishment of Single Islet Insulin Secretion Assay Using Proinsulin-NanoLuc Gaussia Luciferase Assay System It was previously published that a reporter construct, in which the Gaussia luciferase is placed within the c-peptide portion of proinsulin accurately measures insulin secretion without affecting β-cell function (Burns et al., 2015, Cell metabolism 21, 126-137). Using a lentiviral system, INS-1 cells stably expressing this Gaussia luciferase were generated (FIGS. 3A-3F). Luciferase secretion from INS-1 cells stably expressing Proinsulin-NanoLuc increased with high-glucose (20 mM), high glucose with Exendin-4 (G20 mM+Ex4), and the depolarizing agent, potassium chloride (FIGS. 3A-3B), confirming the utility of this reporter system. Next, the usefulness of this reporter to measure insulin secretion in mouse or human islets transiently infected with the Proinsulin-NanoLuc reporter was evaluated. Luciferase secretion in response to 20 mM high glucose was detected in both transiently infected mouse and human islets were detected (FIGS. 3C-3F). Importantly, the assay sensitivity was sufficient that insulin secretion could be qualified at the level of single islets. These results indicate that the Proinsulin-NanoLuc luciferase reporter based insulin secretion assay is applicable to not only the rat beta cell line INS-1 cells, but also to primary mouse and human primary β cells.

Figure 5A:
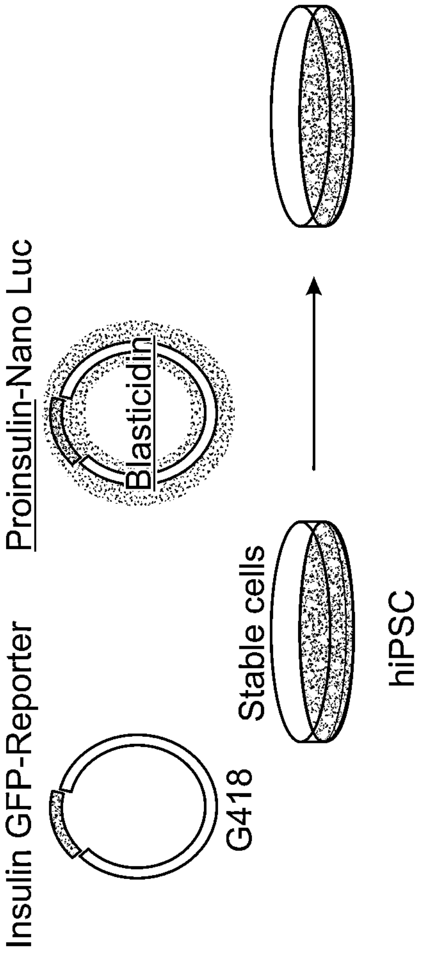
FIGS. 5A-5E are diagrams and plots showing the generation of functional islet-like organoids in 3D gellan gum cultures.
Figure 5B:
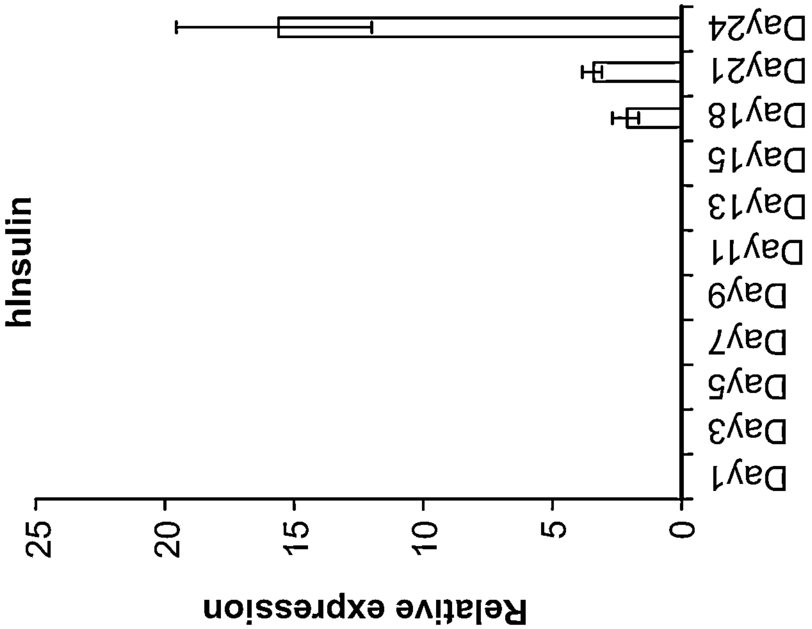

Establishment of hiPSC and hESC Cells Incorporating Dual Lineage and Functional Reporters Human iPSCs and hESCs stably expressing reporters for βcell lineage (human insulin reporter) and β cell function (proinsulin-NanoLuc reporter) were generated, hiPSC$^{hINS-GFP/Sec-Luc}$ and hESC$^{hINS-GFP/Sec-Luc}$, respectively (FIG. 5A). First, a neomycin resistant construct of human insulin GFP reporter was generated by inserting human insulin promoter sequence of pGreenZeo lenti-reporter (SR10028PA-1, System Bioscience) into pGreenFire Lenti-Reporter plasmid (TR019PA-1, System Bioscience) (named as hINS-GFP-EF1a-Neo). hINS-GFP-EF1a-Neo lenti virus was infected into hiPSC and hESC by spin fection (800 g, 1 hour, 37 degree) followed by a media changed to fresh STEMCELL™ TeSR™ media. Three (3) days after the first infection, the cells were treated with 100 µg/ml G418 in STEMCELL™ TeSR™ media for 7 days. Selected hiPSC and hESC cells stably expressing hINS-GFP-EF1a-Neo were subsequently infected with the Proinsulin-NanoLuc (Addgene, Plasmid #62057) lenti-virus by spin fection (800 g, 1 hour, 37 degree) followed by a media change to fresh STEMCELL™ TeSR™ media. Three (3) days after the second infection, the cells were treated with 5 µg/ml blasticysin and 100 m/ml G418 in STEMCELL™ TeSR™ media for 7 days. Subsequently, cells were maintained in STEMCELL™ TeSR™ media (FIG. 5A). The generated stable cell lines incorporating the dual reporters maintained self-renewal and pluripotency capabilities, as well as the capacity to differentiate into insulin producing β like cells (FIG. 5B).

Pooled Human Islet-Like Organoid Cultures Display Consistent Insulin Secretion Despite Variable Functionality Seen in Individual Organoids.

Figure 5C:
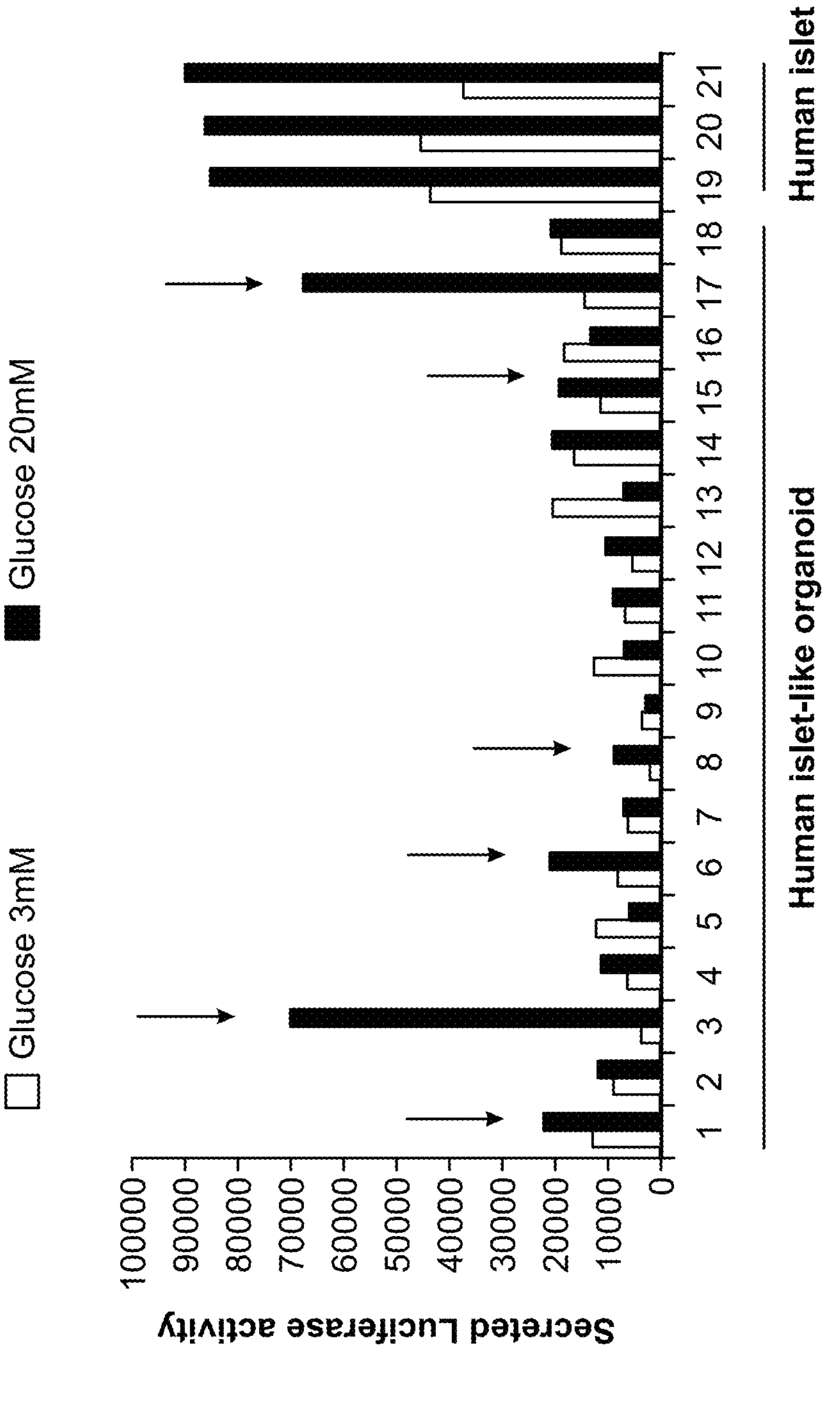
Figure 5D:
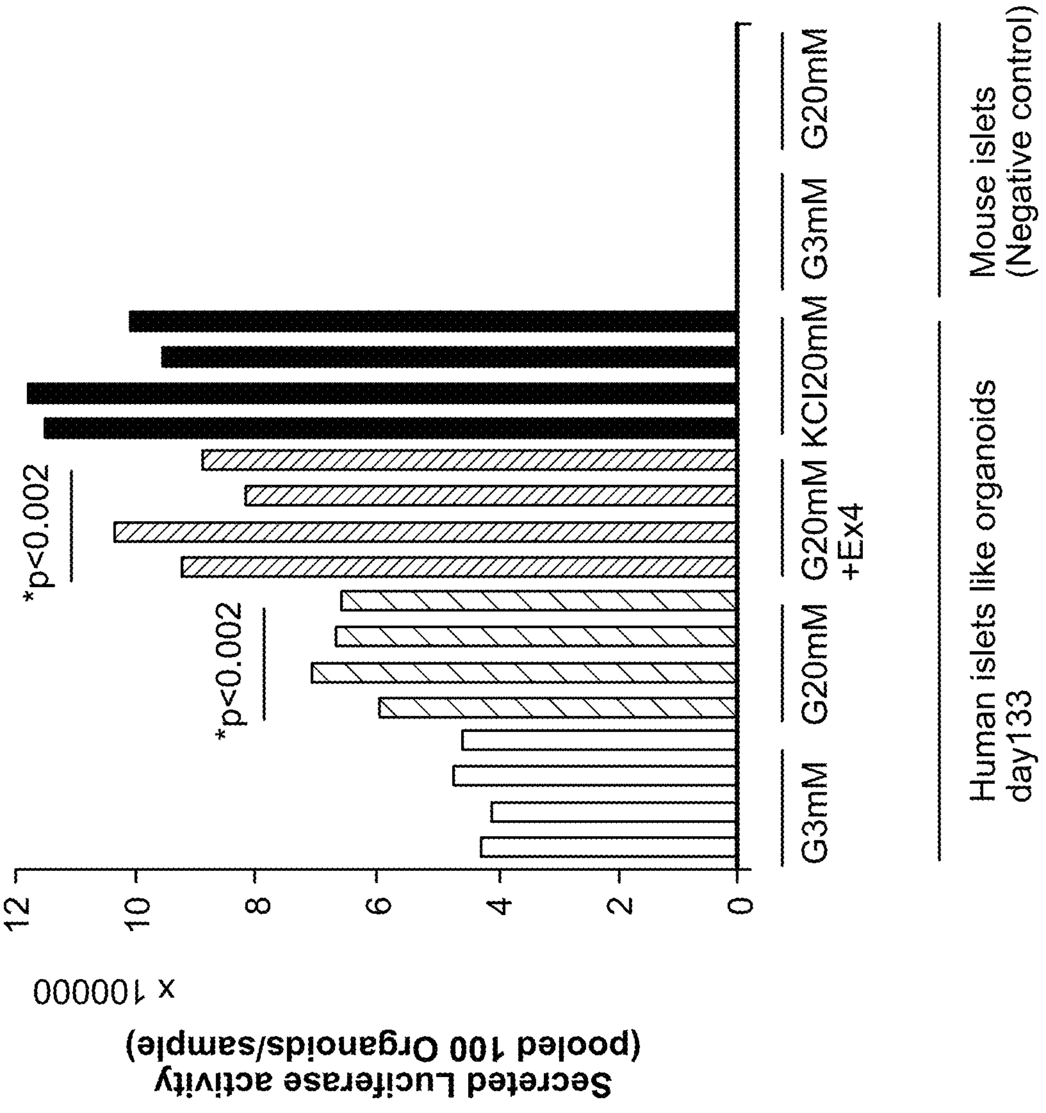
Figure 5E:
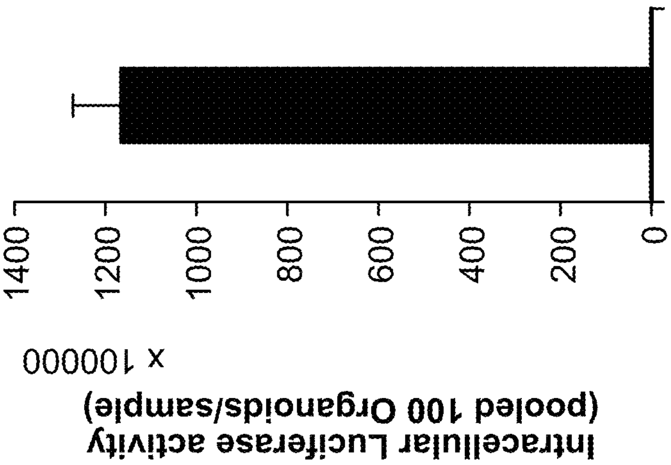

Recent studies have reported the generation of insulin producing β-like cells from hESC and hiPSC capable of secreting insulin in response to glucose (Pagliuca et al. 2014, Cell 159, 428-439; Rezania et al., 2014, Nature Biotechnology November; 32(11):1121-33; Russ et al., 2015, EMBO Journal 34, 1759-1772). However, fully functional human islet-like clusters able to appropriately secrete insulin in response to nutritional signals including glucose, amino acids, fatty acids and incretins such as GLP-1 have yet to be demonstrated. To date efforts have focused on the independent generation of insulin producing β-like cells, glucagon producing α-like cells, and somatostatin producing δ-like cells from hPSC. However, these approaches lack the supporting cells important for regulation, such as mesenchymal cells, adipose cells, and vasculature cells. Since the 3D structure of islets naturally enhances their function, these missing cellular components may compromise the functionality of islet-like cells clusters. In addition, organogenesis of pancreatic islets involves clonal expansion of β-cells, suggesting that these cells may have multiple functions in islet-like organoids. To test this idea, single organoid proinsulin secretion assays were performed. Human islet-like organoids generated by methods described herein are morphologically identical with human islet (FIG. 4C). However, significant variability was seen in the glucose-stimulated insulin secretion (GSIS) capabilities of individual human islet-like organoids compared to human islets, as measured by proinsulin luciferase secretion assay (FIG. 5C) Consistent GSIS functionality was demonstrated in pooled organoids (10 to 100 organoids for assay) (FIG. 5D). Furthermore, pooled human islet like organoids demonstrate enhanced GSIS when co-stimulation with GLP-1, as well as robust KCl-stimulated insulin secretion (FIG. 5D).

In vitro cultured iPSC-derived human pancreatic islet-like organoids generated herein retained their ability to respond to glucose, GLP1 and KCl after extended time (133 days) in culture (FIG. 5D).

Example 2: Generation and Characterization of Human Organoids

Figure 6A:
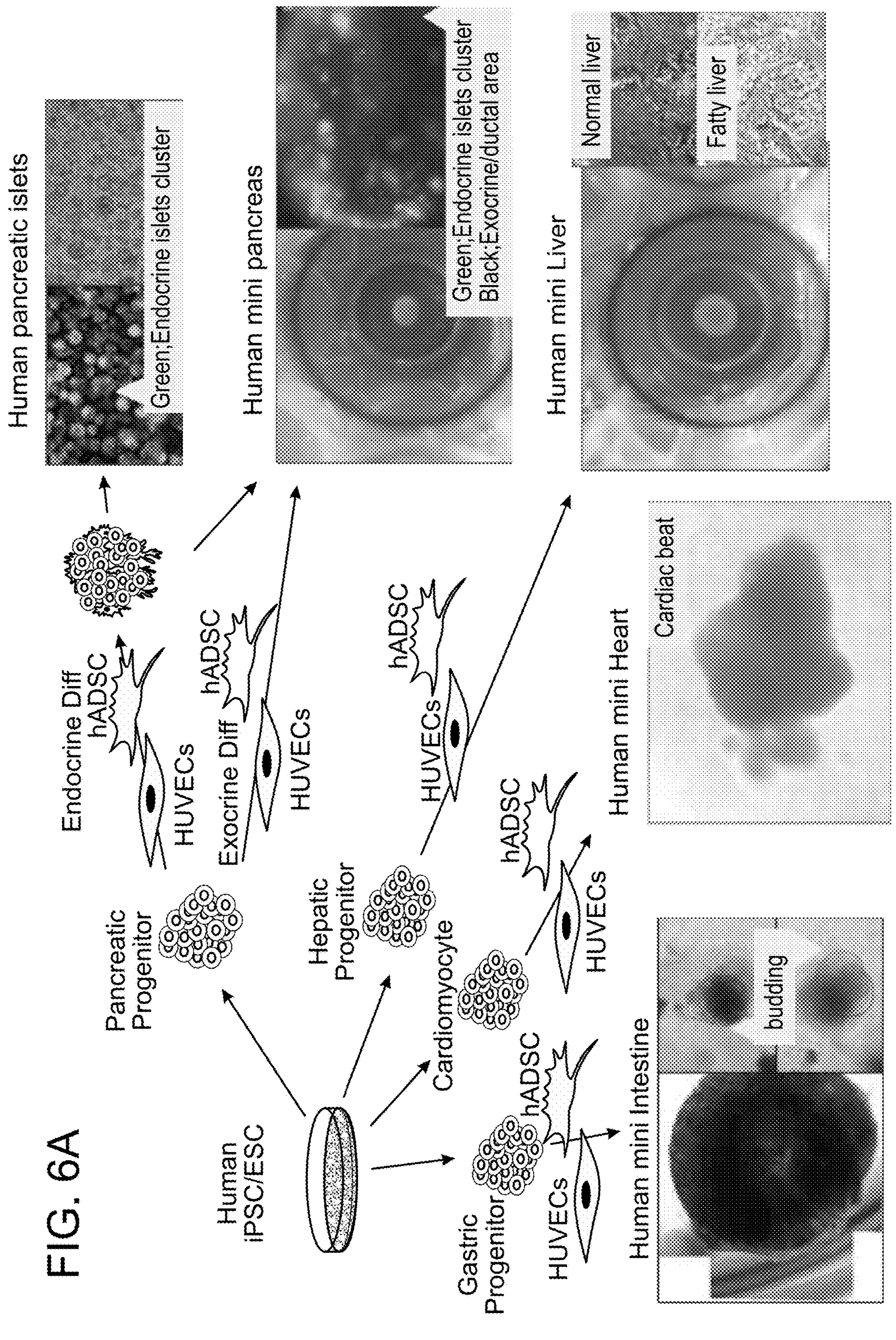
FIGS. 6A-6H are schematics and images showing generation of functional human mini-organs in a dish.

Functional human mini organs, including human islets, pancreas, liver, heart, and intestine, can be generated using the methods described herein (FIG. 6A). FIG. 9 shows a structure of a human pancreas and human pancreatic islets within the pancreas. Using the methods herein, human pancreatic islets mini organs or organoids were generated in about 30 days. The pancreatic islets generated contained human induced pluripotent stem cell (hiPSC)-derived beta cells, alpha cells, delta cells, duct cells, as well as endothelial cells and hADSCs. The pancreatic islet organoids generated express key beta cells transcription factors such as Insulin, Nkx6-1, PCSK1, and UCN3, as well as key mitochondrial metabolic genes including Esrrg, Ndufa 1, Ndufa 12, Cox7a2 and Atp5b (FIGS. 4D-4E). The pancreatic islet organoids exhibited at least partial GSIS, KCl-stimulated insulin secretion, GLP-1 stimulated insulin secretion, vascularization, somatostatin secretion, and glucagon secretion (FIGS. 4G, 5D).

Figure 6B:
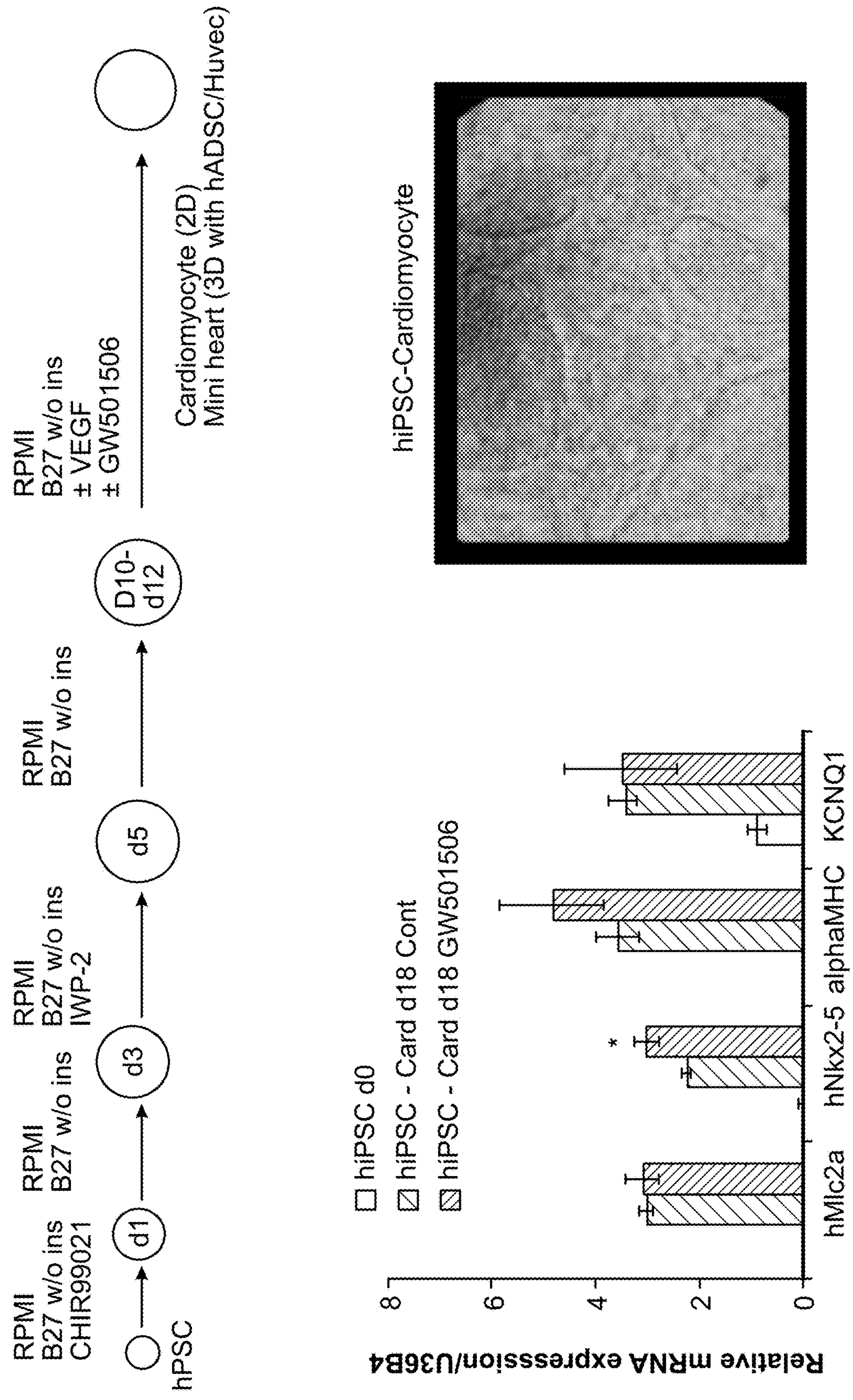
Figure 6C:
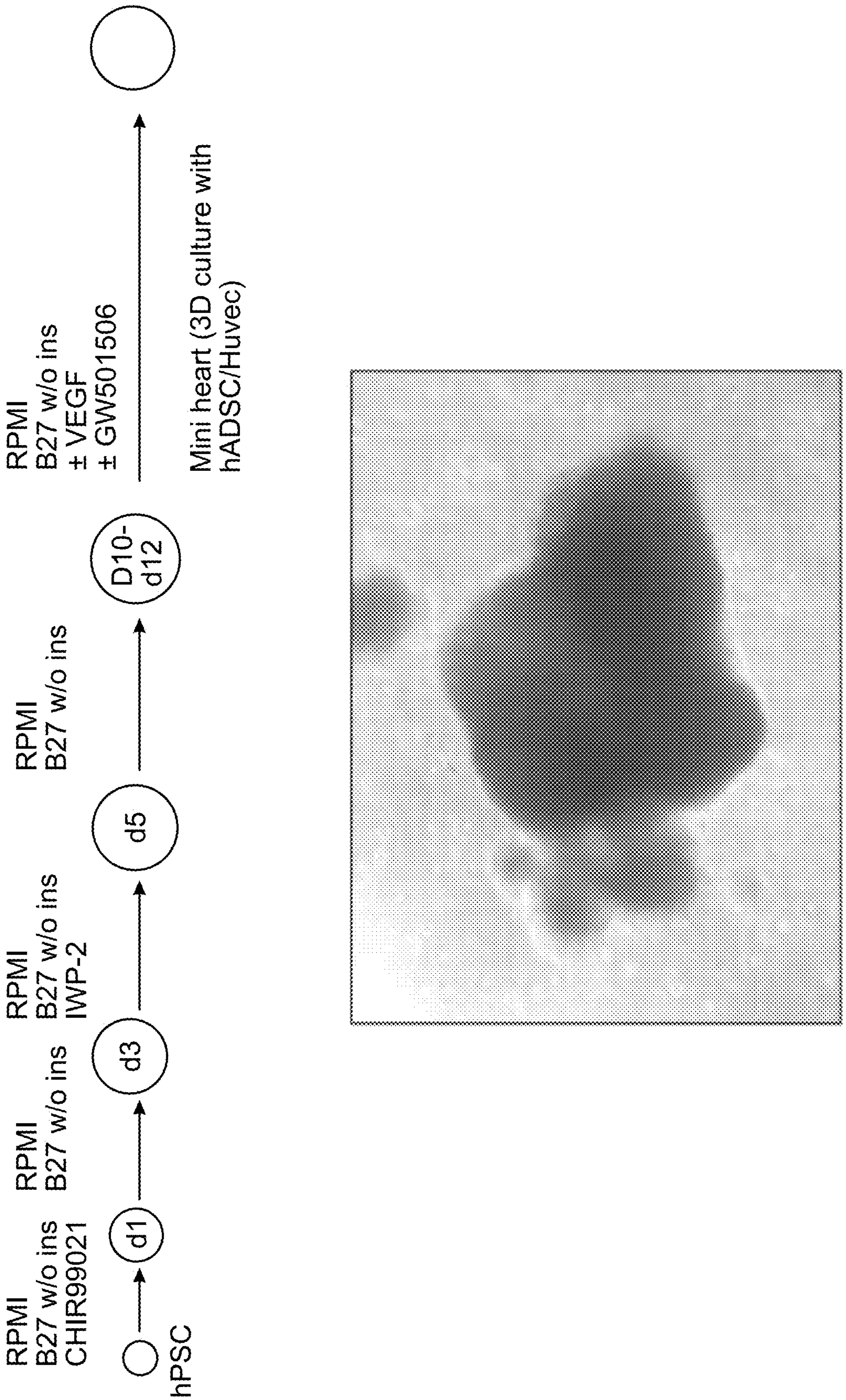
Figure 6D:
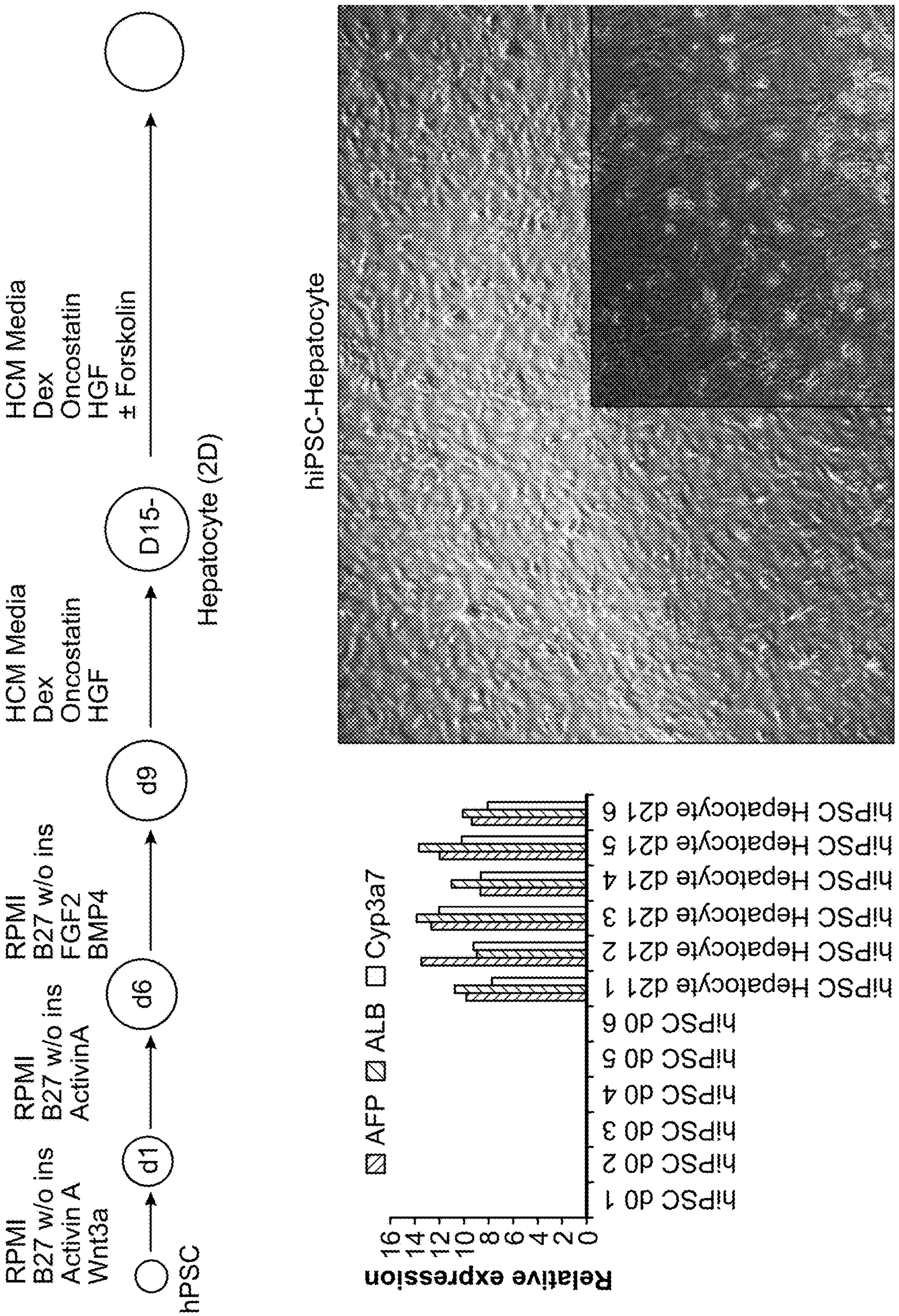
Figure 6E:
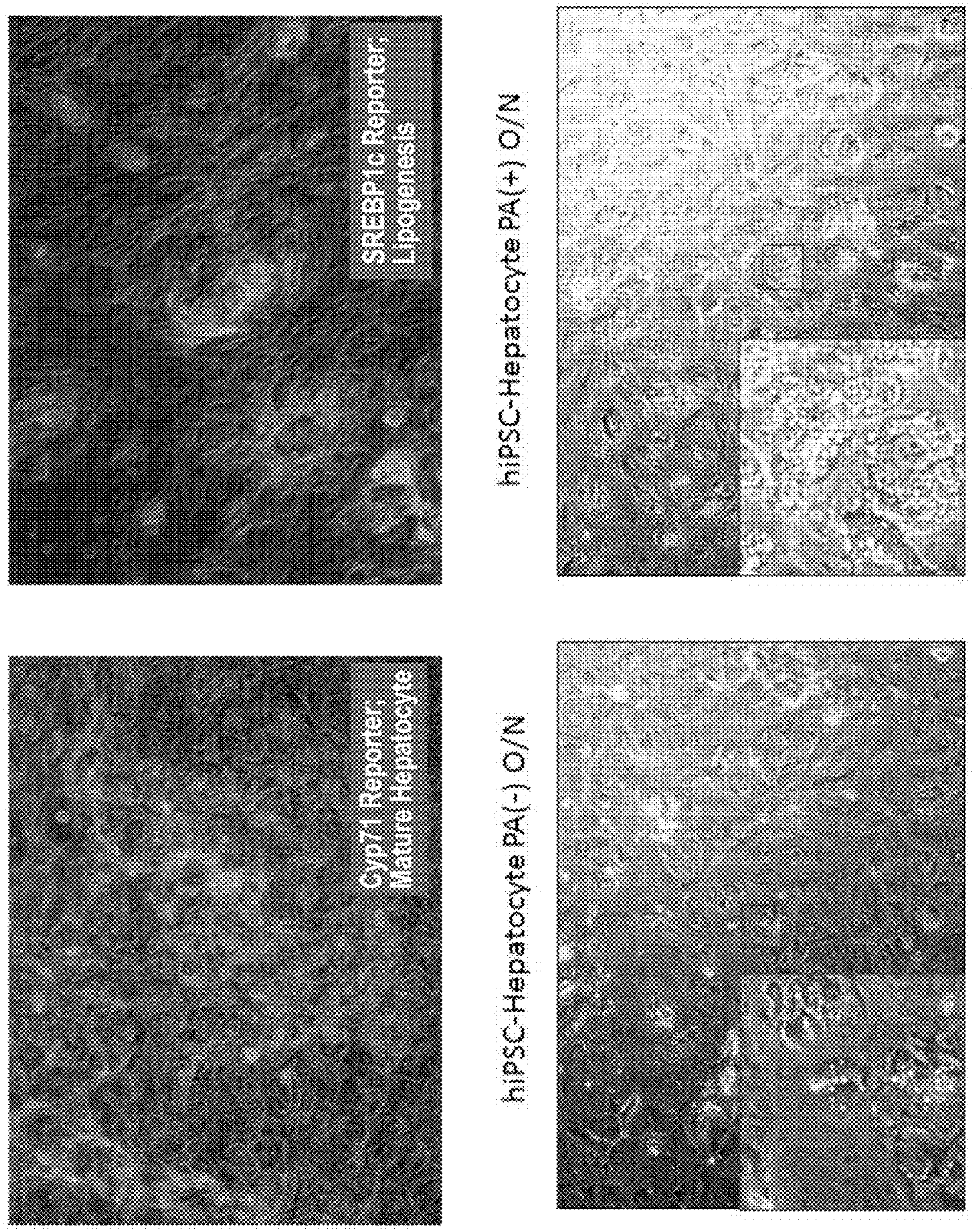
Figure 6F:
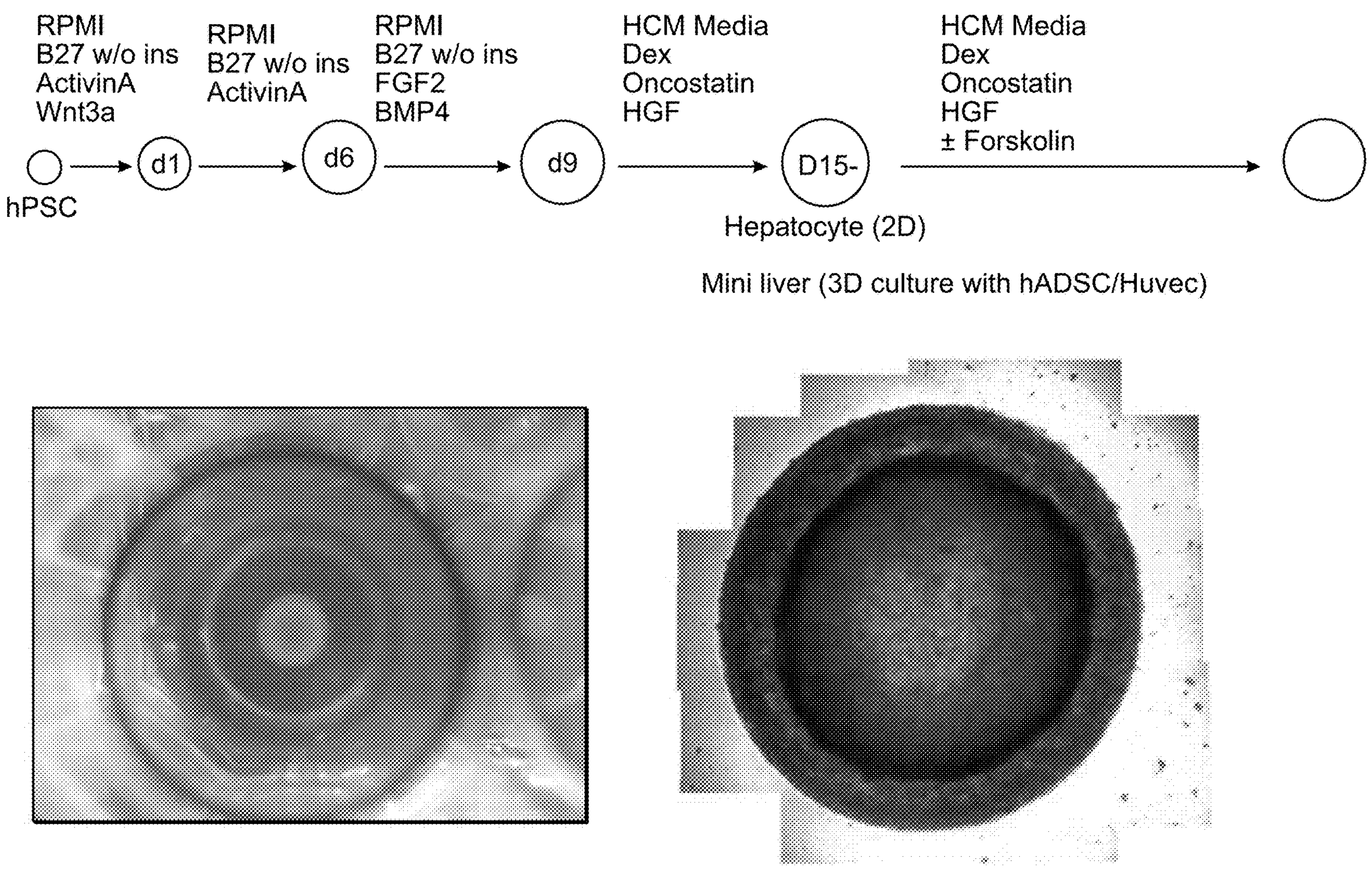
Figure 6G:
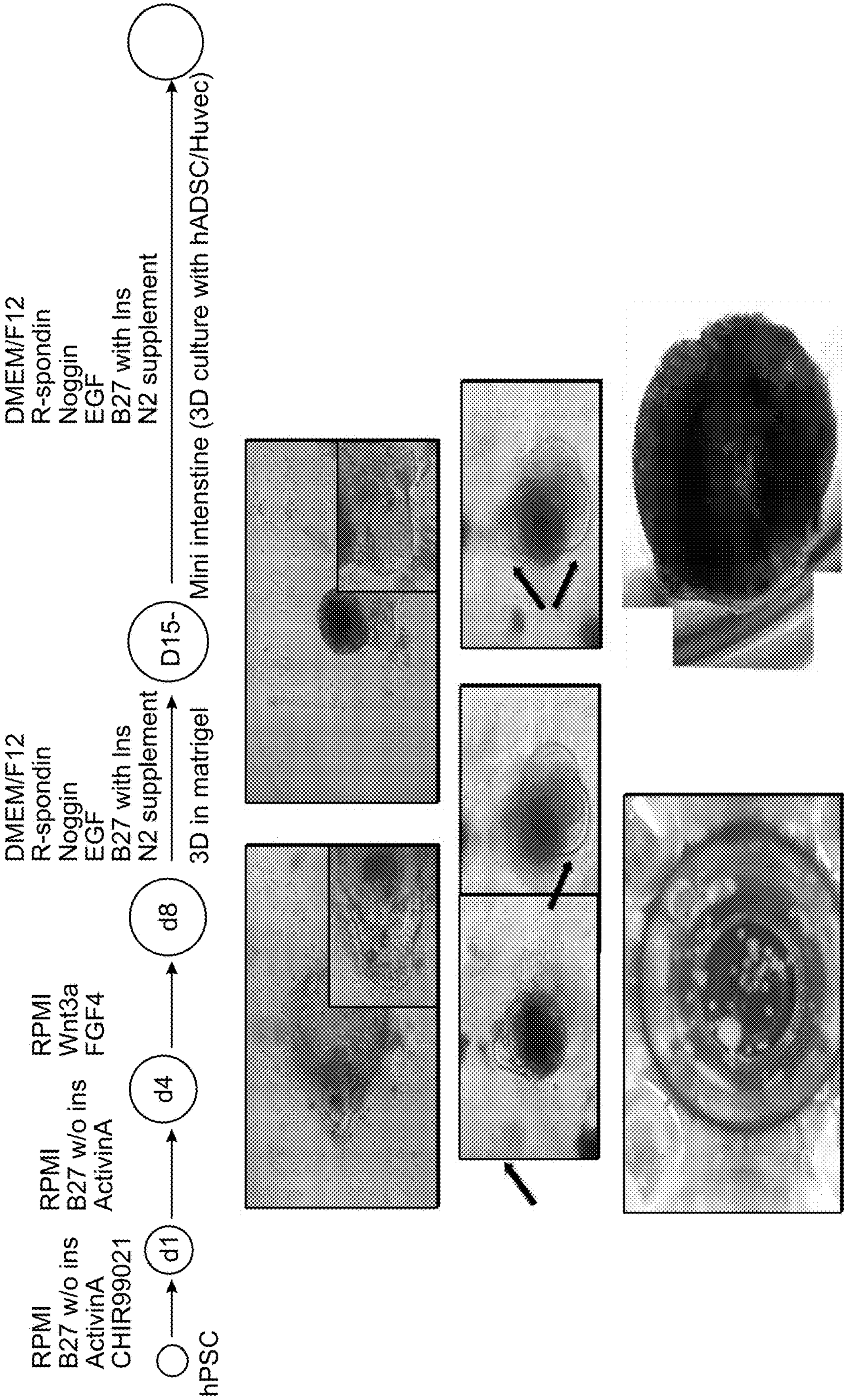
Figure 6H:
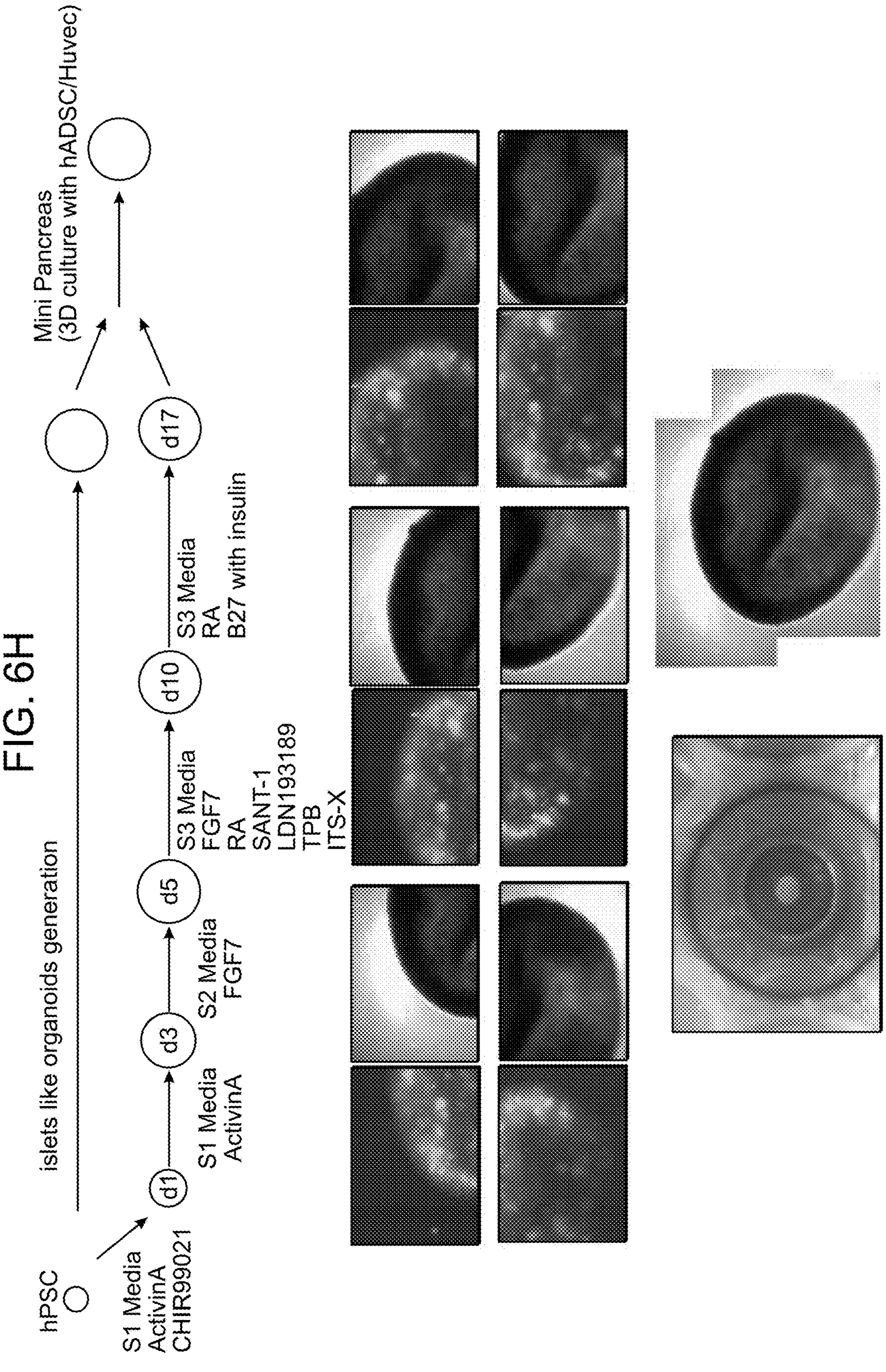

A human mini pancreas or human pancreatic organoid was generated in about 30 days (FIG. 6H). The human pancreatic organoid contained hiPSC-derived islets clustered within the interior of the organoid and a hiPSC-derived exocrine component surrounding the islets (FIG. 6H). The pancreatic organoid also contained endothelial cells and hADSC. Function of the human pancreatic organoid was demonstrated using an amylase secretion test, among other tests.

A human mini liver was generated in about 15 days (FIGS. 6D-6F). The human mini liver contained hiPSC derived hepatocytes, endothelial cells, and hADSCs. Analysis of functional characteristics of the human mini liver revealed that the mini liver expressed AFP, ALB, and Cyp3a7 (FIG. 6D), as well as the mature hepatocyte marker Cyp7a1 and lipogenesis marker SREBP1c (FIG. 6E). The human mini liver also exhibited insulin signaling, insulin resistance by palmitic acids, and lipid accumulation. The human mini liver is further tested for gluconeogenesis and metabolic function for drug metabolism.

A human mini heart was generated in about 15 days (FIGS. 6B-6C). The human mini heart contained hiPSC derived cardiomyocytes, endothelial cells, and hADSCs. The human mini heart expressed key cardiomyocyte genes such as hMlc2a, hNkx2-5, alpha MHC and KCNQ1 (FIG. 6B), and was seen to beat in cultures.

A human mini intestine was generated in about 30 days (FIG. 6G). The human mini intestine contained hiPSC derived intestinal cells, endothelial cells, and hADSCs. The human mini intestine expressed small intestine markers CDX2, Muc2, and Lgr5, and exhibited budding of intestinal organoids in response to R-Spondin.

Example 3: Transplantation of Functional Pancreatic Islet Organoids Rescued Type 1 Diabetic Mice Expression of specific functional islets marker such as MAFA, UCN3 and mitochondrial oxidative genes such as ERRγ (Esrrg), Ndufa 1, Ndufa 12, Cox7a2 and Atp5b in hiPSC-derived human islet-like organoids was observed. Notably, these islet-like organoids recapture both human islets development as well as the pathogenesis of diabetes in a dish. Transplantation of these functional islet-like organoids rescue type 1 diabetic mice with long survival, rapid vascularization, and reduced immune rejection.

Example 4: Drug Screening and Disease Modeling in Human Islet-Like Organoids

Figure 7:
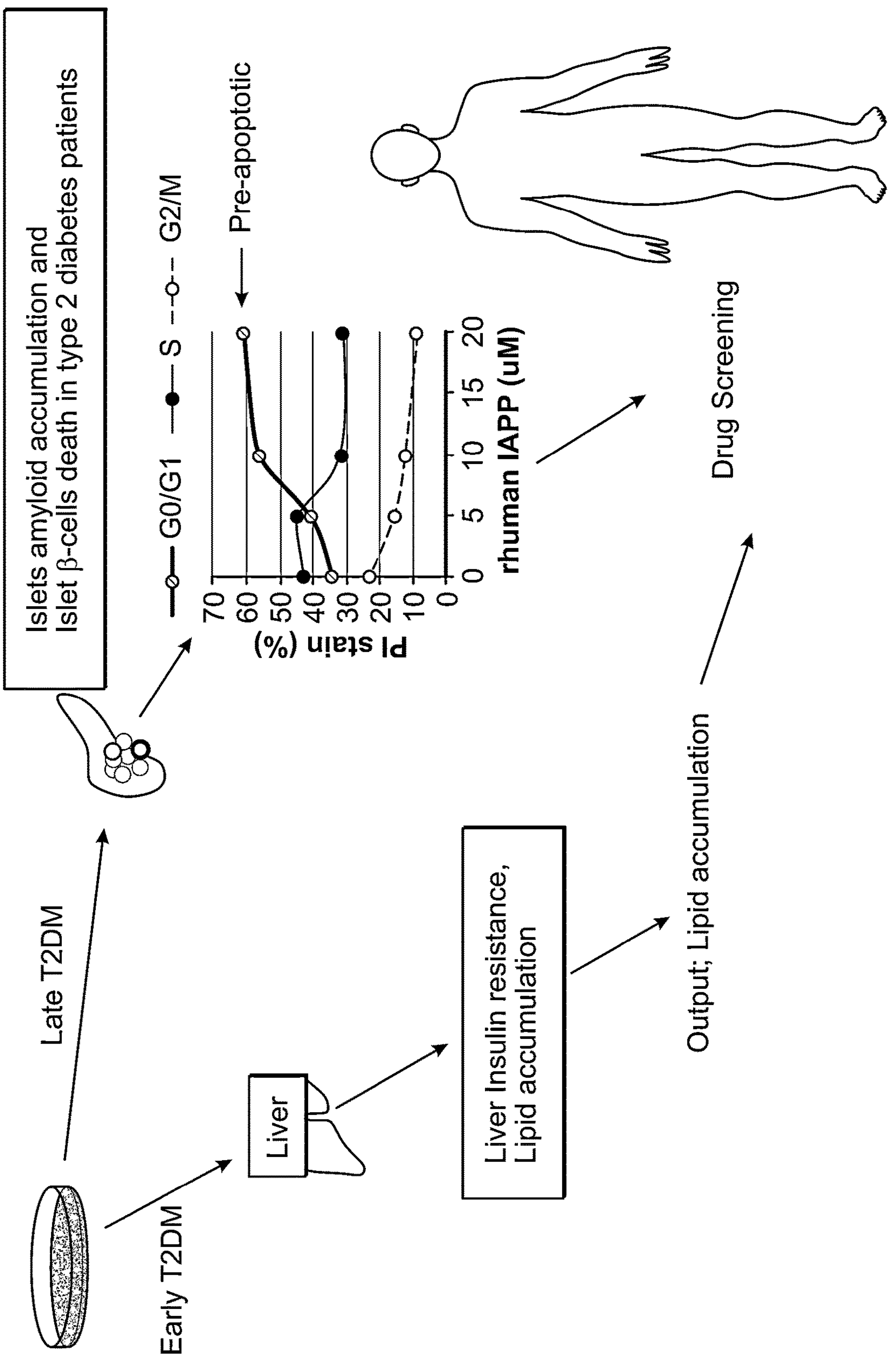
FIG. 7 is a schematic showing modeling of human Type 2 diabetes in a dish. Generation of functional human organs such as a liver, pancreas, and islets provides new therapeutic strategies in drug-screening and modeling of human type 2 diabetes. For example, hepatic organoids with accumulated lipids can be used to study early insulin resistance phenotypes, while human islet-like organoids can be used to study β cell death seen in late stage type 2 diabetes. Inserted graph shows the response of islet-like organoids to increasing concentrations of human amyloid polypeptide (hIAPP). The increase in propidium iodide (PI) staining in G0/G1 stage cells indicates that hIAPP induces apoptosis in islet-like organoids.

Generation of functional human organs according to methods described herein provides new strategies for drug-screening and disease modeling. Specifically, functional organoids can be used as models of type 2 diabetes for drug screening (FIG. 7). Human islet-like organoids responded to amyloid polypeptide (hIAPP) toxicity, an inducer of β cell loss in type 2 diabetic patients and islet dysfunction after transplantation in hyperglycemic patients, hIAPP dose-dependently induced G0/G1 arrest in 24 hours in human islet-like organoids (FIG. 7).

Figure 8A:
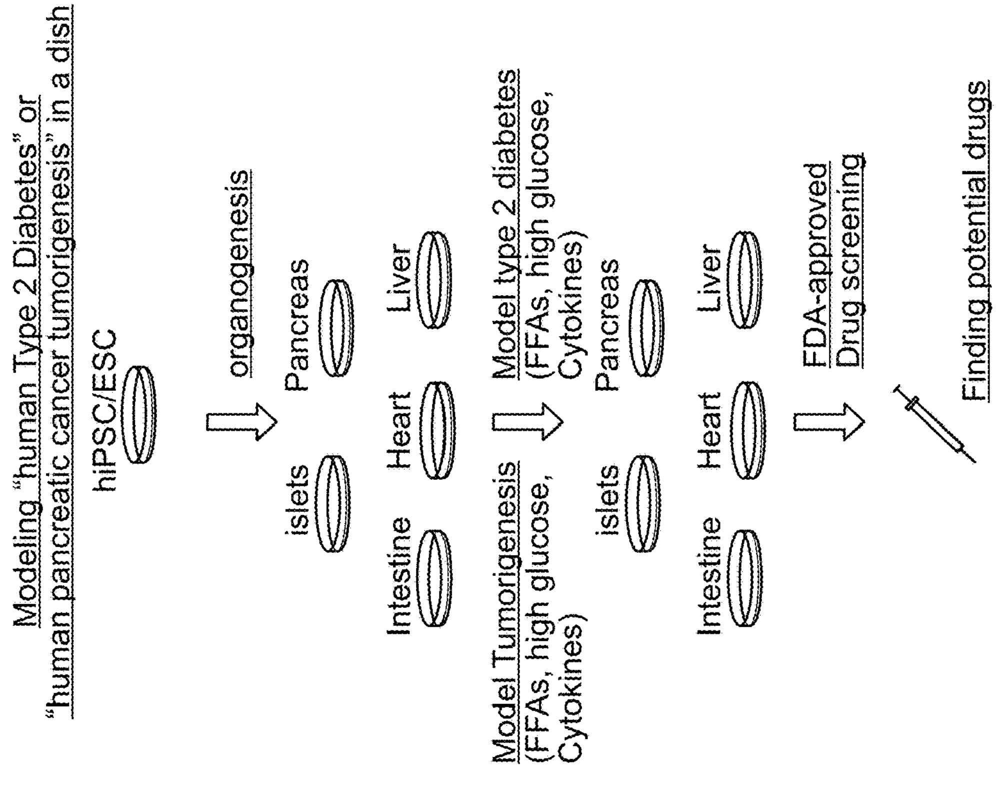
FIGS. 8A and 8B are schematics showing platforms for drug screening and the subsequent evaluation of potential candidates for human type 2 diabetes and pancreatic cancer.

FIG. 8A provides a schematic showing experimental approaches to model type 2 diabetes and potentially screen for drugs using pancreatic islet and/or pancreatic organoids generated by the methods herein. In an exemplary assay, 3D mini organs are exposed to stressors that induce type 2 diabetes, such as high levels of free fatty acids (FFAs) and/or, glucose and selected cytokines. The stressed 3D mini organs are then treated with various drugs. In some embodiments, the drug is approved by the Food and Drug Administration (FDA).

As output, the following are assayed in human pancreatic islet organoids: insulin secretion, beta cell apoptosis (PI stain), lactate dehydrogenase A (LDHA) expression via a luciferase reporter, and changes in expression of marker genes including NDUFA4 (Mitochondrial oxidative phosphorylation), ESRRG (Mitochondrial function), KCNK3 (Katp channel activity) and MAFA (beta cell fate marker). For the human pancreas organoid, amylase secretion and apoptosis of exocrine cells (PI stain) are assayed. For the liver organoid, lipid accumulation is assayed using oil red O or histology. In the case of heart organoid, heart beat and heart size (hypertrophy) are measured. The intestine organoid is analyzed by measuring lipid accumulation using oil red O or histology.

FIG. 8A also shows modeling of human pancreatic cancer tumorigenesis and metastasis in a dish and the potential to screen for drugs that target those diseases. In an exemplary assay, a 3D mini human pancreas is co-cultured with pancreatic cancer cells, stellate cells, and immune cells to create human pancreatic cancer microenvironment in a dish. Various drugs (e.g., FDA-approved drugs) are then screened to find compounds which effectively suppress pancreatic cancer growth or metastasis in a mini human pancreas microenvironment. As output, the following are measured for the pancreas organoid: apoptosis of exocrine cells (PI stain), collagen synthesis (Trichrome stain) and stellate cells activation (GFAP-reporter). Potential candidate drugs identified in these assays are tested in pancreatic cancer tumorigenesis and metastasis mouse models. Genes expression and morphology as well as the degree of cell death, cell growth, and metastasis are investigated.

Figure 8B:
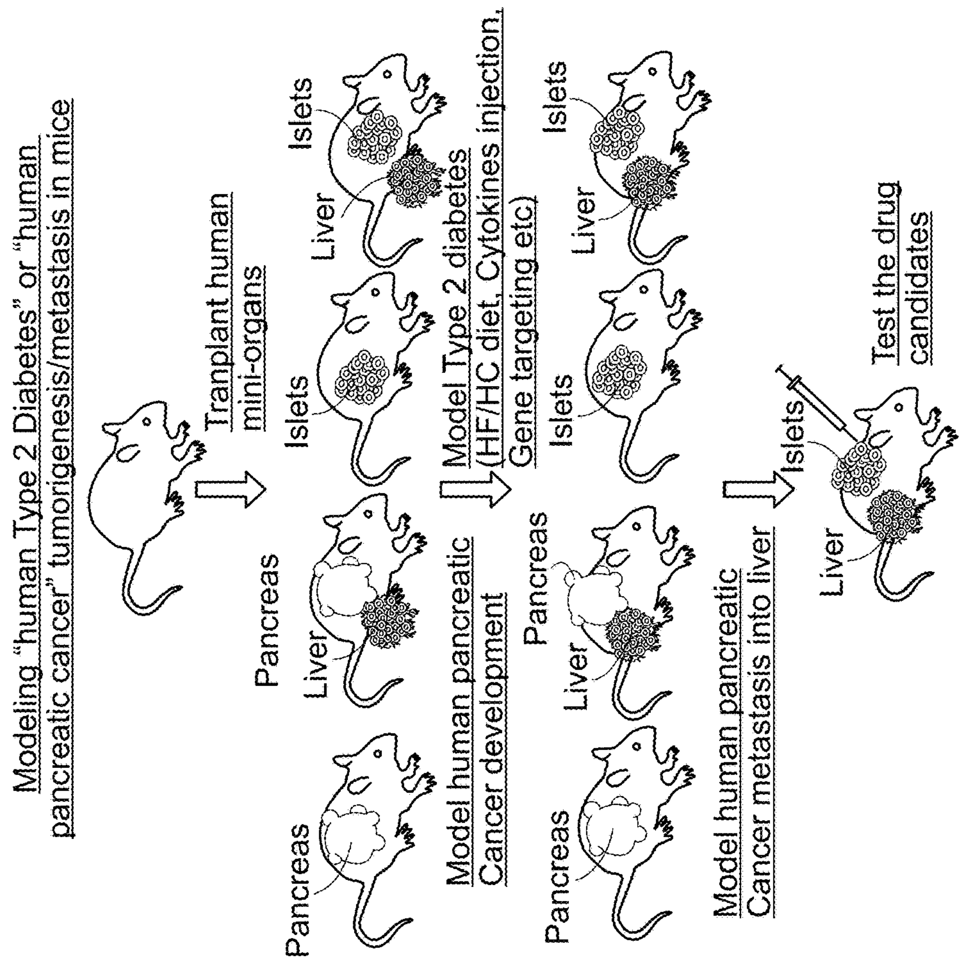

FIG. 8B provides a schematic showing modeling of human Type 2 diabetes in mice. In an exemplary assay, human islet organoids and/or human liver organoids are transplanted into mice. The mice are then administered various stressors that induce type 2 diabetes, such as a high fat diet (HFD) or cytokines injection. The potential candidate drugs identified in this assay are further tested in human type 2 diabetic mouse model. Genes expression and morphology as well as the degree of diabetes are investigated.

FIG. 8B also shows modeling of human pancreatic cancer tumorigenesis and metastasis in mice. In an exemplary assay, human pancreas organoids and/or human liver organoids are transplanted into mice. Mice transplanted with a mini pancreas are used to study human pancreatic cancer growth in human pancreas microenvironment. In another exemplary assay, a mini pancreas and mini liver are co-transplanted in mice. The liver is a major site for metastasis of pancreatic cancer. In vivo, endothelial cells in the mini pancreas and in the mini liver create a pancreas-liver vasculature network for pancreatic cancer metastasis. Thus, mice co-transplanted with a mini pancreas and mini liver are used to study the metastasis of human pancreatic cancer into the human liver.

An ultimate goal of the generation of functional organ-like clusters from pluripotent stem cells (PSC) is to gain insight into the mechanisms underlying human diseases. Although great advances have been made in terms of developing disease models in animals, many of these models fail to faithfully recapture the human condition. In the case of pancreatic islets, their development, cytoarchitecture, and physiology in rodents and human are notably different.

Results herein were obtained using the following materials and methods.

3D Kelcogel® (3DKG) Culture Media

Kelcogel® F low acyl gellan gum (GG-LA) obtained from Modernist Pantry is suspended in pure water 0.3% (w/v) and dissolved by stirring at 90° C. or by microwave. The aqueous solution is sterilized at 121° C. for 20 minutes in an autoclave. The solution is added to TeSR™ (Ludwid et al., Nature methods 3, 637-646) or custom TeSR™ media (800 ml DMEM/F12, 13.28 g BSA. 10 ml Glutamax, 560 mg $NaHCO_3$, 330 mg thiamine, 100 mg reduced glutathione, 3300 mg Vitamin C, 14 μg Selenium, 10 ml NEAA, 2 ml Trace element B, 1 ml Trace Element C, 7 μl β-ME, 2 ml DLC, 2 ml GABA, 2 ml LiCl, 129.7 μg pipecolic acid, Insulin 2 mg up to 1000 ml) at final concentration of 0.015%. Methylcellulose (MC) stock solution is added to a final concentration of 0.3% (R&D systems) (e.g., 0.3% Kelcogel® stock: Kelcogel® F low acyl GG-LA 300 mg+MilliQ water 100 ml; 3DKG Stem TeSR™ Base Media: STEMCELL™ TeSR™ 95 ml+0.3% Kelcogel® stock 5 ml+MC stock solution 300 ul; 3DKG Custom TeSR™ Base Media: custom TeSR™ media 95 ml+0.3% Kelcogel® stock 5 ml+MC stock solution 300ul; 1% final concentration of Penicillin/streptozocin is added for 3DKG media).

Preparation of Human Pancreatic Endocrine Progenitors and β-Like Cells In Vitro

Pancreatic endocrine cells (hiPSC-PEs) were prepared from human iPSC using differentiation methods as previously described. Briefly, human induced pluripotent stem cells (hiPSC) derived from HUVECs were obtained from the Stem Cell Core (Salk Institute). Cells were maintained on MATRIGEL® (BD)-coated dishes in complete STEMCELL™ TeSR™ media at 37 degree in a humidified 5% $CO_2$ incubator. For pancreatic differentiation, hiPSC were infected with a human insulin reporter lentivirus (pGreenZero lenti reporter human insulin, System Biosciences) by Spinfection (800 g, 1 hour). Methods 1: Media was changed to 100 ng/ml human Activin (R&D Systems), 25 ng/ml recombinant human Wnt3a (R&D Systems) in custom TeSR™ media (800 ml DMEM/F12, 13.28 g BSA, 10 ml Glutamax, 560 mg $NaHCO_3$, 330 mg thiamine, 100 mg reduced glutathione, 3300 mg Vitamin C, 14 μg Selenium, 10 ml NEAA, 2 ml Trace Element B, 1 ml Trace Element C, 7 μl (3-ME, 2 ml DLC, 2 ml GABA, 2 ml LiCl, 129.7 μg PA, Insulin 2 mg up to 1000 ml) for 2 days and then 100 ng/ml human Activin in differentiation media for another 2 days (Stage 1, Pancreatic Endoderm). Subsequently, media was replaced with custom TeSR™ media with 1 uM dorsomorphin (Calbiochem), 2 μM Retinoic Acid (Sigma), 10 μM SB431542 and 1% of B27 supplement for 7 days (Stage 2). Media was then replaced with custom TeSR™ media with 10 uM forskolin (Sigma), 10 μM dexamethasone (Stemgent), 10 μM TGFβ RI Kinase inhibitor II/Alk5 inhibitor II (Calbiochem or Enzo), 10 μM Nicotinamide (Sigma), 1 μM 3,3',5-Triiodo-L-thyronine sodium salt (T3) and 1% of B27 supplement for 4-5 days (day 15-day 21, Pancreatic endocrine progenitors). Media was replaced every day (stage 1) or every other day (stage 2 & stage 3).

Methods 2: Media was changed to 100 ng/ml human Activin (R&D Systems), 25 ng/ml recombinant human Wnt3a (R&D Systems) or 3 μM CHIR99021 (Axon or Selleckchem) in differentiation media (51) for 1 day and then 100 ng/ml human Activin in differentiation media (51) for another 2 days (Stage 1, Pancreatic Endoderm). Subsequently, media was replaced with differentiation media (S2) with 50 ng/ml FGF7 (R&D Systems) for 2 days and then differentiation media (S3) with 50 ng/ml FGF7, 0.25 μM SANT-1 (Sigma), 1 μM Retinoic Acid (Sigma), 100 nM LDN193189 and 100 nM α-Amyloid Precursor Protein Modulator TPB for 3 days. Subsequently, media was replaced with differentiation media (S4) with 0.25 μM SANT-1, 50 nM Retinoic Acid, 10 μM Alk5 inhibitor II, 1 μM T3 for 3 days. Subsequently, media was replaced with differentiation media (S5) with 100 nM LDN193189, 100 nM Gamma Secretase inhibitor XX GSiXX (Millipore), 10 μM Alk5 inhibitor II, 1 μM T3 for 7 days. Subsequently, media was replaced with differentiation media (S5) with 10 μM Trolox (Calbiochem), 2 μM R428 (Selleckchem), 1 mM N-acetyl cysteine, 10 μM Alk5 inhibitor II, 1 μM T3 for additional 7 to 20 days.

S1 Media (MCDB131 Media, 8 mM glucose, 2.46 g/L $NaHCO_3$, 2% Fatty acid free BSA, 0.25 mM L-Ascorbic acid 0.002% Insulin-Transferrin-Selenium ITS-X (GIBCO), 2 mM Glutamax, 1% Penicillin-Streptomycin), S2 Media (MCDB131 Media, 8 mM glucose, 1.23 g/L $NaHCO_3$, 2% Fatty acid free BSA, 0.25 mM L-Ascorbic acid, 0.002%

Insulin-Transferrin-Selenium ITS-X (GIBCO), 2 mM Glutamax, 1% Penicillin-Streptomycin), S3 Media (MCDB131 Media, 8 mM glucose, 1.23 g/L $NaHCO_3$, 2% Fatty acid free BSA, 0.25 mM L-Ascorbic acid, 0.5% Insulin-Transferrin-Selenium ITS-X (GIBCO), 2 mM Glutamax, 1% Penicillin-Streptomycin), S4 Media (MCDB131 Media, 8 mM glucose, 1.23 g/L $NaHCO_3$, 2% Fatty acid free BSA, 0.25 mM L-Ascorbic acid, 0.002% Insulin-Transferrin-Selenium ITS-X (GIBCO), 2 mM Glutamax, 1% Penicillin-Streptomycin, 10 μg/ml Heparin, 10 μM Zinc Sulfate), S5 Media (MCDB131 Media or BLAR Media, 20 mM glucose, 1.754 g/L $NaHCO_3$, 2% Fatty acid free BSA, 0.25 mM L-Ascorbic acid, 0.002% Insulin-Transferrin-Selenium ITS-X (GIBCO), 2 mM Glutamax, 1% Penicillin-Streptomycin). For 3 dimensional culture, hiPSC or hESC were cultured in 3DKG Stem TeSR™ Base Media with 10 μM Y-27632 for 5 to 7 days and then Media were replaced each Differentiation media with 0.015% Kelcogel and 0.3% Methylcellulose.

Generation of Three-Dimensional Pancreatic Islet Bud In Vitro: Islet-Like Organoids in Matrigel Through Co-Culture with hADSCs and HUVECs Primary HUVECs and human Adipose-derived stem cells (hADSC) (Invitrogen or PromoCell) were cultured in 15 cm dish with EBM Medium (Ronza, cc-3121) or MesenProRS™ Medium (GIBCO, 12747-010 or Preadipocyte Growth Medium Kit, C-27417), respectively, at 37 degree Celsius in a humidified 5% $CO_2$ incubator. For co-culturing experiments, pancreatic endocrine progenitors derived from human iPSC were treated with Accutase, while HUVECs and hADSC were treated with TrypLE (GIBCO, 12604-013) and cells collected into a 50 ml tube respectively. After the cells were counted, $1\times10^6$ cells of hiPS-PP, $7\times10^6$ cells of HUVEC and $1\text{-}2\times10^5$ cells of hADSC were co-cultured in 1 well of 24 well with 300 ul of MATRIGEL® matrix. For the purpose of scalable generation of human islets like organoids, $1\times10^6$ cells of hiPS-PP (day 15-day 21), $7\times10^6$ cells of HUVEC and $1\text{-}2\times10^5$ cells of hADSC were co-cultured in 3DKG Custom TeSR® media with 10 uM forskolin (Sigma), 10 μM dexamethasone (Stemgent), 10 uM TGFβ RI Kinase inhibitor II/Alk5 inhibitor II (Calbiochem or Enzo), 10 uM Nicotinamide (Sigma), 1 uM 3,3',5-Triiodo-L-thyronine sodium salt (T3) and 1% of B27 supplement, R428 (204), Zinc sulfate (10 μM) and N-Cys (1 mM). (Methods 1) or co-cultured in differentiation media (S5) with 100 nM LDN193189, 100 nM Gamma Secretase inhibitor XX GSiXX (Millipore), 10 μM Alk5 inhibitor II, 1 μM T3 for 7 days. Subsequently, media was replaced with differentiation media (S5) with 10 μM Trolox (Calbiochem), 2 μM R428 (Selleckchem), 1 mM N-acetyl cysteine, 10 μM Alk5 inhibitor II, 1 μM T3 for additional 7 to 20 days (Methods 2). Mixed cells formed spherical, islet-like clusters within a few days. Media was changed every other day.

Generation of 3D (Three-Dimensional) Pancreatic Islet Buds In Vitro: Islet-Like Organoids in Scalable Gellan Gum Through Co-Culture with hADSCs and HUVECs Cells were prepared as described above. Briefly, $1\times10^8$ cells of hiPS-PP, $2\text{-}7\times10^7$ cells of HUVECs and $5\text{-}7\times10^6$ cells of hADSC were co-cultured in 60-100 ml of 3DKG Custom TeSR™ with 10 μM forskolin (Sigma), 10 μM dexamethasone (Stemgent), 10 μM TGFβ RI Kinase inhibitor II/Alk5 inhibitor II (Calbiochem or Enzo), 10 μM Nicotinamide (Sigma), 1 μM 3,3',5-Triiodo-L-thyronine sodium salt (T3) and 1% of B27 supplement, R428 (2 μM), Zinc sulfate (10 μM) and N-Cys (1 mM) (Methods 1) or co-cultured in differentiation media (S5) with 100 nM LDN193189, 100 nM Gamma Secretase inhibitor XX GSiXX (Millipore), 10 μM Alk5 inhibitor II, 1 μM T3 for 7 days. Subsequently, media was replaced with differentiation media (S5) with 10 μM Trolox (Calbiochem), 2 μM R428 (Selleckchem), 1 mM N-acetyl cysteine, 10 μM Alk5 inhibitor II, 1 μM T3 for additional 7 to 20 days (Methods 2). Mixed cells formed spherical, islet-like clusters within a few days. Media was changed every day or every other day.

Generation of 3D (Three-Dimensional) Pancreatic Islets Bud In Vitro: Islet-Like Organoids in Scalable Gellan Gum 3D Culture Methods without (w/o) Using hADSC and HUVECs Human PSCs, including iPSC or ESC, were initially cultured in matrigel-coated plates (2 dimensional (2D) cultures. Cells were then treated with Accutase (Innovative Cell Technologies, Inc., San Diego, Calif.) to generate a single cell suspension, washed with PBS and centrifuged at 1000-1300 rpm for 5 minutes to pellet cells. Cells were resuspended with 3DKG Stem TeSR™ Base Medium (Stemcell Technologies, Cambridge, Mass.) with 10 μM Y-27632 (a RHO/ROCK pathway inhibitor compound) and cultured for an additional for 5 to 7 days until PSC sphere growth reached 50-100 μm diameter. Media was then replaced with differentiation media supplemented with 0.015% Kelcogel and 0.3% Methylcellulose. The culture medium was changed to differentiation medium (51) containing 100 ng/ml human Activin (R&D Systems), 25 ng/ml recombinant human Wnt3a (R&D Systems) or 3 μM CHIR99021, a glycogen synthase kinase GSK-3 inhibitor (Axon Medchem, Reston, Va.; or Selleckchem) for 1 day and then to differentiation medium (S1) containing 100 ng/ml human Activin for another 2 days (Stage 1, Pancreatic Endoderm). Subsequently, the medium was replaced with differentiation medium (S2) containing 50 ng/ml FGF7 (R&D Systems) for 2 days, and then with differentiation medium (S3) containing 50 ng/ml FGF7, 0.25 μM SANT-1 (Sigma), 1 μM Retinoic Acid (Sigma), 100 nM LDN193189 (an ALK2 and ALK3 inhibitor, Sigma) and 100 nM α-Amyloid Precursor Protein Modulator TPB for 3 days. Subsequently, this medium was replaced with differentiation medium (S4) containing 0.25 μM SANT-1, 50 nM Retinoic Acid, 10 μM Alk5 inhibitor II, 1 μM T3 for 3 days. Subsequently, the medium was replaced with differentiation medium (S5) containing 100 nM LDN193189, 100 nM Gamma Secretase inhibitor XX GSiXX (Millipore) 10 μM Alk5 inhibitor II, 1 μM T3 for 7 days. Subsequently, the medium was replaced with differentiation medium (S5) containing 10 uM Trolox (Calbiochem), 2 μM R428 (Selleckchem), 1 mM N-acetyl cysteine, 10 μM Alk5 inhibitor II, 1 μM T3 for an additional 7 to 20 days. After confirmation of the insulin gene expression by either reporter expression or qPCR (typically on day 20-30), the medium was changed to differentiation medium (S5) containing 10 μM Trolox (Calbiochem), 2 μM R428 (Selleckchem), 1 mM N-acetyl cysteine, 10 μM Alk5 inhibitor II, 1 μM T3 and 100 ng/ml recombinant human (rh)Wnt4 (R&D Systems), 400 ng/ml rhWnt5a, or 50% Wnt5a conditioned medium for 1-20 days. Wnt5a conditioned medium was prepared by culturing an L-Wnt5a cell line (ATCC, CRL-2814) in DMEM with 10% FBS, 1% Penicillin-streptomycin for 4 days after cells had reached 70-100% confluence in T175-T225 Frasko cell culture flasks.

Generation of 3D (Three-Dimensional) Liver Bud In Vitro: Organ Buds

Hepatocyte cells (hiPSC-HEs) from human iPSC were prepared using differentiation methods as previously described. Briefly, hiPSCs were maintained on MATRIGEL® (BD)-coated dishes in complete STEMCELL™ TeSR™ media at 37 degrees Celsius in a humidified 5%

$CO_2$ incubator. For hepatic differentiation, hiPSC (90% confluence in 6 well) were cultured with 100 ng/ml human Activin (Sigma) and 25 ng/ml recombinant human Wnt3a (R&D systems) or 3 μM CHIR99021 and 1% B27 supplement minus Insulin in RPMI1640 media for 1 day and then 100 ng/ml human Activin and 1% B27 supplement minus Insulin in RPMI media for another 4 days (Stage 1 Hepatic-Endoderm). Subsequently, media was replaced with differentiation media with 10 ng/ml bFGF, 20 ng/ml BMP4 and 1% of B27 supplement in RPMI1640 media for 3 days (Stage 2). Media was then replaced with differentiation media with 0.1 μM Dexamethasone, 20 ng/ml OncostatinM (R&D Systems) and 10-20 ng/ml Hepatic Growth Factor (HGF, R&D Systems) and 1% of B27 supplement in Hepatocyte Culture Media (Lonza, MD, CC-3198, withdraw EGF and Gentamicin/Amphotericin-B) for 4-22 days (day 15-day 19, Pancreatic endocrine progenitors). Media was replaced every day (stage 1) or every other day (stage 2 & stage 3). Primary HUVECs cells and human Adipose-derived stem cells (hADSC) (InVitrogen or PromoCell) were cultured in 15 cm dish with EBM Media (Ronza, cc-3121) or MesenProRS Media (GIBCO, 12747-010 or Preadipocyte Growth Medium Kit, C-27417), respectively, at 37 degree Celsius in a humidified 5% $CO_2$ incubator. For co-culturing experiments, day 10-hepatocytes derived from human iPSC were treated with Accutase, while HUVECs and hADSC were treated with TrypLE (GIBCO, 12604-013) and cells were collected into 50 ml tube, respectively. After the cells were counted, $1\times10^6$ cells of hiPS-PP, $7\times10^6$ cells of HUVEC and $1\text{-}2\times10^5$ cells of hADSC were co-cultured in 1 well of 24 well with 300 ul of matrigel. Liver-like organoids were formed within 1 to 2 days. Then, liver-like organoids were taken out from MATRIGEL® matrix and cultured in in 3DKG Custom TeSR™.

Generation of 3D (Three-Dimensional) Heart Bud In Vitro: Organ Buds

Cardiomyocyte cells (hiPSC-CDs) were prepared from human iPSC using differentiation methods as previously described. Briefly, hiPSCs were maintained on MATRIGEL® (BD)-coated dishes in complete Stemcell™ TeSR™ media at 37 degree Celsius in a humidified 5% $CO_2$ incubator. For hepatic differentiation, hiPSC (90% confluence in 6 well) were cultured with 100 ng/ml human Activin (R&D Systems) and 10 uM CHIR99021 and 1% B27 supplement minus Insulin in RPMI1640 media for 1 days and then 1% B27 supplement minus Insulin in RPMI media for another 2 days (Stage 1 cardiac-Mesoderm). Subsequently, media was replaced with RPMI1640 with 5 uM IWP-2 and 1% B27 supplement minus Insulin in RPMI media for 1 days (Stage 2). Media was then replaced with 1% B27 supplement minus Insulin in RPMI Media for 6 days or more (Stage 3). Cardiac contraction started around day 13. Media was replaced every day (stage 1) or every other day (stage 2 & stage 3). Primary HUVECs cells and human Adipose-derived stem cells (hADSC) (Invitrogen or PromoCell) were cultured in 15 cm dish with EBM Media (Ronza, cc-3121) or MesenProRS™ Media (GIBCO, 12747-010 or Preadipocyte Growth Medium Kit, C-27417), respectively at 37 degrees Celsius in a humidified 5% $CO_2$ incubator. For co-culturing experiments, day 13 to day 15 cardiomyocytes derived from human iPSC were treated with Dispase, while HUVECs and hADSC were treated with TrypLE (GIBCO, 12604-013) and cells collected into 50 ml tube respectively. After the cells were counted, $1\times10^6$ cells of hiPS-PP, $7\times10^6$ cells of HUVEC and $1\text{-}2\times10^5$ cells of hADSC were co-cultured in 3DKG Custom TeSR™ media. Mini heart like organs capable of contracting were formed within a few days.

Generation of 3D (Three-Dimensional) Intestine Bud In Vitro: Organ Buds

Intestinal cells (hiPSC-ITs) were prepared from human iPSC using differentiation methods as previously described. Briefly, hiPSCs were maintained on Matrigel® (BD)-coated dishes in complete Stemcell™ TeSR™ Media at 37 degrees Celsius in a humidified 5% $CO_2$ incubator. For hepatic differentiation, hiPSC (90% confluence in 6 well) were cultured with 100 ng/ml human Activin (R&D Systems), 3 uM CHIR99021, 2 mM Glutamax and 1% B27 supplement minus Insulin in RPMI1640 media for 1 day and then 100 ng/ml human Activin (R&D Systems), 2 mM Glutamax and 1% B27 supplement minus Insulin in RPMI1640 media for another 3 days (Stage 1 Forgut-Endoderm). Subsequently, media was replaced with 500 ng/ml Wnt3a, 500 ng/ml FGF4 and 1% B27 supplement in RPMI 1640 media for 4 days (Stage 2). Cells were transferred to Matrigel® matrix and then a 3D-spheroid Matrigel® dorm was made in the bottom of 24 well. Media was then replaced with 1% B27 supplement, 1% N2 supplement, 500 ng/ml R-spondin, 100 ng/ml Noggin, 50 ng/ml EGF, 2 mM Glutamax™ supplement, 10 uM HEPES in DMEM/F12 Media for 7 days or more (stage 3). Intestinal-like organoid spheroids were observed within a week. Media was replaced every day (stage 1) and every other day (stage 2 & stage 3). Primary HUVECs cells and human Adipose-derived stem cells (hADSC) (Invitrogen or PromoCell) were cultured in a 15 cm dish with EBM Media (Ronza, cc-3121) or MesenProRS™ Media (GIBCO®, 12747-010 or Preadipocyte Growth Medium Kit, C-27417), respectively, at 37 degrees Celsius in a humidified 5% $CO_2$ incubator. For co-culturing experiments, intestinal progenitors (day 7) derived from human iPSC were treated with Accutase, while HUVECs and hADSC were treated with TrypLE (GIBCO®, 12604-013) and cells collected into a 50 ml tube respectively. After counting the cells, $1\times10^6$ cells of hiPS-PP, $7\times10^6$ HUVEC cells and $1\text{-}2\times10^5$ hADSC cells were co-cultured in 3DKG Custom TeSR™ media.

Insulin Secretion Assay (Primary Mouse and Human Pancreatic Islets and Human iPSC-Derived Cells)

Insulin release from intact islets was monitored using batch incubation methods (Yoshihara et al., 2010, Nat. Commun. 1:127). Briefly, overnight-cultured isolated pancreatic islets (RPMI-1640 supplemented with 10% (v/v) fetal bovine serum and 1% (v/v) Antibiotic-Antimycotic (Gibco)) were pre-cultured at 37° C. for 30 min (Krebs-Ringer bicarbonate buffer (KRBB) containing 129.4 mM NaCl, 3.7 mM KCl, 2.7 mM $CaCl_2$, 1.3 mM $KH_2PO_4$, 1.3 mM $MgSO_4$, 24.8 mM $NaHCO_3$ (equilibrated with 5% $CO_2$, 95% $O_2$, pH7.4), 10 mM HEPES and 0.2% (v/v) BSA (fraction V, Sigma) (KRBH) with 3 mM glucose). Pancreatic islets were then incubated in KRBH buffer (500 μl/10 islets) with 3 mM or 20 mM glucose to determine insulin secretion levels. After 30 min, islets were pelleted by centrifugation and insulin levels determined by ELISA (Rat/mouse Insulin ELISA KIT (Millipore) and Human Insulin ELISA KIT (Millipore) for mouse and human islets, respectively). For human iPSC derived cells, the cells ($1\times10^6$ cells/well in 24 well) were pre-cultured in 3 mM glucose KRBH buffer (500 μl/well). The cells were then incubated in KRBB (200 μl/well) with 3 mM or 20 mM glucose to determine c-peptide secretion levels as indicator of insulin secretion levels. After 30 min, the cells were pelleted by centrifugation and c-peptide levels were determined by human c-peptide ELISA KIT (Millipore).

Quantitative RT-PCR Analysis

Total RNA was extracted using TRIzol reagent (Invitrogen) and RNeasy KIT (Qiagen). Reverse transcription was performed with a SuperScript III First-Strand Synthesis System kit (Invitrogen) or PrimeScript RT reagent kit (TAKARA). Real time quantitative RT-PCR (qPCR) was performed using SYBR Green (Bio-Rad).

Lentivirus Production for Proinsulin-NanoLuc

Proinsulin-NanoLuc in pLX304 (Addgene, #62057) was obtained from Addgene. Proinsulin-NanoLuc lentivirus was produced using a second-generation viral packaging system. Briefly, 14 μg of Proinsulin-NanoLuc, 6.6 μg of PsPAX2 packaging plasmid (Addgene 12260), 5.4 μg of pMD2.G envelope plasmid (Addgene 12259) and 54 μl Lipofectamin2000 (Invitrogen) were used to transfect a T75 flask of HEK293LTV packaging cells. Twenty-four (24) hours after transfection, media was changed to fresh DMEM with 10% FBS and 1% Penicillin/Streptozocine. Forty-eight (48) hours and 96 hours after transfection, viruses were collected as day 1 and day 3, respectively and passed through 0.2 μm cellulose acetate filters (VWR). Viruses were aliquoted and frozen at −80 degrees Celsius until use.

Gaussia Luciferase Assay for Insulin Secretion Measurement

Mouse islets, human islets and human islets like organoids were plated in their respective growth media with 10 μg/ml Polybrene® polymer (Santacruz). Viruses were then added. After overnight culture, cells were placed in fresh growth media. Forty-eight (48) to 72 hours after infection, mouse islets, human islets and human islet-like organoids were picked up by hand and then placed into 96 wells with single islet or organoid. Then, insulin secretion assays were performed. Briefly, a single islet or organoid was pre-incubated with 3 mM glucose KRBB at 37° C. for 30 min to 1 hour. The cells were then incubated in KRBB (100 μl/well) with 3 mM for 30 min and then sequentially incubated with 20 mM glucose with or without 100 nM Exendin-4 or 3 mM glucose with 20 mM KCl (100 μl/well). To determine Gaussia Luciferase activity as indicator of insulin secretion levels, 10 μl of samples are used for Luciferase assay using Pierce Gaussia Luciferase Flash Assay Kit (Prod #16159, Thermo Scientific).

INS-1 cells were infected with the virus by spinfection (800 g, 1 hour at 37 degrees Celsius) and then changed to fresh INS-1 growth media. Seventy-two (72) hours after transfection, INS-1 cells were treated with 5 μg/ml Blasticidin (Invitrogen) for 7 days to select for Proinsulin-NanoLuc expressing cells. For insulin secretion assay, the cells ($5\times10^4$-$1\times10^5$ cells/well in 96 well) were pre-cultured in 3 mM glucose KRBB (100 μl/well). The cells were then incubated in KRBB (100 μl/well) with 3 mM and then sequentially incubated with 20 mM glucose with or without 100 nM Exendine-4 or 3 mM glucose with 20 mM KCl (100 μl/well). To determine Gaussia Luciferase activity as indicator of insulin secretion levels, 10 μl of samples are used for Luciferase assay using Pierce Gaussia Luciferase Flash Assay Kit (Prod #16159, Thermo Scientific).

Vascularization Test In Vitro

Human islet-like organoids were embedded in 1 well of 24 well plate with 300 μl of Matrigel® matrix with EBM Media (Ronza, cc-3121). Vascularization was observed within 24-72 hours.

3D Culture of hADSCs and WNT Protein Expression hADSCs undergo changes in the expression of Wnt genes, in particular genes in the Wnt5a pathway, during the spontaneous self-organization that occurs in 3D culture. (FIG. 11A). Wnt5a was found to be the predominant protein expressed among the Wnt proteins in hADSC 3D culture over time. (FIG. 11B).

Example 5: Wnt Proteins in the Metabolic Maturation of iPSC-Derived Islet Organoids Fltp and Esrrg genes were found to be expressed in iPSC-derived islet organoids (day 21, generated without co-culture with hADSCs or HUVECs) after treatment with PBS, WNT3a (500 ng/ml), recombinant human (rh)WNT4 (100 ng/ml), or rhWNT5a (400 ng/ml) for 5 days. (FIG. 12A). As shown in FIG. 12B, Esrrg gene expression was induced in hiPSC-derived islet organoids that were generated in the absence of supporting hADSC or HUVECs, in response to increasing doses of rhWNT4 (0, 10, 25, 50, 100, 200 ng/ml) and rhWNT5a (0, 25, 50, 100, 200, 400 ng/ml). In addition, mitochondrial genes involved in oxidative phosphorylation (Cox7a2, Ndufa1, Ndufa7), lactate dehydrogenase (Ldha) and Fltp (a Wnt/planar cell polarity (PCP) effector and reporter gene) were induced in hiPSC-derived islet organoids that were generated in the absence of supporting hADSC or HUVECs, in response to increasing doses of rhWNT4 (0, 10, 25, 50, 100, 200 ng/ml) and rhWNT5a (0, 25, 50, 100, 200, 400 ng/ml), (FIG. 12C). Mitochondrial (Mitotracker; Mito-Red) and insulin (Insulin-GFP) levels were increased in hiPSC-derived islet organoids (day 27) after 8 days treatment with PBS or WNT4 (100 ng/ml). (FIG. 12D). Human iPSC-derived islet organoids (day 27) were generated after 8 days treatment with PBS or WNT4 (100 ng/ml). (FIG. 12E). Insulin production was found in hiPSC-derived islet organoids (day 27) after 8 days treatment with rhWNT4 (100 ng/ml), rhWNT5a (400 ng/ml), or WNT5a secreting fibroblast conditioned media (50%), compared with PBS and control fibroblast conditioned media (50%). (FIGS. 12F-12H). Human iPSC (hiPSC)-derived islet organoids (day 22) treated with rhWnt4 (100 ng/ml) for 12 days showed functional maturation based on their secretion of human c-peptide, as measured in response to low glucose βmM, "G3 mM"), high glucose (20 mM, "G20 mM"), or high KCl levels (20 mM, "KCL20 mM"), (FIG. 13).

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A method of generating a functionally mature pancreatic islet organoid, the method comprising culturing an induced pluripotent stem cell (iPSC)-derived pancreatic islet organoid comprising an iPSC-derived beta-like cell in a medium comprising a Wnt4 or a Wnt5a polypeptide, or a fragment thereof, thereby generating the functionally mature pancreatic islet organoid.

2. The method of claim 1, wherein the induced pluripotent stem cell (iPSC)-derived beta-like cell is cultured in a 3-dimensional matrix to generate the pancreatic islet organoid.

3. The method of claim 1, wherein the Wnt4 or Wnt5a polypeptide, or a fragment thereof, is a recombinant human Wnt4 or Wnt5a polypeptide, or a fragment thereof.

4. The method of claim 3, wherein the medium comprises a recombinant human Wnt4 polypeptide, or a fragment thereof.

5. The method of claim 1, wherein the pancreatic islet organoid further comprises one or more cell types selected from the group consisting of an iPSC-derived alpha cell, an iPSC-derived delta cell, an iPSC-derived duct cell, an adipose-derived stem cell (hADSC), and an endothelial cell.

6. The method of claim 1, wherein the pancreatic islet organoid is vascularized.

7. The method of claim 1, wherein the pancreatic islet organoid exhibits one or more of glucose-stimulated insulin secretion (GSIS), c-peptide secretion, KCl-stimulated insulin secretion, GLP-1 stimulated insulin secretion, somatostatin secretion, and glucagon secretion.

8. The method of claim 1, wherein the pancreatic islet organoid expresses one or more mitochondrial genes involved in oxidative phosphorylation selected from the group consisting of Cox7a2, Ndufa1, Ndufa7, and lactate dehydrogenase (Ldha).

9. The method of claim 1, wherein the pancreatic islet organoid is surrounded by an iPSC-derived exocrine component.

10. The method of claim 1, wherein the pancreatic islet organoid expresses a beta cell transcription factor selected from the group consisting of PDX1, MAFA, PAX4, PAX6, NEUROD1, NKX6-1, GATA6, and FOXA2.

11. The method of claim 1, wherein the pancreatic islet organoid expresses Estrogen-related receptor gamma (Esrrg).

12. The method of claim 1, wherein the pancreatic islet organoid is cultured in the medium for at least 4 days.

13. The method of claim 1, wherein the medium comprises a Wnt4 or Wnt5a polypeptide, or a fragment thereof, in a concentration of between 10-400 ng/ml.

14. The method of claim 1, wherein upon implantation into a subject suffering from Type I or Type II diabetes, the pancreatic islet organoid is capable of ameliorating, reducing, and/or stabilizing the Type I diabetes or Type II diabetes in the subject.

15. The method of claim 14, wherein the subject is human.

16. The method of claim 1, wherein the iPSC-derived beta-like cell is a human iPSC-derived beta-like cell.

17. The method of claim 5, wherein the one or more cell types selected from the group consisting of an iPSC-derived alpha cell, an iPSC-derived delta cell, an iPSC-derived duct cell, an adipose-derived stem cell (hADSC), and an endothelial cell is human.

18. The method of claim 1, wherein the Wnt4 or Wnt5a polypeptide, or a fragment thereof, is present in culture medium of a Wnt4- or Wnt5a-producing cell line.

19. The method of claim 1, wherein the iPSC-derived pancreatic islet organoid is a human iPSC (hiPSC)-derived pancreatic islet organoid.

* * * * *